US008445229B2

(12) United States Patent
Grasso et al.

(10) Patent No.: US 8,445,229 B2
(45) Date of Patent: *May 21, 2013

(54) METHODS OF GENERATING HIGH-PRODUCTION OF ANTIBODIES FROM HYBRIDOMAS CREATED BY IN VITRO IMMUNIZATION

(75) Inventors: Luigi Grasso, Bala Cynwyd, PA (US); Shaohong Liang, West Chester, PA (US); Nicholas C. Nicolaides, Garnett Valley, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 318 days.

This patent is subject to a terminal disclaimer.

(21) Appl. No.: 12/786,530

(22) Filed: May 25, 2010

(65) Prior Publication Data

US 2010/0311169 A1  Dec. 9, 2010

Related U.S. Application Data

(62) Division of application No. 10/714,228, filed on Nov. 14, 2003, now Pat. No. 7,754,450.

(60) Provisional application No. 60/427,165, filed on Nov. 15, 2002, provisional application No. 60/501,650, filed on Sep. 10, 2003.

(51) Int. Cl.
*C12N 15/01* (2006.01)
*C12N 15/06* (2006.01)

(52) U.S. Cl.
USPC ....... 435/69.1; 435/70.21; 435/441; 435/449; 435/455

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,376,110 A | 3/1983 | David et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,720,459 A | 1/1988 | Winkelhake |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III et al. |

(Continued)

FOREIGN PATENT DOCUMENTS

| | | |
|---|---|---|
| CA | 2240609 A1 | 10/1999 |
| WO | PCT/US92/09196 | 10/1992 |

(Continued)

OTHER PUBLICATIONS

Low et al (Journal of Molecular Biology, 1996, vol. 260, pp. 359-368).*
Allen et al., "MutS mediates heteroduplex loop formation by a translocation mechanism," EMBO J., Jul. 1997, 1(14), 4467-4476.
Antoni et al., "An interactive computer program for the determination of the binding constants of monoclonal antibodies by non-linear regression analysis of radioimmunoassay data," J. of Immunol. Meth., Oct. 1985, 83, 61-68.
Ausubel et al. (Eds.), Current Protocols in Molecular Biology, John Wiley & Sons, NY, 1998.

(Continued)

*Primary Examiner* — Karen Canella
(74) *Attorney, Agent, or Firm* — Woodcock Washburn, LLP

(57) ABSTRACT

The invention provides methods for generating high titers of high-affinity antibodies from hybridoma cells produced by fusing myeloma cells with in vitro immunized donor cells. The hybridoma cells or mammalian expression cells with cloned antibody genes from the hybridomas producing the high-affinity antibodies may be mismatch repair defective due to defects of endogenous mismatch repair subunits of through expression of a dominant negative allele of a mismatch repair gene which allows the hybridoma cell to be hypermutable, may be rendered hypermutable by chemical means, or may be naturally mismatch repair deficient. High-affinity antibodies and high titer producer cells producing antibodies may be prepared by the methods of the invention.

41 Claims, 13 Drawing Sheets

U.S. PATENT DOCUMENTS

| | | | |
|---|---|---|---|
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Mateucci |
| 5,264,564 A | 11/1993 | Mateucci |
| 5,272,250 A | 12/1993 | Spielvogel et al. |
| 5,276,019 A | 1/1994 | Cohen et al. |
| 5,276,423 A | 1/1994 | Breit et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,530,101 A | 6/1996 | Queen et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cok et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler et al. |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,146,894 A | 11/2000 | Nicolaides et al. |
| 6,333,318 B1 | 12/2001 | Evans et al. |
| 6,808,894 B1 | 10/2004 | Nicolaides et al. |
| 7,754,450 B2 | 7/2010 | Grasso et al. |
| 2003/0143682 A1 | 7/2003 | Nicolaides et al. |

FOREIGN PATENT DOCUMENTS

| | | |
|---|---|---|
| WO | WO 93/21952 A1 | 11/1993 |
| WO | WO 98/39352 | 9/1998 |
| WO | WO 99/14226 | 3/1999 |
| WO | WO 01/59092 A2 | 8/2001 |
| WO | WO 01/88192 A3 | 11/2001 |
| WO | WO 02/37967 A1 | 5/2002 |
| WO | WO 02/054856 A1 | 7/2002 |
| WO | WO 03/012130 A1 | 2/2003 |
| WO | WO 03/062435 A1 | 7/2003 |
| WO | WO 2004/009782 A3 | 1/2004 |
| WO | WO 2004/024871 A2 | 3/2004 |
| WO | WO 2005/011735 A1 | 2/2005 |

OTHER PUBLICATIONS

Belmont et al., "Synthesis and study of new adenine-acridine tandem, inhibitor of exonuclease III," Bioorg. Med. Chem. Lett., Feb. 7, 2000, 10(3), 293-295.

Bigger et al., "Mutational spectra for polycyclic aromatic hydrocarbons in the supF target gene," Mutation Research, May 2000, 450(1-2), 75-93.

Bjornson, "Modulation of MutS ATP hydrolysis by DNA cofactors," Biochemistry, Mar. 21, 2000, 39(11), 3176-3183.

Borrebaeck, "Critical appraisal of the in vitro immunization technology for the production of mouse and human monoclonal antibodies", Adv Drug Delivery Reviews, Nov. 1988, 2(2), 143-165.

Borrebaeck, "Human mAbs Produced by primary in-vitro, immunization," Trends in Immunology, Jan. 1, 1988, 9(1), 355-359.

Borrebaeck et al., "Human monoclonal antibodies produced by primary in vitro immunization of peripheral blood lymphocytes," Proc. Natl. Acad. Sci, USA, Jun. 1988, 85(11), 3995-3999.

Brown et al., "Protein antigens of normal and malignant human cells identified by immunoprecipitation with monoclonal antibodies," J. Biol. Chem., Jun. 10, 1980, 255(11), 4980-4983.

Brown et al., "Structural characterization of human melanoma-associated antigen p97 with monoclonal antibodies," J. of Immunol., Aug. 1981, 127(2), 539-546.

Cascalho et al., "Mismatch Repair Co-opted by Hypermutation," Science, Feb. 20, 1998, 279, 1207-1210.

Chino et al., "Effect of a noval antibiotic, heliquinomycin, on DNA helicase and cell growth," J. Antibiot. (Tokyo), May 1998, 51(5A), 480-486.

Cole et al., "The EBV-hybridoma technique and its application to human lung cancer," Monoclonal antibodies and Cancer Therapy, Alan R. Liss, Inc., 1985, 77-96.

Cote et al "Generation of human monoclonal antibodies reactive with cellular antigens," Proc. Natl. Acad. Sci. USA, Apr. 1983, 80(7), 2026-2030.

Crooke et al., "Pharmacokinetic properties of several novel oligonucleotide analogs in mice," J. Pharmacol. Exp. Ther., May 1996, 277(2), 923-937.

Emery et al., "Strategies for humanizing antibodies," in: Antibody Engineering, Borrebaeck, C.A.K. (Ed), Oxford University Press, NY, 1995, 159-183.

Englisch et al., "Chemically modified oligonucleotides as probes and inhibitors," Angewandte Chemie (International Edition), Jun. 1991, 30(6), 613-722.

Fiedler et al., "High-level production and long-term storage of engineered antibodies in transgentic tobacco seeds," Biotechnology, Oct. 1995, 13(10), 1090-1093.

Fire et al., "Potent and specific genetic interference by double-stranded RNA in Caenorhabditis elegans," Nature, Feb. 19, 1998, 391(6669), 806-811.

Gait, "Oligoribonucleotides as drugs?," Antisense research and Applications, Crooke, S.T., et al. (Eds.), CRC Press, 1993, Chapter 16, 289-302.

Galfre et al., "Antibodies to major histocompatibility antigens produced by hybrid cell lines," Nature, Apr. 7, 1977, 266(5602), 550-552.

Galio et al., "ATP hydrolysis-dependent formation of a dynamic ternary nucleoprotein comples with MutS and MutL," Nucl. Acids Res., Jun. 1999, 27(11), 2325-2331.

Gefter et al., "A simple Method for polyethylene glycol-promoted hybridization of mouse myeloma cells," Somatic Cell Genet., Mar. 1977, 3(2), 233-236.

Glaser, "Can ReoPro repolish tarnished monoclonal therapeutics?," Nat. Biotechnol., Oct. 1996, 14, 1216-1217.

Graham et al., "Characteristics of human cell line transformed by DNA from human adenovirus type 5," J. Gen. Virol., Jul. 1977, 36, 59-72.

Green et al., "Immunoglobulin hypermutation in cultured cells," Immunol. Rev., Apr. 1998, 162(1), 77-87.

Grishok et al., "Genetic requirements for inheritance of RNAi in *C. elegans*," Science, Mar. 31, 2001, 287(5462), 2494-2497.

Guzman et al., "In vitro immunization: generation of neutralizing monoclonal antibodies to human interleukin-10," J. of Immunol. Methods, Feb. 27, 1995, 179(2), 265-268.

Herbert et al., "Dictionary of immunology", 1985, p. 221.

Ho et al "In vitro immunization of human lymphocytes. I Production of human monoclonal antibodies against bombes in and tetanus toxoid," J. of Immunology, Dec. 1985, 135(6), 3831-3838.

Horii et al "Cloning, characterization and chromosomal assignment of the human genes homologous to yeast PMS1, a member of mis match repair genes," Biochem. Biophys. Res. Commun., Nov. 1994, 204(3), 1257-1264.

Huang et al "N-ethylmaleimide profile of yeast NADP-dependent isocitrate dehydrogenase," Arch. Biophys., Jan. 10, 1995, 316(1), 485-492.

Irving, et al "Affinity maturation of recombinant antibodies using *E. coli* mutator cells," Immunotechnology, Jun. 1996, 2(2), 127-143.

Kabanov et al., "A new class of antivirals: antisense oligonucleotides combined with a hydrophobic substituent effectively inhibit influenza virus reproduction and synthesis of virus-specific proteins in MDCK cells," FEBS Lett., Jan. 1, 1990, 259(2), 327-330.

Kaufman et al.(Eds.), Handbook of Molecular and Cellular Methods in Biology and Medicine, First Edition, CRC Press, Jul. 15, 1995, 496 pages.

Kennett et al. (Eds.), "Monoclonal antibodies. Hybridomas: A new dimension in biological analyses", Plenum Publishing Corp., NY, 1980, 423 pages.

Khazaeli et al., "Human immune response to monoclonal antibodies," J. Immunother. Emphasis Tumor Immunol, Jan. 1994, 15(1), 42-52.

Kim et al., "The role of DNA repair in somatic hypermutation of immunoglobulin genes," J. of Experimental Medicine, Jun. 1998, 187(11), 1729-1733.

Kitagawa et al., "Enzyme coupled immunoassay of insulin using a novel coupling reagent," J. Biochem., Jan. 1976, 79(1), 233-236.

Köhler and Milstein, "Continuous cultures of fused cells secreting antibody of predefines specificity," Nature, Aug. 7, 1975, 256(5517), 495-497.

Kozbor et al., "The production of monoclonal antibodies from human lymphocytes" Immunology Today, Mar. 1983, 4(3), 72-79.

Kroshwitz (Ed.), "Polynucleotide's," The Concise Encyclopedia of Polymer Science and Engineering, John Wiley & Sons, NY, 1990, 858-859.

Kukhanova et al., "Unique Inhibitory Effect of 1-(2'-Deoxy-2'-fluoro-62 -L, -arabinofuranosyl)-5-methyluracil 5'-Triphosphate on Epstein-Barr Virus and Human DNA Polymerases," Biochem. Pharmacol., Apr. 15, 1998, 55(8), 1181-1187.

Kuwakado et al., "Aphicolin potentiates apoptosis induced by arabinosyl nucleosides in human myeloid leukemia cell lines," Biochem. Pharmacol., Dec. 3, 1993, 46(11), 1909-1916.

Lehninger, "The molecular basis of cell structure and function," Biochemistry, $2^{nd}$ Ed., Worth Publishers, Inc., 1975, 72-77.

Lerner, "How to make a hybridoma," Yale J. Biol. and Med., Sep.-Oct. 1981, 54(5), 387-402.

Letsinger et al., "Cholesteryl-conjugated oligonucleotides: synthesis, properties and activity as inhibitors of replication of human immunodeficiency virus in cell culture," Proc. Natl. Acad. Sci. USA, Sep. 1989, 86(17), 6553-6556.

Ma et al., "Creation of Isogenic Mismatch Repair Deficient Cell Lines From a Non-RER Human Colon Cancer," Environmental and Molecular Mutagensis, 1998, 31(suppl 29), P19, 1 page.

Manoharan et al., "Chemical modifications to improve uptake and Bioavailability of antisense oligonucleotides," Ann. NY Acad. Sci., Oct. 28, 1992, 660, 306-309.

Manoharan et al., "Cholic acid-oligonucliotide conjugates for antisense applications," Bioorg. Med. Chem. Let., Apr. 21, 1994, 4(8), 1053-1060.

Manoharan et al., "Introduction of a lipophilic thioether tether in the mirror groove of nucleic acids for antisense applications," Bioorg. Med. Chem. Let., Dec. 1993, 3(12), 2765-2770.

Manoharan et al., "Lipidic nucleic acids," Tetrahedron Lett., May 1995, 36(21), 3651-3654.

Manoharan et al., "Oligonucleotide conjugates: alteration of the pharmacokinetic properties of antisense agents," Nucleosides & Nucleotides, May 1995, 14(3-5), 969-973.

Martin et al., " A new access to 2'-O-Alkylribonucleosiden oligonucleotides and their properties," Helv. Chim. Acta, 1995, 78, 486-504 (English abstract).

Martin et al., "Aid and mismatch repair in antibody diversification," Nature Reviews. Immunology, Aug. 2002, 2(8), 605-614.

Martin et al., "Induction of apoptosis (programmed cell death) in human leukemic HL-60 cells by inhibition of RNA or Protein synthesis," J. of Immunol., Sep. 15, 1990, 145(5), 1859-1867.

Marx, "Interfering with gene expression," Science, May 26, 2000, 288, 1370-1372.

Mather, "Establishment and characterization of two distinct mouse testicular epithelial cell lines," Biol. of Reprod., Aug. 23, 1980, 23(1), 243-252.

Mather et al., "Culture of testicular cells in hormone-supplemented serum-free medium," Annals N.Y. Acad. Sci., Jun. 1982, 383 (The Cell Biology of Testis), 44-68.

McPherson (ed.), "Directed Mutagenesis: A Practical Approach", Oxford University Press, USA, Aug. 1, 1991, 282 pages.

Mironov et al., "Introduction of mutations in mismatch repair-proficient and—deficient human colon cancer cell lines by carcinogens producing different types of DNA damage," Proc. of the Amer. Assoc. for Cancer Res., 1999, 40, 625.

Mishra et al., "Improved leishmanicidal effect of phosphorotiote antisense oligonucleotides by LDL-medicated delivery," Biochim. Et Biophysica, Feb. 1995, 1264, 229-237.

Müller, "Calculation of average antibody affinity in anti-hapten sera from data obtained by competitive radioimmunoassay," J. Immunol. Meth., Jun. 26, 1980, 34, 345-352.

Neuberger et al., "Mice perform a human repertoire," Nature, Mar. 6, 1997, 386, 25-26.

Nicolaides, "A naturally occurring hPMS2 Mutation can confer a dominant negative mutator phenotype," Mol. Cell. Biol., Mar. 1998, 18(3), 1635-1641.

Nicolaides et al., "Genomic organization of the human PMS2 gene family," Genomics, Nov. 1995, 30, 195-206.

Nicolaides et al., "Morphogenics as a Tool for Target Discovery and Drug Development," Ann. N.Y. Acad. Sci, Nov. 2005, 1059, 86-96.

Nielsen et al., "Sequence-selective recognition of DNA by strand Displacement with a thymine-substituted polymide," Science, Dec. 1991, 254,1497-1500.

Oberhauser et al., "Effective incorporation of 2'-O-methyl-oligoribonucleotides into liposomes and enhanced cell associated through modification with thiocholestrol," Nucl. Acids Res., Feb. 1992, 20(3), 533-538.

Ono et al., "Inhibition of DNA polymerase a by 2',3'-dideoxyribonucleoside 5'triphosphates: effect of manganese ion," Biomed. & Pharmacotherapy., 1984, 38(8), 382-389.

Pardue et al., "Production of monoclonal antibodies against calmodulin by in vitro immunization of spleen cells," J. of Cell Biology, Apr. 1983, 96(4), 1149-1154.

Reff, "High-level production of recombinant immunoglobulins in mammalian cells," Curr. Opin. Biotechnol., Oct. 1993, 4(5), 573-576.

Reynaud et al., "Mismatch repair and immunoglobulin gene hypermutation did we learn something?" Immunology Today, Nov. 1999, 20, 522-527.

Saez-Llorens et al., "Safety and pharmacokinetics of an intramuscular humanized monoclonal antibody to respiratory syncytial virus in premature infants and infants with bronchopulmonary dysplasia," Pediat. Infect. Disc. J., Sep. 1998, 17(9), 787-791.

Saison-Behmoaras et al., "Short modified antisense oligonucleotides directed against Ha-ras point mutation induced selective cleavage of the mRNA and inhibit T24 cells proliferation," EMBO J., May 1991, 10(5), 1111-1118.

Sambrook et al., "Molecular Cloning: A Laboratory Manual", 2nd Ed., Cold Spring Harbor Laboratory Press, Plainview, Dec. 1989, 1659 pages.

Sanghvi, "Heterocyclic base modifications in nucleic acids and their applications in antions in antisense oligonucleotides," Antisense Research and Applications, Crooke, et al. (Eds.), CRC Press, 1993, 273-288.

Sharon, "Structural correlates of high antibody affinity: three engineered amino acid substitutions can increase the affinity of an anti-p-azophenylarsonate antibody 200-fold", PNAS, Jun. 1990, 87, 4814-4817.

Sharp et al., "RNA Interference," Science, Mar. 31, 2000, 287, 2431,2433.

Shea et al.,"Synthesis, hybridization properties and antiviral activiral activity of lipid oligodeoxynucleotide conjugates," Nucl. Acids Res., Jul. 1990, 18, 3777-3783.

Shield et al., "A cost-effectiveness analysis of OKT3 induction therapy in cadaveric kidney transplantation," Am. J. Kidney Dis., Jun. 1996, 27(6), 855-864.

Spencer et al., "Characteristics of Sequences Around Indivdual Nucleotide Substitutions I IgVH Genes Suggest different GC and AT mutators," Journal of Immunology, Jun. 1999, 162, 6596-6601.

Svinarchuk et al., "Inhibition of HIV proliferation in MT-4 cells by antisense oligonucleotide conjugated to lipophilic groups," Biochimie, 1993, 75(1-2), 49-54.

Thorell, "Radioimmunoassay and related techniques: Methodology and Clinical Applications," Jan. 1978, 298.

Urlaub et al., "Isolation of Chinese hamster cell mutants deficient in dihydrofolate," Proc. Natl. Acad. Sci. USA, Jul. 1980, 77(7), 4216-4220.

Waldman et al., "p21 is necessary for the p53-mediated G1 arrest in human cancer cells," Cancer Res., Nov. 15, 1995, 55, 5187-5190.

Weiner, "Monoclonal antibody therapy of cancer," Semin. In Oncol., Oct. 1999, 26(5), 43-51.

Wiesendanger et al., "Somatic Hypermutation, Transcription, and DNA Mismatch Repair," Cell, Aug. 1998, 94(4), 415-418.

Yeh et al., "A cell-surfaced antigen which is present in the ganglioside fraction and shared by human melanomas," Int. J. Cancer, Mar. 1982, 29, 269-275.

Yeh et al., "Cell Surface antigens of human melanoma identified by monoclonal antibody," Proc. Natl. Acad. Sci. USA, Jun. 1979, 76(6), 2927-2931.

Yelton et al. "Affinity maturation of the BR96 anti-carcinoma antibody by codon-based mutagenesis," Journal of Immunology, Aug. 15, 1995, 155, 1994-2004.

Zafiropoulos et al., "Induction of antigen-specific isotype switching by in vitro Immunization of human naïve B Lymphocytes," J. of Immunological Methods, Jan. 1997, 200, 181-190.

Zan et al. "The translesion DNA polymerase ζ plays a major role in Ig and bcl-6 somatic hypermutation." Immunity, May 2001, 14, 643-653.

* cited by examiner

```
                        SEQUENCE LISTING

<160> NUMBER OF SEQ ID NOS: 50

<210> SEQ ID NO 1
<211> LENGTH: 3063
<212> TYPE: DNA
<213> ORGANISM: Homo sapiens

<400> SEQUENCE: 1
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctcctttcaa     120
gttctcagat catcacttcg gtggtcagtg ttgtaaaaga gcttattgaa aactccttgg     180
atgctggtgc cacaagcgta gatgttaaac tggagaacta tggatttgat aaaattgagg     240
tgcgagataa cggggagggt atcaaggctg ttgatgcacc tgtaatggca atgaagtact     300
acacctcaaa aataaatagt catgaagatc ttgaaaattt gacaacttac ggttttcgtg     360
gagaagcctt ggggtcaatt tgttgtatag ctgaggtttt aattacaaca agaacggctg     420
ctgataattt tagcacccag tatgttttag atggcagtgg ccacatactt tctcagaaac     480
cttcacatct tggtcaaggt acaactgtaa ctgctttaag attatttaag aatctacctg     540
taagaaagca gttttactca actgcaaaaa aatgtaaaga tgaaataaaa aagatccaag     600
atctcctcat gagctttggt atccttaaac ctgacttaag gattgtcttt gtacataaca     660
aggcagttat ttggcagaaa agcagagtat cagatcacaa gatggctctc atgtcagttc     720
tggggactgc tgttatgaac aatatggaat cctttcagta ccactctgaa gaatctcaga     780
tttatctcag tggatttctt ccaaagtgtg atgcagacca ctctttcact agtctttcaa     840
caccagaaag aagtttcatc ttcataaaca gtcgaccagt acatcaaaaa gatatcttaa     900
agttaatccg acatcattac aatctgaaat gcctaaagga atctactcgt ttgtatcctg     960
ttttcttctt gaaaatcgat gttcctacag ctgatgttga tgtaaattta acaccagata    1020
aaagccaagt attattacaa aataaggaat ctgttttaat tgctcttgaa aatctgatga    1080
cgacttgtta tggaccatta cctagtacaa attcttatga aaataataaa acagatgttt    1140
ccgcagctga catcgttctt agtaaaacag cagaaacaga tgtgctttt aataaagtgg     1200 aatcatctgg aaagaattat tcaaatgttg atacttcagt cattccattc caaaatgata    1260
tgcataatga tgaatctgga aaaacactg atgattgttt aaatcaccag ataagtattg     1320
gtgactttgg ttatggtcat tgtagtagtg aaatttctaa cattgataaa aacactaaga    1380
atgcatttca ggacatttca atgagtaatg tatcatggga gaactctcag acggaatata    1440
gtaaaacttg ttttataagt tccgttaagc acacccagtc agaaaatggc aataaagacc    1500
atatagatga gagtgggaa aatgaggaag aagcaggtct tgaaaactct tcggaaattt     1560
ctgcagatga gtggagcagg ggaaatatac ttaaaaattc agtgggagag aatattgaac    1620
ctgtgaaaat tttagtgcct gaaaaagtt taccatgtaa agtaagtaat aataattatc     1680
```

```
caatccctga acaaatgaat cttaatgaag attcatgtaa caaaaaatca aatgtaatag   1740
ataataaatc tggaaaagtt acagcttatg atttacttag caatcgagta atcaagaaac   1800
ccatgtcagc aagtgctctt tttgttcaag atcatcgtcc tcagtttctc atagaaaatc   1860
ctaagactag tttagaggat gcaacactac aaattgaaga actgtggaag acattgagtg   1920
aagaggaaaa actgaaatat gaagagaagg ctactaaaga cttggaacga tacaatagtc   1980
aaatgaagag agccattgaa caggagtcac aaatgtcact aaaagatggc agaaaaaaga   2040
taaaacccac cagcgcatgg aatttggccc agaagcacaa gttaaaaacc tcattatcta   2100
atcaaccaaa acttgatgaa ctccttcagt cccaaattga aaaagaagg agtcaaaata   2160 ttaaaatggt acagatcccc ttttctatga aaaacttaaa aataaatttt aagaaacaaa   2220
acaaagttga cttagaagag aaggatgaac cttgcttgat ccacaatctc aggtttcctg   2280
atgcatggct aatgacatcc aaaacagagg taatgttatt aaatccatat agagtagaag   2340
aagccctgct atttaaaaga cttcttgaga atcataaact tcctgcagag ccactggaaa   2400
agccaattat gttaacagag agtcttttta atggatctca ttatttagac gttttatata   2460
aaatgacagc agatgaccaa agatacagtg gatcaactta cctgtctgat cctcgtctta   2520
cagcgaatgg tttcaagata aaattgatac caggagtttc aattactgaa aattacttgg   2580
aaatagaagg aatggctaat tgtctcccat tctatggagt agcagattta aaagaaattc   2640
ttaatgctat attaaacaga aatgcaaagg aagtttatga atgtagacct cgcaaagtga   2700
taagttattt agagggagaa gcagtgcgtc tatccagaca attacccatg tacttatcaa   2760
aagaggacat ccaagacatt atctacagaa tgaagcacca gtttggaaat gaaattaaag   2820
agtgtgttca tggtcgccca ttttttcatc atttaaccta tcttccagaa actacatgat   2880
taaatatgtt taagaagatt agttaccatt gaaattggtt ctgtcataaa acagcatgag   2940
tctggtttta aattatcttt gtattatgtg tcacatggtt atttttttaaa tgaggattca   3000 ctgacttgtt tttatattga aaaaagttcc acgtattgta gaaaacgtaa ataaactaat   3060
aac                                                                 3063
```

<210> SEQ ID NO 2
<211> LENGTH: 932
<212> TYPE: PRT
<213> ORGANISM: Homo sapiens

<400> SEQUENCE: 2

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125
```

-continued

```
Ile Leu Ser Gln Lys Pro Ser His Leu Gly Gln Gly Thr Thr Val Thr
130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
        355                 360                 365

Leu Phe Asn Lys Val Glu Ser Ser Gly Lys Asn Tyr Ser Asn Val Asp
370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
        515                 520                 525

Ser Asn Asn Asn Tyr Pro Ile Pro Glu Gln Met Asn Leu Asn Glu Asp
530                 535                 540

Ser Cys Asn Lys Lys Ser Asn Val Ile Asp Asn Lys Ser Gly Lys Val
545                 550                 555                 560
```

```
        Thr Ala Tyr Asp Leu Leu Ser Asn Arg Val Ile Lys Lys Pro Met Ser
                        565                 570                 575

Ala Ser Ala Leu Phe Val Gln Asp His Arg Pro Gln Phe Leu Ile Glu
                    580                 585                 590

Asn Pro Lys Thr Ser Leu Glu Asp Ala Thr Leu Gln Ile Glu Glu Leu
                595                 600                 605

Trp Lys Thr Leu Ser Glu Glu Lys Leu Lys Tyr Glu Glu Lys Ala
            610                 615                 620

Thr Lys Asp Leu Glu Arg Tyr Asn Ser Gln Met Lys Arg Ala Ile Glu
        625                 630                 635                 640

Gln Glu Ser Gln Met Ser Leu Lys Asp Gly Arg Lys Ile Lys Pro
                        645                 650                 655

Thr Ser Ala Trp Asn Leu Ala Gln Lys His Lys Leu Lys Thr Ser Leu
                        660                 665                 670

Ser Asn Gln Pro Lys Leu Asp Glu Leu Leu Gln Ser Gln Ile Glu Lys
                    675                 680                 685

Arg Arg Ser Gln Asn Ile Lys Met Val Gln Ile Pro Phe Ser Met Lys
                690                 695                 700

Asn Leu Lys Ile Asn Phe Lys Lys Gln Asn Lys Val Asp Leu Glu Glu
        705                 710                 715                 720

Lys Asp Glu Pro Cys Leu Ile His Asn Leu Arg Phe Pro Asp Ala Trp
                        725                 730                 735

Leu Met Thr Ser Lys Thr Glu Val Met Leu Leu Asn Pro Tyr Arg Val
                        740                 745                 750

Glu Glu Ala Leu Leu Phe Lys Arg Leu Leu Glu Asn His Lys Leu Pro
                    755                 760                 765

Ala Glu Pro Leu Glu Lys Pro Ile Met Leu Thr Glu Ser Leu Phe Asn
                770                 775                 780

Gly Ser His Tyr Leu Asp Val Leu Tyr Lys Met Thr Ala Asp Asp Gln
        785                 790                 795                 800

Arg Tyr Ser Gly Ser Thr Tyr Leu Ser Asp Pro Arg Leu Thr Ala Asn
                        805                 810                 815

Gly Phe Lys Ile Lys Leu Ile Pro Gly Val Ser Ile Thr Glu Asn Tyr
                        820                 825                 830

Leu Glu Ile Glu Gly Met Ala Asn Cys Leu Pro Phe Tyr Gly Val Ala
                    835                 840                 845

Asp Leu Lys Glu Ile Leu Asn Ala Ile Leu Asn Arg Asn Ala Lys Glu
                850                 855                 860

Val Tyr Glu Cys Arg Pro Arg Lys Val Ile Ser Tyr Leu Glu Gly Glu
        865                 870                 875                 880

Ala Val Arg Leu Ser Arg Gln Leu Pro Met Tyr Leu Ser Lys Glu Asp
                        885                 890                 895

Ile Gln Asp Ile Ile Tyr Arg Met Lys His Gln Phe Gly Asn Glu Ile
                    900                 905                 910

Lys Glu Cys Val His Gly Arg Pro Phe Phe His His Leu Thr Tyr Leu
                915                 920                 925

Pro Glu Thr Thr
            930

<210> SEQ ID NO 3
<211> LENGTH: 2771
<212> TYPE: DNA
<213> ORGANISM: Homo sapiens

<400> SEQUENCE: 3
```

```
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240
tgtggggtag aagaagaaaa cttcgaaggc ttaactctga acatcacac atctaagatt   300
caagagtttg ccgacctaac tcaggttgaa acttttggct ttcgggggga agctctgagc   360
tcactttgtg cactgagcga tgtcaccatt tctacctgcc acgcatcggc gaaggttgga   420
actcgactga tgtttgatca caatgggaaa attatccaga aaaccccta ccccgcccc    480
agagggacca cagtcagcgt gcagcagtta ttttccacac tacctgtgcg ccataaggaa   540
tttcaaagga atattaagaa ggagtatgcc aaaatggtcc aggtcttaca tgcatactgt   600
atcatttcag caggcatccg tgtaagttgc accaatcagc ttggacaagg aaaacgacag   660
cctgtggtat gcacaggtgg aagccccagc ataaggaaa atatcggctc tgtgtttggg   720
cagaagcagt tgcaaagcct cattccttt gttcagctgc cccctagtga ctccgtgtgt   780
gaagagtacg gtttgagctg ttcggatgct ctgcataatc ttttttacat ctcaggtttc   840
atttcacaat gcacgcatgg agttggaagg agttcaacag acagacagtt tttctttatc   900
aaccggcggc cttgtgaccc agcaaaggtc tgcagactcg tgaatgaggt ctaccacatg   960
tataatcgac accagtatcc atttgttgtt cttaacattt ctgttgattc agaatgcgtt  1020
gatatcaatg ttactccaga taaaaggcaa attttgctac aagaggaaaa gcttttgttg  1080
gcagttttaa agacctcttt gataggaatg tttgatagtg atgtcaacaa gctaaatgtc  1140
agtcagcagc cactgctgga tgttgaaggt aacttaataa aaatgcatgc agcggatttg  1200
gaaaagccca tggtagaaaa gcaggatcaa tccccttcat taaggactgg agaagaaaaa  1260
aaagacgtgt ccatttccag actgcgagag gccttttctc ttcgtcacac aacagagaac  1320
aagcctcaca gcccaaagac tccagaacca agaaggagcc ctctaggaca gaaaaggggt  1380
atgctgtctt ctagcacttc aggtgccatc tctgacaaag gcgtcctgag acctcagaaa  1440
gaggcagtga gttccagtca cggacccagt gaccctacgg acagagcgga ggtggagaag  1500
gactcggggc acggcagcac ttccgtggat tctgaggggt tcagcatccc agacacgggc  1560
agtcactgca gcagcgagta tgcggccagc tccccagggg acaggggctc gcaggaacat  1620
gtggactctc aggagaaagc gcctgaaact gacgactctt tttcagatgt ggactgccat  1680
tcaaaccagg aagataccgg atgtaaattt cgagttttgc ctcagccaac taatctcgca  1740
accccaaaca caaagcgttt taaaaaagaa gaaattcttt ccagttctga catttgtcaa  1800
aagttagtaa atactcagga catgtcagcc tctcaggttg atgtagctgt gaaaattaat  1860
aagaaagttg tgcccctgga cttttctatg agttctttag ctaaacgaat aaagcagtta  1920
catcatgaag cacagcaaag tgaagggaa cagaattaca ggaagtttag ggcaaagatt  1980
tgtcctggag aaaatcaagc agccgaagat gaactaagaa aagagataag taaaacgatg  2040
tttgcagaaa tggaaatcat tggtcagttt aacctgggat ttataataac caaactgaat  2100
gaggatatct tcatagtgga ccagcatgcc acggacgaga gtataacctt cgagatgctg  2160
cagcagcaca ccgtgctcca ggggcagagg ctcatagcac ctcagactct caacttaact  2220
gctgttaatg aagctgttct gatagaaaat ctggaaatat ttagaaagaa tggctttgat  2280
tttgttatcg atgaaaatgc tccagtcact gaaagggcta aactgattc cttgccaact  2340
agtaaaaact ggaccttcgg accccaggac gtcgatgaac tgatcttcat gctgagcgac  2400
```

-continued

```
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca ccctggaac tgtccccatg aaggccaac catgagacac      2580 atcgccaacc tgggtgtcat ttctcagaac tgaccgtagt cactgtatgg aataattggt    2640
tttatcgcag attttatgt tttgaaagac agagtcttca ctaaccttt ttgttttaaa      2700 atgaaacctg ctacttaaaa aaatacaca tcacacccat ttaaaagtga tcttgagaac     2760
cttttcaaac c                                                          2771
```

```
<210> SEQ ID NO 4
<211> LENGTH: 932
<212> TYPE: PRT
<213> ORGANISM: Homo sapiens

<400> SEQUENCE: 4
```

```
Met Lys Gln Leu Pro Ala Ala Thr Val Arg Leu Leu Ser Ser Ser Gln
 1               5                  10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
           100                 105                 110

Ala Ala Asp Asn Phe Ser Thr Gln Tyr Val Leu Asp Gly Ser Gly His
       115                 120                 125

Ile Leu Ser Gln Lys Pro Ser His Leu Gly Gln Gly Thr Thr Val Thr
   130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
    290                 295                 300
```

-continued

```
Asp Val Asp Val Asn Leu Thr Pro Asp Lys Ser Gln Val Leu Leu Gln
305                 310                 315                 320
Asn Lys Glu Ser Val Leu Ile Ala Leu Glu Asn Leu Met Thr Thr Cys
            325                 330                 335
Tyr Gly Pro Leu Pro Ser Thr Asn Ser Tyr Glu Asn Asn Lys Thr Asp
            340                 345                 350
Val Ser Ala Ala Asp Ile Val Leu Ser Lys Thr Ala Glu Thr Asp Val
        355                 360                 365
Leu Phe Asn Lys Val Glu Ser Ser Gly Lys Asn Tyr Ser Asn Val Asp
    370                 375                 380
Thr Ser Val Ile Pro Phe Gln Asn Asp Met His Asn Asp Glu Ser Gly
385                 390                 395                 400
Lys Asn Thr Asp Asp Cys Leu Asn His Gln Ile Ser Ile Gly Asp Phe
            405                 410                 415
Gly Tyr Gly His Cys Ser Ser Glu Ile Ser Asn Ile Asp Lys Asn Thr
            420                 425                 430
Lys Asn Ala Phe Gln Asp Ile Ser Met Ser Asn Val Ser Trp Glu Asn
        435                 440                 445
Ser Gln Thr Glu Tyr Ser Lys Thr Cys Phe Ile Ser Ser Val Lys His
    450                 455                 460
Thr Gln Ser Glu Asn Gly Asn Lys Asp His Ile Asp Glu Ser Gly Glu
465                 470                 475                 480
Asn Glu Glu Glu Ala Gly Leu Glu Asn Ser Glu Ile Ser Ala Asp
            485                 490                 495
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
        515                 520                 525
Ser Asn Asn Asn Tyr Pro Ile Pro Glu Gln Met Asn Leu Asn Glu Asp
    530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
            565                 570                 575
Ala Ser Ala Leu Phe Val Gln Asp His Arg Pro Gln Phe Leu Ile Glu
        580                 585                 590
Asn Pro Lys Thr Ser Leu Glu Asp Ala Thr Leu Gln Ile Glu Glu Leu
    595                 600                 605
Trp Lys Thr Leu Ser Glu Glu Lys Leu Lys Tyr Glu Glu Lys Ala
610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Ile Lys Pro
            645                 650                 655
Thr Ser Ala Trp Asn Leu Ala Gln Lys His Lys Leu Lys Thr Ser Leu
            660                 665                 670
Ser Asn Gln Pro Lys Leu Asp Glu Leu Leu Gln Ser Gln Ile Glu Lys
        675                 680                 685
Arg Arg Ser Gln Asn Ile Lys Met Val Gln Ile Pro Phe Ser Met Lys
    690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
            725                 730                 735
```

```
Leu Met Thr Ser Lys Thr Glu Val Met Leu Asn Pro Tyr Arg Val
            740                 745                 750

Glu Glu Ala Leu Leu Phe Lys Arg Leu Leu Glu Asn His Lys Leu Pro
        755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
                820                 825                 830

Leu Glu Ile Glu Gly Met Ala Asn Cys Leu Pro Phe Tyr Gly Val Ala
            835                 840                 845

Asp Leu Lys Glu Ile Leu Asn Ala Ile Leu Asn Arg Asn Ala Lys Glu
850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
                900                 905                 910

Lys Glu Cys Val His Gly Arg Pro Phe Phe His His Leu Thr Tyr Leu
            915                 920                 925

Pro Glu Thr Thr
        930

<210> SEQ ID NO 5
<211> LENGTH: 426
<212> TYPE: DNA
<213> ORGANISM: Homo sapiens

<400> SEQUENCE: 5
cgaggcggat cgggtgttgc atccatggag cgagctgaga gctcgagtac agaacctgct      60
aaggccatca aacctattga tcggaagtca gtccatcaga tttgctctgg caggtggta     120 ctgagtctaa gcactgcggt aaaggagtta gtagaaaaca gtctggatgc tggtgccact     180
aatattgatc taaagcttaa ggactatgga gtggatctta ttgaagtttc agacaatgga     240
tgtggggtag aagaagaaaa cttcgaaggc ttaactctga acatcacac atctaagatt     300 caagagtttg ccgacctaac tcaggttgaa acttttggct tcggggggga agctctgagc     360
tcactttgtg cactgagcga tgtcaccatt tctacctgcc acgcatcggc gaaggttgga     420
acttga                                                               426

<210> SEQ ID NO 6
<211> LENGTH: 133
<212> TYPE: PRT
<213> ORGANISM: Homo sapiens

<400> SEQUENCE: 6

Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45
```

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys
    130

<210> SEQ ID NO 7
<211> LENGTH: 1408
<212> TYPE: DNA
<213> ORGANISM: Homo sapiens

<400> SEQUENCE: 7
ggcgctccta cctgcaagtg gctagtgcca agtgctgggc cgccgctcct gccgtgcatg       60
ttggggagcc agtacatgca ggtgggctcc acacggagag gggcgcagac ccggtgacag      120
ggctttacct ggtacatcgg catggcgcaa ccaaagcaag agagggtggc gcgtgccaga      180
caccaacggt cggaaaccgc cagacaccaa cggtcggaaa ccgccaagac accaacgctc      240
ggaaaccgcc agacaccaac gctcggaaac cgccagacac caaggctcgg aatccacgcc      300
aggccacgac ggagggcgac tacctcccct ctgaccctgc tgctggcgtt cggaaaaaac      360
gcagtccggt gtgctctgat ggtccaggc tctttgacgt cacggactcg acctttgaca      420
gagccactag gcgaaaagga gagacgggaa gtatttttt cgccccgccc ggaaagggtg      480
gagcacaacg tcgaaagcag ccgttgggag cccaggaggc ggggcgcctg tgggagccgt      540
ggagggaact ttcccagtcc ccgaggcgga tccggtgttg catccttgga gcgagctgag      600
aactcgagta cagaacctgc taaggccatc aaacctattg atcggaagtc agtccatcag      660
atttgctctg ggccggtggt accgagtcta aggccgaatg cggtgaagga gttagtagaa      720
aacagtctgg atgctggtgc cactaatgtt gatctaaagc ttaaggacta tggagtggat      780
ctcattgaag tttcaggcaa tggatgtggg gtagaagaag aaaacttcga aggctttact      840
ctgaaacatc acacatgtaa gattcaagag tttgccgacc taactcaggt ggaaactttt      900
ggctttcggg gggaagctct gagctcactt tgtgcactga gtgatgtcac catttctacc      960
tgccgtgtat cagcgaaggt tgggactcga ctggtgtttg atcactatgg gaaaatcatc     1020
cagaaaaccc cctaccccg ccccagaggg atgacagtca gcgtgaagca gttatttctc      1080
acgctacctg tgcaccataa agaatttcaa aggaatatta agaagaaacg tgcctgcttc     1140
cccttcgcct tctgccgtga ttgtcagttt cctgaggcct ccccagccat gcttcctgta     1200
cagcctgtag aactgactcc tagaagtacc caccccacc cctgctcctt ggaggacaac     1260
gtgatcactg tattcagctc tgtcaagaat ggtccaggtt cttctagatg atctgcacaa     1320
atggttcctc cctccttcc tgatgtctgc cattagcatt ggaataaagt tcctgctgaa     1380
aatccaaaaa aaaaaaaaaa aaaaaaaa                                       1408

<210> SEQ ID NO 8
<211> LENGTH: 389
<212> TYPE: PRT
<213> ORGANISM: Homo sapiens

<400> SEQUENCE: 8

```
Met Ala Gln Pro Lys Gln Glu Arg Val Ala Arg Ala Arg His Gln Arg
1               5                   10                  15
Ser Glu Thr Ala Arg His Gln Arg Ser Glu Thr Ala Lys Thr Pro Thr
            20                  25                  30
Leu Gly Asn Arg Gln Thr Pro Thr Leu Gly Asn Arg Gln Thr Pro Arg
        35                  40                  45
Leu Gly Ile His Ala Arg Pro Arg Arg Ala Thr Thr Ser Leu Leu
    50                  55                  60
Thr Leu Leu Leu Ala Phe Gly Lys Asn Ala Val Arg Cys Ala Leu Ile
65                  70                  75                  80
Gly Pro Gly Ser Leu Thr Ser Arg Thr Arg Pro Leu Thr Glu Pro Leu
                85                  90                  95
Gly Glu Lys Glu Arg Arg Glu Val Phe Phe Pro Pro Arg Pro Glu Arg
            100                 105                 110
Val Glu His Asn Val Glu Ser Arg Trp Glu Pro Arg Arg Arg Gly
        115                 120                 125
Ala Cys Gly Ser Arg Gly Gly Asn Phe Pro Ser Pro Arg Gly Gly Ser
    130                 135                 140
Gly Val Ala Ser Leu Glu Arg Ala Glu Asn Ser Ser Thr Glu Pro Ala
145                 150                 155                 160
Lys Ala Ile Lys Pro Ile Asp Arg Lys Ser Val His Gln Ile Cys Ser
                165                 170                 175
Gly Pro Val Val Pro Ser Leu Arg Pro Asn Ala Val Lys Glu Leu Val
            180                 185                 190
Glu Asn Ser Leu Asp Ala Gly Ala Thr Asn Val Asp Leu Lys Leu Lys
        195                 200                 205
Asp Tyr Gly Val Asp Leu Ile Glu Val Ser Gly Asn Gly Cys Gly Val
    210                 215                 220
Glu Glu Glu Asn Phe Glu Gly Phe Thr Leu Lys His His Thr Cys Lys
225                 230                 235                 240
Ile Gln Glu Phe Ala Asp Leu Thr Gln Val Glu Thr Phe Gly Phe Arg
                245                 250                 255
Gly Glu Ala Leu Ser Ser Leu Cys Ala Leu Ser Asp Val Thr Ile Ser
            260                 265                 270
Thr Cys Arg Val Ser Ala Lys Val Gly Thr Arg Leu Val Phe Asp His
        275                 280                 285
Tyr Gly Lys Ile Ile Gln Lys Thr Pro Tyr Pro Arg Pro Arg Gly Met
    290                 295                 300
Thr Val Ser Val Lys Gln Leu Phe Ser Thr Leu Pro Val His His Lys
305                 310                 315                 320
Glu Phe Gln Arg Asn Ile Lys Lys Arg Ala Cys Phe Pro Phe Ala
                325                 330                 335
Phe Cys Arg Asp Cys Gln Phe Pro Glu Ala Ser Pro Ala Met Leu Pro
    340                 345                 350
Val Gln Pro Val Glu Leu Thr Pro Arg Ser Thr Pro His Pro Cys
        355                 360                 365
Ser Leu Glu Asp Asn Val Ile Thr Val Phe Ser Val Lys Asn Gly
    370                 375                 380
Pro Gly Ser Ser Arg
385
```

<210> SEQ ID NO 9

<211> LENGTH: 1785
<212> TYPE: DNA
<213> ORGANISM: Homo sapiens

<400> SEQUENCE: 9

```
tttttagaaa ctgatgttta ttttccatca accattttc catgctgctt aagagaatat      60
gcaagaacag cttaagacca gtcagtggtt gctcctaccc attcagtggc ctgagcagtg     120
gggagctgca gaccagtctt ccgtggcagg ctgagcgctc cagtcttcag tagggaattg     180
ctgaataggc acagagggca cctgtacacc ttcagaccag tctgcaacct caggctgagt     240
agcagtgaac tcaggagcgg gagcagtcca ttcaccctga aattcctcct tggtcactgc     300
cttctcagca gcagcctgct cttctttttc aatctcttca ggatctctgt agaagtacag     360
atcaggcatg acctcccatg ggtgttcacg ggaaatggtg ccacgcatgc gcagaacttc     420
ccgagccagc atccaccaca ttaaacccac tgagtgagct cccttgttgt tgcatgggat     480
ggcaatgtcc acatagcgca gaggagaatc tgtgttacac agcgcaatgg taggtaggtt     540
aacataagat gcctccgtga gaggcgaagg ggcggcggga cccgggcctg gcccgtatgt     600
gtccttggcg gcctagacta ggccgtcgct gtatggtgag cccagggag gcggatctgg      660
gcccccagaa ggacacccgc ctggatttgc cccgtagccc ggcccgggcc cctcgggagc     720
agaacagcct tggtgaggtg gacaggaggg gacctcgcga gcagacgcgc gcgccagcga     780
cagcagcccc gccccggcct ctcgggagcc gggggcaga ggctgcggag ccccaggagg      840
gtctatcagc cacagtctct gcatgtttcc aagagcaaca ggaaatgaac acattgcagg     900
ggccagtgtc attcaaagat gtggctgtgg atttcaccca ggaggagtgg cggcaactgg     960
accctgatga agatagca tacggggatg tgatgttgga gaactacagc catctagttt     1020
ctgtggggta tgattatcac caagccaaac atcatcatgg agtggaggtg aaggaagtgg    1080
agcagggaga ggagccgtgg ataatgaag gtgaatttcc atgtcaacat agtccagaac     1140
ctgctaaggc catcaaacct attgatcgga agtcagtcca tcagatttgc tctgggccag    1200
tggtactgag tctaagcact gcagtgaagg agttagtaga aaacagtctg gatgctggtg    1260
ccactaatat tgatctaaag cttaaggact atggagtgga tctcattgaa gtttcagaca    1320
atggatgtgg ggtagaagaa gaaaactttg aaggcttaat ctctttcagc tctgaaacat    1380
cacacatgta agattcaaga gtttgccgac ctaactgaag ttgaaacttt cggttttcag    1440
ggggaagctc tgagctcact gtgtgcactg agcgatgtca ccatttctac ctgccacgcg    1500
ttggtgaagt ttgggactcg actggtgttt gatcacgatg gaaaatcat ccaggaaacc     1560
ccctaccccc acccagagg gaccacagtc agcgtgaagc agttatttc tacgctacct      1620
gtgcgccata aggaatttca aggaatatt aagaagacgt gcctgcttcc ccttcgcctt     1680
ctgccgtgat tgtcagtttc ctgaggcctc cccagccatg cttcctgtac agcctgcaga    1740
actgtgagtc aattaaacct cttttcttca taaattaaaa aaaaa                    1785
```

<210> SEQ ID NO 10
<211> LENGTH: 264
<212> TYPE: PRT
<213> ORGANISM: Homo sapiens

<400> SEQUENCE: 10

```
Met Cys Pro Trp Arg Pro Arg Leu Gly Arg Arg Cys Met Val Ser Pro
1               5                   10                  15

Arg Glu Ala Asp Leu Gly Pro Gln Lys Asp Thr Arg Leu Asp Leu Pro
            20                  25                  30
```

```
Arg Ser Pro Ala Arg Ala Pro Arg Glu Gln Asn Ser Leu Gly Glu Val
         35                  40                  45

Asp Arg Arg Gly Pro Arg Glu Gln Thr Arg Ala Pro Ala Thr Ala Ala
 50                  55                  60

Pro Pro Arg Pro Leu Gly Ser Arg Gly Ala Glu Ala Ala Glu Pro Gln
 65                  70                  75                  80

Glu Gly Leu Ser Ala Thr Val Ser Ala Cys Phe Gln Glu Gln Gln Glu
                 85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255

Phe Ser Ser Glu Thr Ser His Met
            260

<210> SEQ ID NO 11
<211> LENGTH: 2271
<212> TYPE: DNA
<213> ORGANISM: Homo sapiens

<400> SEQUENCE: 11
atgtcgttcg tggcagggg tattcggcgg ctggacgaga cagtggtgaa ccgcatcgcg      60 gcggggaag ttatccagcg gccagctaat gctatcaaag agatgattga aactgttta     120 gatgcaaaat ccacaagtat tcaagtgatt gttaaagagg gaggcctgaa gttgattcag     180
atccaagaca atggcaccgg gatcaggaaa gaagatctgg atattgtatg tgaaaggttc     240
actactagta aactgcagtc ctttgaggat ttagccagta tttctaccta tggctttcga     300
ggtgaggctt tggccagcat aagccatgtg gctcatgtta ctattacaac gaaaacagct     360 gatgaaagt gtgcatacag agcaagttac tcagatggaa aactgaaagc ccctcctaaa     420
ccatgtgctg caatcaagg acccagatc acggtggagg accttttta caacatagcc     480 acgaggagaa aagctttaaa aaatccaagt gaagaatatg gaaaatttt ggaagttgtt     540 ggcaggtatt cagtacacaa tgcaggcatt agtttctcag ttaaaaaca aggagagaca     600 gtagctgatg ttaggacact acccaatgcc tcaaccgtgg acaatattcg ctccatcttt     660
ggaaatgctg ttagtcgaga actgatagaa attggatgtg aggataaaac cctagccttc     720
aaaatgaatg gttacatatc caatgcaaac tactcagtga agaagtgcat cttcttactc     780
ttcatcaacc atcgtctggt agaatcaact tccttgagaa aagccataga aacagtgtat     840
```

```
gcagcctatt tgcccaaaaa cacacaccca ttcctgtacc tcagtttaga aatcagtccc    900
cagaatgtgg atgttaatgt gcaccccaca aagcatgaag ttcacttcct gcacgaggag    960
agcatcctgg agcgggtgca gcagcacatc gagagcaagc tcctgggctc caattcctcc   1020
aggatgtact tcacccagac tttgctacca ggacttgctg gccctctgg ggagatggtt   1080 aaatccacaa caagtctgac ctcgtcttct acttctggaa gtagtgataa ggtctatgcc   1140
caccagatgg ttcgtacaga ttcccgggaa cagaagcttg atgcatttct gcagcctctg   1200
agcaaacccc tgtccagtca gcccaggcc attgtcacag aggataagac agatatttct   1260
agtggcaggg ctaggcagca agatgaggag atgcttgaac tcccagcccc tgctgaagtg   1320
gctgccaaaa atcagagctt ggaggggat acaacaaagg ggacttcaga aatgtcagag   1380
aagagaggac ctacttccag caaccccaga agagacatc gggaagattc tgatgtggaa   1440
atggtggaag atgattcccg aaaggaaatg actgcagctt gtaccccccg gagaaggatc   1500
attaacctca ctagtgtttt gagtctccag gaagaaatta atgagcaggg acatgaggtt   1560
ctccgggaga tgttgcataa ccactccttc gtgggctgtg tgaatcctca gtgggccttg   1620
gcacagcatc aaaccaagtt ataccttctc aacaccacca agcttagtga agaactgttc   1680
taccagatac tcatttatga ttttgccaat tttggtgttc tcaggttatc ggagccagca   1740
ccgctctttg accttgccat gcttgcctta gatagtccag agagtggctg acagaggaa   1800 gatggtccca agaaggact tgctgaatac attgttgagt ttctgaagaa gaaggctgag   1860
atgcttgcag actatttctc tttggaaatt gatgaggaag gaacctgat tggattaccc   1920 cttctgattg acaactatgt gcccccttg gagggactgc ctatcttcat tcttcgacta   1980
gccactgagg tgaattggga cgaagaaaag gaatgttttg aaagcctcag taaagaatgc   2040
gctatgttct attccatccg gaagcagtac atatctgagg agtcgaccct ctcaggccag   2100
cagagtgaag tgcctggctc cattccaaac tcctggaagt ggactgtgga acacattgtc   2160
tataaagcct gcgctcaca cattctgcct cctaaacatt tcacagaaga tggaaatatc   2220
ctgcagcttg ctaacctgcc tgatctatac aaagtctttg agaggtgtta a            2271
```

<210> SEQ ID NO 12
<211> LENGTH: 2484
<212> TYPE: PRT
<213> ORGANISM: Homo sapiens

<400> SEQUENCE: 12

```
Cys Thr Thr Gly Gly Cys Thr Cys Thr Thr Cys Thr Gly Gly Cys Gly
1               5                   10                  15

Cys Cys Ala Ala Ala Ala Thr Gly Thr Cys Gly Thr Thr Cys Gly Thr
            20                  25                  30

Gly Gly Cys Ala Gly Gly Gly Gly Thr Thr Ala Thr Thr Cys Gly Gly
        35                  40                  45

Cys Gly Gly Cys Thr Gly Gly Ala Cys Gly Ala Gly Ala Cys Ala Gly
    50                  55                  60

Thr Gly Gly Thr Gly Ala Ala Cys Cys Gly Cys Ala Thr Cys Gly Cys
65                  70                  75                  80

Gly Gly Cys Gly Gly Gly Gly Ala Ala Gly Thr Thr Ala Thr Cys
                85                  90                  95

Cys Ala Gly Cys Gly Gly Cys Cys Ala Gly Cys Thr Ala Ala Thr Gly
            100                 105                 110

Cys Thr Ala Thr Cys Ala Ala Ala Gly Ala Gly Ala Thr Gly Ala Thr
        115                 120                 125
```

```
Thr Gly Ala Gly Ala Ala Cys Thr Gly Thr Thr Thr Ala Gly Ala Thr
    130                 135                 140
Gly Cys Ala Ala Ala Ala Thr Cys Cys Ala Cys Ala Ala Gly Thr Ala
145                 150                 155                 160
Thr Thr Cys Ala Ala Gly Thr Gly Ala Thr Thr Gly Thr Thr Ala Ala
                165                 170                 175

Ala Gly Ala Gly Gly Gly Ala Gly Gly Cys Cys Thr Gly Ala Ala Gly
            180                 185                 190
Thr Thr Gly Ala Thr Thr Cys Ala Gly Ala Thr Cys Cys Ala Ala Gly
        195                 200                 205

Ala Cys Ala Ala Thr Gly Gly Cys Ala Cys Cys Gly Gly Gly Ala Thr
    210                 215                 220
Cys Ala Gly Gly Ala Ala Ala Gly Ala Ala Gly Ala Thr Cys Thr Gly
225                 230                 235                 240
Gly Ala Thr Ala Thr Thr Gly Thr Ala Thr Gly Thr Gly Ala Ala Ala
                245                 250                 255
Gly Gly Thr Thr Cys Ala Cys Thr Ala Cys Thr Ala Gly Thr Ala Ala
            260                 265                 270
Ala Cys Thr Gly Cys Ala Gly Thr Cys Cys Thr Thr Thr Gly Ala Gly
        275                 280                 285
Gly Ala Thr Thr Thr Ala Gly Cys Cys Ala Gly Thr Ala Thr Thr Thr
    290                 295                 300
Cys Thr Ala Cys Cys Thr Ala Thr Gly Gly Cys Thr Thr Thr Cys Gly
305                 310                 315                 320

Ala Gly Gly Thr Gly Ala Gly Gly Cys Thr Thr Thr Gly Gly Cys Cys
                325                 330                 335

Ala Gly Cys Ala Thr Ala Ala Gly Cys Cys Ala Thr Gly Thr Gly Gly
            340                 345                 350

Cys Thr Cys Ala Thr Gly Thr Thr Ala Cys Thr Ala Thr Thr Ala Cys
        355                 360                 365

Ala Ala Cys Gly Ala Ala Ala Ala Cys Ala Gly Cys Thr Gly Ala Thr
    370                 375                 380

Gly Gly Ala Ala Ala Gly Thr Gly Thr Gly Cys Ala Thr Ala Cys Ala
385                 390                 395                 400

Gly Ala Gly Cys Ala Ala Gly Thr Thr Ala Cys Thr Cys Ala Gly Ala
                405                 410                 415

Thr Gly Gly Ala Ala Ala Ala Cys Thr Gly Ala Ala Ala Gly Cys Cys
            420                 425                 430

Cys Cys Thr Cys Cys Thr Ala Ala Ala Cys Cys Ala Thr Gly Thr Gly
        435                 440                 445

Cys Thr Gly Gly Cys Ala Ala Thr Cys Ala Ala Gly Gly Gly Ala Cys
    450                 455                 460

Cys Cys Ala Gly Ala Thr Cys Ala Cys Gly Gly Thr Gly Gly Ala Gly
465                 470                 475                 480

Gly Ala Cys Cys Thr Thr Thr Thr Thr Thr Ala Cys Ala Ala Cys Ala
                485                 490                 495

Thr Ala Gly Cys Cys Ala Cys Gly Ala Gly Gly Ala Gly Ala Ala Ala
            500                 505                 510

Ala Gly Cys Thr Thr Thr Ala Ala Ala Ala Ala Ala Thr Cys Cys Ala
        515                 520                 525

Ala Gly Thr Gly Ala Ala Gly Ala Ala Thr Ala Thr Gly Gly Gly Ala
    530                 535                 540

Ala Ala Ala Thr Thr Thr Thr Gly Gly Ala Ala Gly Thr Thr Gly Thr
```

-continued

```
545                 550                 555                 560

Thr Gly Gly Cys Ala Gly Gly Thr Ala Thr Thr Cys Ala Gly Thr Ala
                565                 570                 575

Cys Ala Cys Ala Ala Thr Gly Cys Ala Gly Gly Cys Ala Thr Thr Ala
            580                 585                 590

Gly Thr Thr Thr Cys Thr Cys Ala Gly Thr Thr Ala Ala Ala Ala Ala
        595                 600                 605

Ala Cys Ala Ala Gly Gly Ala Gly Ala Gly Ala Cys Ala Gly Thr Ala
    610                 615                 620

Gly Cys Thr Gly Ala Thr Gly Thr Thr Ala Gly Gly Ala Cys Ala Cys
625                 630                 635                 640

Thr Ala Cys Cys Cys Ala Ala Thr Gly Cys Cys Thr Cys Ala Ala Cys
                645                 650                 655

Cys Gly Thr Gly Gly Ala Cys Ala Ala Thr Ala Thr Thr Cys Gly Cys
            660                 665                 670

Thr Cys Cys Ala Thr Cys Thr Thr Thr Gly Gly Ala Ala Ala Thr Gly
        675                 680                 685

Cys Thr Gly Thr Thr Ala Gly Thr Cys Gly Ala Gly Ala Ala Cys Thr
    690                 695                 700

Gly Ala Thr Ala Gly Ala Ala Ala Thr Thr Gly Gly Ala Thr Gly Thr
705                 710                 715                 720

Gly Ala Gly Gly Ala Thr Ala Ala Ala Ala Cys Cys Cys Thr Ala Gly
                725                 730                 735

Cys Cys Thr Thr Cys Ala Ala Ala Ala Thr Gly Ala Ala Thr Gly Gly
            740                 745                 750

Thr Thr Ala Cys Ala Thr Ala Thr Cys Cys Ala Ala Thr Gly Cys Ala
        755                 760                 765

Ala Ala Cys Thr Ala Cys Thr Cys Ala Gly Thr Gly Ala Ala Gly Ala
    770                 775                 780

Ala Gly Thr Gly Cys Ala Thr Cys Thr Thr Cys Thr Thr Ala Cys Thr
785                 790                 795                 800

Cys Thr Thr Cys Ala Thr Cys Ala Ala Cys Cys Ala Thr Cys Gly Thr
                805                 810                 815

Cys Thr Gly Gly Thr Ala Gly Ala Ala Thr Cys Ala Ala Cys Thr Thr
            820                 825                 830

Cys Cys Thr Thr Gly Ala Gly Ala Ala Ala Ala Gly Cys Cys Ala Thr
        835                 840                 845

Ala Gly Ala Ala Ala Cys Ala Gly Thr Gly Thr Ala Thr Gly Cys Ala
    850                 855                 860

Gly Cys Cys Thr Ala Thr Thr Thr Gly Cys Cys Cys Ala Ala Ala Ala
865                 870                 875                 880

Ala Cys Ala Cys Ala Cys Ala Cys Cys Cys Ala Thr Thr Cys Cys Thr
                885                 890                 895

Gly Thr Ala Cys Cys Thr Cys Ala Gly Thr Thr Thr Ala Gly Ala Ala
            900                 905                 910

Ala Thr Cys Ala Gly Thr Cys Cys Cys Cys Ala Gly Ala Ala Thr Gly
        915                 920                 925

Thr Gly Gly Ala Thr Gly Thr Thr Ala Ala Thr Gly Thr Gly Cys Ala
    930                 935                 940

Cys Cys Cys Cys Ala Cys Ala Ala Ala Gly Cys Ala Thr Gly Ala Ala
945                 950                 955                 960

Gly Thr Thr Cys Ala Cys Thr Thr Cys Cys Thr Gly Cys Ala Cys Gly
                965                 970                 975
```

```
Ala Gly Gly Ala Gly Ala Gly Cys Ala Thr Cys Cys Thr Gly Gly Ala
            980                 985                 990

Gly Cys Gly Gly Gly Thr Gly Cys  Ala Gly Cys Ala Gly  Cys Ala Cys
            995                 1000                1005

Ala Thr  Cys Gly Ala Gly  Ala  Gly Cys Ala Ala Gly  Cys Thr Cys
            1010                1015                1020

Cys Thr  Gly Gly Gly Cys  Thr  Cys Cys Ala Ala  Thr  Thr Cys Cys
            1025                1030                1035

Thr Cys  Cys Ala Gly Gly Ala  Thr Gly Thr Ala Cys  Thr Thr Cys
            1040                1045                1050

Ala Cys  Cys Cys Ala Gly Ala  Cys Thr Thr Thr Gly  Cys Thr Ala
            1055                1060                1065

Cys Cys  Ala Gly Gly Ala Cys  Thr Thr Gly Cys Thr  Gly Gly Cys
            1070                1075                1080

Cys Cys  Cys Thr Cys Thr Gly  Gly Gly Ala Gly  Ala Thr Gly
            1085                1090                1095

Gly Thr  Thr Ala Ala Ala Thr  Cys Cys Ala Cys Ala  Ala Cys Ala
            1100                1105                1110

Ala Gly  Thr Cys Thr Gly Ala  Cys Cys Thr Cys Gly  Thr Cys Thr
            1115                1120                1125

Thr Cys  Thr Ala Cys Thr Thr  Cys Thr Gly Gly Ala  Ala Gly Thr
            1130                1135                1140

Ala Gly  Thr Gly Ala Thr Ala  Ala Gly Gly Thr Cys  Thr Ala Thr
            1145                1150                1155

Gly Cys  Cys Cys Ala Cys Cys  Ala Gly Ala Thr Gly  Gly Thr Thr
            1160                1165                1170

Cys Gly  Thr Ala Cys Ala Gly  Ala Thr Thr Cys Cys  Cys Gly Gly
            1175                1180                1185

Gly Ala  Ala Cys Ala Gly Ala  Ala Gly Cys Thr Thr  Gly Ala Thr
            1190                1195                1200

Gly Cys  Ala Thr Thr Thr Cys  Thr Gly Cys Ala Gly  Cys Cys Thr
            1205                1210                1215

Cys Thr  Gly Ala Gly Cys Ala  Ala Ala Cys Cys Cys  Cys Thr Gly
            1220                1225                1230

Thr Cys  Cys Ala Gly Thr Cys  Ala Gly Cys Cys Cys  Cys Ala Gly
            1235                1240                1245

Gly Cys  Cys Ala Thr Thr Gly  Thr Cys Ala Cys Ala  Gly Ala Gly
            1250                1255                1260

Gly Ala  Thr Ala Ala Gly Ala  Cys Ala Gly Ala Thr  Ala Thr Thr
            1265                1270                1275

Thr Cys  Thr Ala Gly Thr Gly  Gly Cys Ala Gly Gly  Gly Cys Thr
            1280                1285                1290

Ala Gly  Gly Cys Ala Gly Cys  Ala Ala Gly Ala Thr  Gly Ala Gly
            1295                1300                1305

Gly Ala  Gly Ala Thr Gly Cys  Thr Thr Gly Ala Ala  Cys Thr Cys
            1310                1315                1320

Cys Cys  Ala Gly Cys Cys Cys  Cys Thr Gly Cys Thr  Gly Ala Ala
            1325                1330                1335

Gly Thr  Gly Gly Cys Thr Gly  Cys Cys Ala Ala Ala  Ala Ala Thr
            1340                1345                1350

Cys Ala  Gly Ala Gly Cys Thr  Thr Gly Gly Ala Gly  Gly Gly Gly
            1355                1360                1365

Gly Ala  Thr Ala Cys Ala Ala  Cys Ala Ala Ala Gly  Gly Gly Gly
            1370                1375                1380
```

-continued

Ala Cys Thr Thr Cys Ala Gly Ala Ala Ala Thr Gly Thr Cys Ala
1385 1390 1395

Gly Ala Gly Ala Ala Gly Ala Gly Ala Gly Gly Ala Cys Cys Thr
1400 1405 1410

Ala Cys Thr Thr Cys Cys Ala Gly Cys Ala Ala Cys Cys Cys Cys
1415 1420 1425

Ala Gly Ala Ala Ala Gly Ala Gly Ala Cys Ala Thr Cys Gly Gly
1430 1435 1440

Gly Ala Ala Gly Ala Thr Thr Cys Thr Gly Ala Thr Gly Thr Gly
1445 1450 1455

Gly Ala Ala Ala Thr Gly Gly Thr Gly Gly Ala Ala Gly Ala Thr
1460 1465 1470

Gly Ala Thr Thr Cys Cys Cys Gly Ala Ala Ala Gly Gly Ala Ala
1475 1480 1485

Ala Thr Gly Ala Cys Thr Gly Cys Ala Gly Cys Thr Thr Gly Thr
1490 1495 1500

Ala Cys Cys Cys Cys Cys Cys Gly Gly Ala Gly Ala Ala Gly Gly
1505 1510 1515

Ala Thr Cys Ala Thr Thr Ala Ala Cys Cys Thr Cys Ala Cys Thr
1520 1525 1530

Ala Gly Thr Gly Thr Thr Thr Thr Gly Ala Gly Thr Cys Thr Cys
1535 1540 1545

Cys Ala Gly Gly Ala Ala Gly Ala Ala Ala Thr Thr Ala Ala Thr
1550 1555 1560

Gly Ala Gly Cys Ala Gly Gly Gly Ala Cys Ala Thr Gly Ala Gly
1565 1570 1575

Gly Thr Thr Cys Thr Cys Cys Gly Gly Gly Ala Gly Ala Thr Gly
1580 1585 1590

Thr Thr Gly Cys Ala Thr Ala Ala Cys Cys Ala Cys Thr Cys Cys
1595 1600 1605

Thr Thr Cys Gly Thr Gly Gly Gly Cys Thr Gly Thr Gly Thr Gly
1610 1615 1620

Ala Ala Thr Cys Cys Thr Cys Ala Gly Thr Gly Gly Gly Cys Cys
1625 1630 1635

Thr Thr Gly Gly Cys Ala Cys Ala Gly Cys Ala Thr Cys Ala Ala
1640 1645 1650

Ala Cys Cys Ala Ala Gly Thr Thr Ala Thr Ala Cys Cys Thr Thr
1655 1660 1665

Cys Thr Cys Ala Ala Cys Ala Cys Cys Ala Cys Cys Ala Ala Gly
1670 1675 1680

Cys Thr Thr Ala Gly Thr Gly Ala Ala Gly Ala Ala Cys Thr Gly
1685 1690 1695

Thr Thr Cys Thr Ala Cys Cys Ala Gly Ala Thr Ala Cys Thr Cys
1700 1705 1710

Ala Thr Thr Thr Ala Thr Gly Ala Thr Thr Thr Thr Gly Cys Cys
1715 1720 1725

Ala Ala Thr Thr Thr Thr Gly Gly Thr Gly Thr Thr Cys Thr Cys
1730 1735 1740

Ala Gly Gly Thr Thr Ala Thr Cys Gly Gly Ala Gly Cys Cys Ala
1745 1750 1755

Gly Cys Ala Cys Cys Gly Cys Thr Cys Thr Thr Thr Gly Ala Cys
1760 1765 1770

Cys Thr Thr Gly Cys Cys Ala Thr Gly Cys Thr Thr Gly Cys Cys

-continued

|  |  |  | 1775 |  |  |  | 1780 |  |  | 1785 |  |
|---|---|---|---|---|---|---|---|---|---|---|---|
| Thr | Thr | Ala | Gly | Ala | Thr | Ala | Gly | Thr | Cys | Cys | Ala | Gly | Ala | Gly |
|  | 1790 |  |  |  | 1795 |  |  |  |  | 1800 |  |
| Ala | Gly | Thr | Gly | Gly | Cys | Thr | Gly | Gly | Ala | Cys | Ala | Gly | Ala | Gly |
|  | 1805 |  |  |  | 1810 |  |  |  |  | 1815 |  |
| Gly | Ala | Ala | Gly | Ala | Thr | Gly | Gly | Thr | Cys | Cys | Ala | Ala | Ala |
|  | 1820 |  |  |  | 1825 |  |  |  |  | 1830 |  |
| Gly | Ala | Ala | Gly | Gly | Ala | Cys | Thr | Thr | Gly | Cys | Thr | Gly | Ala | Ala |
|  | 1835 |  |  |  | 1840 |  |  |  |  | 1845 |  |
| Thr | Ala | Cys | Ala | Thr | Thr | Gly | Thr | Thr | Gly | Ala | Gly | Thr | Thr | Thr |
|  | 1850 |  |  |  | 1855 |  |  |  |  | 1860 |  |
| Cys | Thr | Gly | Ala | Ala | Gly | Ala | Ala | Gly | Ala | Ala | Gly | Gly | Cys | Thr |
|  | 1865 |  |  |  | 1870 |  |  |  |  | 1875 |  |
| Gly | Ala | Gly | Ala | Thr | Gly | Cys | Thr | Thr | Gly | Cys | Ala | Gly | Ala | Cys |
|  | 1880 |  |  |  | 1885 |  |  |  |  | 1890 |  |
| Thr | Ala | Thr | Thr | Thr | Cys | Thr | Cys | Thr | Thr | Thr | Gly | Gly | Ala | Ala |
|  | 1895 |  |  |  | 1900 |  |  |  |  | 1905 |  |
| Ala | Thr | Thr | Gly | Ala | Thr | Gly | Ala | Gly | Gly | Ala | Ala | Gly | Gly | Gly |
|  | 1910 |  |  |  | 1915 |  |  |  |  | 1920 |  |
| Ala | Ala | Cys | Cys | Thr | Gly | Ala | Thr | Thr | Gly | Gly | Ala | Thr | Thr | Ala |
|  | 1925 |  |  |  | 1930 |  |  |  |  | 1935 |  |
| Cys | Cys | Cys | Cys | Thr | Thr | Cys | Thr | Gly | Ala | Thr | Thr | Gly | Ala | Cys |
|  | 1940 |  |  |  | 1945 |  |  |  |  | 1950 |  |
| Ala | Ala | Cys | Thr | Ala | Thr | Gly | Thr | Gly | Cys | Cys | Cys | Cys | Cys | Thr |
|  | 1955 |  |  |  | 1960 |  |  |  |  | 1965 |  |
| Thr | Thr | Gly | Gly | Ala | Gly | Gly | Gly | Ala | Cys | Thr | Gly | Cys | Cys | Thr |
|  | 1970 |  |  |  | 1975 |  |  |  |  | 1980 |  |
| Ala | Thr | Cys | Thr | Thr | Cys | Ala | Thr | Thr | Cys | Thr | Thr | Cys | Gly | Ala |
|  | 1985 |  |  |  | 1990 |  |  |  |  | 1995 |  |
| Cys | Thr | Ala | Gly | Cys | Cys | Ala | Cys | Thr | Gly | Ala | Gly | Gly | Thr | Gly |
|  | 2000 |  |  |  | 2005 |  |  |  |  | 2010 |  |
| Ala | Ala | Thr | Thr | Gly | Gly | Gly | Ala | Cys | Gly | Ala | Ala | Gly | Ala | Ala |
|  | 2015 |  |  |  | 2020 |  |  |  |  | 2025 |  |
| Ala | Ala | Gly | Gly | Ala | Ala | Thr | Gly | Thr | Thr | Thr | Gly | Ala | Ala |
|  | 2030 |  |  |  | 2035 |  |  |  |  | 2040 |  |
| Ala | Gly | Cys | Cys | Thr | Cys | Ala | Gly | Thr | Ala | Ala | Ala | Gly | Ala | Ala |
|  | 2045 |  |  |  | 2050 |  |  |  |  | 2055 |  |
| Thr | Gly | Cys | Gly | Cys | Thr | Ala | Thr | Gly | Thr | Thr | Cys | Thr | Ala | Thr |
|  | 2060 |  |  |  | 2065 |  |  |  |  | 2070 |  |
| Thr | Cys | Cys | Ala | Thr | Cys | Cys | Gly | Gly | Ala | Ala | Gly | Cys | Ala | Gly |
|  | 2075 |  |  |  | 2080 |  |  |  |  | 2085 |  |
| Thr | Ala | Cys | Ala | Thr | Ala | Thr | Cys | Thr | Gly | Ala | Gly | Gly | Ala | Gly |
|  | 2090 |  |  |  | 2095 |  |  |  |  | 2100 |  |
| Thr | Cys | Gly | Ala | Cys | Cys | Cys | Thr | Cys | Thr | Cys | Ala | Gly | Gly | Cys |
|  | 2105 |  |  |  | 2110 |  |  |  |  | 2115 |  |
| Cys | Ala | Gly | Cys | Ala | Gly | Ala | Gly | Thr | Gly | Ala | Ala | Gly | Thr | Gly |
|  | 2120 |  |  |  | 2125 |  |  |  |  | 2130 |  |
| Cys | Cys | Thr | Gly | Gly | Cys | Thr | Cys | Cys | Ala | Thr | Thr | Cys | Cys | Ala |
|  | 2135 |  |  |  | 2140 |  |  |  |  | 2145 |  |
| Ala | Ala | Cys | Thr | Cys | Cys | Thr | Gly | Gly | Ala | Ala | Gly | Thr | Gly | Gly |
|  | 2150 |  |  |  | 2155 |  |  |  |  | 2160 |  |
| Ala | Cys | Thr | Gly | Thr | Gly | Gly | Ala | Ala | Cys | Ala | Cys | Ala | Thr | Thr |
|  | 2165 |  |  |  | 2170 |  |  |  |  | 2175 |  |

| Gly | Thr | Cys | Thr | Ala | Thr | Ala | Ala | Gly | Cys | Cys | Thr | Thr | Gly |
|---|---|---|---|---|---|---|---|---|---|---|---|---|---|
| | | | | 2180 | | | | 2185 | | | | | 2190 |
| Cys | Gly | Cys | Thr | Cys | Ala | Cys | Ala | Cys | Ala | Thr | Thr | Cys | Thr | Gly |
| 2195 | | | | | 2200 | | | | | 2205 | | | | |
| Cys | Cys | Thr | Cys | Thr | Ala | Ala | Ala | Cys | Ala | Thr | Thr | Thr | Cys |
| 2210 | | | | | 2215 | | | | | 2220 | | | |
| Ala | Cys | Ala | Gly | Ala | Ala | Gly | Ala | Thr | Gly | Gly | Ala | Ala | Ala | Thr |
| | 2225 | | | | 2230 | | | | | 2235 | | | | |
| Ala | Thr | Cys | Cys | Thr | Gly | Cys | Ala | Gly | Cys | Thr | Thr | Gly | Cys | Thr |
| | 2240 | | | | 2245 | | | | | 2250 | | | | |
| Ala | Ala | Cys | Cys | Thr | Gly | Cys | Cys | Thr | Gly | Ala | Thr | Cys | Thr | Ala |
| | 2255 | | | | 2260 | | | | | 2265 | | | | |
| Thr | Ala | Cys | Ala | Ala | Ala | Gly | Thr | Cys | Thr | Thr | Thr | Gly | Ala | Gly |
| | 2270 | | | | 2275 | | | | | 2280 | | | | |
| Ala | Gly | Gly | Thr | Gly | Thr | Thr | Ala | Ala | Ala | Thr | Ala | Thr | Gly | Gly |
| | 2285 | | | | 2290 | | | | | 2295 | | | | |
| Thr | Thr | Ala | Thr | Thr | Thr | Ala | Thr | Gly | Cys | Ala | Cys | Thr | Gly | Thr |
| | 2300 | | | | 2305 | | | | | 2310 | | | | |
| Gly | Gly | Gly | Ala | Thr | Gly | Thr | Gly | Thr | Thr | Cys | Thr | Thr | Cys | Thr |
| | 2315 | | | | 2320 | | | | | 2325 | | | | |
| Thr | Thr | Cys | Thr | Cys | Thr | Gly | Thr | Ala | Thr | Thr | Cys | Cys | Gly | Ala |
| | 2330 | | | | 2335 | | | | | 2340 | | | | |
| Thr | Ala | Cys | Ala | Ala | Ala | Gly | Thr | Gly | Thr | Thr | Gly | Thr | Ala | Thr |
| | 2345 | | | | 2350 | | | | | 2355 | | | | |
| Cys | Ala | Ala | Ala | Gly | Thr | Gly | Thr | Gly | Ala | Thr | Ala | Thr | Ala | Cys |
| | 2360 | | | | 2365 | | | | | 2370 | | | | |
| Ala | Ala | Ala | Gly | Thr | Gly | Thr | Ala | Cys | Cys | Ala | Ala | Cys | Ala | Thr |
| | 2375 | | | | 2380 | | | | | 2385 | | | | |
| Ala | Ala | Gly | Thr | Gly | Thr | Gly | Gly | Thr | Ala | Gly | Cys | Ala | Cys |
| | 2390 | | | | 2395 | | | | | 2400 | | | | |
| Thr | Thr | Ala | Ala | Gly | Ala | Cys | Thr | Thr | Ala | Thr | Ala | Cys | Thr | Thr |
| | 2405 | | | | 2410 | | | | | 2415 | | | | |
| Gly | Cys | Cys | Thr | Thr | Cys | Thr | Gly | Ala | Thr | Ala | Gly | Thr | Ala | Thr |
| | 2420 | | | | 2425 | | | | | 2430 | | | | |
| Thr | Cys | Cys | Thr | Thr | Thr | Ala | Thr | Ala | Cys | Ala | Cys | Ala | Gly | Thr |
| | 2435 | | | | 2440 | | | | | 2445 | | | | |
| Gly | Gly | Ala | Thr | Thr | Gly | Ala | Thr | Thr | Ala | Thr | Ala | Ala | Ala | Thr |
| | 2450 | | | | 2455 | | | | | 2460 | | | | |
| Ala | Ala | Ala | Thr | Ala | Gly | Ala | Thr | Gly | Thr | Gly | Thr | Cys | Thr | Thr |
| | 2465 | | | | 2470 | | | | | 2475 | | | | |
| Ala | Ala | Cys | Ala | Thr | Ala |
| | 2480 | | | | |

<210> SEQ ID NO 13
<211> LENGTH: 4895
<212> TYPE: DNA
<213> ORGANISM: Homo sapiens

<400> SEQUENCE: 13

```
gtcggcgtcc gaggcggttg gtgtcggaga atttgttaag cgggactcca ggcaattatt      60
tccagtcaga gaaggaaacc agtgcctggc attctcacca tctttctacc taccatgatc    120
aagtgcttgt cagttgaagt acaagccaaa ttgcgttctg gtttggccat aagctccttg    180
ggccaatgtg ttgaggaact tgccctcaac agtattgatg ctgaagcaaa atgtgtggct    240
gtcagggtga atatggaaac cttccaagtt caagtgatag acaatggatt tgggatgggg    300
```

```
agtgatgatg tagagaaagt gggaaatcgt tatttcacca gtaaatgcca ctcggtacag    360
gacttggaga atccaaggtt ttatggtttc cgaggagagg ccttggcaaa tattgctgac    420
atggccagtg ctgtggaaat ttcgtccaag aaaaacagga caatgaaaac ttttgtgaaa    480
ctgtttcaga gtggaaaagc cctgaaagct tgtgaagctg atgtgactag agcaagcgct    540
gggactactg taacagtgta taacctattt taccagcttc ctgtaaggag gaaatgcatg    600
gaccctagac tggagtttga aaggttaggg cagagaatag aagctctctc actcatgcac    660
ccttccattt ctttctcttt gagaaatgat gtttctggtt ccatggttct tcagctccct    720
aaaaccaaag acgtatgttc ccgattttgt caaatttatg gattgggaaa gtcccaaaag    780
ctaagagaaa taagttttaa atataaagag tttgagctta gtggctatat cagctctgaa    840
gcacattaca acaagaatat gcagttttg  tttgtgaaca aaagactagt tttaaggaca    900
aagctacata aactcattga ctttttatta aggaagaaa  gtattatatg caagccaaag    960
aatggtccca ccagtaggca aatgaattca agtcttcggc accggtctac cccagaactc   1020
tatggcatat atgtaattaa tgtgcagtgc caattctgtg agtatgatgt gtgcatggag   1080
ccagccaaaa ctctgattga atttcagaac tgggacactc tcttgttttg cattcaggaa   1140
ggagtgaaaa tgttttaaa  gcaagaaaaa ttatttgtgg aattatcagg tgaggatatt   1200
aaggaattta gtgaagataa tggttttagt ttatttgatg ctactcttca gaagcgtgtg   1260
acttccgatg agaggagcaa tttccaggaa gcatgtaata atattttaga ttcctatgag   1320
atgtttaatt tgcagtcaaa agctgtgaaa agaaaaacta ctgcagaaaa cgtaaacaca   1380
cagagttcta gggattcaga agctaccaga aaaaatacaa atgatgcatt tttgtacatt   1440
tatgaatcag gtggtccagg ccatagcaaa atgacagagc catctttaca aaacaaagac   1500
agctcttgct cagaatcaaa gatgttagaa caagagacaa ttgtagcatc agaagctggt   1560
gaaaatgaga acataaaaa  atctttcctg gaacgtagct ctttagaaaa tccgtgtgga   1620
accagtttag aaatgttttt aagccctttt cagacaccat gtcactttga ggagagtggg   1680
caggatctag aaatatggaa agaaagtact actgttaatg gcatggctgc caacatcttg   1740
aaaaataata gaattcagaa tcaaccaaag agatttaaag atgctactga agtgggatgc   1800
cagcctctgc cttttgcaac aacattatgg ggagtacata gtgctcagac agagaaagag   1860
aaaaaaaaag aatctagcaa ttgtggaaga agaaatgttt ttagttatgg gcgagttaaa   1920
ttatgttcca ctggctttat aactcatgta gtacaaaatg aaaaaactaa atcaactgaa   1980
acagaacatt catttaaaaa ttatgttaga cctggtccca cacgtgccca agaaacattt   2040
ggaaatagaa cacgtcattc agttgaaact ccagacatca agatttagc  cagcacttta   2100 agtaaagaat ctggtcaatt gcccaacaaa aaaaattgca gaacgaatat aagttatggg   2160
ctagagaatg aacctacagc aacttataca atgttttctg cttttcagga aggtagcaaa   2220
aaatcacaaa cagattgcat attatctgat acatcccct  ctttcccctg gtatagacac   2280
gtttccaatg atagtaggaa aacagataaa ttaattggtt ctccaaacc  aatcgtccgt   2340 aagaagctaa gcttgagttc acagctagga tctttagaga agtttaagag gcaatatggg   2400
aaggttgaaa atcctctgga tacagaagta gaggaaagta atggagtcac taccaatctc   2460
agtcttcaag ttgaacctga cattctgctg aaggacaaga accgcttaga gaactctgat   2520
gtttgtaaaa tcactactat ggagcatagt gattcagata gtagttgtca accagcaagc   2580
cacatccttg actcagagaa gttttccattc tccaaggat  aagattgttt agaacaacag   2640
atgcctagtt tgagagaaag tcctatgacc ctgaaggagt tatctctctt taatagaaaa   2700
```

```
cctttggacc ttgagaagtc atctgaatca ctagcctcta aattatccag actgaagggt    2760
tccgaaagag aaactcaaac aatggggatg atgagtcgtt ttaatgaact tccaaattca    2820
gattccagta ggaaagacag caagttgtgc agtgtgttaa cacaagattt ttgtatgtta    2880
tttaacaaca agcatgaaaa aacagagaat ggtgtcatcc caacatcaga ttctgccaca    2940
caggataatt cctttaataa aaatagtaaa acacattcta acagcaatac aacagagaac    3000
tgtgtgatat cagaaactcc tttggtattg ccctataata attctaaagt taccggtaaa    3060
gattcagatg ttcttatcag agcctcagaa caacagatag gaagtcttga ctctcccagt    3120
ggaatgttaa tgaatccggt agaagatgcc acaggtgacc aaaatggaat ttgttttcag    3180
agtgaggaat ctaaagcaag agcttgttct gaaactgaag agtcaaacac gtgttgttca    3240
gattggcagc ggcatttcga tgtagccctg ggaagaatgg tttatgtcaa caaaatgact    3300
ggactcagca cattcattgc cccaactgag gacattcagg ctgcttgtac taaagacctg    3360
acaactgtgg ctgtggatgt tgtacttgag aatgggtctc agtacaggtg tcaaccttt    3420 agaagcgacc ttgttcttcc tttccttccg agagctcgag cagagaggac tgtgatgaga    3480
caggataaca gagatactgt ggatgatact gttagtagcg aatcgcttca gtctttgttc    3540
tcagaatggg acaatccagt atttgcccgt tatccagagg ttgctgttga tgtaagcagt    3600
ggccaggctg agagcttagc agttaaaatt cacaacatct tgtatcccta tcgtttcacc    3660
aaaggaatga ttcattcaat gcaggttctc cagcaagtag ataacaagtt tattgcctgt    3720
ttgatgagca ctaagactga agagaatggc gaggcagatt cctacgagaa gcaacaggca    3780
caaggctctg gtcggaaaaa attactgtct tctactctaa ttcctccgct agagataaca    3840
gtgacagagg aacaaaggag actcttatgg tgttaccaca aaaatctgga agatctgggc    3900
cttgaatttg tatttccaga cactagtgat tctctggtcc ttgtgggaaa agtaccacta    3960
tgttttgtgg aaagagaagc caatgaactt cggagaggaa gatctactgt gaccaagagt    4020
attgtggagg aatttatccg agaacaactg gagctactcc agaccaccgg aggcatccaa    4080
gggacattgc cactgactgt ccagaaggtg ttggcatccc aagcctgcca tggggccatt    4140
aagtttaatg atggcctgag cttacaggaa agttgccgcc ttattgaagc tctgtcctca    4200
tgccagctgc cattccagtg tgctcacggg agaccttcta tgctgccgtt agctgacata    4260
gaccacttgg aacaggaaaa acagattaaa cccaacctca ctaaacttcg caaaatggcc    4320
caggcctggc gtctctttgg aaaagcagag tgtgatacaa ggcagagcct gcagcagtcc    4380
atgcctccct gtgagccacc atgagaacag aatcactggt ctaaaaggaa caagggatg    4440 ttcactgtat gcctctgagc agagagcagc agcagcaggt accagcacgg ccctgactga    4500
atcagcccag tgtccctgag cagcttagac agcagggctc tctgtatcag tctttcttga    4560
gcagatgatt cccctagttg agtagccaga tgaaattcaa gcctaaagac aattcattca    4620
tttgcatcca tgggcacaga aggttgctat atagtatcta ccttttgcta cttatttaat    4680
gataaaattt aatgacagtt taaaaaaaaa aaaaaaaaaa attatttgaa ggggtgggtg    4740 attttttgttt ttgtacagtt tttttcaag cttcacattt gcgtgtatct aattcagctg    4800
atgctcaagt ccaaggggta gtctgccttc ccaggctgcc cccagggttt ctgcactggt    4860
cccctctttt cccttcagtc ttcttcactt cccctt                              4895

<210> SEQ ID NO 14
<211> LENGTH: 1429
<212> TYPE: PRT
<213> ORGANISM: Homo sapiens
```

```
<400> SEQUENCE: 14

Met Ile Lys Cys Leu Ser Val Glu Val Gln Ala Lys Leu Arg Ser Gly
 1               5                  10                  15

Leu Ala Ile Ser Ser Leu Gly Gln Cys Val Glu Glu Leu Ala Leu Asn
            20                  25                  30

Ser Ile Asp Ala Glu Ala Lys Cys Val Ala Val Arg Val Asn Met Glu
            35                  40                  45

Thr Phe Gln Val Gln Val Ile Asp Asn Gly Phe Gly Met Gly Ser Asp
        50                  55                  60

Asp Val Glu Lys Val Gly Asn Arg Tyr Phe Thr Ser Lys Cys His Ser
65                  70                  75                  80

Val Gln Asp Leu Glu Asn Pro Arg Phe Tyr Gly Phe Arg Gly Glu Ala
                85                  90                  95

Leu Ala Asn Ile Ala Asp Met Ala Ser Ala Val Glu Ile Ser Ser Lys
            100                 105                 110

Lys Asn Arg Thr Met Lys Thr Phe Val Lys Leu Phe Gln Ser Gly Lys
            115                 120                 125

Ala Leu Lys Ala Cys Glu Ala Asp Val Thr Arg Ala Ser Ala Gly Thr
        130                 135                 140

Thr Val Thr Val Tyr Asn Leu Phe Tyr Gln Leu Pro Val Arg Arg Lys
145                 150                 155                 160

Cys Met Asp Pro Arg Leu Glu Phe Glu Lys Val Arg Gln Arg Ile Glu
                165                 170                 175

Ala Leu Ser Leu Met His Pro Ser Ile Ser Phe Ser Leu Arg Asn Asp
            180                 185                 190

Val Ser Gly Ser Met Val Leu Gln Leu Pro Lys Thr Lys Asp Val Cys
            195                 200                 205

Ser Arg Phe Cys Gln Ile Tyr Gly Leu Gly Lys Ser Gln Lys Leu Arg
        210                 215                 220

Glu Ile Ser Phe Lys Tyr Lys Glu Phe Glu Leu Ser Gly Tyr Ile Ser
225                 230                 235                 240

Ser Glu Ala His Tyr Asn Lys Asn Met Gln Phe Leu Phe Val Asn Lys
                245                 250                 255

Arg Leu Val Leu Arg Thr Lys Leu His Lys Leu Ile Asp Phe Leu Leu
            260                 265                 270

Arg Lys Glu Ser Ile Ile Cys Lys Pro Lys Asn Gly Pro Thr Ser Arg
            275                 280                 285

Gln Met Asn Ser Ser Leu Arg His Arg Ser Thr Pro Glu Leu Tyr Gly
        290                 295                 300

Ile Tyr Val Ile Asn Val Gln Cys Gln Phe Cys Glu Tyr Asp Val Cys
305                 310                 315                 320

Met Glu Pro Ala Lys Thr Leu Ile Glu Phe Gln Asn Trp Asp Thr Leu
                325                 330                 335

Leu Phe Cys Ile Gln Glu Gly Val Lys Met Phe Leu Lys Gln Glu Lys
            340                 345                 350

Leu Phe Val Glu Leu Ser Gly Glu Asp Ile Lys Glu Phe Ser Glu Asp
            355                 360                 365

Asn Gly Phe Ser Leu Phe Asp Ala Thr Leu Gln Lys Arg Val Thr Ser
        370                 375                 380

Asp Glu Arg Ser Asn Phe Gln Glu Ala Cys Asn Asn Ile Leu Asp Ser
385                 390                 395                 400

Tyr Glu Met Phe Asn Leu Gln Ser Lys Ala Val Lys Arg Lys Thr Thr
                405                 410                 415
```

```
Ala Glu Asn Val Asn Thr Gln Ser Ser Arg Asp Ser Glu Ala Thr Arg
            420                 425                 430

Lys Asn Thr Asn Asp Ala Phe Leu Tyr Ile Tyr Ser Gly Gly Pro
            435                 440                 445

Gly His Ser Lys Met Thr Glu Pro Ser Leu Gln Asn Lys Asp Ser Ser
450                 455                 460

Cys Ser Glu Ser Lys Met Leu Glu Gln Glu Thr Ile Val Ala Ser Glu
465                 470                 475                 480

Ala Gly Glu Asn Glu Lys His Lys Lys Ser Phe Leu Glu Arg Ser Ser
                485                 490                 495

Leu Glu Asn Pro Cys Gly Thr Ser Leu Glu Met Phe Leu Ser Pro Phe
                500                 505                 510

Gln Thr Pro Cys His Phe Glu Glu Ser Gly Gln Asp Leu Glu Ile Trp
            515                 520                 525

Lys Glu Ser Thr Thr Val Asn Gly Met Ala Ala Asn Ile Leu Lys Asn
            530                 535                 540

Asn Arg Ile Gln Asn Gln Pro Lys Arg Phe Lys Asp Ala Thr Glu Val
545                 550                 555                 560

Gly Cys Gln Pro Leu Pro Phe Ala Thr Thr Leu Trp Gly Val His Ser
                565                 570                 575

Ala Gln Thr Glu Lys Glu Lys Lys Lys Glu Ser Ser Asn Cys Gly Arg
                580                 585                 590

Arg Asn Val Phe Ser Tyr Gly Arg Val Lys Leu Cys Ser Thr Gly Phe
                595                 600                 605

Ile Thr His Val Val Gln Asn Glu Lys Thr Lys Ser Thr Glu Thr Glu
            610                 615                 620

His Ser Phe Lys Asn Tyr Val Arg Pro Gly Pro Thr Arg Ala Gln Glu
625                 630                 635                 640

Thr Phe Gly Asn Arg Thr Arg His Ser Val Glu Thr Pro Asp Ile Lys
                645                 650                 655

Asp Leu Ala Ser Thr Leu Ser Lys Glu Ser Gly Gln Leu Pro Asn Lys
                660                 665                 670

Lys Asn Cys Arg Thr Asn Ile Ser Tyr Gly Leu Glu Asn Glu Pro Thr
            675                 680                 685

Ala Thr Tyr Thr Met Phe Ser Ala Phe Gln Glu Gly Ser Lys Lys Ser
            690                 695                 700

Gln Thr Asp Cys Ile Leu Ser Asp Thr Ser Pro Ser Phe Pro Trp Tyr
705                 710                 715                 720

Arg His Val Ser Asn Asp Ser Arg Lys Thr Asp Lys Leu Ile Gly Phe
                725                 730                 735

Ser Lys Pro Ile Val Arg Lys Lys Leu Ser Leu Ser Ser Gln Leu Gly
                740                 745                 750

Ser Leu Glu Lys Phe Lys Arg Gln Tyr Gly Lys Val Glu Asn Pro Leu
                755                 760                 765

Asp Thr Glu Val Glu Glu Ser Asn Gly Val Thr Thr Asn Leu Ser Leu
            770                 775                 780

Gln Val Glu Pro Asp Ile Leu Leu Lys Asp Lys Asn Arg Leu Glu Asn
785                 790                 795                 800

Ser Asp Val Cys Lys Ile Thr Thr Met Glu His Ser Asp Ser Asp Ser
                805                 810                 815

Ser Cys Gln Pro Ala Ser His Ile Leu Asp Ser Glu Lys Phe Pro Phe
                820                 825                 830

Ser Lys Asp Glu Asp Cys Leu Glu Gln Gln Met Pro Ser Leu Arg Glu
```

```
                    835            840              845
Ser Pro Met Thr Leu Lys Glu Leu Ser Leu Phe Asn Arg Lys Pro Leu
850                     855                 860
Asp Leu Glu Lys Ser Ser Glu Ser Leu Ala Ser Lys Leu Ser Arg Leu
865             870                  875                     880
Lys Gly Ser Glu Arg Glu Thr Gln Thr Met Gly Met Met Ser Arg Phe
                    885                 890                 895
Asn Glu Leu Pro Asn Ser Asp Ser Arg Lys Asp Ser Lys Leu Cys
                900                 905                 910
Ser Val Leu Thr Gln Asp Phe Cys Met Leu Phe Asn Asn Lys His Glu
            915                 920                 925
Lys Thr Glu Asn Gly Val Ile Pro Thr Ser Asp Ser Ala Thr Gln Asp
930                 935                 940
Asn Ser Phe Asn Lys Asn Ser Lys Thr His Ser Asn Ser Asn Thr Thr
945                 950                 955                 960
Glu Asn Cys Val Ile Ser Glu Thr Pro Leu Val Leu Pro Tyr Asn Asn
                965                 970                 975
Ser Lys Val Thr Gly Lys Asp Ser Asp Val Leu Ile Arg Ala Ser Glu
            980                 985                 990
Gln Gln Ile Gly Ser Leu Asp Ser  Pro Ser Gly Met Leu  Met Asn Pro
            995                 1000                1005
Val Glu  Asp Ala Thr Gly  Asp Gln Asn Gly Ile Cys  Phe Gln Ser
    1010                1015                1020
Glu Glu  Ser Lys Ala Arg  Ala  Cys Ser Glu Thr Glu  Glu Ser Asn
    1025                1030                1035
Thr Cys  Cys Ser Asp Trp Gln  Arg His Phe Asp Val  Ala Leu Gly
    1040                1045                1050
Arg Met  Val Tyr Val Asn Lys  Met Thr Gly Leu Ser  Thr Phe Ile
    1055                1060                1065
Ala Pro  Thr Glu Asp Ile Gln  Ala Ala Cys Thr Lys  Asp Leu Thr
    1070                1075                1080
Thr Val  Ala Val Asp Val Val  Leu Glu Asn Gly Ser  Gln Tyr Arg
    1085                1090                1095
Cys Gln  Pro Phe Arg Ser Asp  Leu Val Leu Pro Phe  Leu Pro Arg
    1100                1105                1110
Ala Arg  Ala Glu Arg Thr Val  Met Arg Gln Asp Asn  Arg Asp Thr
    1115                1120                1125
Val Asp  Asp Thr Val Ser Ser  Glu Ser Leu Gln Ser  Leu Phe Ser
    1130                1135                1140
Glu Trp  Asp Asn Pro Val Phe  Ala Arg Tyr Pro Glu  Val Ala Val
    1145                1150                1155
Asp Val  Ser Ser Gly Gln Ala  Glu Ser Leu Ala Val  Lys Ile His
    1160                1165                1170
Asn Ile  Leu Tyr Pro Tyr Arg  Phe Thr Lys Gly Met  Ile His Ser
    1175                1180                1185
Met Gln  Val Leu Gln Gln Val  Asp Asn Lys Phe Ile  Ala Cys Leu
    1190                1195                1200
Met Ser  Thr Lys Thr Glu Glu  Asn Gly Glu Ala Asp  Ser Tyr Glu
    1205                1210                1215
Lys Gln  Gln Ala Gln Gly Ser  Gly Arg Lys Lys Leu  Leu Ser Ser
    1220                1225                1230
Thr Leu  Ile Pro Pro Leu Glu  Ile Thr Val Thr Glu  Glu Gln Arg
    1235                1240                1245
```

| | | | | | | | | | | |
|---|---|---|---|---|---|---|---|---|---|---|
|Arg|Leu|Leu|Trp|Cys|Tyr|His|Lys|Asn|Leu|Glu|Asp|Leu|Gly|Leu|
| |1250| | | | |1255| | | |1260| | | | |

Glu Phe Val Phe Pro Asp Thr Ser Asp Ser Leu Val Leu Val Gly
    1265             1270                1275

Lys Val Pro Leu Cys Phe Val Glu Arg Glu Ala Asn Glu Leu Arg
    1280             1285                1290

Arg Gly Arg Ser Thr Val Thr Lys Ser Ile Val Glu Glu Phe Ile
    1295             1300                1305

Arg Glu Gln Leu Glu Leu Leu Gln Thr Thr Gly Gly Ile Gln Gly
    1310             1315                1320

Thr Leu Pro Leu Thr Val Gln Lys Val Leu Ala Ser Gln Ala Cys
    1325             1330                1335

His Gly Ala Ile Lys Phe Asn Asp Gly Leu Ser Leu Gln Glu Ser
    1340             1345                1350

Cys Arg Leu Ile Glu Ala Leu Ser Ser Cys Gln Leu Pro Phe Gln
    1355             1360                1365

Cys Ala His Gly Arg Pro Ser Met Leu Pro Leu Ala Asp Ile Asp
    1370             1375                1380

His Leu Glu Gln Glu Lys Gln Ile Lys Pro Asn Leu Thr Lys Leu
    1385             1390                1395

Arg Lys Met Ala Gln Ala Trp Arg Leu Phe Gly Lys Ala Glu Cys
    1400             1405                1410

Asp Thr Arg Gln Ser Leu Gln Gln Ser Met Pro Pro Cys Glu Pro
    1415             1420                1425

Pro

```
<210> SEQ ID NO 15
<211> LENGTH: 3145
<212> TYPE: DNA
<213> ORGANISM: Homo sapiens

<400> SEQUENCE: 15
ggcgggaaac agcttagtgg gtgtggggtc gcgcattttc ttcaaccagg aggtgaggag    60
gtttcgacat ggcggtgcag ccgaaggaga cgctgcagtt ggagagcgcg gccgaggtcg   120
gcttcgtgcg cttctttcag ggcatgccgg agaagccgac caccacagtg cgccttttcg   180
accggggcga cttctatacg gcgcacggcg aggacgcgct gctggccgcc gggaggtgt    240
tcaagaccca gggggtgatc aagtacatgg ggccggcagg agcaaagaat ctgcagagtg   300
ttgtgcttag taaatgaat tttgaatctt ttgtaaaaga tcttcttctg gttcgtcagt    360
atagagttga agtttataag aatagagctg gaaataaggc atccaaggag aatgattggt   420
atttggcata taaggcttct cctggcaatc tctctcagtt tgaagacatt ctctttggta   480
acaatgatat gtcagcttcc attggtgttg tgggtgttaa aatgtccgca gttgatggcc   540
agagacaggt tggagttggg tatgtggatt ccatacagag gaaactagga ctgtgtgaat   600
tccctgataa tgatcagttc tccaatcttg aggctctcct catccagatt ggaccaaagg   660
aatgtgtttt acccggagga gagactgctg gagacatggg gaaactgaga cagataattc   720
aaagaggagg aattctgatc acagaaagaa aaaagctga cttttccaca aaagacattt   780
atcaggacct caaccggttg ttgaaaggca aaaaggaga gcagatgaat agtgctgtat   840
tgccagaaat ggagaatcag gttgcagttt catcactgtc tgcggtaatc aagttttag    900
aactcttatc agatgattcc aactttggac agtttgaact gactactttt gacttcagcc   960
agtatatgaa attggatatt gcagcagtca gagcccttaa ccttttcag ggttctgttg   1020
```

| | | | | |
|---|---|---|---|---|
| aagataccac | tggctctcag | tctctggctg | ccttgctgaa | taagtgtaaa | accccctcaag | 1080 |
| gacaaagact | tgttaaccag | tggattaagc | agcctctcat | ggataagaac | agaatagagg | 1140 |
| agagattgaa | tttagtggaa | gcttttgtag | aagatgcaga | attgaggcag | actttacaag | 1200 |
| aagatttact | tcgtcgattc | ccagatctta | accgacttgc | caagaagttt | caaagacaag | 1260 |
| cagcaaactt | acaagattgt | taccgactct | atcagggtat | aaatcaacta | cctaatgtta | 1320 |
| tacaggctct | ggaaaaacat | gaaggaaaac | accagaaatt | attgttggca | gttttttgtga | 1380 |
| ctcctcttac | tgatcttcgt | tctgacttct | ccaagtttca | ggaaatgata | gaaacaactt | 1440 |
| tagatatgga | tcaggtggaa | aaccatgaat | tccttgtaaa | accttcattt | gatcctaatc | 1500 |
| tcagtgaatt | aagagaaata | atgaatgact | tggaaaagaa | gatgcagtca | acattaataa | 1560 |
| gtgcagccag | agatcttggc | ttggaccctg | gcaaacagat | taaactggat | tccagtgcac | 1620 |
| agtttggata | ttactttcgt | gtaacctgta | aggaagaaaa | agtccttcgt | aacaataaaa | 1680 |
| actttagtac | tgtagatatc | cagaagaatg | gtgttaaatt | taccaacagc | aaattgactt | 1740 |
| ctttaaatga | agagtatacc | aaaaataaaa | cagaatatga | agaagcccag | gatgccattg | 1800 |
| ttaaagaaat | tgtcaatatt | tcttcaggct | atgtagaacc | aatgcagaca | ctcaatgatg | 1860 |
| tgttagctca | gctagatgct | gttgtcagct | ttgctcacgt | gtcaaatgga | gcacctgttc | 1920 |
| catatgtacg | accagccatt | ttggagaaag | gacaaggaag | aattatatta | aaagcatcca | 1980 |
| ggcatgcttg | tgttgaagtt | caagatgaaa | ttgcatttat | tcctaatgac | gtatactttg | 2040 |
| aaaaagataa | acagatgttc | cacatcatta | ctggccccaa | tatgggaggt | aaatcaacat | 2100 |
| atattcgaca | aactggggtg | atagtactca | tggcccaaat | tgggtgtttt | gtgccatgtg | 2160 |
| agtcagcaga | agtgtccatt | gtggactgca | tcttagcccg | agtaggggct | ggtgacagtc | 2220 |
| aattgaaagg | agtctccacg | ttcatggctg | aaatgttgga | aactgcttct | atcctcaggt | 2280 |
| ctgcaaccaa | agattcatta | ataatcatag | atgaattggg | aagaggaact | tctacctacg | 2340 |
| atggatttgg | gttagcatgg | gctatatcag | aatacattgc | aacaaagatt | ggtgcttttt | 2400 |
| gcatgtttgc | aacccatttt | catgaactta | ctgccttggc | caatcagata | ccaactgtta | 2460 |
| ataatctaca | tgtcacagca | ctcaccactg | aagagacctt | aactatgctt | tatcaggtga | 2520 |
| agaaaggtgt | ctgtgatcaa | agttttggga | ttcatgttgc | agagcttgct | aatttcccta | 2580 |
| agcatgtaat | agagtgtgct | aaacagaaag | ccctggaact | tgaggagttt | cagtatattg | 2640 |
| gagaatcgca | aggatatgat | atcatggaac | cagcagcaaa | gaagtgctat | ctggaaagag | 2700 |
| agcaaggtga | aaaattatt | caggagttcc | tgtccaaggt | gaaacaaatg | cccttactg | 2760 |
| aaatgtcaga | agaaacatc | acaataaagt | taaacagct | aaaagctgaa | gtaatagcaa | 2820 |
| agaataatag | ctttgtaaat | gaaatcattt | cacgaataaa | agttactacg | tgaaaaatcc | 2880 |
| cagtaatgga | atgaaggtaa | tattgataag | ctattgtctg | taatagtttt | atattgtttt | 2940 |
| atattaaccc | tttttccata | gtgttaactg | tcagtgccca | tgggctatca | acttaataag | 3000 |
| atatttagta | atattttact | ttgaggacat | tttcaaagat | ttttattttg | aaaaatgaga | 3060 |
| gctgtaactg | aggactgttt | gcaattgaca | taggcaataa | taagtgatgt | gctgaatttt | 3120 |
| ataaataaaa | tcatgtagtt | tgtgg | | | | 3145 |

<210> SEQ ID NO 16
<211> LENGTH: 934
<212> TYPE: PRT
<213> ORGANISM: Homo sapiens

<400> SEQUENCE: 16

```
Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
            115                 120                 125

Ser Gln Phe Glu Asp Ile Leu Phe Gly Asn Asn Asp Met Ser Ala Ser
        130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Thr Ala Gly
        195                 200                 205

Asp Met Gly Lys Leu Arg Gln Ile Ile Gln Arg Gly Gly Ile Leu Ile
210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
            275                 280                 285

Phe Glu Leu Thr Thr Phe Asp Phe Ser Gln Tyr Met Lys Leu Asp Ile
        290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
            325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
            355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430
```

-continued

```
Leu Ala Val Phe Val Thr Pro Leu Thr Asp Leu Arg Ser Asp Phe Ser
            435                 440                 445

Lys Phe Gln Glu Met Ile Glu Thr Thr Leu Asp Met Asp Gln Val Glu
            450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
                500                 505                 510

Leu Asp Ser Ser Ala Gln Phe Gly Tyr Tyr Phe Arg Val Thr Cys Lys
                515                 520                 525

Glu Glu Lys Val Leu Arg Asn Asn Lys Asn Phe Ser Thr Val Asp Ile
            530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Ala Gln Asp Ala
                565                 570                 575

Ile Val Lys Glu Ile Val Asn Ile Ser Ser Gly Tyr Val Glu Pro Met
                580                 585                 590

Gln Thr Leu Asn Asp Val Leu Ala Gln Leu Asp Ala Val Val Ser Phe
            595                 600                 605

Ala His Val Ser Asn Gly Ala Pro Val Pro Tyr Val Arg Pro Ala Ile
            610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
                660                 665                 670

Gly Gly Lys Ser Thr Tyr Ile Arg Gln Thr Gly Val Ile Val Leu Met
                675                 680                 685

Ala Gln Ile Gly Cys Phe Val Pro Cys Glu Ser Ala Glu Val Ser Ile
            690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
                740                 745                 750

Gly Thr Ser Thr Tyr Asp Gly Phe Gly Leu Ala Trp Ala Ile Ser Glu
                755                 760                 765

Tyr Ile Ala Thr Lys Ile Gly Ala Phe Cys Met Phe Ala Thr His Phe
                770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
                820                 825                 830

Leu Ala Asn Phe Pro Lys His Val Ile Glu Cys Ala Lys Gln Lys Ala
                835                 840                 845

Leu Glu Leu Glu Glu Phe Gln Tyr Ile Gly Glu Ser Gln Gly Tyr Asp
```

```
                    850                 855                 860
Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
        915                 920                 925

Arg Ile Lys Val Thr Thr
    930

<210> SEQ ID NO 17
<211> LENGTH: 4374
<212> TYPE: DNA
<213> ORGANISM: Homo sapiens

<400> SEQUENCE: 17
gggcacgagc cctgccatgt ctcgccggaa gcctgcgtcg ggcggcctcg ctgcctccag      60
ctcagcccct gcgaggcaag cggttttgag ccgattcttc cagtctacgg gaagcctgaa     120
atccacctcc tcctccacag gtgcagccga ccaggtggac cctggcgctg cagcggccgc     180
agcgccccca gcgcccgcct tcccgcccca gctgccgccg cacgtagcta cagaaattga     240
cagaagaaag aagagaccat tggaaaatga tgggcctgtt aaaagaaag taaagaaagt      300 ccaacaaaag gaaggaggaa gtgatctggg aatgtctggc aactctgagc aaagaaatg      360 tctgaggacc aggaatgttt caaagtctct ggaaaaattg aaagaattct gctgcgattc     420
tgcccttcct caaagtagag tccagacaga atctctgcag gagagatttg cagttctgcc     480
aaaatgtact gattttgatg atatcagtct tctacacgca aagaatgcag tttcttctga     540
agattcgaaa cgtcaaatta tcaaaaggaca caacacttt tttgatctca gtcagtttgg    600
atcatcaaat acaagtcatg aaaattaca gaaaactgct tccaaatcag ctaacaaacg     660
gtccaaaagc atctatacgc cgctagaatt acaatacata gaaatgaagc agcagcacaa     720
agatgcagtt ttgtgtgtgg aatgtggata taagtataga ttcttgggg aagatgcaga     780 gattgcagcc cgagagctca atatttattg ccattttagat cacaacttta tgacagcaag     840
tatacctact cacagactgt tgttcatgt acgccgcctg gtggcaaaag gatataaggt      900
gggagttgtg aagcaaactg aaactgcagc attaaaggcc attggagaca acagaagttc     960
actcttttcc cggaaattga ctgccctta tacaaaatct acacttattg gagaagatgt    1020
gaatccccta atcaagctgg atgatgctgt aaatgttgat gagataatga ctgatacttc    1080
taccagctat cttctgtgca tctctgaaaa taaggaaaat gttagggaca aaaaaaaggg    1140
caacattttt attggcattg tgggagtgca gcctgccaca ggcgaggttg tgtttgatag    1200
tttccaggac tctgcttctc gttcagagct agaaacccgg atgtcaagcc tgcagccagt    1260
agagctgctg cttccttcgg ccttgtccga gcaaacagag gcgctcatcc acagagccac    1320
atctgttagt gtgcaggatg acagaattcg agtcgaaagg atggataaca tttatttga    1380 atacagccat gctttccagg cagttacaga gttttatgca aagatacag ttgacatcaa    1440 aggttctcaa attatttctg gcattgttaa cttagagaag cctgtgattt gctctttggc    1500
tgccatcata aaatacctca aagaattcaa cttggaaaag atgctctcca acctgagaa    1560 ttttaaacag ctatcaagta aaatggaatt tatgacaatt aatggaacaa cattaaggaa    1620
tctggaaatc ctacagaatc agactgatat gaaaaccaaa ggaagtttgc tgtgggtttt    1680
```

```
agaccacact aaaacttcat ttgggagacg gaagttaaag aagtgggtga cccagccact    1740
ccttaaatta agggaaataa atgcccggct tgatgctgta tcggaagttc tccattcaga    1800
atctagtgtg tttggtcaga tagaaaatca tctacgtaaa ttgcccgaca tagagagggg    1860
actctgtagc atttatcaca aaaaatgttc tacccaagag ttcttcttga ttgtcaaaac    1920
tttatatcac ctaaagtcag aatttcaagc aataatacct gctgttaatt cccacattca    1980
gtcagacttg ctccggaccg ttattttaga aattcctgaa ctcctcagtc cagtggagca    2040
ttacttaaag atactcaatg aacaagctgc caaagttggg gataaaactg aattatttaa    2100
agacctttct gacttcccct taataaaaaa gaggaaggat gaaattcaag gtgttattga    2160
cgagatccga atgcatttgc aagaaatacg aaaaatacta aaaaatcctt ctgcacaata    2220
tgtgacagta tcaggacagg agtttatgat agaaataaag aactctgctg tatcttgtat    2280
accaactgat tgggtaaagg ttggaagcac aaaagctgtg agccgctttc actctccttt    2340
tattgtagaa aattacagac atctgaatca gctccgggag cagctagtcc ttgactgcag    2400
tgctgaatgg cttgattttc tagagaaatt cagtgaacat tatcactcct tgtgtaaagc    2460
agtgcatcac ctagcaactg ttgactgcat tttctccctg gccaaggtcg ctaagcaagg    2520
agattactgc agaccaactg tacaagaaga agaaaaaatt gtaataaaaa atggaaggca    2580
ccctgtgatt gatgtgttgc tgggagaaca ggatcaatat gtcccaaata atacagattt    2640
atcagaggac tcagagagag taatgataat taccggacca acatgggtg gaaagagctc    2700 ctacataaaa caagttgcat tgattaccat catggctcag attggctcct atgttcctgc    2760
agaagaagcg acaattggga ttgtggatgg catttcaca aggatgggtg ctgcagacaa    2820
tatatataaa ggacggagta catttatgga agaactgact gacacagcag aaataatcag    2880
aaaagcaaca tcacagtcct tggttatctt ggatgaacta ggaagaggga cgagcactca    2940
tgatggaatt gccattgcct atgctacact tgagtatttc atcagagatg tgaaatcctt    3000
aaccctgttt gtcacccatt atccgccagt ttgtgaacta gaaaaaaatt actcacacca    3060
ggtggggaat taccacatgg gattcttggt cagtgaggat gaaagcaaac tggatccagg    3120
cgcagcagaa caagtccctg attttgtcac cttcctttac caaataacta gaggaattgc    3180
agcaaggagt tatggattaa atgtggctaa actagcagat gttcctggag aaattttgaa    3240
gaaagcagct cacaagtcaa aagagctgga aggattaata aatacgaaaa gaaagagact    3300
caagtatttt gcaaagttat ggacgatgca taatgcacaa gacctgcaga agtggacaga    3360
ggagttcaac atggaagaaa cacagacttc tcttcttcat taaaatgaag actacatttg    3420
tgaacaaaaa atggagaatt aaaaatacca actgtacaaa ataactctcc agtaacagcc    3480
tatctttgtg tgacatgtga gcataaaatt atgaccatgg tatattccta ttggaaacag    3540
agaggttttt ctgaagacag tcttttcaa gtttctgtct tcctaactt tctacgtata    3600 aacactcttg aatagacttc cactttgtaa ttagaaaatt ttatggacag taagtccagt    3660
aaagccttaa gtggcagaat ataattccca agcttttgga gggtgatata aaaatttact    3720
tgatattttt atttgtttca gttcagataa ttggcaactg ggtgaatctg caggaatct    3780 atccattgaa ctaaaataat tttattatgc aaccagttta tccaccaaga acataagaat    3840
tttttataag tagaaagaat tggccaggca tggtggctca tgcctgtaat cccagcactt    3900
tgggaggcca aggtaggcag atcacctgag gtcaggagtt caagaccagc ctggccaaca    3960
tggcaaaacc ccatctttac taaaaatata agtacatct ctactaaaaa tacgaaaaaa    4020
ttagctgggc atggtggcgc acacctgtag tcccagctac tccggaggct gaggcaggag    4080
```

```
aatctcttga acctgggagg cggaggttgc aatgagccga gatcacgtca ctgcactcca    4140
gcttgggcaa cagagcaaga ctccatctca aaaagaaaaa aagaaaagaa atagaattat    4200
caagctttta aaaactagag cacagaagga ataaggtcat gaaatttaaa aggttaaata    4260
ttgtcatagg attaagcagt ttaaagattg ttggatgaaa ttatttgtca ttcattcaag    4320
taataaatat ttaatgaata cttgctataa aaaaaaaaaa aaaaaaaaaa aaaa          4374
```

```
<210> SEQ ID NO 18
<211> LENGTH: 1128
<212> TYPE: PRT
<213> ORGANISM: Homo sapiens

<400> SEQUENCE: 18
```

```
Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
            20                  25                  30

Ser Leu Lys Ser Thr Ser Ser Thr Gly Ala Ala Asp Gln Val Asp
        35                  40                  45

Pro Gly Ala Ala Ala Ala Ala Pro Pro Ala Pro Ala Phe Pro Pro
    50                  55                  60

Gln Leu Pro Pro His Val Ala Thr Glu Ile Asp Arg Arg Lys Lys Arg
65                  70                  75                  80

Pro Leu Glu Asn Asp Gly Pro Val Lys Lys Val Lys Val Gln
                85                  90                  95

Gln Lys Glu Gly Gly Ser Asp Leu Gly Met Ser Gly Asn Ser Glu Pro
                100                 105                 110

Lys Lys Cys Leu Arg Thr Arg Asn Val Ser Lys Ser Leu Glu Lys Leu
            115                 120                 125

Lys Glu Phe Cys Cys Asp Ser Ala Leu Pro Gln Ser Arg Val Gln Thr
        130                 135                 140

Glu Ser Leu Gln Glu Arg Phe Ala Val Leu Pro Lys Cys Thr Asp Phe
145                 150                 155                 160

Asp Asp Ile Ser Leu Leu His Ala Lys Asn Ala Val Ser Ser Glu Asp
                165                 170                 175

Ser Lys Arg Gln Ile Asn Gln Lys Asp Thr Thr Leu Phe Asp Leu Ser
            180                 185                 190

Gln Phe Gly Ser Ser Asn Thr Ser His Glu Asn Leu Gln Lys Thr Ala
        195                 200                 205

Ser Lys Ser Ala Asn Lys Arg Ser Lys Ser Ile Tyr Thr Pro Leu Glu
    210                 215                 220

Leu Gln Tyr Ile Glu Met Lys Gln Gln His Lys Asp Ala Val Leu Cys
225                 230                 235                 240

Val Glu Cys Gly Tyr Lys Tyr Arg Phe Phe Gly Glu Asp Ala Glu Ile
                245                 250                 255

Ala Ala Arg Glu Leu Asn Ile Tyr Cys His Leu Asp His Asn Phe Met
            260                 265                 270

Thr Ala Ser Ile Pro Thr His Arg Leu Phe Val His Val Arg Arg Leu
        275                 280                 285

Val Ala Lys Gly Tyr Lys Val Gly Val Val Lys Gln Thr Glu Thr Ala
    290                 295                 300

Ala Leu Lys Ala Ile Gly Asp Asn Arg Ser Ser Leu Phe Ser Arg Lys
305                 310                 315                 320

Leu Thr Ala Leu Tyr Thr Lys Ser Thr Leu Ile Gly Glu Asp Val Asn
```

-continued

```
                325                 330                 335
Pro Leu Ile Lys Leu Asp Asp Ala Val Asn Val Asp Glu Ile Met Thr
                340                 345                 350

Asp Thr Ser Thr Ser Tyr Leu Leu Cys Ile Ser Glu Asn Lys Glu Asn
                355                 360                 365

Val Arg Asp Lys Lys Gly Asn Ile Phe Ile Gly Ile Val Gly Val
    370                 375                 380

Gln Pro Ala Thr Gly Glu Val Val Phe Asp Ser Phe Gln Asp Ser Ala
385                 390                 395                 400

Ser Arg Ser Glu Leu Glu Thr Arg Met Ser Ser Leu Gln Pro Val Glu
                405                 410                 415

Leu Leu Leu Pro Ser Ala Leu Ser Glu Gln Thr Glu Ala Leu Ile His
                420                 425                 430

Arg Ala Thr Ser Val Ser Val Gln Asp Asp Arg Ile Arg Val Glu Arg
                435                 440                 445

Met Asp Asn Ile Tyr Phe Glu Tyr Ser His Ala Phe Gln Ala Val Thr
    450                 455                 460

Glu Phe Tyr Ala Lys Asp Thr Val Asp Ile Lys Gly Ser Gln Ile Ile
465                 470                 475                 480

Ser Gly Ile Val Asn Leu Glu Lys Pro Val Ile Cys Ser Leu Ala Ala
                485                 490                 495

Ile Ile Lys Tyr Leu Lys Glu Phe Asn Leu Glu Lys Met Leu Ser Lys
                500                 505                 510

Pro Glu Asn Phe Lys Gln Leu Ser Ser Lys Met Glu Phe Met Thr Ile
                515                 520                 525

Asn Gly Thr Thr Leu Arg Asn Leu Glu Ile Leu Gln Asn Gln Thr Asp
    530                 535                 540

Met Lys Thr Lys Gly Ser Leu Leu Trp Val Leu Asp His Thr Lys Thr
545                 550                 555                 560

Ser Phe Gly Arg Arg Lys Leu Lys Lys Trp Val Thr Gln Pro Leu Leu
                565                 570                 575

Lys Leu Arg Glu Ile Asn Ala Arg Leu Asp Ala Val Ser Glu Val Leu
                580                 585                 590

His Ser Glu Ser Ser Val Phe Gly Gln Ile Glu Asn His Leu Arg Lys
                595                 600                 605

Leu Pro Asp Ile Glu Arg Gly Leu Cys Ser Ile Tyr His Lys Lys Cys
    610                 615                 620

Ser Thr Gln Glu Phe Phe Leu Ile Val Lys Thr Leu Tyr His Leu Lys
625                 630                 635                 640

Ser Glu Phe Gln Ala Ile Ile Pro Ala Val Asn Ser His Ile Gln Ser
                645                 650                 655

Asp Leu Leu Arg Thr Val Ile Leu Glu Ile Pro Glu Leu Leu Ser Pro
                660                 665                 670

Val Glu His Tyr Leu Lys Ile Leu Asn Glu Gln Ala Ala Lys Val Gly
                675                 680                 685

Asp Lys Thr Glu Leu Phe Lys Asp Leu Ser Asp Phe Pro Leu Ile Lys
    690                 695                 700

Lys Arg Lys Asp Glu Ile Gln Gly Val Ile Asp Glu Ile Arg Met His
705                 710                 715                 720

Leu Gln Glu Ile Arg Lys Ile Leu Lys Asn Pro Ser Ala Gln Tyr Val
                725                 730                 735

Thr Val Ser Gly Gln Glu Phe Met Ile Glu Ile Lys Asn Ser Ala Val
                740                 745                 750
```

```
Ser Cys Ile Pro Thr Asp Trp Val Lys Val Gly Ser Thr Lys Ala Val
        755                 760                 765

Ser Arg Phe His Ser Pro Phe Ile Val Glu Asn Tyr Arg His Leu Asn
    770                 775                 780

Gln Leu Arg Glu Gln Leu Val Leu Asp Cys Ser Ala Glu Trp Leu Asp
785                 790                 795                 800

Phe Leu Glu Lys Phe Ser Glu His Tyr His Ser Leu Cys Lys Ala Val
                805                 810                 815

His His Leu Ala Thr Val Asp Cys Ile Phe Ser Leu Ala Lys Val Ala
                820                 825                 830

Lys Gln Gly Asp Tyr Cys Arg Pro Thr Val Gln Glu Arg Lys Ile
            835                 840                 845

Val Ile Lys Asn Gly Arg His Pro Val Ile Asp Val Leu Leu Gly Glu
    850                 855                 860

Gln Asp Gln Tyr Val Pro Asn Asn Thr Asp Leu Ser Glu Asp Ser Glu
865                 870                 875                 880

Arg Val Met Ile Ile Thr Gly Pro Asn Met Gly Lys Ser Ser Tyr
                885                 890                 895

Ile Lys Gln Val Ala Leu Ile Thr Ile Met Ala Gln Ile Gly Ser Tyr
                900                 905                 910

Val Pro Ala Glu Glu Ala Thr Ile Gly Ile Val Asp Gly Ile Phe Thr
                915                 920                 925

Arg Met Gly Ala Ala Asp Asn Ile Tyr Lys Gly Arg Ser Thr Phe Met
930                 935                 940

Glu Glu Leu Thr Asp Thr Ala Glu Ile Ile Arg Lys Ala Thr Ser Gln
945                 950                 955                 960

Ser Leu Val Ile Leu Asp Glu Leu Gly Arg Gly Thr Ser Thr His Asp
                965                 970                 975

Gly Ile Ala Ile Ala Tyr Ala Thr Leu Glu Tyr Phe Ile Arg Asp Val
                980                 985                 990

Lys Ser Leu Thr Leu Phe Val Thr His Tyr Pro Pro Val Cys Glu Leu
                995                 1000                1005

Glu Lys Asn Tyr Ser His Gln Val Gly Asn Tyr His Met Gly Phe
    1010                1015                1020

Leu Val Ser Glu Asp Glu Ser Lys Leu Asp Pro Gly Ala Ala Glu
    1025                1030                1035

Gln Val Pro Asp Phe Val Thr Phe Leu Tyr Gln Ile Thr Arg Gly
    1040                1045                1050

Ile Ala Ala Arg Ser Tyr Gly Leu Asn Val Ala Lys Leu Ala Asp
    1055                1060                1065

Val Pro Gly Glu Ile Leu Lys Lys Ala Ala His Lys Ser Lys Glu
    1070                1075                1080

Leu Glu Gly Leu Ile Asn Thr Lys Arg Lys Arg Leu Lys Tyr Phe
    1085                1090                1095

Ala Lys Leu Trp Thr Met His Asn Ala Gln Asp Leu Gln Lys Trp
    1100                1105                1110

Thr Glu Glu Phe Asn Met Glu Thr Gln Thr Ser Leu Leu His
    1115                1120                1125

<210> SEQ ID NO 19
<211> LENGTH: 3095
<212> TYPE: DNA
<213> ORGANISM: Homo sapiens

<400> SEQUENCE: 19
```

```
cagaaacctc atacttctcg ggtcagggaa ggtttgggag gatgctgagg cctgagatct    60
catcaacctc gccttctgcc ccggcggttt cccccgtcgt cggagaaacc cgctcacctc   120
agggtccccg ctacaatttc ggactccagg agactccaca gagccgccct tcggtccagg   180
tggtctctgc atccacctgt cctggcacgt caggagctgc gggcgaccgg agcagcagca   240
gcagcagcct tccctgcccc gcgccaaact cccggccagc tcaaggttca tactttggaa   300 acaaagagc ttatgcagaa aacacagttg catcaaattt tacttttggt gcaagctcat    360
cttctgcacg agatactaat tatcctcaaa cacttaaaac tccattgtct actggaaatc   420
ctcagagatc aggttataag agctggacac cacaagtggg atattcagct tcatcctcat   480
ctgcgatttc tgcacactcc ccatcagtta ttgtagctgt tgtagaaggg agaggacttg   540
ccagaggtga ataggaatg gcaagtattg atttaaaaaa ccccaaatt atactatccc    600 agtttgcaga caacacaaca tatgcaaagg tgatcactaa acttaaaatt ttatcacctt   660
tggaaataat aatgtcaaat actgcttgtg ctgtggggaa ttccaccaag ttgttcactc   720
tgatcacaga aaatttcaag aatgttaatt tcactactat ccaaaggaaa tacttcaatg   780
aaacaaaagg attagagtac attgaacagt tatgcatagc agaattcagc actgtcctaa   840
tggaggttca gtccaagtat tactgccttg cagctgttgc agctttgtta aaatatgttg   900
aatttattca aaattcagtt tatgcaccaa aatcactgaa gatttgtttc cagggtagtg   960
aacagacagc catgatagat tcatcatcag cccaaaacct tgaattgtta attaataatc  1020
aagactatag gaataatcac actctctttg gtgttctaaa ttatactaag actcctggag  1080
ggagtagacg acttcgttct aatatattag agcctctagt tgatattgaa accattaaca  1140
tgcgcttaga ttgtgttcaa gaactacttc aagatgagga actatttttt ggacttcaat  1200
cagttatatc aagatttctt gatacagagc agcttctttc tgttttagtc caaattccag  1260
agcaagacac ggtcaatgct gctgaatcaa agataacaaa tttaatatac ttaaaacata  1320
ccttggaact tgtggatcct ttaaagattg ctatgaagaa ctgtaacaca cctttattaa  1380
gagcttacta tggttccttg gaagacaaga ggttttggaat catacttgaa aagattaaaa  1440
cagtaattaa tgatgatgca agatacatga aaggatgcct aaacatgagg actcagaagt  1500
gctatgcagt gaggtctaac ataaatgaat tcttgacat agcaagaaga acatacacag  1560
agattgtaga tgcatagca ggaatgatat cacaacttgg agaaaaatat agtctacctt   1620
taaggacaag tcttagctct gttcgaggat tttcatcca gatgactaca gattgtatag    1680
ccctacctag tgatcaactt ccttcagaat ttattaagat ttctaaagtg aaaaattctt   1740
acagctttac atcagcagat ttaattaaaa tgaatgaaag atgccaagaa tctttgagag  1800
aaatctatca catgacttat atgatagtgt gcaaactgct tagtgagatt tatgaacata  1860
ttcattgctt atataaacta tctgacactg tgtcaatgct ggatatgcta ctgtcatttg  1920
ctcatgcctg cactctttct gactatgttc gaccagaatt tactgatact ttagcaatca  1980
aacagggatg gcatcctatt cttgaaaaaa tatctgcgga aaaacctatt gccaacaata  2040
cctatgttac agaagggagt aattttttga tcataactgg accaaacatg agtggaaaat  2100
ccacatattt aaaacagatt gctctttgtc agattatggc ccagattgga tcatatgttc  2160
cagcagaata ttcttccttt agaattgcta acagattttt tacaagaatt agtactgatg  2220
atgatatcga aacaaattca tcaacattta tgaaagaaat gaagagata gcatatattc   2280 tacataatgc taatgacaaa tcgctcatat taattgatga acttggcaga ggtactaata  2340
cggaagaagg tattggcatt tgttatgctg tttgtgaata tctactgagc ttaaaggcat  2400
```

| | | | |
|---|---|---|---|
| ttacactgtt tgctacacat ttcctggaac tatgccatat tgatgccctg tatcctaatg | | | 2460 |
| tagaaaacat gcattttgaa gttcaacatg taaagaatac ctcaagaaat aaagaagcaa | | | 2520 |
| ttttgtatac ctacaaactt tctaagggac tcacagaaga gaaaaattat ggattaaaag | | | 2580 |
| ctgcagaggt gtcatcactt ccaccatcaa ttgtcttgga tgccaaggaa atcacaactc | | | 2640 |
| aaattacgag acaaattttg caaaaccaaa ggagtacccc tgagatggaa agacagagag | | | 2700 |
| ctgtgtacca tctagccact aggcttgttc aaactgctcg aaactctcaa ttggatccag | | | 2760 |
| acagtttacg aatatattta agtaacctca agaagaagta caagaagat tttcccagga | | | 2820 |
| ccgaacaagt tccagaaaag actgaagaat aatcacaatt ctaatgtaat aatatatctt | | | 2880 |
| aattcaagga acctagaatt tattttctc cttagagata aggaaaataa catttgccaa | | | 2940 |
| atttcatatt ttaattgaaa attacattat attaacatca caattgtcat ctatatattc | | | 3000 |
| tatatgaaaa atatttatta taacttaaca aatgagaact acttaaagga atggttttta | | | 3060 |
| tgttaggaga aaatacaata caccacaaaa aaaaa | | | 3095 |

<210> SEQ ID NO 20
<211> LENGTH: 936
<212> TYPE: PRT
<213> ORGANISM: Homo sapiens

<400> SEQUENCE: 20

Met Leu Arg Pro Glu Ile Ser Ser Thr Ser Pro Ser Ala Pro Ala Val
1               5                   10                  15

Ser Pro Val Val Gly Glu Thr Arg Ser Pro Gln Gly Pro Arg Tyr Asn
            20                  25                  30

Phe Gly Leu Gln Glu Thr Pro Gln Ser Arg Pro Ser Val Gln Val Val
        35                  40                  45

Ser Ala Ser Thr Cys Pro Gly Thr Ser Gly Ala Ala Gly Asp Arg Ser
    50                  55                  60

Ser Ser Ser Ser Ser Leu Pro Cys Pro Ala Pro Asn Ser Arg Pro Ala
65                  70                  75                  80

Gln Gly Ser Tyr Phe Gly Asn Lys Arg Ala Tyr Ala Glu Asn Thr Val
                85                  90                  95

Ala Ser Asn Phe Thr Phe Gly Ala Ser Ser Ser Ala Arg Asp Thr
            100                 105                 110

Asn Tyr Pro Gln Thr Leu Lys Thr Pro Leu Ser Thr Gly Asn Pro Gln
        115                 120                 125

Arg Ser Gly Tyr Lys Ser Trp Thr Pro Gln Val Gly Tyr Ser Ala Ser
    130                 135                 140

Ser Ser Ser Ala Ile Ser Ala His Ser Pro Ser Val Ile Val Ala Val
145                 150                 155                 160

Val Glu Gly Arg Gly Leu Ala Arg Gly Glu Ile Gly Met Ala Ser Ile
                165                 170                 175

Asp Leu Lys Asn Pro Gln Ile Ile Leu Ser Gln Phe Ala Asp Asn Thr
            180                 185                 190

Thr Tyr Ala Lys Val Ile Thr Lys Leu Lys Ile Leu Ser Pro Leu Glu
        195                 200                 205

Ile Ile Met Ser Asn Thr Ala Cys Ala Val Gly Asn Ser Thr Lys Leu
    210                 215                 220

Phe Thr Leu Ile Thr Glu Asn Phe Lys Asn Val Asn Phe Thr Thr Ile
225                 230                 235                 240

Gln Arg Lys Tyr Phe Asn Glu Thr Lys Gly Leu Glu Tyr Ile Glu Gln
                245                 250                 255

-continued

```
Leu Cys Ile Ala Glu Phe Ser Thr Val Leu Met Glu Val Gln Ser Lys
            260                 265                 270
Tyr Tyr Cys Leu Ala Ala Val Ala Leu Leu Lys Tyr Val Glu Phe
        275                 280                 285
Ile Gln Asn Ser Val Tyr Ala Pro Lys Ser Leu Lys Ile Cys Phe Gln
    290                 295                 300
Gly Ser Glu Gln Thr Ala Met Ile Asp Ser Ser Ala Gln Asn Leu
305                 310                 315                 320
Glu Leu Leu Ile Asn Asn Gln Asp Tyr Arg Asn His Thr Leu Phe
                325                 330                 335
Gly Val Leu Asn Tyr Thr Lys Thr Pro Gly Gly Ser Arg Arg Leu Arg
            340                 345                 350
Ser Asn Ile Leu Glu Pro Leu Val Asp Ile Glu Thr Ile Asn Met Arg
        355                 360                 365
Leu Asp Cys Val Gln Glu Leu Leu Gln Asp Glu Glu Leu Phe Phe Gly
    370                 375                 380
Leu Gln Ser Val Ile Ser Arg Phe Leu Asp Thr Glu Gln Leu Leu Ser
385                 390                 395                 400
Val Leu Val Gln Ile Pro Glu Gln Asp Thr Val Asn Ala Ala Glu Ser
                405                 410                 415
Lys Ile Thr Asn Leu Ile Tyr Leu Lys His Thr Leu Glu Leu Val Asp
            420                 425                 430
Pro Leu Lys Ile Ala Met Lys Asn Cys Asn Thr Pro Leu Leu Arg Ala
        435                 440                 445
Tyr Tyr Gly Ser Leu Glu Asp Lys Arg Phe Gly Ile Ile Leu Glu Lys
    450                 455                 460
Ile Lys Thr Val Ile Asn Asp Asp Ala Arg Tyr Met Lys Gly Cys Leu
465                 470                 475                 480
Asn Met Arg Thr Gln Lys Cys Tyr Ala Val Arg Ser Asn Ile Asn Glu
                485                 490                 495
Phe Leu Asp Ile Ala Arg Arg Thr Tyr Thr Glu Ile Val Asp Asp Ile
            500                 505                 510
Ala Gly Met Ile Ser Gln Leu Gly Glu Lys Tyr Ser Leu Pro Leu Arg
        515                 520                 525
Thr Ser Leu Ser Ser Val Arg Gly Phe Phe Ile Gln Met Thr Thr Asp
    530                 535                 540
Cys Ile Ala Leu Pro Ser Asp Gln Leu Pro Ser Glu Phe Ile Lys Ile
545                 550                 555                 560
Ser Lys Val Lys Asn Ser Tyr Ser Phe Thr Ser Ala Asp Leu Ile Lys
                565                 570                 575
Met Asn Glu Arg Cys Gln Glu Ser Leu Arg Glu Ile Tyr His Met Thr
            580                 585                 590
Tyr Met Ile Val Cys Lys Leu Leu Ser Glu Ile Tyr Glu His Ile His
        595                 600                 605
Cys Leu Tyr Lys Leu Ser Asp Thr Val Ser Met Leu Asp Met Leu Leu
    610                 615                 620
Ser Phe Ala His Ala Cys Thr Leu Ser Asp Tyr Val Arg Pro Glu Phe
625                 630                 635                 640
Thr Asp Thr Leu Ala Ile Lys Gln Gly Trp His Pro Ile Leu Glu Lys
                645                 650                 655
Ile Ser Ala Glu Lys Pro Ile Ala Asn Asn Thr Tyr Val Thr Glu Gly
            660                 665                 670
Ser Asn Phe Leu Ile Ile Thr Gly Pro Asn Met Ser Gly Lys Ser Thr
        675                 680                 685
```

Tyr Leu Lys Gln Ile Ala Leu Cys Gln Ile Met Ala Gln Ile Gly Ser
        690                 695                 700

Tyr Val Pro Ala Glu Tyr Ser Ser Phe Arg Ile Ala Lys Gln Ile Phe
705                 710                 715                 720

Thr Arg Ile Ser Thr Asp Asp Ile Glu Thr Asn Ser Ser Thr Phe
            725                 730                 735

Met Lys Glu Met Lys Glu Ile Ala Tyr Ile Leu His Asn Ala Asn Asp
            740                 745                 750

Lys Ser Leu Ile Leu Ile Asp Glu Leu Gly Arg Gly Thr Asn Thr Glu
            755                 760                 765

Glu Gly Ile Gly Ile Cys Tyr Ala Val Cys Glu Tyr Leu Leu Ser Leu
        770                 775                 780

Lys Ala Phe Thr Leu Phe Ala Thr His Phe Leu Glu Leu Cys His Ile
785                 790                 795                 800

Asp Ala Leu Tyr Pro Asn Val Glu Asn Met His Phe Glu Val Gln His
                805                 810                 815

Val Lys Asn Thr Ser Arg Asn Lys Glu Ala Ile Leu Tyr Thr Tyr Lys
            820                 825                 830

Leu Ser Lys Gly Leu Thr Glu Glu Lys Asn Tyr Gly Leu Lys Ala Ala
        835                 840                 845

Glu Val Ser Ser Leu Pro Pro Ser Ile Val Leu Asp Ala Lys Glu Ile
850                 855                 860

Thr Thr Gln Ile Thr Arg Gln Ile Leu Gln Asn Gln Arg Ser Thr Pro
865                 870                 875                 880

Glu Met Glu Arg Gln Arg Ala Val Tyr His Leu Ala Thr Arg Leu Val
                885                 890                 895

Gln Thr Ala Arg Asn Ser Gln Leu Asp Pro Asp Ser Leu Arg Ile Tyr
            900                 905                 910

Leu Ser Asn Leu Lys Lys Lys Tyr Lys Glu Asp Phe Pro Arg Thr Glu
        915                 920                 925

Gln Val Pro Glu Lys Thr Glu Glu
    930                 935

<210> SEQ ID NO 21
<211> LENGTH: 2726
<212> TYPE: DNA
<213> ORGANISM: Homo sapiens

<400> SEQUENCE: 21
gcggtcggtc agcggggcgt tctcccacct gtagcgactc agagcctcca agctcatggc    60
ctccttagga gcgaacccaa ggaggacacc gcagggaccg agacctgggg cggcctcctc   120
cggcttcccc agcccggccc cagtgccggg ccccagggag gccgaggagg aggaagtcga   180
ggaggaggag gagctggccg agatccatct gtgtgtgctg tggaattcag gatacttggg   240
cattgcctac tatgatacta gtgactccac tatccacttc atgccagatg ccccagacca   300
cgagagcctc aagcttctcc agagagttct ggatgagatc aatccccagt ctgttgttac   360
gagtgccaaa caggatgaga atatgactcg atttctggga agcttgcct cccaggagca   420 cagagagcct aaaagacctg aaatcatatt tttgccaagt gtggattttg gtctggagat   480
aagcaaacaa cgcctccttt ctggaaacta ctccttcatc ccagacgcca tgactgccac   540
tgagaaaatc ctcttcctct cttccattat tcccttlgac tgcctcctca cagttcgagc   600
acttggaggg ctgctgaagt tcctgggtcg aagaagaatc ggggttgaac tggaagacta   660
taatgtcagc gtccccatcc tgggctttaa gaaatttatg ttgactcatc tggtgaacat   720

```
agatcaagac acttacagtg ttctacagat ttttaagagt gagtctcacc cctcagtgta    780
caaagtggcc agtggactga aggaggggct cagcctcttt ggaatcctca acagatgcca    840
ctgtaagtgg ggagagaagc tgctcaggct atggttcaca cgtccgactc atgacctggg    900
ggagctcagt tctcgtctgg acgtcattca gttttttctg ctgccccaga atctggacat    960
ggctcagatg ctgcatcggc tcctgggtca catcaagaac gtgcctctga ttctgaaacg   1020
catgaagttg tcccacacca aggtcagcga ctggcaggtt ctctacaaga ctgtgtacag   1080
tgccctgggc ctgagggatg cctgccgctc cctgccgcag tccatccagc tctttcggga   1140
cattgcccaa gagttctctg atgacctgca ccatatcgcc agcctcattg ggaaagtagt   1200
ggactttgag ggcagccttg ctgaaaatcg cttcacagtc ctccccaaca tagatcctga   1260
aattgatgag aaaaagcgaa gactgatggg acttcccagt ttccttactg aggttgcccg   1320
caaggagctg gagaatctgg actcccgtat tccttcatgc agtgtcatct acatccctct   1380
gattggcttc cttcttttcta ttccccgcct gcctccatg gtagaggcca gtgactttga   1440
gattaatgga ctggacttca tgtttctctc agaggagaag ctgcactatc gtagtgcccg   1500
aaccaaggag ctggatgcat tgctggggga cctgcactgc gagatccggg accaggagac   1560
gctgctgatg taccagctac agtgccaggt gctggcacga gcagctgtct aacccgagt   1620 attggacctt gcctcccgcc tggacgtcct gctggctctt gccagtgctg cccgggacta   1680
tggctactca aggccgcgtt actccccaca agtccttggg gtacgaatcc agaatggcag   1740
acatcctctg atgaactct gtgcccgaac ctttgtgccc aactccacag aatgtggtgg   1800
ggacaaaggg agggtcaaag tcatcactgg acccaactca tcagggaaga gcatatacct   1860
caaacaggta ggcttgatca cattcatggc cctggtaggc agctttgtgc agcagagga   1920 ggccgaaatt ggggcagtag acgccatctt cacacgaatt catagctgcg aatccatctc   1980
ccttggcctc tccaccttca tgatcgacct caaccagcag gtggcgaaag cagtgaacaa   2040
tgccactgca cagtcgctgg tccttattga tgaatttgga aagggaacca acacggtgga   2100
tgggctcgcg cttctggccg ctgtgctccg acactggctg gcacgtggac ccacatgccc   2160 ccacatctttt gtggccacca actttctgag ccttgttcag ctacaactgc tgccacaagg   2220
gcccctggtg cagtatttga ccatgggagac ctgtgaggat ggcaacgatc ttgtcttctt   2280
ctatcaggtt tgcgaaggtg ttgcgaaggc cagccatgcc tcccacacag ctgcccaggc   2340
tgggcttcct gacaagcttg tggctcgtgg caaggaggtc tcagacttga tccgcagtgg   2400
aaaacccatc aagcctgtca aggatttgct aaagaagaac caaatggaaa attgccagac   2460
attagtggat aagtttatga aactggattt ggaagatcct aacctggact tgaacgtttt   2520
catgagccag gaagtgctgc ctgctgccac cagcatcctc tgagagtcct tccagtgtcc   2580
tccccagcct cctgagactc cggtgggctg ccatgccctc tttgtttcct tatctccctc   2640
agacgcagag tttttagttt ctctagaaat tttgtttcat attaggaata aagtttattt   2700
tgaagaaaaa aaaaaaaaaa aaaaaa                                        2726
```

<210> SEQ ID NO 22  
<211> LENGTH: 835  
<212> TYPE: PRT  
<213> ORGANISM: Homo sapiens

<400> SEQUENCE: 22

```
Met Ala Ser Leu Gly Ala Asn Pro Arg Arg Thr Pro Gln Gly Pro Arg
1               5                   10                  15
```

-continued

```
Pro Gly Ala Ala Ser Ser Gly Phe Pro Ser Pro Ala Pro Val Pro Gly
             20                  25                  30

Pro Arg Glu Ala Glu Glu Glu Val Glu Glu Glu Glu Leu Ala
         35                  40                  45

Glu Ile His Leu Cys Val Leu Trp Asn Ser Gly Tyr Leu Gly Ile Ala
 50                  55                  60

Tyr Tyr Asp Thr Ser Asp Ser Thr Ile His Phe Met Pro Asp Ala Pro
 65                  70                  75                  80

Asp His Glu Ser Leu Lys Leu Leu Gln Arg Val Leu Asp Glu Ile Asn
             85                  90                  95

Pro Gln Ser Val Val Thr Ser Ala Lys Gln Asp Glu Asn Met Thr Arg
                 100                 105                 110

Phe Leu Gly Lys Leu Ala Ser Gln Glu His Arg Glu Pro Lys Arg Pro
             115                 120                 125

Glu Ile Ile Phe Leu Pro Ser Val Asp Phe Gly Leu Glu Ile Ser Lys
         130                 135                 140

Gln Arg Leu Leu Ser Gly Asn Tyr Ser Phe Ile Pro Asp Ala Met Thr
145                 150                 155                 160

Ala Thr Glu Lys Ile Leu Phe Leu Ser Ser Ile Ile Pro Phe Asp Cys
                 165                 170                 175

Leu Leu Thr Val Arg Ala Leu Gly Gly Leu Leu Lys Phe Leu Gly Arg
             180                 185                 190

Arg Arg Ile Gly Val Glu Leu Glu Asp Tyr Asn Val Ser Val Pro Ile
         195                 200                 205

Leu Gly Phe Lys Lys Phe Met Leu Thr His Leu Val Asn Ile Asp Gln
210                 215                 220

Asp Thr Tyr Ser Val Leu Gln Ile Phe Lys Ser Glu Ser His Pro Ser
225                 230                 235                 240

Val Tyr Lys Val Ala Ser Gly Leu Lys Glu Gly Leu Ser Leu Phe Gly
                 245                 250                 255

Ile Leu Asn Arg Cys His Cys Lys Trp Gly Glu Lys Leu Leu Arg Leu
             260                 265                 270

Trp Phe Thr Arg Pro Thr His Asp Leu Gly Glu Leu Ser Ser Arg Leu
         275                 280                 285

Asp Val Ile Gln Phe Phe Leu Leu Pro Gln Asn Leu Asp Met Ala Gln
         290                 295                 300

Met Leu His Arg Leu Leu Gly His Ile Lys Asn Val Pro Leu Ile Leu
305                 310                 315                 320

Lys Arg Met Lys Leu Ser His Thr Lys Val Ser Asp Trp Gln Val Leu
                 325                 330                 335

Tyr Lys Thr Val Tyr Ser Ala Leu Gly Leu Arg Asp Ala Cys Arg Ser
             340                 345                 350

Leu Pro Gln Ser Ile Gln Leu Phe Arg Asp Ile Ala Gln Glu Phe Ser
         355                 360                 365

Asp Asp Leu His His Ile Ala Ser Leu Ile Gly Lys Val Val Asp Phe
         370                 375                 380

Glu Gly Ser Leu Ala Glu Asn Arg Phe Thr Val Leu Pro Asn Ile Asp
385                 390                 395                 400

Pro Glu Ile Asp Glu Lys Lys Arg Arg Leu Met Gly Leu Pro Ser Phe
                 405                 410                 415

Leu Thr Glu Val Ala Arg Lys Glu Leu Glu Asn Leu Asp Ser Arg Ile
             420                 425                 430

Pro Ser Cys Ser Val Ile Tyr Ile Pro Leu Ile Gly Phe Leu Leu Ser
         435                 440                 445
```

```
Ile Pro Arg Leu Pro Ser Met Val Glu Ala Ser Asp Phe Glu Ile Asn
450                 455                 460
Gly Leu Asp Phe Met Phe Leu Ser Glu Glu Lys Leu His Tyr Arg Ser
465                 470                 475                 480
Ala Arg Thr Lys Glu Leu Asp Ala Leu Leu Gly Asp Leu His Cys Glu
                485                 490                 495
Ile Arg Asp Gln Glu Thr Leu Leu Met Tyr Gln Leu Gln Cys Gln Val
            500                 505                 510
Leu Ala Arg Ala Ala Val Leu Thr Arg Val Leu Asp Leu Ala Ser Arg
        515                 520                 525
Leu Asp Val Leu Leu Ala Leu Ala Ser Ala Ala Arg Asp Tyr Gly Tyr
    530                 535                 540
Ser Arg Pro Arg Tyr Ser Pro Gln Val Leu Gly Val Arg Ile Gln Asn
545                 550                 555                 560
Gly Arg His Pro Leu Met Glu Leu Cys Ala Arg Thr Phe Val Pro Asn
                565                 570                 575
Ser Thr Glu Cys Gly Asp Lys Gly Arg Val Lys Val Ile Thr Gly
            580                 585                 590
Pro Asn Ser Ser Gly Lys Ser Ile Tyr Leu Lys Gln Val Gly Leu Ile
            595                 600                 605
Thr Phe Met Ala Leu Val Gly Ser Phe Val Pro Ala Glu Glu Ala Glu
        610                 615                 620
Ile Gly Ala Val Asp Ala Ile Phe Thr Arg Ile His Ser Cys Glu Ser
625                 630                 635                 640
Ile Ser Leu Gly Leu Ser Thr Phe Met Ile Asp Leu Asn Gln Gln Val
                645                 650                 655
Ala Lys Ala Val Asn Asn Ala Thr Ala Gln Ser Leu Val Leu Ile Asp
            660                 665                 670
Glu Phe Gly Lys Gly Thr Asn Thr Val Asp Gly Leu Ala Leu Leu Ala
        675                 680                 685
Ala Val Leu Arg His Trp Leu Ala Arg Gly Pro Thr Cys Pro His Ile
    690                 695                 700
Phe Val Ala Thr Asn Phe Leu Ser Leu Val Gln Leu Gln Leu Leu Pro
705                 710                 715                 720
Gln Gly Pro Leu Val Gln Tyr Leu Thr Met Glu Thr Cys Glu Asp Gly
                725                 730                 735
Asn Asp Leu Val Phe Phe Tyr Gln Val Cys Glu Gly Val Ala Lys Ala
            740                 745                 750
Ser His Ala Ser His Thr Ala Ala Gln Ala Gly Leu Pro Asp Lys Leu
        755                 760                 765
Val Ala Arg Gly Lys Glu Val Ser Asp Leu Ile Arg Ser Gly Lys Pro
    770                 775                 780
Ile Lys Pro Val Lys Asp Leu Leu Lys Asn Gln Met Glu Asn Cys
785                 790                 795                 800
Gln Thr Leu Val Asp Lys Phe Met Lys Leu Asp Leu Glu Asp Pro Asn
                805                 810                 815
Leu Asp Leu Asn Val Phe Met Ser Gln Glu Val Leu Pro Ala Ala Thr
            820                 825                 830
Ser Ile Leu
        835

<210> SEQ ID NO 23
<211> LENGTH: 4264
<212> TYPE: DNA
```

<213> ORGANISM: Homo sapiens

<400> SEQUENCE: 23

| | | |
|---|---|---|
| atttcccgcc agcaggagcc gcgcggtaga tgcggtgctt ttaggagctc cgtccgacag | 60 |
| aacggttggg ccttgccggc tgtcggtatg tcgcgacaga gcaccctgta cagcttcttc | 120 |
| cccaagtctc cggcgctgag tgatgccaac aaggcctcgg ccagggcctc acgcgaaggc | 180 |
| ggccgtgccg ccgctgcccc cggggcctct ccttccccag gcggggatgc ggcctggagc | 240 |
| gaggctgggc ctgggcccag gcccttggcg cgatccgcgt caccgcccaa ggcgaagaac | 300 |
| ctcaacggag ggctgcggag atcggtagcg cctgctgccc ccaccagttg tgacttctca | 360 |
| ccaggagatt tggtttgggc caagatggag ggttacccct ggtggccttg tctggtttac | 420 |
| aaccacccct ttgatggaac attcatccgc gagaaaggga aatcagtccg tgttcatgta | 480 |
| cagttttttg atgacagccc aacaaggggc tgggttagca aaaggctttt aaagccatat | 540 |
| acaggttcaa aatcaaagga agcccagaag ggaggtcatt tttacagtgc aaagcctgaa | 600 |
| atactgagag caatgcaacg tgcagatgaa gccttaaata aagacaagat taagaggctt | 660 |
| gaattggcag tttgtgatga gccctcagag ccagaagagg aagaagagat ggaggtaggc | 720 |
| acaacttacg taacagataa gagtgaagaa gataatgaaa ttgagagtga agaggaagta | 780 |
| cagcctaaga cacaaggatc taggcgaagt agccgccaaa taaaaaaacg aagggtcata | 840 |
| tcagattctg agagtgacat tggtggctct gatgtggaat ttaagccaga cactaaggag | 900 |
| gaaggaagca gtgatgaaat aagcagtgga gtggggata gtgagagtga aggcctgaac | 960 |
| agccctgtca agttgctcg aaagcggaag agaatggtga ctggaaatgg ctctcttaaa | 1020 |
| aggaaaagct ctaggaagga aacgccctca gccaccaaac aagcaactag catttcatca | 1080 |
| gaaaccaaga atactttgag agcttctctct gcccctcaaa attctgaatc ccaagcccac | 1140 |
| gttagtggag gtggtgatga cagtagtcgc cctactgttt ggtatcatga aactttagaa | 1200 |
| tggcttaagg aggaaaagag aagagatgag cacaggagga ggcctgatca ccccgatttt | 1260 |
| gatgcatcta cactctatgt gcctgaggat ttcctcaatt cttgtactcc tgggatgagg | 1320 |
| aagtggtggc agattaagtc tcagaacttt gatcttgtca tctgttacaa ggtggggaaa | 1380 |
| ttttatgagc tgtaccacat ggatgctctt attggagtca gtgaactggg gctggtattc | 1440 |
| atgaaaggca actgggccca ttctggcttt cctgaaattg catttggccg ttattcagat | 1500 |
| tccctggtgc agaagggcta taaagtagca cgagtggaac agactgagac tccagaaatg | 1560 |
| atggaggcac gatgtagaaa gatggcacat atatccaagt atgatagagt ggtgaggagg | 1620 |
| gagatctgta ggatcattac caagggtaca cagacttaca gtgtgctgga aggtgatccc | 1680 |
| tctgagaact acagtaagta tcttcttagc ctcaaagaaa aagaggaaga ttcttctggc | 1740 |
| catactcgtg catatggtgt gtgctttgtt gatacttcac tgggaaagtt tttcataggt | 1800 |
| cagttttcag atgatcgcca ttgttcgaga tttaggactc tagtggcaca ctatccccca | 1860 |
| gtacaagttt tatttgaaaa aggaaatctc tcaaaggaaa ctaaaacaat tctaaagagt | 1920 |
| tcattgtcct gttctcttca ggaaggtctg ataccccggct cccagttttg ggatgcatcc | 1980 |
| aaaactttga gaactctcct tgaggaagaa tattttaggg aaaagctaag tgatggcatt | 2040 |
| ggggtgatgt tacccccaggt gcttaaaggt atgacttcag agtctgattc cattgggttg | 2100 |
| acaccaggag agaaaagtga attggccctc tctgctctag tggttgtgt cttctacctc | 2160 |
| aaaaaatgcc ttattgatca ggagctttta tcaatggcta attttgaaga atatattccc | 2220 |
| ttggattctg acacagtcag cactacaaga tctggtgcta tcttcaccaa agcctatcaa | 2280 |

```
cgaatggtgc tagatgcagt gacattaaac aacttggaga tttttctgaa tggaacaaat    2340
ggttctactg aaggaaccct actagagagg gttgatactt gccatactcc ttttggtaag    2400
cggctcctaa agcaatggct ttgtgcccca ctctgtaacc attatgctat taatgatcgt    2460
ctagatgcca tagaagacct catggttgtg cctgacaaaa tctccgaagt tgtagagctt    2520
ctaaagaagc ttccagatct tgagaggcta ctcagtaaaa ttcataatgt tgggtctccc    2580
ctgaagagtc agaaccaccc agacagcagg gctataatgt atgaagaaac tacatacagc    2640
aagaagaaga ttattgattt tcttttctgct ctggaaggat tcaaagtaat gtgtaaaatt    2700
atagggatca tggaagaagt tgctgatggt tttaagtcta aaatccttaa gcaggtcatc    2760
tctctgcaga caaaaaatcc tgaaggtcgt tttcctgatt tgactgtaga attgaaccga    2820
tgggatacag cctttgacca tgaaaaggct cgaaagactg gacttattac tcccaaagca    2880
ggctttgact ctgattatga ccaagctctt gctgacataa gagaaaatga acagagcctc    2940
ctggaatacc tagagaaaca gcgcaacaga attggctgta ggaccatagt ctattggggg    3000
attggtagga accgttacca gctggaaatt cctgagaatt tcaccactcg caatttgcca    3060
gaagaatacg agttgaaatc taccaagaag ggctgtaaac gatactggac caaaactatt    3120
gaaaagaagt tggctaatct cataaatgct gaagaacgga gggatgtatc attgaaggac    3180
tgcatgcggc gactgttcta taactttgat aaaaattaca aggactggca gtctgctgta    3240
gagtgtatcg cagtgttgga tgttttactg tgcctggcta actatagtcg aggggtgat    3300 ggtcctatgt gtcgcccagt aattctgttg ccggaagata ccccccctt cttagagctt    3360 aaaggatcac gccatccttg cattacgaag acttttttg gagatgattt tattcctaat    3420
gacattctaa taggctgtga ggaagaggag caggaaaatg gcaaagccta ttgtgtgctt    3480
gttactggac caaatatggg gggcaagtct acgcttatga gacaggctgg cttattagct    3540
gtaatggccc agatggggttg ttacgtccct gctgaagtgt gcaggctcac accaattgat    3600
agagtgttta ctagacttgg tgcctcagac agaataatgt caggtgaaag tacattttt    3660 gttgaattaa gtgaaactgc cagcatactc atgcatgcaa cagcacattc tctggtgctt    3720
gtggatgaat taggaagagg tactgcaaca ttgatggga cggcaatagc aaatgcagtt    3780
gttaaagaac ttgctgagac tataaaatgt cgtacattat tttcaactca ctaccattca    3840
ttagtagaag attattctca aaatgttgct gtgcgcctag acatatggc atgcatggta    3900 gaaaatgaat gtgaagaccc cagccaggag actattacgt tcctctataa attcattaag    3960
ggagcttgtc ctaaaagcta tggctttaat gcagcaaggc ttgctaatct cccagaggaa    4020
gttattcaaa agggacatag aaaagcaaga gaatttgaga agatgaatca gtcactacga    4080
ttatttcggg aagtttgcct ggctagtgaa aggtcaactg tagatgctga agctgtccat    4140
aaattgctga ctttgattaa ggaattatag actgactaca ttggaagctt tgagttgact    4200
tctgaccaaa ggtggtaaat tcagacaaca ttatgatcta ataaacttta tttttttaaaa    4260 atga                                                                4264
```

<210> SEQ ID NO 24
<211> LENGTH: 1360
<212> TYPE: PRT
<213> ORGANISM: Homo sapiens

<400> SEQUENCE: 24

Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly

```
                   20                  25                  30
Arg Ala Ala Ala Pro Gly Ala Ser Pro Pro Gly Gly Asp Ala
                35                  40                  45
Ala Trp Ser Glu Ala Gly Pro Gly Pro Arg Pro Leu Ala Arg Ser Ala
 50                  55                  60
Ser Pro Pro Lys Ala Lys Asn Leu Asn Gly Gly Leu Arg Arg Ser Val
 65                  70                  75                  80
Ala Pro Ala Ala Pro Thr Ser Cys Asp Phe Ser Pro Gly Asp Leu Val
                85                  90                  95
Trp Ala Lys Met Glu Gly Tyr Pro Trp Trp Pro Cys Leu Val Tyr Asn
                100                 105                 110
His Pro Phe Asp Gly Thr Phe Ile Arg Glu Lys Gly Lys Ser Val Arg
            115                 120                 125
Val His Val Gln Phe Phe Asp Asp Ser Pro Thr Arg Gly Trp Val Ser
            130                 135                 140
Lys Arg Leu Leu Lys Pro Tyr Thr Gly Ser Lys Ser Lys Glu Ala Gln
145                 150                 155                 160
Lys Gly Gly His Phe Tyr Ser Ala Lys Pro Glu Ile Leu Arg Ala Met
                165                 170                 175
Gln Arg Ala Asp Glu Ala Leu Asn Lys Asp Lys Ile Lys Arg Leu Glu
            180                 185                 190
Leu Ala Val Cys Asp Glu Pro Ser Glu Pro Glu Glu Glu Glu Glu Met
            195                 200                 205
Glu Val Gly Thr Thr Tyr Val Thr Asp Lys Ser Glu Glu Asp Asn Glu
210                 215                 220
Ile Glu Ser Glu Glu Glu Val Gln Pro Lys Thr Gln Gly Ser Arg Arg
225                 230                 235                 240
Ser Ser Arg Gln Ile Lys Lys Arg Arg Val Ile Ser Asp Ser Glu Ser
                245                 250                 255
Asp Ile Gly Gly Ser Asp Val Glu Phe Lys Pro Asp Thr Lys Glu Glu
                260                 265                 270
Gly Ser Ser Asp Glu Ile Ser Ser Gly Val Gly Asp Ser Glu Ser Glu
            275                 280                 285
Gly Leu Asn Ser Pro Val Lys Val Ala Arg Lys Arg Lys Arg Met Val
            290                 295                 300
Thr Gly Asn Gly Ser Leu Lys Arg Lys Ser Ser Arg Lys Glu Thr Pro
305                 310                 315                 320
Ser Ala Thr Lys Gln Ala Thr Ser Ile Ser Ser Glu Thr Lys Asn Thr
                325                 330                 335
Leu Arg Ala Phe Ser Ala Pro Gln Asn Ser Glu Ser Gln Ala His Val
                340                 345                 350
Ser Gly Gly Gly Asp Asp Ser Ser Arg Pro Thr Val Trp Tyr His Glu
            355                 360                 365
Thr Leu Glu Trp Leu Lys Glu Lys Arg Arg Asp Glu His Arg Arg
            370                 375                 380
Arg Pro Asp His Pro Asp Phe Asp Ala Ser Thr Leu Tyr Val Pro Glu
385                 390                 395                 400
Asp Phe Leu Asn Ser Cys Thr Pro Gly Met Arg Lys Trp Trp Gln Ile
                405                 410                 415
Lys Ser Gln Asn Phe Asp Leu Val Ile Cys Tyr Lys Val Gly Lys Phe
                420                 425                 430
Tyr Glu Leu Tyr His Met Asp Ala Leu Ile Gly Val Ser Glu Leu Gly
            435                 440                 445
```

```
Leu Val Phe Met Lys Gly Asn Trp Ala His Ser Gly Phe Pro Glu Ile
450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
                500                 505                 510

Ile Cys Arg Ile Ile Thr Lys Gly Thr Gln Thr Tyr Ser Val Leu Glu
            515                 520                 525

Gly Asp Pro Ser Glu Asn Tyr Ser Lys Tyr Leu Leu Ser Leu Lys Glu
            530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
                580                 585                 590

Gln Val Leu Phe Glu Lys Gly Asn Leu Ser Lys Glu Thr Lys Thr Ile
            595                 600                 605

Leu Lys Ser Ser Leu Ser Cys Ser Leu Gln Glu Gly Leu Ile Pro Gly
            610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
                660                 665                 670

Pro Gly Glu Lys Ser Glu Leu Ala Leu Ser Ala Leu Gly Gly Cys Val
            675                 680                 685

Phe Tyr Leu Lys Lys Cys Leu Ile Asp Gln Glu Leu Leu Ser Met Ala
            690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
                740                 745                 750

Ser Thr Glu Gly Thr Leu Leu Glu Arg Val Asp Thr Cys His Thr Pro
            755                 760                 765

Phe Gly Lys Arg Leu Leu Lys Gln Trp Leu Cys Ala Pro Leu Cys Asn
            770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
                805                 810                 815

Asp Leu Glu Arg Leu Leu Ser Lys Ile His Asn Val Gly Ser Pro Leu
                820                 825                 830

Lys Ser Gln Asn His Pro Asp Ser Arg Ala Ile Met Tyr Glu Glu Thr
            835                 840                 845

Thr Tyr Ser Lys Lys Lys Ile Ile Asp Phe Leu Ser Ala Leu Glu Gly
            850                 855                 860

Phe Lys Val Met Cys Lys Ile Ile Gly Ile Met Glu Glu Val Ala Asp
865                 870                 875                 880
```

```
Gly Phe Lys Ser Lys Ile Leu Lys Gln Val Ile Ser Leu Gln Thr Lys
                885                 890                 895

Asn Pro Glu Gly Arg Phe Pro Asp Leu Thr Val Glu Leu Asn Arg Trp
            900                 905                 910

Asp Thr Ala Phe Asp His Glu Lys Ala Arg Lys Thr Gly Leu Ile Thr
        915                 920                 925

Pro Lys Ala Gly Phe Asp Ser Asp Tyr Asp Gln Ala Leu Ala Asp Ile
    930                 935                 940

Arg Glu Asn Glu Gln Ser Leu Leu Glu Tyr Leu Glu Lys Gln Arg Asn
945                 950                 955                 960

Arg Ile Gly Cys Arg Thr Ile Val Tyr Trp Gly Ile Gly Arg Asn Arg
                965                 970                 975

Tyr Gln Leu Glu Ile Pro Glu Asn Phe Thr Thr Arg Asn Leu Pro Glu
            980                 985                 990

Glu Tyr Glu Leu Lys Ser Thr Lys Lys Gly Cys Lys Arg Tyr Trp Thr
        995                 1000                1005

Lys Thr Ile Glu Lys Lys Leu Ala Asn Leu Ile Asn Ala Glu Glu
    1010                1015                1020

Arg Arg Asp Val Ser Leu Lys Asp Cys Met Arg Arg Leu Phe Tyr
    1025                1030                1035

Asn Phe Asp Lys Asn Tyr Lys Asp Trp Gln Ser Ala Val Glu Cys
    1040                1045                1050

Ile Ala Val Leu Asp Val Leu Leu Cys Leu Ala Asn Tyr Ser Arg
    1055                1060                1065

Gly Gly Asp Gly Pro Met Cys Arg Pro Val Ile Leu Leu Pro Glu
    1070                1075                1080

Asp Thr Pro Pro Phe Leu Glu Leu Lys Gly Ser Arg His Pro Cys
    1085                1090                1095

Ile Thr Lys Thr Phe Phe Gly Asp Asp Phe Ile Pro Asn Asp Ile
    1100                1105                1110

Leu Ile Gly Cys Glu Glu Glu Gln Glu Asn Gly Lys Ala Tyr
    1115                1120                1125

Cys Val Leu Val Thr Gly Pro Asn Met Gly Gly Lys Ser Thr Leu
    1130                1135                1140

Met Arg Gln Ala Gly Leu Leu Ala Val Met Ala Gln Met Gly Cys
    1145                1150                1155

Tyr Val Pro Ala Glu Val Cys Arg Leu Thr Pro Ile Asp Arg Val
    1160                1165                1170

Phe Thr Arg Leu Gly Ala Ser Asp Arg Ile Met Ser Gly Glu Ser
    1175                1180                1185

Thr Phe Phe Val Glu Leu Ser Glu Thr Ala Ser Ile Leu Met His
    1190                1195                1200

Ala Thr Ala His Ser Leu Val Leu Val Asp Glu Leu Gly Arg Gly
    1205                1210                1215

Thr Ala Thr Phe Asp Gly Thr Ala Ile Ala Asn Ala Val Val Lys
    1220                1225                1230

Glu Leu Ala Glu Thr Ile Lys Cys Arg Thr Leu Phe Ser Thr His
    1235                1240                1245

Tyr His Ser Leu Val Glu Asp Tyr Ser Gln Asn Val Ala Val Arg
    1250                1255                1260

Leu Gly His Met Ala Cys Met Val Glu Asn Glu Cys Glu Asp Pro
    1265                1270                1275

Ser Gln Glu Thr Ile Thr Phe Leu Tyr Lys Phe Ile Lys Gly Ala
```

Cys Pro Lys Ser Tyr Gly Phe Asn Ala Ala Arg Leu Ala Asn Leu
　　　　　1295　　　　　　　　　　　1300　　　　　　　　　　　1305

Pro Glu Glu Val Ile Gln Lys Gly His Arg Lys Ala Arg Glu Phe
1310　　　　　　　　　　　1315　　　　　　　　　　　1320

Glu Lys Met Asn Gln Ser Leu Arg Leu Phe Arg Glu Val Cys Leu
　　　　　1325　　　　　　　　　　　1330　　　　　　　　　　　1335

Ala Ser Glu Arg Ser Thr Val Asp Ala Glu Ala Val His Lys Leu
　　　　　1340　　　　　　　　　　　1345　　　　　　　　　　　1350

Leu Thr Leu Ile Lys Glu Leu
　　　　　1355　　　　　　　　　　　1360

<210> SEQ ID NO 25
<211> LENGTH: 1445
<212> TYPE: DNA
<213> ORGANISM: Homo sapiens

<400> SEQUENCE: 25

```
tttttttttt tgatgttctc cagtgcctca gtggcagcag aactggccct gtatcaggcc      60
gctaccgcca ctccatgacc aacctccctg catacccccc ccccagcac ccctcccaca     120
ggaccgcttc tgtgtttggg acccaccagg cctttgcacc atacaacaaa ccctcactct     180
ccggggcccg gtctgcgccc aggctgaaca ccacgaacgc ctgggacgca gctcctcctt     240
ccctggggag ccagcccctc taccgctcca gcctctccca cctgggaccg cagcacctgc     300
ccccaggatc ctccacctcc ggtgcagtca gtgcctccct ccccagcggt ccctcaagca     360
gcccaggcga gcgtccctgc cactgtgccc atgcagatgc caagccagca gagtcagcag     420
gcgctcgctg gagcgacccg aagccagagc agagcagagc aggtcataaa actcacgga     480
agagctgaaa gtgccccag atgaggactg catcatctgc atggagaagc tgtccgcagc     540
gtctggatac agcgatgtga ctgacagcaa ggcaatgggg ccctggctg tgggctgcct     600
caccaagtgc agccacgcct ccacctgct gtgcctcctg gccatgtact gcaacggcaa     660
taagggccct gagcaccca atcccggaaa gccgttcact gccagagggt ttcccgccag     720
tgctaccttc cagacaacgc cagggccgca agcctccagg ggcttccaga acccggagac     780
actggctgac attccggcct ccccacagct gctgaccgat ggccactaca tgacgctgcc     840
cgtgtctccg gaccagctgc cctgtgacga ccccatgggcg ggcagcggag gcgcccccgt     900
gctgcgggtg ggccatgacc acggctgcca ccagcagcca cgtatctgca acgcgcccct     960
ccctggccct ggaccctatc gtacagaacc tgctaaggcc atcaaaccta ttgatcggaa    1020
gtcagtccat cagatttgct ctgggccagt ggtactgagt ctaagcactg cagtgaagga    1080
gttagtagaa aacagtctgg atgctggtgc cactaatatt gatctaaagc ttaaggacta    1140
tggaatggat ctcattgaag tttcaggcaa tggatgtggg gtagaagaag aaaacttcga    1200
aggcttaatg atgtcaccat ttctacctgc cacgtctcgg cgaaggttgg gactcgactg    1260
gtgtttgatc acgatgggaa aatcatccag aagacccct accccaccc cagagggacc    1320
acagtcagcg tgaagcagtt atttctacg ctacctgtgc gccataagga atttcaaagg    1380
aatattaaga agaaacatgc tgcttcccct tcgccttctg ccgtgattgt cagttttaac    1440
cggaa                                                                1445
```

<210> SEQ ID NO 26
<211> LENGTH: 270
<212> TYPE: PRT
<213> ORGANISM: Homo sapiens

<400> SEQUENCE: 26

| | | | | | | | | | | | | | | |
|---|---|---|---|---|---|---|---|---|---|---|---|---|---|---|
| Met | Glu | Lys | Leu | Ser | Ala | Ala | Ser | Gly | Tyr | Ser | Asp | Val | Thr | Asp | Ser |
| 1 | | | | 5 | | | | | 10 | | | | | 15 | |
| Lys | Ala | Met | Gly | Pro | Leu | Ala | Val | Gly | Cys | Leu | Thr | Lys | Cys | Ser | His |
| | | | 20 | | | | | 25 | | | | | 30 | | |
| Ala | Phe | His | Leu | Leu | Cys | Leu | Leu | Ala | Met | Tyr | Cys | Asn | Gly | Asn | Lys |
| | | 35 | | | | | 40 | | | | | 45 | | | |
| Gly | Pro | Glu | His | Pro | Asn | Pro | Gly | Lys | Pro | Phe | Thr | Ala | Arg | Gly | Phe |
| | 50 | | | | | 55 | | | | | 60 | | | | |
| Pro | Ala | Ser | Ala | Thr | Phe | Gln | Thr | Thr | Pro | Gly | Pro | Gln | Ala | Ser | Arg |
| 65 | | | | | 70 | | | | | 75 | | | | | 80 |
| Gly | Phe | Gln | Asn | Pro | Glu | Thr | Leu | Ala | Asp | Ile | Pro | Ala | Ser | Pro | Gln |
| | | | | 85 | | | | | 90 | | | | | 95 | |
| Leu | Leu | Thr | Asp | Gly | His | Tyr | Met | Thr | Leu | Pro | Val | Ser | Pro | Asp | Gln |
| | | | 100 | | | | | 105 | | | | | 110 | | |
| Leu | Pro | Cys | Asp | Asp | Pro | Met | Ala | Gly | Ser | Gly | Ala | Pro | Val | Leu |
| | | 115 | | | | | 120 | | | | | 125 | | | |
| Arg | Val | Gly | His | Asp | His | Gly | Cys | His | Gln | Gln | Pro | Arg | Ile | Cys | Asn |
| | 130 | | | | | 135 | | | | | 140 | | | | |
| Ala | Pro | Leu | Pro | Gly | Pro | Gly | Pro | Tyr | Arg | Thr | Glu | Pro | Ala | Lys | Ala |
| 145 | | | | | 150 | | | | | 155 | | | | | 160 |
| Ile | Lys | Pro | Ile | Asp | Arg | Lys | Ser | Val | His | Gln | Ile | Cys | Ser | Gly | Pro |
| | | | | 165 | | | | | 170 | | | | | 175 | |
| Val | Val | Leu | Ser | Leu | Ser | Thr | Ala | Val | Lys | Glu | Leu | Val | Glu | Asn | Ser |
| | | | 180 | | | | | 185 | | | | | 190 | | |
| Leu | Asp | Ala | Gly | Ala | Thr | Asn | Ile | Asp | Leu | Lys | Leu | Lys | Asp | Tyr | Gly |
| | | 195 | | | | | 200 | | | | | 205 | | | |
| Met | Asp | Leu | Ile | Glu | Val | Ser | Gly | Asn | Gly | Cys | Gly | Val | Glu | Glu | Glu |
| | 210 | | | | | 215 | | | | | 220 | | | | |
| Asn | Phe | Glu | Gly | Leu | Met | Met | Ser | Pro | Phe | Leu | Pro | Ala | Thr | Ser | Arg |
| 225 | | | | | 230 | | | | | 235 | | | | | 240 |
| Arg | Arg | Leu | Gly | Leu | Asp | Trp | Cys | Leu | Ile | Thr | Met | Gly | Lys | Ser | Ser |
| | | | | 245 | | | | | 250 | | | | | 255 | |
| Arg | Arg | Pro | Pro | Thr | Pro | Thr | Pro | Glu | Gly | Pro | Gln | Ser | Ala |
| | | | 260 | | | | | 265 | | | | | 270 | | |

<210> SEQ ID NO 27
<211> LENGTH: 795
<212> TYPE: DNA
<213> ORGANISM: Homo sapiens

<400> SEQUENCE: 27

```
atgtgtcctt ggcggcctag actaggccgt cgctgtatgg tgagcccag ggaggcggat      60
ctgggccccc agaaggacac ccgcctggat ttgccccgta gccggcccg ggcccctcgg     120
gagcagaaca gccttggtga ggtggacagg aggggacctc gcgagcagac gcgcgcgcca    180
gcgacagcag ccccgccccg gcctctcggg agccggggg cagaggctgc ggagccccag    240
gagggtctat cagccacagt ctctgcatgt tccaagagc aacaggaaat gaacacattg    300
caggggccag tgtcattcaa agatgtggct gtggatttca cccaggagga gtggcggcaa    360
ctggaccctg atgagaagat agcatacggg gatgtgatgt tggagaacta cagccatcta    420
gtttctgtgg ggtatgatta tcaccaagcc aaacatcatc atggagtgga ggtgaaggaa    480
gtggagcagg gagaggagcc gtggataatg gaaggtgaat tccatgtcac acatagtcca    540
```

```
gaacctgcta aggccatcaa acctattgat cggaagtcag tccatcagat ttgctctggg      600
ccagtggtac tgagtctaag cactgcagtg aaggagttag tagaaaacag tctggatgct      660
ggtgccacta atattgatct aaagcttaag gactatggag tggatctcat gaagtttca       720 gacaatggat gtggggtaga agaagaaaac tttgaaggct taatctcttt cagctctgaa      780
acatcacaca tgtaa                                                      795

<210> SEQ ID NO 28
<211> LENGTH: 260
<212> TYPE: PRT
<213> ORGANISM: Homo sapiens

<400> SEQUENCE: 28

Met Cys Pro Trp Arg Pro Arg Leu Gly Arg Arg Cys Met Val Ser Pro
1               5                   10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255

Phe Ser Ser Glu
            260

<210> SEQ ID NO 29
<211> LENGTH: 3218
<212> TYPE: DNA
<213> ORGANISM: Saccharomyces cerevisiae

<400> SEQUENCE: 29
aaataggaat gtgataccct ctattgcatg caaagatagt gtaggaggcg ctgctattgc      60
caaagacttt tgagaccgct tgctgtttca ttatagttga ggagttctcg aagacgagaa      120
```

```
attagcagtt ttcggtgttt agtaatcgcg ctagcatgct aggacaattt aactgcaaaa    180 tttttgatacg atagtgatag taaatggaag gtaaaaataa catagaccta tcaataagca   240
atgtctctca gaataaaagc acttgatgca tcagtggtta acaaaattgc tgcaggtgag    300
atcataatat cccccgtaaa tgctctcaaa gaaatgatgg agaattccat cgatgcgaat    360
gctacaatga ttgatattct agtcaaggaa ggaggaatta aggtacttca ataacagat    420 aacggatctg gaattaataa agcagacctg ccaatcttat gtgagcgatt cacgacgtcc    480
aaattacaaa aattcgaaga tttgagtcag attcaaacgt atggattccg aggagaagct    540
ttagccagta tctcacatgt ggcaagagtc acagtaacga caaaagttaa agaagacaga    600
tgtgcatgga gagtttcata tgcagaaggt aagatgttgg aaagccccaa acctgttgct    660
ggaaaagacg gtaccacgat cctagttgaa gacctttttt tcaatattcc ttctagatta    720
agggccttga ggtcccataa tgatgaatac tctaaaatat tagatgttgt cgggcgatac    780
gccattcatt ccaaggacat tggcttttct tgtaaaaagt tcggagactc taattattct    840
ttatcagtta aaccttcata tacagtccag gataggatta ggactgtgtt caataaatct    900
gtggcttcga atttaattac ttttcatatc agcaaagtag aagatttaaa cctggaaagc    960
gttgatggaa aggtgtgtaa tttgaatttc atatccaaaa agtccatttc attaattttt   1020
ttcattaata atagactagt gacatgtgat cttctaagaa gagctttgaa cagcgtttac   1080
tccaattatc tgccaaaggg cttcagacct tttatttatt tgggaattgt tatagatccg   1140
gcggctgttg atgttaacgt tcacccgaca aagagagagg ttcgtttcct gagccaagat   1200
gagatcatag agaaaatcgc caatcaattg cacgccgaat tatctgccat tgatacttca   1260
cgtactttca aggcttcttc aatttcaaca aacaagccag agtcattgat accatttaat   1320
gacaccatag aaagtgatag gaataggaag agtctccgac aagcccaagt ggtagagaat   1380
tcatatacga cagccaatag tcaactaagg aaagcgaaaa gacaagagaa taaactagtc   1440
agaatagatg cttcacaagc taaaattacg tcatttttat cctcaagtca acagttcaac   1500
tttgaaggat cgtctacaaa gcgacaactg agtgaaccca aggtaacaaa tgtaagccac   1560
tcccaagagg cagaaaagct gacactaaat gaaagcgaac aaccgcgtga tgccaataca   1620
atcaatgata atgacttgaa ggatcaacct aagaagaaac aaaagttggg ggattataaa   1680
gttccaagca ttgccgatga cgaaaagaat gcactcccga tttcaaaaga cgggtatatt   1740
agagtaccta aggagcgagt taatgttaat cttacgagta tcaagaaatt gcgtgaaaaa   1800
gtagatgatt cgatacatcg agaactaaca gacatttttg caaatttgaa ttacgttggg   1860
gttgtagatg aggaaagaag attagccgct attcagcatg acttaaagct tttttttaata   1920 gattacggat ctgtgtgcta tgagctattc tatcagattg gtttgacaga cttcgcaaac   1980
tttggtaaga taaacctaca gagtacaaat gtgtcagatg atatagtttt gtataatctc   2040
ctatcagaat ttgacgagtt aaatgacgat gcttccaaag aaaaaataat tagtaaaata   2100
tgggacatga gcagtatgct aaatgagtac tattccatag aattggtgaa tgatggtcta   2160
gataatgact taaagtctgt gaagctaaaa tctctaccac tactttttaaa aggctacatt   2220 ccatctctgg tcaagttacc attttttata tatcgcctgg gtaaagaagt tgattgggag   2280
gatgaacaag agtgtctaga tggtatttta agagagattg cattactcta tacctgat    2340 atggttccga aagtcgatac actcgatgca tcgttgtcag aagacgaaaa agcccagttt   2400
ataaatagaa aggaacacat atcctcatta ctagaacacg ttctcttccc ttgtatcaaa   2460
cgaaggttcc tggcccctag acacattctc aaggatgtcg tggaaatagc caaccttcca   2520
```

```
gatctataca aagttttga gaggtgttaa ctttaaaacg ttttggctgt aataccaaag     2580 ttttgttta tttcctgagt gtgattgtgt tcatttgaa agtgtatgcc ctttccttta     2640
acgattcatc cgcgagattt caaaggatat gaaatatggt tgcagttagg aaagtatgtc   2700
agaaatgtat attcggattg aaactcttct aatagttctg aagtcacttg gttccgtatt   2760
gttttcgtcc tcttcctcaa gcaacgattc ttgtctaagc ttattcaacg gtaccaagaa   2820
cccgagtcct tttatgagag aaaacatttc atcatttttc aactcaatta tcttaatatc   2880
attttgtagt atttttgaaaa caggatggta aaacgaatca cctgaatcta gaagctgtac   2940
cttgtcccat aaaagtttta atttactgag cctttcggtc aagtaaacta gtttatctag   3000
ttttgaaccg aatattgtgg gcagatttgc agtaagttca gttagatcta ctaaaagttg   3060
tttgacagca gccgattcca caaaaatttg gtaaaaggag atgaaagaga cctcgcgcgt   3120
aatggtttgc atcaccatcg gatgtctgtt gaaaaactca cttttgcat ggaagttatt     3180 aacaataaga ctaatgatta ccttagaata atgtataa                             3218
```

<210> SEQ ID NO 30
<211> LENGTH: 769
<212> TYPE: PRT
<213> ORGANISM: Saccharomyces cerevisiae

<400> SEQUENCE: 30

```
Met Ser Leu Arg Ile Lys Ala Leu Asp Ala Ser Val Val Asn Lys Ile
1               5                   10                  15

Ala Ala Gly Glu Ile Ile Ser Pro Val Asn Ala Leu Lys Glu Met
            20                  25                  30

Met Glu Asn Ser Ile Asp Ala Asn Ala Thr Met Ile Asp Ile Leu Val
        35                  40                  45

Lys Glu Gly Gly Ile Lys Val Leu Gln Ile Thr Asp Asn Gly Ser Gly
    50                  55                  60

Ile Asn Lys Ala Asp Leu Pro Ile Leu Cys Glu Arg Phe Thr Thr Ser
65                  70                  75                  80

Lys Leu Gln Lys Phe Glu Asp Leu Ser Gln Ile Gln Thr Tyr Gly Phe
                85                  90                  95

Arg Gly Glu Ala Leu Ala Ser Ile Ser His Val Ala Arg Val Thr Val
            100                 105                 110

Thr Thr Lys Val Lys Glu Asp Arg Cys Ala Trp Arg Val Ser Tyr Ala
        115                 120                 125

Glu Gly Lys Met Leu Glu Ser Pro Lys Pro Val Ala Gly Lys Asp Gly
    130                 135                 140

Thr Thr Ile Leu Val Glu Asp Leu Phe Phe Asn Ile Pro Ser Arg Leu
145                 150                 155                 160

Arg Ala Leu Arg Ser His Asn Asp Glu Tyr Ser Lys Ile Leu Asp Val
                165                 170                 175

Val Gly Arg Tyr Ala Ile His Ser Lys Asp Ile Gly Phe Ser Cys Lys
            180                 185                 190

Lys Phe Gly Asp Ser Asn Tyr Ser Leu Ser Val Lys Pro Ser Tyr Thr
        195                 200                 205

Val Gln Asp Arg Ile Arg Thr Val Phe Asn Lys Ser Val Ala Ser Asn
    210                 215                 220

Leu Ile Thr Phe His Ile Ser Lys Val Glu Asp Leu Asn Leu Glu Ser
225                 230                 235                 240

Val Asp Gly Lys Val Cys Asn Leu Asn Phe Ile Ser Lys Lys Ser Ile
                245                 250                 255
```

```
Ser Leu Ile Phe Phe Ile Asn Asn Arg Leu Val Thr Cys Asp Leu Leu
            260                 265                 270

Arg Arg Ala Leu Asn Ser Val Tyr Ser Asn Tyr Leu Pro Lys Gly Phe
275                 280                 285

Arg Pro Phe Ile Tyr Leu Gly Ile Val Ile Asp Pro Ala Ala Val Asp
            290                 295                 300

Val Asn Val His Pro Thr Lys Arg Glu Val Arg Phe Leu Ser Gln Asp
305                 310                 315                 320

Glu Ile Ile Glu Lys Ile Ala Asn Gln Leu His Ala Glu Leu Ser Ala
                325                 330                 335

Ile Asp Thr Ser Arg Thr Phe Lys Ala Ser Ser Ile Ser Thr Asn Lys
            340                 345                 350

Pro Glu Ser Leu Ile Pro Phe Asn Asp Thr Ile Glu Ser Asp Arg Asn
            355                 360                 365

Arg Lys Ser Leu Arg Gln Ala Gln Val Val Glu Asn Ser Tyr Thr Thr
370                 375                 380

Ala Asn Ser Gln Leu Arg Lys Ala Lys Arg Gln Glu Asn Lys Leu Val
385                 390                 395                 400

Arg Ile Asp Ala Ser Gln Ala Lys Ile Thr Ser Phe Leu Ser Ser Ser
                405                 410                 415

Gln Gln Phe Asn Phe Glu Gly Ser Ser Thr Lys Arg Gln Leu Ser Glu
            420                 425                 430

Pro Lys Val Thr Asn Val Ser His Ser Gln Glu Ala Glu Lys Leu Thr
            435                 440                 445

Leu Asn Glu Ser Glu Gln Pro Arg Asp Ala Asn Thr Ile Asn Asp Asn
450                 455                 460

Asp Leu Lys Asp Gln Pro Lys Lys Gln Lys Leu Gly Asp Tyr Lys
465                 470                 475                 480

Val Pro Ser Ile Ala Asp Asp Glu Lys Asn Ala Leu Pro Ile Ser Lys
                485                 490                 495

Asp Gly Tyr Ile Arg Val Pro Lys Glu Arg Val Asn Val Asn Leu Thr
            500                 505                 510

Ser Ile Lys Lys Leu Arg Glu Lys Val Asp Asp Ser Ile His Arg Glu
            515                 520                 525

Leu Thr Asp Ile Phe Ala Asn Leu Asn Tyr Val Gly Val Val Asp Glu
530                 535                 540

Glu Arg Arg Leu Ala Ala Ile Gln His Asp Leu Lys Leu Phe Leu Ile
545                 550                 555                 560

Asp Tyr Gly Ser Val Cys Tyr Glu Leu Phe Tyr Gln Ile Gly Leu Thr
                565                 570                 575

Asp Phe Ala Asn Phe Gly Lys Ile Asn Leu Gln Ser Thr Asn Val Ser
            580                 585                 590

Asp Asp Ile Val Leu Tyr Asn Leu Leu Ser Glu Phe Asp Glu Leu Asn
            595                 600                 605

Asp Asp Ala Ser Lys Glu Lys Ile Ile Ser Lys Ile Trp Asp Met Ser
610                 615                 620

Ser Met Leu Asn Glu Tyr Tyr Ser Ile Glu Leu Val Asn Asp Gly Leu
625                 630                 635                 640

Asp Asn Asp Leu Lys Ser Val Lys Leu Lys Ser Leu Pro Leu Leu Leu
                645                 650                 655

Lys Gly Tyr Ile Pro Ser Leu Val Lys Leu Pro Phe Phe Ile Tyr Arg
            660                 665                 670

Leu Gly Lys Glu Val Asp Trp Glu Asp Glu Gln Glu Cys Leu Asp Gly
```

```
                 675                 680                 685
Ile Leu Arg Glu Ile Ala Leu Leu Tyr Ile Pro Asp Met Val Pro Lys
            690                 695                 700

Val Asp Thr Leu Asp Ala Ser Leu Ser Glu Asp Glu Lys Ala Gln Phe
705                 710                 715                 720

Ile Asn Arg Lys Glu His Ile Ser Ser Leu Leu Glu His Val Leu Phe
                725                 730                 735

Pro Cys Ile Lys Arg Arg Phe Leu Ala Pro Arg His Ile Leu Lys Asp
                740                 745                 750

Val Val Glu Ile Ala Asn Leu Pro Asp Leu Tyr Lys Val Phe Glu Arg
            755                 760                 765

Cys

<210> SEQ ID NO 31
<211> LENGTH: 3056
<212> TYPE: DNA
<213> ORGANISM: Mus musculus

<400> SEQUENCE: 31
gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
catccatgga gcaaaccgaa ggcgtgagta cagaatgtgc taaggccatc aagcctattg     240
atgggaagtc agtccatcaa atttgttctg gcaggtgat actcagttta agcaccgctg      300
tgaaggagtt gatagaaaat agtgtagatg ctggtgctac tactattgat ctaaggctta     360
aagactatgg ggtggacctc attgaagttt cagacaatgg atgtggggta gaagaagaaa     420
actttgaagg tctagctctg aaacatcaca catctaagat tcaagagttt gccgacctca     480
cgcaggttga aactttcggc tttcgggggg aagctctgag ctctctgtgt gcactaagtg     540
atgtcactat atctacctgc cacgggtctg caagcgttgg gactcgactg gtgtttgacc     600
ataatgggaa atcacccag aaaactccct accccgacc taaggaacc acagtcagtg       660 tgcagcactt attttataca ctacccgtgc gttacaaaga gtttcagagg aacattaaaa     720
aggagtattc caaaatggtg caggtcttac aggcgtactg tatcatctca gcaggcgtcc     780
gtgtaagctg cactaatcag ctcggacagg ggaagcggca cgctgtggtg tgcacaagcg     840
gcacgtctgg catgaaggaa aatatcgggt ctgtgtttgg ccagaagcag ttgcaaagcc     900
tcattccttt tgttcagctg cccctagtg acgctgtgtg tgaagagtac ggcctgagca     960
cttcaggacg ccacaaaacc ttttctacgt ttcgggcttc atttcacagt gcacgcacgg    1020
cgccgggagg agtgcaacag acaggcagtt tttcttcatc aatcagaggc cctgtgaccc    1080
agcaaaggtc tctaagcttg tcaatgaggt tttatcacat gtataaccgg catcagtacc    1140
catttgtcgt ccttaacgtt tccgttgact cagaatgtgt ggatattaat gtaactccag    1200
ataaaaggca aattctacta caagaagaga agctattgct ggccgttta aagacctcct     1260 tgataggaat gtttgacagt gatgcaaaca agcttaatgt caaccagcag ccactgctag    1320
atgttgaagg taacttagta aagctgcata ctgcagaact agaaaagcct gtgccaggaa    1380
agcaagataa ctctccttca ctgaagagca cagcagacga gaaagggta gcatccatct     1440 ccaggctgag agaggccttt tctcttcatc ctactaaaga gatcaagtct aggggtccag    1500
agactgctga actgacacgg agtttttcaa gtgagaaaag gggcgtgtta tcctcttatc    1560
cttcagacgt catctcttac agaggcctcc gtggctcgca ggacaaattg gtgagtccca    1620
```

```
cggacagccc tggtgactgt atggacagag agaaaataga aaaagactca gggctcagca    1680
gcacctcagc tggctctgag aagagttca  gcacccaga  agtggccagt agctttagca    1740
gtgactataa cgtgagctcc ctagaagaca gaccttctca ggaaaccata aactgtggtg    1800
acctggactg ccgtcctcca ggtacaggac agtccttgaa gccagaagac catggatatc    1860
aatgcaaagc tctacctcta gctcgtctgt cacccacaaa tgccaagcgc ttcaagacag    1920
aggaaagacc ctcaaatgtc aacatttctc aaagattgcc tggtcctcag agcacctcag    1980
cagctgaggt cgatgtagcc ataaaaatga ataagagaat cgtgctcctc gagttctctc    2040
tgagttctct agctaagcga atgaagcagt tacagcacct aaaggcgcag aacaaacatg    2100
aactgagtta cagaaaattt agggccaaga tttgccctgg agaaaaccaa gcagcagaag    2160
atgaactcag aaaagagatt agtaaatcga tgtttgcaga gatggagatc ttgggtcagt    2220
ttaacctggg attttatagta accaaactga agaggacct  cttcctggtg accagcatg    2280 ctgcggatga gaagtacaac tttgagatgc tgcagcagca cacggtgctc caggcgcaga    2340
ggctcatcac accccagact ctgaacttaa ctgctgtcaa tgaagctgta ctgatagaaa    2400
atctggaaat attcagaaag aatggcttg  actttgtcat tgatgaggat gctccagtca    2460
ctgaaagggc taaattgatt tccttaccaa ctagtaaaaa ctggaccttt ggaccccaag    2520
atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagatggac cacccctgga    2700
actgccccca cggcaggcca accatgaggc acgttgccaa tctggatgtc atctctcaga    2760
actgacacac cccttgtagc atagagttta ttacagattg ttcggtttgc aaagagaagg    2820
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc cacattcatg    3000
agactcaatt caaggacaaa aaaaaaaaga tattttgaa  gccttttaaa aaaaaa        3056
```

<210> SEQ ID NO 32
<211> LENGTH: 859
<212> TYPE: PRT
<213> ORGANISM: Mus musculus

<400> SEQUENCE: 32

```
Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125
```

```
Ala Ser Val Gly Thr Arg Leu Val Phe Asp His Asn Gly Lys Ile Thr
    130                 135                 140
Gln Lys Thr Pro Tyr Pro Arg Pro Lys Gly Thr Thr Val Ser Val Gln
145                 150                 155                 160
His Leu Phe Tyr Thr Leu Pro Val Arg Tyr Lys Glu Phe Gln Arg Asn
                165                 170                 175
Ile Lys Lys Glu Tyr Ser Lys Met Val Gln Val Leu Gln Ala Tyr Cys
            180                 185                 190
Ile Ile Ser Ala Gly Val Arg Val Ser Cys Thr Asn Gln Leu Gly Gln
        195                 200                 205
Gly Lys Arg His Ala Val Val Cys Thr Ser Gly Thr Ser Gly Met Lys
    210                 215                 220
Glu Asn Ile Gly Ser Val Phe Gly Gln Lys Gln Leu Gln Ser Leu Ile
225                 230                 235                 240
Pro Phe Val Gln Leu Pro Pro Ser Asp Ala Val Cys Glu Glu Tyr Gly
                245                 250                 255
Leu Ser Thr Ser Gly Arg His Lys Thr Phe Ser Thr Phe Arg Ala Ser
            260                 265                 270
Phe His Ser Ala Arg Thr Ala Pro Gly Val Gln Gln Thr Gly Ser
    275                 280                 285
Phe Ser Ser Ile Arg Gly Pro Val Thr Gln Gln Arg Ser Leu Ser
290                 295                 300
Leu Ser Met Arg Phe Tyr His Met Tyr Asn Arg His Gln Tyr Pro Phe
305                 310                 315                 320
Val Val Leu Asn Val Ser Val Asp Ser Glu Cys Val Asp Ile Asn Val
                325                 330                 335
Thr Pro Asp Lys Arg Gln Ile Leu Leu Gln Glu Lys Leu Leu Leu
            340                 345                 350
Ala Val Leu Lys Thr Ser Leu Ile Gly Met Phe Asp Ser Asp Ala Asn
        355                 360                 365
Lys Leu Asn Val Asn Gln Gln Pro Leu Leu Asp Val Glu Gly Asn Leu
370                 375                 380
Val Lys Leu His Thr Ala Glu Leu Glu Lys Pro Val Pro Gly Lys Gln
385                 390                 395                 400
Asp Asn Ser Pro Ser Leu Lys Ser Thr Ala Asp Glu Lys Arg Val Ala
                405                 410                 415
Ser Ile Ser Arg Leu Arg Glu Ala Phe Ser Leu His Pro Thr Lys Glu
            420                 425                 430
Ile Lys Ser Arg Gly Pro Glu Thr Ala Glu Leu Thr Arg Ser Phe Pro
        435                 440                 445
Ser Glu Lys Arg Gly Val Leu Ser Ser Tyr Pro Ser Asp Val Ile Ser
    450                 455                 460
Tyr Arg Gly Leu Arg Gly Ser Gln Asp Lys Leu Val Ser Pro Thr Asp
465                 470                 475                 480
Ser Pro Gly Asp Cys Met Asp Arg Glu Lys Ile Glu Lys Asp Ser Gly
                485                 490                 495
Leu Ser Ser Thr Ser Ala Gly Ser Glu Glu Phe Ser Thr Pro Glu
            500                 505                 510
Val Ala Ser Ser Phe Ser Ser Asp Tyr Asn Val Ser Ser Leu Glu Asp
        515                 520                 525
Arg Pro Ser Gln Glu Thr Ile Asn Cys Gly Asp Leu Asp Cys Arg Pro
    530                 535                 540
Pro Gly Thr Gly Gln Ser Leu Lys Pro Glu Asp His Gly Tyr Gln Cys
```

|     |     |     |     | 545 |     |     |     | 550 |     |     |     | 555 |     |     |     | 560 |
|-----|-----|-----|-----|-----|-----|-----|-----|-----|-----|-----|-----|-----|-----|-----|-----|-----|

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
                580                 585                 590

Gly Pro Gln Ser Thr Ser Ala Ala Glu Val Asp Val Ala Ile Lys Met
                595                 600                 605

Asn Lys Arg Ile Val Leu Leu Glu Phe Ser Leu Ser Ser Leu Ala Lys
                610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
                660                 665                 670

Met Glu Ile Leu Gly Gln Phe Asn Leu Gly Phe Ile Val Thr Lys Leu
                675                 680                 685

Lys Glu Asp Leu Phe Leu Val Asp Gln His Ala Ala Asp Glu Lys Tyr
690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
                740                 745                 750

Asp Glu Asp Ala Pro Val Thr Glu Arg Ala Lys Leu Ile Ser Leu Pro
                755                 760                 765

Thr Ser Lys Asn Trp Thr Phe Gly Pro Gln Asp Ile Asp Glu Leu Ile
770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
                820                 825                 830

Glu Met Asp His Pro Trp Asn Cys Pro His Gly Arg Pro Thr Met Arg
                835                 840                 845

His Val Ala Asn Leu Asp Val Ile Ser Gln Asn
850                 855

<210> SEQ ID NO 33
<211> LENGTH: 399
<212> TYPE: DNA
<213> ORGANISM: Mus musculus

<400> SEQUENCE: 33

```
atggagcaaa ccgaaggcgt gagtacagaa tgtgctaagg ccatcaagcc tattgatggg      60
aagtcagtcc atcaaatttg ttctgggcag gtgatactca gtttaagcac cgctgtgaag     120
gagttgatag aaaatagtgt agatgctggt gctactacta ttgatctaag gcttaaagac     180 tatgggtgg  acctcattga agtttcagac aatggatgtg gggtagaaga agaaaacttt     240
gaaggtctag ctctgaaaca tcacacatct aagattcaag agtttgccga cctcacgcag     300
gttgaaactt tcggctttcg gggggaagct ctgagctctc tgtgtgcact aagtgatgtc     360
actatatcta cctgccacgg gtctgcaagc gttgggact                            399
```

<210> SEQ ID NO 34
<211> LENGTH: 133
<212> TYPE: PRT
<213> ORGANISM: Mus musculus

<400> SEQUENCE: 34

```
Met Glu Gln Thr Glu Gly Val Ser Thr Glu Cys Ala Lys Ala Ile Lys
1               5                   10                  15
Pro Ile Asp Gly Lys Ser Val His Gln Ile Cys Ser Gly Gln Val Ile
            20                  25                  30
Leu Ser Leu Ser Thr Ala Val Lys Glu Leu Ile Glu Asn Ser Val Asp
        35                  40                  45
Ala Gly Ala Thr Thr Ile Asp Leu Arg Leu Lys Asp Tyr Gly Val Asp
    50                  55                  60
Leu Ile Glu Val Ser Asp Asn Gly Cys Gly Val Glu Glu Asn Phe
65                  70                  75                  80
Glu Gly Leu Ala Leu Lys His His Thr Ser Lys Ile Gln Glu Phe Ala
                85                  90                  95
Asp Leu Thr Gln Val Glu Thr Phe Gly Phe Arg Gly Glu Ala Leu Ser
            100                 105                 110
Ser Leu Cys Ala Leu Ser Asp Val Thr Ile Ser Thr Cys His Gly Ser
        115                 120                 125
Ala Ser Val Gly Thr
    130
```

<210> SEQ ID NO 35
<211> LENGTH: 3099
<212> TYPE: DNA
<213> ORGANISM: Arabidopsis thaliana

<400> SEQUENCE: 35

```
gtcttcttct tcatccttgt ctcaccttcg attttggcgg caaaacataa accctaaggg      60
ttttctcact ctctctctct cttctcacac acacagtccc agagtacggt ggtgttgatt     120
cgattgagga gattcatctg tttatagggt ttagcaaatg caaggagatt cttctccgtc     180
tccgacgact actagctctc ctttgataag acctataaac agaaacgtaa ttcacagaat     240
ctgttccggt caagtcatct tagacctctc ttcggccgtc aaggagcttg tcgagaatag     300
tctcgacgcc ggcgccacca gtatagagat taacctccga gactacggcg aagactattt     360
tcaggtcatt gacaatggtt gtggcatttc cccaaccaat ttcaaggttc ttgcacttaa     420
gcatcatact tctaaattag aggatttcac agatcttttg aatttgacta cttatggttt     480
tagaggagaa gccttgagct ctctctgtgc attgggaaat ctcactgtgg aaacaagaac     540
aaagaatgag ccagttgcta cgctcttgac gtttgatcat tctggtttgc ttactgctga     600
aaagaagact gctcgccaaa ttggtaccac tgtcactgtt aggaagttgt tctctaattt     660
acctgtacga agcaaagagt ttaagcggaa atacgcaaa gaatatggga agcttgtatc     720
tttattgaac gcatatgcgc ttattgcgaa aggagtgcgg tttgtctgct ctaacacgac     780
tgggaaaaac ccaaagtctg ttgtgctgaa cacacaaggg aggggttcac ttaaagataa     840
tatcataaca gttttcggca ttagtacctt tacaagtcta cagcctgtaa gtatatgtgt     900
atcagaagat tgtagagttg aagggttttct tccaagcct ggacagggta ctggacgcaa     960
tttagcagat cgacagtatt tctttataaa tggtcggcct gtagatatgc caaaagtcag    1020
caagttggtg aatgagttat ataaagatac aagttctcgg aaatatccag ttaccattct    1080
```

```
ggatttttatt gtgcctggtg gagcatgtga tttgaatgtc acgcccgata aagaaaggt    1140 gttctttttct gacgagactt ctgttatcgg ttctttgagg gaaggtctga acgagatata   1200
ttcctccagt aatgcgtctt atattgttaa taggttcgag gagaattcgg agcaaccaga   1260
taaggctgga gtttcgtcgt ttcagaagaa atcaaatctt ttgtcagaag ggatagttct   1320
ggatgtcagt tctaaaacaa gactagggga agctattgag aaagaaaatc catccttaag   1380
ggaggttgaa attgataata gttcgccaat ggagaagttt aagtttgaga tcaaggcatg   1440
tgggacgaag aaaggggaag gttctttatc agtccatgat gtaactcacc ttgacaagac   1500
acctagcaaa ggtttgcctc agttaaatgt gactgagaaa gttactgatg caagtaaaga   1560
cttgagcagc cgctctagct ttgcccagtc aactttgaat acttttgtta ccatgggaaa   1620
aagaaaacat gaaacataa gcaccatcct ctctgaaaca cctgtcctca gaaaccaaac    1680
ttctagttat cgtgtggaga aaagcaaatt tgaagttcgt gccttagctt caaggtgtct   1740
cgtggaaggc gatcaacttg atgatatggt catctcaaag gaagatatga caccaagcga   1800
aagagattct gaactaggca atcggatttc tcctggaaca caagctgata atgttgaaag   1860
acatgagaga gaacatgaaa agcctataag gtttgaagaa ccaacatcag ataacacact   1920
caccaagggg gatgtggaaa gggtttcaga ggacaatcca cggtgcagtc agccactgcg   1980
atctgtggcc acagtgctgg attccccagc tcagtcaacc ggtcctaaaa tgttttccac   2040
attagaattt agtttccaaa acctcaggac aaggaggtta gagaggctgt cgagattgca   2100
gtccacaggt tatgtatcta aatgtatgaa tacgccacag cctaaaaagt gctttgccgc   2160
tgcaacatta gagttatctc aaccggatga tgaagagcga aaagcaaggg ctttagctgc   2220
agctacttct gagctggaaa ggcttttcg aaaagaggat ttcaggagaa tgcaggtact   2280
cgggcaattc aatcttgggt tcatcattgc aaaattggag cgagatctgt tcattgtgga   2340
tcagcatgca gctgatgaga aattcaactt cgaacattta gcaaggtcaa ctgtcctgaa   2400
ccagcaaccc ttactccagc ctttgaactt ggaactctct ccagaagaag aagtaactgt   2460
gttaatgcac atggatatta tcagggaaaa tggctttctt ctagaggaga atccaagtgc   2520
tcctcccgga aaacacttta gactacgagc cattccttat agcaagaata tcacctttgg   2580
agtcgaagat cttaaagacc tgatctcaac tctaggagat aaccatgggg aatgttcggt   2640
tgctagtagc tacaaaacca gcaaaacaga ttcgatttgt ccatcacgag tccgtgcaat   2700
gctagcatcc cgagcatgca gatcatctgt gatgatcgga gatccactca gaaaaaacga   2760
aatgcagaag atagtagaac acttggcaga tctcgaatct ccttggaatt gcccacacgg   2820
acgaccaaca atgcgtcatc ttgtggactt gacaactta ctcacattac ctgatgacga   2880
caatgtcaat gatgatgatg atgatgatgc aaccatctca ttggcatgaa cactcaaaag   2940
tcttaacgta tttagatgtg agaatcctta agattaacat tgaggaacac tcggttataa   3000
ctacaatcgt aaatgtaaat tgtcttagtc tatatgatct ttttggtcac aacaggtaat   3060
ttcattttcc tttgattact tctcgtgaaa aaacaaatt                          3099
```

<210> SEQ ID NO 36
<211> LENGTH: 923
<212> TYPE: PRT
<213> ORGANISM: Arabidopsis thaliana

<400> SEQUENCE: 36

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln

-continued

```
                20                  25                  30
Val Ile Leu Asp Leu Ser Ser Ala Val Lys Glu Leu Val Glu Asn Ser
            35                  40                  45
Leu Asp Ala Gly Ala Thr Ser Ile Glu Ile Asn Leu Arg Asp Tyr Gly
        50                  55                  60
Glu Asp Tyr Phe Gln Val Ile Asp Asn Gly Cys Gly Ile Ser Pro Thr
65                  70                  75                  80
Asn Phe Lys Val Leu Ala Leu Lys His His Thr Ser Lys Leu Glu Asp
                85                  90                  95
Phe Thr Asp Leu Leu Asn Leu Thr Thr Tyr Gly Phe Arg Gly Glu Ala
            100                 105                 110
Leu Ser Ser Leu Cys Ala Leu Gly Asn Leu Thr Val Glu Thr Arg Thr
        115                 120                 125
Lys Asn Glu Pro Val Ala Thr Leu Leu Thr Phe Asp His Ser Gly Leu
130                 135                 140
Leu Thr Ala Glu Lys Lys Thr Ala Arg Gln Ile Gly Thr Thr Val Thr
145                 150                 155                 160
Val Arg Lys Leu Phe Ser Asn Leu Pro Val Arg Ser Lys Glu Phe Lys
                165                 170                 175
Arg Asn Ile Arg Lys Glu Tyr Gly Lys Leu Val Ser Leu Leu Asn Ala
            180                 185                 190
Tyr Ala Leu Ile Ala Lys Gly Val Arg Phe Val Cys Ser Asn Thr Thr
        195                 200                 205
Gly Lys Asn Pro Lys Ser Val Val Leu Asn Thr Gln Gly Arg Gly Ser
210                 215                 220
Leu Lys Asp Asn Ile Ile Thr Val Phe Gly Ile Ser Thr Phe Thr Ser
225                 230                 235                 240
Leu Gln Pro Val Ser Ile Cys Val Ser Glu Asp Cys Arg Val Glu Gly
                245                 250                 255
Phe Leu Ser Lys Pro Gly Gln Thr Gly Arg Asn Leu Ala Asp Arg
            260                 265                 270
Gln Tyr Phe Phe Ile Asn Gly Arg Pro Val Asp Met Pro Lys Val Ser
        275                 280                 285
Lys Leu Val Asn Glu Leu Tyr Lys Asp Thr Ser Ser Arg Lys Tyr Pro
290                 295                 300
Val Thr Ile Leu Asp Phe Ile Val Pro Gly Gly Ala Cys Asp Leu Asn
305                 310                 315                 320
Val Thr Pro Asp Lys Arg Lys Val Phe Phe Ser Asp Glu Thr Ser Val
                325                 330                 335
Ile Gly Ser Leu Arg Glu Gly Leu Asn Glu Ile Tyr Ser Ser Ser Asn
            340                 345                 350
Ala Ser Tyr Ile Val Asn Arg Phe Glu Glu Asn Ser Glu Gln Pro Asp
        355                 360                 365
Lys Ala Gly Val Ser Ser Phe Gln Lys Ser Asn Leu Leu Ser Glu
370                 375                 380
Gly Ile Val Leu Asp Val Ser Ser Lys Thr Arg Leu Gly Glu Ala Ile
385                 390                 395                 400
Glu Lys Glu Asn Pro Ser Leu Arg Glu Val Glu Ile Asp Asn Ser Ser
                405                 410                 415
Pro Met Glu Lys Phe Lys Phe Glu Ile Lys Ala Cys Gly Thr Lys Lys
            420                 425                 430
Gly Glu Gly Ser Leu Ser Val His Asp Val Thr His Leu Asp Lys Thr
        435                 440                 445
```

```
Pro Ser Lys Gly Leu Pro Gln Leu Asn Val Thr Glu Lys Val Thr Asp
450                 455                 460

Ala Ser Lys Asp Leu Ser Ser Arg Ser Ser Phe Ala Gln Ser Thr Leu
465                 470                 475                 480

Asn Thr Phe Val Thr Met Gly Lys Arg Lys His Glu Asn Ile Ser Thr
                    485                 490                 495

Ile Leu Ser Glu Thr Pro Val Leu Arg Asn Gln Thr Ser Ser Tyr Arg
                500                 505                 510

Val Glu Lys Ser Lys Phe Glu Val Arg Ala Leu Ala Ser Arg Cys Leu
                515                 520                 525

Val Glu Gly Asp Gln Leu Asp Asp Met Val Ile Ser Lys Glu Asp Met
530                 535                 540

Thr Pro Ser Glu Arg Asp Ser Glu Leu Gly Asn Arg Ile Ser Pro Gly
545                 550                 555                 560

Thr Gln Ala Asp Asn Val Glu Arg His Glu Arg Glu His Glu Lys Pro
                565                 570                 575

Ile Arg Phe Glu Glu Pro Thr Ser Asp Asn Thr Leu Thr Lys Gly Asp
                580                 585                 590

Val Glu Arg Val Ser Glu Asp Asn Pro Arg Cys Ser Gln Pro Leu Arg
                595                 600                 605

Ser Val Ala Thr Val Leu Asp Ser Pro Ala Gln Ser Thr Gly Pro Lys
                610                 615                 620

Met Phe Ser Thr Leu Glu Phe Ser Phe Gln Asn Leu Arg Thr Arg Arg
625                 630                 635                 640

Leu Glu Arg Leu Ser Arg Leu Gln Ser Thr Gly Tyr Val Ser Lys Cys
                645                 650                 655

Met Asn Thr Pro Gln Pro Lys Lys Cys Phe Ala Ala Ala Thr Leu Glu
                660                 665                 670

Leu Ser Gln Pro Asp Asp Glu Arg Lys Ala Arg Ala Leu Ala Ala
                675                 680                 685

Ala Thr Ser Glu Leu Glu Arg Leu Phe Arg Lys Glu Asp Phe Arg Arg
690                 695                 700

Met Gln Val Leu Gly Gln Phe Asn Leu Gly Phe Ile Ile Ala Lys Leu
705                 710                 715                 720

Glu Arg Asp Leu Phe Ile Val Asp Gln His Ala Ala Asp Glu Lys Phe
                725                 730                 735

Asn Phe Glu His Leu Ala Arg Ser Thr Val Leu Asn Gln Gln Pro Leu
                740                 745                 750

Leu Gln Pro Leu Asn Leu Glu Leu Ser Pro Glu Glu Val Thr Val
                755                 760                 765

Leu Met His Met Asp Ile Ile Arg Glu Asn Gly Phe Leu Leu Glu Glu
770                 775                 780

Asn Pro Ser Ala Pro Pro Gly Lys His Phe Arg Leu Arg Ala Ile Pro
785                 790                 795                 800

Tyr Ser Lys Asn Ile Thr Phe Gly Val Glu Asp Leu Lys Asp Leu Ile
                805                 810                 815

Ser Thr Leu Gly Asp Asn His Gly Glu Cys Ser Val Ala Ser Ser Tyr
                820                 825                 830

Lys Thr Ser Lys Thr Asp Ser Ile Cys Pro Ser Arg Val Arg Ala Met
                835                 840                 845

Leu Ala Ser Arg Ala Cys Arg Ser Ser Val Met Ile Gly Asp Pro Leu
850                 855                 860

Arg Lys Asn Glu Met Gln Lys Ile Val Glu His Leu Ala Asp Leu Glu
865                 870                 875                 880
```

```
Ser Pro Trp Asn Cys Pro His Gly Arg Pro Thr Met Arg His Leu Val
                885                 890                 895

Asp Leu Thr Thr Leu Leu Thr Leu Pro Asp Asp Asn Val Asn Asp
                900                 905                 910

Asp Asp Asp Asp Ala Thr Ile Ser Leu Ala
            915                 920

<210> SEQ ID NO 37
<211> LENGTH: 399
<212> TYPE: DNA
<213> ORGANISM: Arabidopsis thaliana

<400> SEQUENCE: 37
atgcaaggag attcttctcc gtctccgacg actactagct ctcctttgat aagacctata      60
aacagaaacg taattcacag aatctgttcc ggtcaagtca tcttagacct ctcttcggcc     120
gtcaaggagc ttgtcgagaa tagtctcgac gccggcgcca ccagtataga gattaacctc     180
cgagactacg gcgaagacta ttttcaggtc attgacaatg gttgtggcat tcccccaacc     240
aatttcaagg ttcttgcact taagcatcat acttctaaat tagaggattt cacagatctt     300
ttgaatttga ctacttatgg ttttagagga gaagccttga gctctctctg tgcattggga     360
aatctcactg tggaaacaag aacaaagaat gagccagtt                            399

<210> SEQ ID NO 38
<211> LENGTH: 133
<212> TYPE: PRT
<213> ORGANISM: Arabidopsis thaliana

<400> SEQUENCE: 38

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser
        35                  40                  45

Leu Asp Ala Gly Ala Thr Ser Ile Glu Ile Asn Leu Arg Asp Tyr Gly
    50                  55                  60

Glu Asp Tyr Phe Gln Val Ile Asp Asn Gly Cys Gly Ile Ser Pro Thr
65                  70                  75                  80

Asn Phe Lys Val Leu Ala Leu Lys His His Thr Ser Lys Leu Glu Asp
                85                  90                  95

Phe Thr Asp Leu Leu Asn Leu Thr Thr Tyr Gly Phe Arg Gly Glu Ala
            100                 105                 110

Leu Ser Ser Leu Cys Ala Leu Gly Asn Leu Thr Val Glu Thr Arg Thr
        115                 120                 125

Lys Asn Glu Pro Val
    130

<210> SEQ ID NO 39
<211> LENGTH: 2772
<212> TYPE: DNA
<213> ORGANISM: Arabidopsis thaliana

<400> SEQUENCE: 39
atgcaaggag attcttctcc gtctccgacg actactagct ctcctttgat aagacctata      60
aacagaaacg taattcacag aatctgttcc ggtcaagtca tcttagacct ctcttcggcc     120
gtcaaggagc ttgtcgagaa tagtctcgac gccggcgcca ccagtataga gattaacctc     180
```

```
cgagactacg gcgaagacta ttttcaggtc attgacaatg gttgtggcat ttccccaacc     240
aatttcaagg ttcttgcact taagcatcat acttctaaat tagaggattt cacagatctt     300
ttgaatttga ctacttatgg ttttagagga gaagccttga gctctctctg tgcattggga     360
aatctcactg tggaaacaag aacaaagaat gagccagttg ctacgctctt gacgtttgat     420
cattctggtt tgcttactgc tgaaaagaag actgctcgcc aaattggtac cactgtcact     480
gttaggaagt tgttctctaa tttacctgta cgaagcaaag agtttaagcg aatatacgc      540 aaagaatatg ggaagcttgt atctttattg aacgcatatg cgcttattgc gaaaggagtg     600
cggtttgtct gctctaacac gactgggaaa acccaaagt ctgttgtgct gaacacacaa      660
gggaggggtt cacttaaaga taatatcata acagttttcg gcattagtac ctttacaagt     720
ctacagcctg taagtatatg tgtatcagaa gattgtagag ttgaagggtt tctttccaag     780
cctggacagg gtactggacg caatttagca gatcgacagt atttctttat aaatggtcgg     840
cctgtagata tgccaaaagt cagcaagttg gtgaatgagt tatataaaga tacaagttct     900
cggaaatatc cagttaccat tctggatttt attgtgcctg gtggagcatg tgatttgaat     960
gtcacgcccg ataaaagaaa ggtgttcttt tctgacgaga cttctgttat cggttctttg     1020
agggaaggtc tgaacgagat atattcctcc agtaatgcgt cttatattgt taataggttc     1080
gaggagaatt cggagcaacc agataaggct ggagtttcgt cgtttcagaa gaaatcaaat     1140
cttttgtcag aagggatagt tctggatgtc agttctaaaa caagactagg ggaagctatt     1200
gagaaagaaa atccatcctt aagggaggtt gaaattgata atagttcgcc aatggagaag     1260
tttaagtttg agatcaaggc atgtgggacg aagaaggggg aaggttcttt atcagtccat     1320
gatgtaactc accttgacaa gacacctagc aaaggtttgc ctcagttaaa tgtgactgag     1380
aaagttactg atgcaagtaa agacttgagc agccgctcta gctttgccca gtcaactttg     1440
aatacttttg ttaccatggg aaaaagaaaa catgaaaaca taagcaccat cctctctgaa     1500
acacctgtcc tcagaaacca aacttctagt tatcgtgtgg agaaaagcaa atttgaagtt     1560
cgtgccttag cttcaaggtg tctcgtggaa ggcgatcaac ttgatgatat ggtcatctca     1620
aaggaagata tgacaccaag cgaaagagat tctgaactag gcaatcggat ttctcctgga     1680
acacaagctg ataatgttga agacatgag agagaacatg aaaagcctat aaggtttgaa     1740
gaaccaacat cagataacac actcaccaag ggggatgtgg aaagggtttc agaggacaat     1800
ccacggtgca gtcagccact gcgatctgtg gccacagtgc tggattcccc agctcagtca     1860
accggtccta aaatgttttc cacattagaa tttagtttcc aaaacctcag gacaaggagg     1920
ttagagaggc tgtcgagatt gcagtccaca ggttatgtat ctaaatgtat gaatacgcca     1980
cagcctaaaa agtgctttgc cgctgcaaca ttagagttat ctcaaccgga tgatgaagag     2040
cgaaaagcaa gggctttagc tgcagctact tctgagctgg aaaggctttt tcgaaaagag     2100
gatttcagga gaatgcaggt actcgggcaa ttcaatcttg ggttcatcat tgcaaaattg     2160
gagcgagatc tgttcattgt ggatcagcat gcagctgatg agaaattcaa cttcgaacat     2220
ttagcaaggt caactgtcct gaaccagcaa cccttactcc agcctttgaa cttggaactc     2280
tctccagaag aagaagtaac tgtgttaatg cacatggata ttatcaggga aaatggcttt     2340
cttctagagg agaatccaag tgctcctccc ggaaaacact ttagactacg agccattcct     2400
tatagcaaga atatcacctt tggagtcgaa gatcttaaag acctgatctc aactctagga     2460
gataaccatg gggaatgttc ggttgctagt agctacaaaa ccagcaaaac agattcgatt     2520
tgtccatcac gagtccgtgc aatgctagca tcccgagcat gcagatcatc tgtgatgatc     2580
```

```
ggagatccac tcagaaaaaa cgaaatgcag aagatagtag aacacttggc agatctcgaa    2640
tctccttgga attgcccaca cggacgacca acaatgcgtc atcttgtgga cttgacaact    2700
ttactcacat tacctgatga cgacaatgtc aatgatgatg atgatgatga tgcaaccatc    2760
tcattggcat ga                                                        2772

<210> SEQ ID NO 40
<211> LENGTH: 923
<212> TYPE: PRT
<213> ORGANISM: Arabidopsis thaliana

<400> SEQUENCE: 40

Met Gln Gly Asp Ser Ser Pro Ser Pro Thr Thr Ser Ser Pro Leu
1               5                   10                  15

Ile Arg Pro Ile Asn Arg Asn Val Ile His Arg Ile Cys Ser Gly Gln
                20                  25                  30

Val Ile Leu Asp Leu Ser Ser Ala Val Lys Glu Leu Val Glu Asn Ser
            35                  40                  45

Leu Asp Ala Gly Ala Thr Ser Ile Glu Ile Asn Leu Arg Asp Tyr Gly
        50                  55                  60

Glu Asp Tyr Phe Gln Val Ile Asp Asn Gly Cys Gly Ile Ser Pro Thr
65                  70                  75                  80

Asn Phe Lys Val Leu Ala Leu Lys His His Thr Ser Lys Leu Glu Asp
                85                  90                  95

Phe Thr Asp Leu Leu Asn Leu Thr Thr Tyr Gly Phe Arg Gly Glu Ala
            100                 105                 110

Leu Ser Ser Leu Cys Ala Leu Gly Asn Leu Thr Val Glu Thr Arg Thr
        115                 120                 125

Lys Asn Glu Pro Val Ala Thr Leu Leu Thr Phe Asp His Ser Gly Leu
130                 135                 140

Leu Thr Ala Glu Lys Lys Thr Ala Arg Gln Ile Gly Thr Thr Val Thr
145                 150                 155                 160

Val Arg Lys Leu Phe Ser Asn Leu Pro Val Arg Ser Lys Glu Phe Lys
                165                 170                 175

Arg Asn Ile Arg Lys Glu Tyr Gly Lys Leu Val Ser Leu Leu Asn Ala
            180                 185                 190

Tyr Ala Leu Ile Ala Lys Gly Val Arg Phe Val Cys Ser Asn Thr Thr
        195                 200                 205

Gly Lys Asn Pro Lys Ser Val Val Leu Asn Thr Gln Gly Arg Gly Ser
210                 215                 220

Leu Lys Asp Asn Ile Ile Thr Val Phe Gly Ile Ser Thr Phe Thr Ser
225                 230                 235                 240

Leu Gln Pro Val Ser Ile Cys Val Ser Glu Asp Cys Arg Val Glu Gly
                245                 250                 255

Phe Leu Ser Lys Pro Gly Gln Gly Thr Gly Arg Asn Leu Ala Asp Arg
            260                 265                 270

Gln Tyr Phe Phe Ile Asn Gly Arg Pro Val Asp Met Pro Lys Val Ser
        275                 280                 285

Lys Leu Val Asn Glu Leu Tyr Lys Asp Thr Ser Ser Arg Lys Tyr Pro
    290                 295                 300

Val Thr Ile Leu Asp Phe Ile Val Pro Gly Gly Ala Cys Asp Leu Asn
305                 310                 315                 320

Val Thr Pro Asp Lys Arg Lys Val Phe Phe Ser Asp Glu Thr Ser Val
                325                 330                 335
```

```
Ile Gly Ser Leu Arg Glu Gly Leu Asn Glu Ile Tyr Ser Ser Ser Asn
            340                 345                 350
Ala Ser Tyr Ile Val Asn Arg Phe Glu Glu Asn Ser Glu Gln Pro Asp
            355                 360                 365
Lys Ala Gly Val Ser Ser Phe Gln Lys Lys Ser Asn Leu Leu Ser Glu
            370                 375                 380
Gly Ile Val Leu Asp Val Ser Ser Lys Thr Arg Leu Gly Glu Ala Ile
385                 390                 395                 400
Glu Lys Glu Asn Pro Ser Leu Arg Glu Val Glu Ile Asp Asn Ser Ser
            405                 410                 415
Pro Met Glu Lys Phe Lys Phe Glu Ile Lys Ala Cys Gly Thr Lys Lys
            420                 425                 430
Gly Glu Gly Ser Leu Ser Val His Asp Val Thr His Leu Asp Lys Thr
            435                 440                 445
Pro Ser Lys Gly Leu Pro Gln Leu Asn Val Thr Glu Lys Val Thr Asp
            450                 455                 460
Ala Ser Lys Asp Leu Ser Ser Arg Ser Ser Phe Ala Gln Ser Thr Leu
465                 470                 475                 480
Asn Thr Phe Val Thr Met Gly Lys Arg Lys His Glu Asn Ile Ser Thr
            485                 490                 495
Ile Leu Ser Glu Thr Pro Val Leu Arg Asn Gln Thr Ser Ser Tyr Arg
            500                 505                 510
Val Glu Lys Ser Lys Phe Glu Val Arg Ala Leu Ala Ser Arg Cys Leu
            515                 520                 525
Val Glu Gly Asp Gln Leu Asp Asp Met Val Ile Ser Lys Glu Asp Met
            530                 535                 540
Thr Pro Ser Glu Arg Asp Ser Glu Leu Gly Asn Arg Ile Ser Pro Gly
545                 550                 555                 560
Thr Gln Ala Asp Asn Val Glu Arg His Glu Arg Glu His Glu Lys Pro
            565                 570                 575
Ile Arg Phe Glu Glu Pro Thr Ser Asp Asn Thr Leu Thr Lys Gly Asp
            580                 585                 590
Val Glu Arg Val Ser Glu Asp Asn Pro Arg Cys Ser Gln Pro Leu Arg
            595                 600                 605
Ser Val Ala Thr Val Leu Asp Ser Pro Ala Gln Ser Thr Gly Pro Lys
            610                 615                 620
Met Phe Ser Thr Leu Glu Phe Ser Phe Gln Asn Leu Arg Thr Arg Arg
625                 630                 635                 640
Leu Glu Arg Leu Ser Arg Leu Gln Ser Thr Gly Tyr Val Ser Lys Cys
            645                 650                 655
Met Asn Thr Pro Gln Pro Lys Lys Cys Phe Ala Ala Ala Thr Leu Glu
            660                 665                 670
Leu Ser Gln Pro Asp Asp Glu Glu Arg Lys Ala Arg Ala Leu Ala Ala
            675                 680                 685
Ala Thr Ser Glu Leu Glu Arg Leu Phe Arg Lys Glu Asp Phe Arg Arg
            690                 695                 700
Met Gln Val Leu Gly Gln Phe Asn Leu Gly Phe Ile Ile Ala Lys Leu
705                 710                 715                 720
Glu Arg Asp Leu Phe Ile Val Asp Gln His Ala Ala Asp Glu Lys Phe
            725                 730                 735
Asn Phe Glu His Leu Ala Arg Ser Thr Val Leu Asn Gln Gln Pro Leu
            740                 745                 750
Leu Gln Pro Leu Asn Leu Glu Leu Ser Pro Glu Glu Val Thr Val
            755                 760                 765
```

```
Leu Met His Met Asp Ile Ile Arg Glu Asn Gly Phe Leu Leu Glu Glu
    770                 775                 780
Asn Pro Ser Ala Pro Pro Gly Lys His Phe Arg Leu Arg Ala Ile Pro
785                 790                 795                 800
Tyr Ser Lys Asn Ile Thr Phe Gly Val Glu Asp Leu Lys Asp Leu Ile
                805                 810                 815
Ser Thr Leu Gly Asp Asn His Gly Glu Cys Ser Val Ala Ser Ser Tyr
            820                 825                 830
Lys Thr Ser Lys Thr Asp Ser Ile Cys Pro Ser Arg Val Arg Ala Met
        835                 840                 845
Leu Ala Ser Arg Ala Cys Arg Ser Ser Val Met Ile Gly Asp Pro Leu
    850                 855                 860
Arg Lys Asn Glu Met Gln Lys Ile Val Glu His Leu Ala Asp Leu Glu
865                 870                 875                 880
Ser Pro Trp Asn Cys Pro His Gly Arg Pro Thr Met Arg His Leu Val
                885                 890                 895
Asp Leu Thr Thr Leu Leu Thr Leu Pro Asp Asp Asn Val Asn Asp
            900                 905                 910
Asp Asp Asp Asp Asp Ala Thr Ile Ser Leu Ala
        915                 920

<210> SEQ ID NO 41
<211> LENGTH: 3466
<212> TYPE: DNA
<213> ORGANISM: Arabidopsis thaliana

<400> SEQUENCE: 41
ttcgaattct ctcagctcaa acatcgtttt ctctctcact ctctctcaca attccaaaaa      60
atgcagcgcc agagatcgat tttgtctttc ttccaaaaac ccacggcggc gactacgaag     120
ggtttggttt ccggcgatgc tgctagcggc ggggcggca gcggaggacc acgatttaat     180
gtgaaggaag gggatgctaa aggcgacgct tctgtacgtt ttgctgtttc gaaatctgtc     240
gatgaggtta gaggaacgga tactccaccg gagaaggttc cgcgtcgtgt cctgccgtct     300
ggatttaagc cggctgaatc cgccggtgat gcttcgtccc tgttctccaa tattatgcat     360
aagtttgtaa aagtcgatga tcgagattgt tctggagaga ggagccgaga agatgttgtt     420
ccgctgaatg attcatctct atgtatgaag gctaatgatg ttattcctca atttcgttcc     480
aataatggta aaactcaaga agaaaccat gcttttagtt tcagtgggag agctgaactt     540
agatcagtag aagatatagg agtagatggc gatgttcctg gtccagaaac accagggatg     600
cgtccacgtg cttctcgctt gaagcgagtt ctggaggatg aaatgacttt taaggaggat     660
aaggttcctg tattggactc taacaaaagg ctgaaaatgc tccaggatcc ggtttgtgga     720
gagaagaaag aagtaaacga aggaaccaaa tttgaatggc ttgagtcttc tcgaatcagg     780
gatgccaata gaagacgtcc tgatgatccc ctttacgata gaaagacctt acacatacca     840
cctgatgttt tcaagaaaat gtctgcatca caaaagcaat attggagtgt taagagtgaa     900
tatatggaca ttgtgctttt ctttaaagtg gggaaatttt atgagctgta tgagctagat     960
gcggaattag gtcacaagga gcttgactgg aagatgacca tgagtggtgt gggaaaatgc    1020
agacaggttg gtatctctga aagtgggata gatgaggcag tgcaaaagct attagctcgt    1080
ggatataaag ttggacgaat cgagcagcta gaaacatctg accaagcaaa agccagaggt    1140
gctaatacta taattccaag gaagctagtt caggtattaa ctccatcaac agcaagcgag    1200
ggaaacatcg ggcctgatgc cgtccatctt cttgctataa aagagatcaa aatggagcta    1260
```

```
caaaagtgtt caactgtgta tggatttgct tttgttgact gtgctgcctt gaggttttgg   1320
gttgggtcca tcagcgatga tgcatcatgt gctgctcttg gagcgttatt gatgcaggtt   1380
tctccaaagg aagtgttata tgacagtaaa gggctatcaa gagaagcaca aaaggctcta   1440
aggaaatata cgttgacagg gtctacggcg gtacagttgg ctccagtacc acaagtaatg   1500
ggggatacag atgctgctgg agttagaaat ataatagaat ctaacggata ctttaaaggt   1560
tcttctgaat catggaactg tgctgttgat ggtctaaatg aatgtgatgt tgcccttagt   1620
gctcttggag agctaattaa tcatctgtct aggctaaagc tagaagatgt acttaagcat   1680
ggggatattt ttccatacca agtttacagg ggttgtctca gaattgatgg ccagacgatg   1740
gtaaatcttg agatatttaa caatagctgt gatggtgtcc ttcagggacc cttgaacaaa   1800
tatcttgaaa actgtgttag tccaactggt aagcgactct taaggaattg gatctgccat   1860
ccactcaaag atgtagaaag catcaataaa cggcttgatg tagttgaaga attcacggca   1920
aactcagaaa gtatgcaaat cactggccag tatctccaca aacttccaga cttagaaaga   1980
ctgctcggac gcatcaagtc tagcgttcga tcatcagcct ctgtgttgcc tgctcttctg   2040
gggaaaaaag tgctgaaaca acgagttaaa gcatttgggc aaattgtgaa agggttcaga   2100
agtggaattg atctgttgtt ggctctacag aaggaatcaa atatgatgag tttgctttat   2160
aaactctgta aacttcctat attagtagga aaaagcgggc tagagttatt tctttctcaa   2220
ttcgaagcag ccatagatag cgactttcca aattatcaga accaagatgt gacagatgaa   2280
aacgctgaaa ctctcacaat acttatcgaa ctttttatcg aaagagcaac tcaatggtct   2340
gaggtcattc acaccataag ctgcctagat gtcctgagat cttttgcaat cgcagcaagt   2400
ctctctgctg gaagcatggc caggcctgtt attttcccg aatcagaagc tacagatcag   2460
aatcagaaaa caaagggcc aatacttaaa atccaaggac tatggcatcc atttgcagtt   2520
gcagccgatg tcaattgcc tgttccgaat gatatactcc ttggcgaggc tagaagaagc   2580
agtggcagca ttcatcctcg gtcattgtta ctgacgggac caaacatggg cggaaaatca   2640
actcttcttc gtgcaacatg tctggccgtt atctttgccc aacttggctg ctacgtgccg   2700
tgtgagtctt gcgaaatctc cctcgtggat actatcttca caaggcttgg cgcatctgat   2760
agaatcatga caggagagag tacctttttg gtagaatgca ctgagacagc gtcagttctt   2820
cagaatgcaa ctcaggattc actagtaatc cttgacgaac tgggcagagg aactagtact   2880
ttcgatggat acgccattgc atactcggtt tttcgtcacc tggtagagaa agttcaatgt   2940
cggatgctct ttgcaacaca ttaccaccct ctcaccaagg aattcgcgtc tcacccacgt   3000
gtcacctcga aacacatggc ttgcgcattc aaatcaagat ctgattatca accacgtggt   3060
tgtgatcaag acctagtgtt cttgtaccgt ttaaccgagg agcttgtcc tgagagctac   3120 ggacttcaag tggcactcat ggctggaata ccaaaccaag tggttgaaac agcatcaggt   3180
gctgctcaag ccatgaagag atcaattggg gaaaacttca agtcaagtga gctaagatct   3240
gagttctcaa gtctgcatga agactggctc aagtcattgg tgggtatttc tcgagtcgcc   3300
cacaacaatg cccccattgg cgaagatgac tacgacactt tgttttgctt atggcatgag   3360
atcaaatcct cttactgtgt tcccaaataa atggctatga cataacacta tctgaagctc   3420
gttaagtctt ttgcttctct gatgtttatt cctcttaaaa aatgcg                  3466
```

<210> SEQ ID NO 42
<211> LENGTH: 1109
<212> TYPE: PRT
<213> ORGANISM: Arabidopsis thaliana -continued

<400> SEQUENCE: 42

```
Met Gln Arg Gln Arg Ser Ile Leu Ser Phe Phe Lys Pro Thr Ala
1               5                   10                  15

Ala Thr Thr Lys Gly Leu Val Ser Gly Asp Ala Ala Ser Gly Gly
            20                  25                  30

Gly Ser Gly Gly Pro Arg Phe Asn Val Lys Glu Gly Asp Ala Lys Gly
        35                  40                  45

Asp Ala Ser Val Arg Phe Ala Val Ser Lys Ser Val Asp Glu Val Arg
    50                  55                  60

Gly Thr Asp Thr Pro Pro Glu Lys Val Pro Arg Arg Val Leu Pro Ser
65                  70                  75                  80

Gly Phe Lys Pro Ala Glu Ser Ala Gly Asp Ala Ser Ser Leu Phe Ser
                85                  90                  95

Asn Ile Met His Lys Phe Val Lys Val Asp Asp Arg Asp Cys Ser Gly
            100                 105                 110

Glu Arg Ser Arg Glu Asp Val Pro Leu Asn Asp Ser Ser Leu Cys
        115                 120                 125

Met Lys Ala Asn Asp Val Ile Pro Gln Phe Arg Ser Asn Asn Gly Lys
130                 135                 140

Thr Gln Glu Arg Asn His Ala Phe Ser Phe Ser Gly Arg Ala Glu Leu
145                 150                 155                 160

Arg Ser Val Glu Asp Ile Gly Val Asp Gly Asp Val Pro Gly Pro Glu
                165                 170                 175

Thr Pro Gly Met Arg Pro Arg Ala Ser Arg Leu Lys Arg Val Leu Glu
            180                 185                 190

Asp Glu Met Thr Phe Lys Glu Asp Lys Val Pro Val Leu Asp Ser Asn
        195                 200                 205

Lys Arg Leu Lys Met Leu Gln Asp Pro Val Cys Gly Glu Lys Lys Glu
210                 215                 220

Val Asn Glu Gly Thr Lys Phe Glu Trp Leu Glu Ser Ser Arg Ile Arg
225                 230                 235                 240

Asp Ala Asn Arg Arg Pro Asp Asp Pro Leu Tyr Asp Arg Lys Thr
                245                 250                 255

Leu His Ile Pro Pro Asp Val Phe Lys Lys Met Ser Ala Ser Gln Lys
            260                 265                 270

Gln Tyr Trp Ser Val Lys Ser Glu Tyr Met Asp Ile Val Leu Phe Phe
        275                 280                 285

Lys Val Gly Lys Phe Tyr Glu Leu Tyr Glu Leu Asp Ala Glu Leu Gly
290                 295                 300

His Lys Glu Leu Asp Trp Lys Met Thr Met Ser Gly Val Gly Lys Cys
305                 310                 315                 320

Arg Gln Val Gly Ile Ser Glu Ser Gly Ile Asp Glu Ala Val Gln Lys
                325                 330                 335

Leu Leu Ala Arg Gly Tyr Lys Val Gly Arg Ile Glu Gln Leu Glu Thr
            340                 345                 350

Ser Asp Gln Ala Lys Ala Arg Gly Ala Asn Thr Ile Ile Pro Arg Lys
        355                 360                 365

Leu Val Gln Val Leu Thr Pro Ser Thr Ala Ser Glu Gly Asn Ile Gly
370                 375                 380

Pro Asp Ala Val His Leu Leu Ala Ile Lys Glu Ile Lys Met Glu Leu
385                 390                 395                 400

Gln Lys Cys Ser Thr Val Tyr Gly Phe Ala Phe Val Asp Cys Ala Ala
                405                 410                 415
```

```
Leu Arg Phe Trp Val Gly Ser Ile Ser Asp Asp Ala Ser Cys Ala Ala
            420                 425                 430

Leu Gly Ala Leu Leu Met Gln Val Ser Pro Lys Glu Val Leu Tyr Asp
            435                 440                 445

Ser Lys Gly Leu Ser Arg Glu Ala Gln Lys Ala Leu Arg Lys Tyr Thr
    450                 455                 460

Leu Thr Gly Ser Thr Ala Val Gln Leu Ala Pro Val Pro Gln Val Met
465                 470                 475                 480

Gly Asp Thr Asp Ala Ala Gly Val Arg Asn Ile Ile Glu Ser Asn Gly
                485                 490                 495

Tyr Phe Lys Gly Ser Ser Glu Ser Trp Asn Cys Ala Val Asp Gly Leu
                500                 505                 510

Asn Glu Cys Asp Val Ala Leu Ser Ala Leu Gly Glu Leu Ile Asn His
            515                 520                 525

Leu Ser Arg Leu Lys Leu Glu Asp Val Leu Lys His Gly Asp Ile Phe
    530                 535                 540

Pro Tyr Gln Val Tyr Arg Gly Cys Leu Arg Ile Asp Gly Gln Thr Met
545                 550                 555                 560

Val Asn Leu Glu Ile Phe Asn Asn Ser Cys Asp Gly Val Leu Gln Gly
                565                 570                 575

Pro Leu Asn Lys Tyr Leu Glu Asn Cys Val Ser Pro Thr Gly Lys Arg
                580                 585                 590

Leu Leu Arg Asn Trp Ile Cys His Pro Leu Lys Asp Val Glu Ser Ile
        595                 600                 605

Asn Lys Arg Leu Asp Val Val Glu Glu Phe Thr Ala Asn Ser Glu Ser
    610                 615                 620

Met Gln Ile Thr Gly Gln Tyr Leu His Lys Leu Pro Asp Leu Glu Arg
625                 630                 635                 640

Leu Leu Gly Arg Ile Lys Ser Ser Val Arg Ser Ser Ala Ser Val Leu
                645                 650                 655

Pro Ala Leu Leu Gly Lys Lys Val Leu Lys Gln Arg Val Lys Ala Phe
                660                 665                 670

Gly Gln Ile Val Lys Gly Phe Arg Ser Gly Ile Asp Leu Leu Leu Ala
            675                 680                 685

Leu Gln Lys Glu Ser Asn Met Met Ser Leu Leu Tyr Lys Leu Cys Lys
    690                 695                 700

Leu Pro Ile Leu Val Gly Lys Ser Gly Leu Glu Leu Phe Leu Ser Gln
705                 710                 715                 720

Phe Glu Ala Ala Ile Asp Ser Asp Phe Pro Asn Tyr Gln Asn Gln Asp
                725                 730                 735

Val Thr Asp Glu Asn Ala Glu Thr Leu Thr Ile Leu Ile Glu Leu Phe
            740                 745                 750

Ile Glu Arg Ala Thr Gln Trp Ser Glu Val Ile His Thr Ile Ser Cys
    755                 760                 765

Leu Asp Val Leu Arg Ser Phe Ala Ile Ala Ser Leu Ser Ala Gly
770                 775                 780

Ser Met Ala Arg Pro Val Ile Phe Pro Glu Ser Glu Ala Thr Asp Gln
785                 790                 795                 800

Asn Gln Lys Thr Lys Gly Pro Ile Leu Lys Ile Gln Gly Leu Trp His
                805                 810                 815

Pro Phe Ala Val Ala Ala Asp Gly Gln Leu Pro Val Pro Asn Asp Ile
            820                 825                 830

Leu Leu Gly Glu Ala Arg Arg Ser Ser Gly Ser Ile His Pro Arg Ser
```

```
                    835                  840                 845
Leu Leu Leu Thr Gly Pro Asn Met Gly Lys Ser Thr Leu Leu Arg
    850                 855                 860

Ala Thr Cys Leu Ala Val Ile Phe Ala Gln Leu Gly Cys Tyr Val Pro
865             870                  875                 880

Cys Glu Ser Cys Glu Ile Ser Leu Val Asp Thr Ile Phe Thr Arg Leu
                885                 890                 895

Gly Ala Ser Asp Arg Ile Met Thr Gly Glu Ser Thr Phe Leu Val Glu
            900                 905                 910

Cys Thr Glu Thr Ala Ser Val Leu Gln Asn Ala Thr Gln Asp Ser Leu
                915                 920                 925

Val Ile Leu Asp Glu Leu Gly Arg Gly Thr Ser Thr Phe Asp Gly Tyr
    930                 935                 940

Ala Ile Ala Tyr Ser Val Phe Arg His Leu Val Glu Lys Val Gln Cys
945             950                 955                 960

Arg Met Leu Phe Ala Thr His Tyr His Pro Leu Thr Lys Glu Phe Ala
                965                 970                 975

Ser His Pro Arg Val Thr Ser Lys His Met Ala Cys Ala Phe Lys Ser
                980                 985                 990

Arg Ser Asp Tyr Gln Pro Arg Gly Cys Asp Gln Asp Leu Val Phe Leu
            995                 1000                1005

Tyr Arg Leu Thr Glu Gly Ala  Cys Pro Glu Ser Tyr  Gly Leu Gln
    1010                1015                1020

Val Ala Leu Met Ala Gly Ile  Pro Asn Gln Val Val  Glu Thr Ala
    1025                1030                1035

Ser Gly Ala Ala Gln Ala Met  Lys Arg Ser Ile Gly  Glu Asn Phe
    1040                1045                1050

Lys Ser Ser Glu Leu Arg Ser  Glu Phe Ser Ser Leu  His Glu Asp
    1055                1060                1065

Trp Leu Lys Ser Leu Val Gly  Ile Ser Arg Val Ala  His Asn Asn
    1070                1075                1080

Ala Pro Ile Gly Glu Asp Asp  Tyr Asp Thr Leu Phe  Cys Leu Trp
    1085                1090                1095

His Glu Ile Lys Ser Ser Tyr  Cys Val Pro Lys
    1100                1105
```

<210> SEQ ID NO 43
<211> LENGTH: 5307
<212> TYPE: DNA
<213> ORGANISM: Arabidopsis thaliana

<400> SEQUENCE: 43

```
aaagataagt tcatacgact tttgtggctc atcaaaggcc atcatcgtcc tctatataca    60
atttagtgct ttatagtaca aaaccttcca cttcccttcg tccaaagttt tccaatttaa   120
tttataaaca ggaataatat tatctatata ataaagtgaa aataactat cattgtccaa    180 ataatttggt cgttgatcat gttactacaa agaaatgaaa tccttagtag aagtatatat   240
atatatatat ttgtaacaca ctcaaaatgg taggtgttgt tacagacaga tgttcgttag   300
cccagtaagc ccaatatgag atttaatggg ccttgatatt ttatagacca aacattgaaa   360
cattgcacgc ctggtctcaa agaacgttaa tacgcgcc gccggttgcc gccaatccgc     420
tttcccgcca aattcgacac cataaatttc ttctagtcgc tttcgattcc agttccactg   480
aaaaaccacg aaagaagaac atttgcaccg tagttgcaga aggtaggtga aggatttagc   540
tttctctatc ttccaatgga gggtaatttc gaggaacaga acaagcttcc ggagctgaaa   600
```

```
ttgggtaatg ttaaaccta gtttttttt tctttctcat tttcgtattc gatttcccaa    660
ttgggtttat gggttttgta aaggtctga tatttgttat gcattttttt tttaattttt    720
ggaagatgca aagcaagctc aagggttct ctcgttctac aaaacccta caaatgtaag    780 ttctcgtttt ctttcgattt ctgggagaag ttagagcttg tacagtgcct ctaattgcaa    840
taaataacac caattctagt cggaaagtag atgctttaaa attagggttt gaagcaattg    900
tagacatttt gttcattggg aagcgaatta ggaaaaaagg cttaagattt tttagcaatt    960
tctcgatctt tgcttatgtg ggttttgatt gttctttgct tcaggatacg agagctgtta   1020
gattctttga tcgcaaggtg agttcattgt tctcaaatgg tctagacttt ggttgtttaa   1080
atgtcgtcat tgatttatgg aaatttttg aatgcatttg caggattatt atacagctca   1140
tggtgaaaat tcagttttca ttgcaaagac ttattatcat acaaccactg ctctacgtca   1200
gctcgggagt ggttcaaatg ctctttcaag cgtaagcatt agtaggaaca tgttcgaaac   1260
gattgctagg gatcttctcc tggagcgtaa tgatcatact gtagaacttt atgaaggaag   1320
cggatcgaat tggagacttg tgaaaacagg ttctcctgga acattggaa gctttgaaga   1380 tgttttgttt gcaaacaatg aaatgcagga cacaccagtt gttgtctcca tatttccaag   1440
ttttcacgat ggcagatgcg ttattgggat ggcctatgtt gatctgacta ggcgagttct   1500
tggactagct gagtttcttg atgatagccg cttcaccaat ctggagtctt cgttgattgc   1560
tctaggcgca aaagaatgca ttttccagc tgaatccggc aaatccaatg aatgcaaaag   1620
cctgtatgat tccctggaga ggtgtgccgt gatgataaca gagaggaaga aacacgagtt   1680
caaaggaaga gatttagatt cagatcttaa gagattggtg aaggggaata ttgagcctgt   1740
tagagatttg gtatccgggt ttgaccttgc gactcctgct ctaggtgcat tactctcgtt   1800
ttctgaactt ctctcaaatg aggataacta tgggaacttc acaatccgca gatatgatat   1860
tggcggattc atgagacttg actctgcagc tatgagggcg ttgaatgtga tggagagcaa   1920
aactgatgct aataagaatt tcagtttgtt tggtctcatg aacagaacat gtaccgcagg   1980
gatgggtaag agactgcttc atatgtggct gaagcaaccc ctcgtggatt tgaatgagat   2040
taagacgaga ttagatatag ttcagtgctt tgttgaagaa gctgggttaa ggcaggatct   2100
tagacagcat ctgaagcgaa tctcagatgt tgagaggctt ttgcgcagtc tcgagagaag   2160
aagaggtggg ttacagcaca ttattaaact ctatcaggta ctttccgcac ttcaatctgc   2220
ttctctcaat gttaacaaaa ttgcattttc attgtcctaa atgtgtttat gcaactctga   2280
agttataggt atgttattaa gttcattact aattaagtct tcatcttttc tctgcagtca   2340
gctataaggc ttccctttcat caaacagct atgcaacagt acaccggaga attcgcatca   2400
ctcatcagcg agaggtacct gaaaaagctt gaggctttat cagatcaaga tcaccttgga   2460
aagttcatcg atttggttga gtgctctgta gatcttgacc agctagaaaa tggagaatac   2520
atgatatctt caaactacga caccaaattg gcatctctga aagatcagaa agaattgctg   2580
gagcagcaga ttcacgaatt gcacaaaaag acagcgatag aacttgatct tcaggtcgac   2640
aaggctctta aacttgacaa agcagcgcaa tttgggcatg tcttcaggat cacgaagaag   2700
gaagagccaa agatcaggaa gaagctgacg acacagttta tagtgctgga gactcgcaaa   2760
gacggagtga agttcacaaa cacaaagcta aaaaactgg gcgaccagta ccaaagtgtt   2820
gtggatgatt ataggagctg tcaaaaggag ctcgttgatc gtgtagttga gactgttacc   2880
agcttctctg aggtatgttt agttattcat attaagcatt ggactgttac agaattggtt   2940
gtttaaaatc atagtaaact atatgtggaa tttatatgta tattgtatgg ttataggtat   3000
```

```
ttgaggactt agctgggtta ctttctgaaa tggatgtttt gttaagcttt gctgatttgg   3060
ctgccagttg ccctactcca tactgtaggc cagaaatcac ctctttggtt agtacaatct   3120
caagttgatt attttgttct gaaaatgaat agttttttct ttccaagttt atgacataat   3180
gttgagagca cggttaataa attgtaggat gctggagata ttgtactaga aggaagcaga   3240
catccatgtg tagaagctca agattgggtg aatttcatac caaatgattg cagactcgta   3300
agtattgaat gtggtaaata aactgagacg tctttgtttt tcttgtttcc cttttgactt   3360
gaacaaatac ttgtttgccc tttactgttc tttgaaatca gatgagaggg aagagttggt   3420
ttcaaatagt aacagggcct aacatgggag ggaagtccac tttcatccgc caggtatgat   3480
gatttcctct agttcagttt tgcttcatag acgtatgact aaagtcggtt tccggccatt   3540
ataaatccca ggttggtgtg attgtgctga tggctcaagt tggttccttt gttccttgtg   3600
ataaagcatc aatttccata agagactgca tctttgcccg tgtaggagca ggcgattgcc   3660
aagtgagttt aagtttagcc ctcaatgaac gaaaaactgc tgatatcctg aacaccctta   3720
ttccaacttt ttttcctttg gtgtgttagc tgcgtggagt gtcaacttttt atgcaagaaa   3780 tgcttgaaac cgcatcgata ttgaaaggcg ctactgataa gtcactgata attatcgatg   3840
aacttggtcg tggaacatca acttatgatg gttttggtta gtttctctgc aatttctctt   3900
ctttcatttg gatgttttta gtaagttttc tattatatat tcatttttat ggtcatatgt   3960
gagatttcag tgctcttgac atcatcgtgg tgaatatatc aggtttagct tgggctatat   4020
gtgagcatct ggttcaagtg aaaagagcac caactctgtt tgctactcac ttccatgaac   4080
ttactgcctt ggctcaagca aactctgagg tctctggtaa cactgttggt gtggcaaact   4140
tccatgtcag cgctcacatt gacactgaaa gccgcaaact caccatgctt tacaaggtct   4200
ggtttataaa ttaaaaaatt gctgatctgt tgcagttaaa agtgtctctg ttttttatgtt   4260 taatctaaat tacttatttg attttcttac aaagatgaaa ttgaaattaa ttttgtgtgg   4320
tgtgttgttt gtctggttag gttgaaccag gggcctgtga ccagagcttt gggattcatg   4380
tggcggaatt tgccaacttc cctgaaagcg tcgtggccct cgcaagagag aaagctgcag   4440
agctggaaga tttctctccc tcctcgatga taatcaacaa tgaggtcttg attcatttcc   4500
ccctttgttt ttggttgatg atggaatcat tctatcattc acccattctg cagtttatgc   4560
tatattatta taaatctatg tgacaaagat ttaattctcg tattgttgtt tgcaggagag   4620
tgggaagaga aagagcagag aagatgatcc agatgaagta tcaagagggg cagagcgagc   4680
tcacaagttt ctgaaagagt ttgcagcgat gccacttgat aaaatggagc ttaaagattc   4740
acttcaacgg gtacgtgaga tgaaagatga gctagagaaa gatgctgcag actgccactg   4800
gctcaggcag tttctgtgaa gaacccctga cgttttttgg tttttggttt tgtaaatagc   4860
ttaaatcggt tcttgtagtt gtggtcgttg cttgggatga aactaaatga gggcaaaaac   4920
ataattctac atttttttgtt agtaaagctc gttaatttac tccctagtgc tatcaattat   4980
tttgcctatt ataattgttg atcaagtact tagagcaacc ccaatggttt ctaaacataa   5040
gtttcttatt ttatagagag aaattttatt ataaaaaaat gtgtgggttt cttgattagt   5100
gaagaaacca tctccaaaat accttatatt cttatataag gtattttgga gagaatttct   5160
aactattcaa gaaacttaca taattaaata ctattatttt tattgtttta atgttaagaa   5220
acttatattt aaaaccacc aatggaattg ctcttagcta ccatacaaat aattataaaa   5280
atatatcgaa aagtagaaga gccatttt                                      5307
```

```
<210> SEQ ID NO 44
<211> LENGTH: 937
<212> TYPE: PRT
<213> ORGANISM: Arabidopsis thaliana

<400> SEQUENCE: 44
```

| | | | | | | | | | | | | | | | |
|---|---|---|---|---|---|---|---|---|---|---|---|---|---|---|---|
| Met | Glu | Gly | Asn | Phe | Glu | Gln | Asn | Lys | Leu | Pro | Glu | Leu | Lys | Leu |
| 1 | | | | 5 | | | | | 10 | | | | | 15 |
| Asp | Ala | Lys | Gln | Ala | Gln | Gly | Phe | Leu | Ser | Phe | Tyr | Lys | Thr | Leu | Pro |
| | | | 20 | | | | | 25 | | | | | 30 | | |
| Asn | Asp | Thr | Arg | Ala | Val | Arg | Phe | Phe | Asp | Arg | Lys | Asp | Tyr | Tyr | Thr |
| | | 35 | | | | | 40 | | | | | 45 | | | |
| Ala | His | Gly | Glu | Asn | Ser | Val | Phe | Ile | Ala | Lys | Thr | Tyr | Tyr | His | Thr |
| | 50 | | | | | 55 | | | | | 60 | | | | |
| Thr | Thr | Ala | Leu | Arg | Gln | Leu | Gly | Ser | Gly | Ser | Asn | Ala | Leu | Ser | Ser |
| 65 | | | | | 70 | | | | | 75 | | | | | 80 |
| Val | Ser | Ile | Ser | Arg | Asn | Met | Phe | Glu | Thr | Ile | Ala | Arg | Asp | Leu | Leu |
| | | | | 85 | | | | | 90 | | | | | 95 | |
| Leu | Glu | Arg | Asn | Asp | His | Thr | Val | Glu | Leu | Tyr | Glu | Gly | Ser | Gly | Ser |
| | | | 100 | | | | | 105 | | | | | 110 | | |
| Asn | Trp | Arg | Leu | Val | Lys | Thr | Gly | Ser | Pro | Gly | Asn | Ile | Gly | Ser | Phe |
| | | | 115 | | | | | 120 | | | | | 125 | | |
| Glu | Asp | Val | Leu | Phe | Ala | Asn | Asn | Glu | Met | Gln | Asp | Thr | Pro | Val | Val |
| 130 | | | | | 135 | | | | | 140 | | | | | |
| Val | Ser | Ile | Phe | Pro | Ser | Phe | His | Asp | Gly | Arg | Cys | Val | Ile | Gly | Met |
| 145 | | | | 150 | | | | | 155 | | | | | 160 | |
| Ala | Tyr | Val | Asp | Leu | Thr | Arg | Arg | Val | Leu | Gly | Leu | Ala | Glu | Phe | Leu |
| | | | | 165 | | | | | 170 | | | | | 175 | |
| Asp | Asp | Ser | Arg | Phe | Thr | Asn | Leu | Glu | Ser | Ser | Leu | Ile | Ala | Leu | Gly |
| | | | 180 | | | | | 185 | | | | | 190 | | |
| Ala | Lys | Glu | Cys | Ile | Phe | Pro | Ala | Glu | Ser | Gly | Lys | Ser | Asn | Glu | Cys |
| | | | 195 | | | | | 200 | | | | | 205 | | |
| Lys | Ser | Leu | Tyr | Asp | Ser | Leu | Glu | Arg | Cys | Ala | Val | Met | Ile | Thr | Glu |
| | 210 | | | | | 215 | | | | | 220 | | | | |
| Arg | Lys | Lys | His | Glu | Phe | Lys | Gly | Arg | Asp | Leu | Asp | Ser | Asp | Leu | Lys |
| 225 | | | | | 230 | | | | | 235 | | | | | 240 |
| Arg | Leu | Val | Lys | Gly | Asn | Ile | Glu | Pro | Val | Arg | Asp | Leu | Val | Ser | Gly |
| | | | | 245 | | | | | 250 | | | | | 255 | |
| Phe | Asp | Leu | Ala | Thr | Pro | Ala | Leu | Gly | Ala | Leu | Leu | Ser | Phe | Ser | Glu |
| | | | 260 | | | | | 265 | | | | | 270 | | |
| Leu | Leu | Ser | Asn | Glu | Asp | Asn | Tyr | Gly | Asn | Phe | Thr | Ile | Arg | Arg | Tyr |
| | | 275 | | | | | 280 | | | | | 285 | | | |
| Asp | Ile | Gly | Gly | Phe | Met | Arg | Leu | Asp | Ser | Ala | Ala | Met | Arg | Ala | Leu |
| | 290 | | | | | 295 | | | | | 300 | | | | |
| Asn | Val | Met | Glu | Ser | Lys | Thr | Asp | Ala | Asn | Lys | Asn | Phe | Ser | Leu | Phe |
| 305 | | | | | 310 | | | | | 315 | | | | | 320 |
| Gly | Leu | Met | Asn | Arg | Thr | Cys | Thr | Ala | Gly | Met | Gly | Lys | Arg | Leu | Leu |
| | | | | 325 | | | | | 330 | | | | | 335 | |
| His | Met | Trp | Leu | Lys | Gln | Pro | Leu | Val | Asp | Leu | Asn | Glu | Ile | Lys | Thr |
| | | | 340 | | | | | 345 | | | | | 350 | | |
| Arg | Leu | Asp | Ile | Val | Gln | Cys | Phe | Val | Glu | Ala | Gly | Leu | Arg | Gln |
| | | 355 | | | | | 360 | | | | | 365 | | | |
| Asp | Leu | Arg | Gln | His | Leu | Lys | Arg | Ile | Ser | Asp | Val | Glu | Arg | Leu | Leu |
| | 370 | | | | | 375 | | | | | 380 | | | | |
| Arg | Ser | Leu | Glu | Arg | Arg | Arg | Gly | Gly | Leu | Gln | His | Ile | Ile | Lys | Leu |

-continued

```
            385                 390                 395                 400

Tyr Gln Ser Ala Ile Arg Leu Pro Phe Ile Lys Thr Ala Met Gln Gln
                405                 410                 415

Tyr Thr Gly Glu Phe Ala Ser Leu Ile Ser Glu Arg Tyr Leu Lys Lys
                420                 425                 430

Leu Glu Ala Leu Ser Asp Gln Asp His Leu Gly Lys Phe Ile Asp Leu
                435                 440                 445

Val Glu Cys Ser Val Asp Leu Asp Gln Leu Glu Asn Gly Glu Tyr Met
            450                 455                 460

Ile Ser Ser Asn Tyr Asp Thr Lys Leu Ala Ser Leu Lys Asp Gln Lys
465                 470                 475                 480

Glu Leu Leu Glu Gln Gln Ile His Glu Leu His Lys Lys Thr Ala Ile
                485                 490                 495

Glu Leu Asp Leu Gln Val Asp Lys Ala Leu Lys Leu Asp Lys Ala Ala
                500                 505                 510

Gln Phe Gly His Val Phe Arg Ile Thr Lys Lys Glu Glu Pro Lys Ile
                515                 520                 525

Arg Lys Lys Leu Thr Thr Gln Phe Ile Val Leu Glu Thr Arg Lys Asp
            530                 535                 540

Gly Val Lys Phe Thr Asn Thr Lys Leu Lys Lys Leu Gly Asp Gln Tyr
545                 550                 555                 560

Gln Ser Val Val Asp Asp Tyr Arg Ser Cys Gln Lys Glu Leu Val Asp
                565                 570                 575

Arg Val Val Glu Thr Val Thr Ser Phe Ser Glu Val Phe Glu Asp Leu
                580                 585                 590

Ala Gly Leu Leu Ser Glu Met Asp Val Leu Leu Ser Phe Ala Asp Leu
                595                 600                 605

Ala Ala Ser Cys Pro Thr Pro Tyr Cys Arg Pro Glu Ile Thr Ser Leu
            610                 615                 620

Asp Ala Gly Asp Ile Val Leu Glu Gly Ser Arg His Pro Cys Val Glu
625                 630                 635                 640

Ala Gln Asp Trp Val Asn Phe Ile Pro Asn Asp Cys Arg Leu Met Arg
                645                 650                 655

Gly Lys Ser Trp Phe Gln Ile Val Thr Gly Pro Asn Met Gly Gly Lys
                660                 665                 670

Ser Thr Phe Ile Arg Gln Val Gly Val Ile Val Leu Met Ala Gln Val
                675                 680                 685

Gly Ser Phe Val Pro Cys Asp Lys Ala Ser Ile Ser Ile Arg Asp Cys
            690                 695                 700

Ile Phe Ala Arg Val Gly Ala Gly Asp Cys Gln Leu Arg Gly Val Ser
705                 710                 715                 720

Thr Phe Met Gln Glu Met Leu Glu Thr Ala Ser Ile Leu Lys Gly Ala
                725                 730                 735

Thr Asp Lys Ser Leu Ile Ile Ile Asp Glu Leu Gly Arg Gly Thr Ser
                740                 745                 750

Thr Tyr Asp Gly Phe Gly Leu Ala Trp Ala Ile Cys Glu His Leu Val
                755                 760                 765

Gln Val Lys Arg Ala Pro Thr Leu Phe Ala Thr His Phe His Glu Leu
                770                 775                 780

Thr Ala Leu Ala Gln Ala Asn Ser Glu Val Ser Gly Asn Thr Val Gly
785                 790                 795                 800

Val Ala Asn Phe His Val Ser Ala His Ile Asp Thr Glu Ser Arg Lys
                805                 810                 815
```

```
Leu Thr Met Leu Tyr Lys Val Glu Pro Gly Ala Cys Asp Gln Ser Phe
            820                 825                 830
Gly Ile His Val Ala Glu Phe Ala Asn Phe Pro Glu Ser Val Val Ala
            835                 840                 845
Leu Ala Arg Glu Lys Ala Ala Glu Leu Glu Asp Phe Ser Pro Ser Ser
    850                 855                 860
Met Ile Ile Asn Asn Glu Glu Ser Gly Lys Arg Lys Ser Arg Glu Asp
865                 870                 875                 880
Asp Pro Asp Glu Val Ser Arg Gly Ala Glu Arg Ala His Lys Phe Leu
                885                 890                 895
Lys Glu Phe Ala Ala Met Pro Leu Asp Lys Met Glu Leu Lys Asp Ser
            900                 905                 910
Leu Gln Arg Val Arg Glu Met Lys Asp Glu Leu Glu Lys Asp Ala Ala
            915                 920                 925
Asp Cys His Trp Leu Arg Gln Phe Leu
        930                 935

<210> SEQ ID NO 45
<211> LENGTH: 3521
<212> TYPE: DNA
<213> ORGANISM: Arabidopsis thaliana

<400> SEQUENCE: 45
ctaagaaagc gcgcgaaaat tggcaaccca agttcgccat agccacgacc acgaccttcc      60
atttctctta aacggaggag attacgaata aagcaattat gggcaagcaa aagcagcaga     120
cgatttctcg tttcttcgct cccaaaccca atccccgac tcacgaaccg aatccggtag      180
ccgaatcatc aacaccgcca ccgaagatat ccgccactgt atccttctct ccttccaagc     240
gtaagcttct ctccgaccac ctcgccgccg cgtcacccaa aaagcctaaa ctttctcctc     300
acactcaaaa cccagtaccc gatcccaatt tacaccaaag attttctccag agatttctgg    360 aaccctcgcc ggaggaatat gttcccgaaa cgtcatcatc gaggaaatac acaccattgg    420
aacagcaagt ggtggagcta agagcaagt acccagatgt ggttttgatg gtggaagttg     480
gttacaggta cagattcttc ggagaagacg cggagatcgc agcacgcgtg ttgggtattt    540
acgctcatat ggatcacaat ttcatgacgg cgagtgtgcc aacatttcga ttgaatttcc    600
atgtgagaag actggtgaat gcaggataca agattggtgt agtgaagcag actgaaactg    660
cagccattaa gtcccatggt gcaaaccgga ccggcccttt tttccgggga ctgtcggcgt    720
tgtataccaa agccacgctt gaagcggctg aggatataag tggtggttgt ggtggtgaag    780
aaggttttgg ttcacagagt aatttcttgg tttgtgttgt ggatgagaga gttaagtcgg    840
agacattagg ctgtggtatt gaaatgagtt ttgatgttag agtcggtgtt gttggcgttg    900
aaatttcgac aggtgaagtt gtttatgaag agttcaatga taatttcatg agaagtggat    960
tagaggctgt gattttgagc ttgtcaccag ctgagctgtt gcttggccag cctcttttcac   1020 aacaaactga aagttttttg gtggcacatg ctggacctac ctcaaacgtt cgagtggaac    1080
gtgcctcact ggattgtttc agcaatggta atgcagtaga tgaggttatt tcattatgtg    1140
aaaaaatcag cgcaggtaac ttagaagatg ataaagaaat gaagctggag gctgctgaaa    1200
aaggaatgtc ttgcttgaca gttcatacaa ttatgaacat gccacatctg actgttcaag    1260
ccctcgccct aacgttttgc catctcaaac agtttggatt tgaaaggatc ctttaccaag    1320
gggcctcatt tcgctctttg tcaagtaaca cagagatgac tctctcagcc aatactctgc    1380
aacagttgga ggttgtgaaa aataattcag atggatcgga atctggctcc ttattccata    1440
```

```
atatgaatca cacacttaca gtatatggtt ccaggcttct tagacactgg gtgactcatc    1500
ctctatgcga tagaaatttg atatctgctc ggcttgatgc tgtttctgag atttctgctt    1560
gcatgggatc tcatagttct tcccagctca gcagtgagtt ggttgaagaa ggttctgaga    1620
gagcaattgt atcacctgag ttttatctcg tgctctcctc agtcttgaca gctatgtcta    1680
gatcatctga tattcaacgt ggaataacaa gaatctttca tcggactgct aaagccacag    1740
agttcattgc agttatggaa gctatttac ttgcggggaa gcaaattcag cggcttggca    1800
taaagcaaga ctctgaaatg aggagtatgc aatctgcaac tgtgcgatct actctttga    1860 gaaaattgat ttctgttatt tcatcccctg ttgtggttga caatgccgga aaacttctct    1920
ctgccctaaa taaggaagcg gctgttcgag gtgacttgct cgacatacta atcacttcca    1980
gcgaccaatt tcctgagctt gctgaagctc gccaagcagt tttagtcatc agggaaaagc    2040
tggattcctc gatagcttca tttcgcaaga agctcgctat tcgaaatttg gaatttcttc    2100
aagtgtcggg gatcacacat ttgatagagc tgcccgttga ttccaaggtc cctatgaatt    2160
gggtgaaagt aaatagcacc aagaagacta ttcgatatca tcccccagaa atagtagctg    2220
gcttggatga gctagctcta gcaactgaac atcttgccat tgtgaaccga gcttcgtggg    2280 atagttttcct caagagtttc agtagatact acacagattt taaggctgcc gttcaagctc    2340
ttgctgcact ggactgtttg cactccctt caactctatc tagaaacaag aactatgtcc    2400
gtcccgagtt tgtggatgac tgtgaaccag ttgagataaa catacagtct ggtcgtcatc    2460
ctgtactgga gactatatta caagataact tcgtcccaaa tgacacaatt ttgcatgcag    2520
aaggggaata ttgccaaatt atcaccggac taacatggg aggaaagagc tgctatatcc    2580
gtcaagttgc tttaatttcc ataatggctc aggttggttc ctttgtacca gcgtcattcg    2640
ccaagctgca cgtgcttgat ggtgttttca ctcggatggg tgcttcagac agtatccagc    2700
atggcagaag tacctttcta gaagaattaa gtgaagcgtc acacataatc agaacctgtt    2760
cttctcgttc gcttgttata ttagatgagc ttggaagagg cactagcaca cacgacggtg    2820
tagccattgc ctatgcaaca ttacagcatc tcctagcaga aaagagatgt ttggttcttt    2880
ttgtcacgca ttaccctgaa atagctgaga tcagtaacgg attcccaggt tctgttggga    2940
cataccatgt ctcgtatctg acattgcaga aggataaagg cagttatgat catgatgatg    3000
tgacctacct atataagctt gtgcgtggtc tttcagcag gagctttggt tttaaggttg    3060
ctcagcttgc ccagatacct ccatcatgta tacgtcgagc catttcaatg gctgcaaaat    3120
tggaagctga ggtacgtgca agagagagaa atacacgcat gggagaacca gaaggacatg    3180
aagaaccgag aggcgcagaa gaatctattt cggctctagg tgacttgttt gcagacctga    3240
aatttgctct ctctgaagag gacccttgga aagcattcga gttttaaag catgcttgga    3300 agattgctgg caaaatcaga ctaaaaccaa cttgttcatt tgatttaat cttaacatta    3360 tagcaactgc aaggtcttga tcatctgtta gttgcgtact aacttatgtg tattagtata    3420
acaagaaaag agaattagag agatggattc taatccggtg ttgcagtaca tcttttctcc    3480
acccgcataa aaaaaaaaaa aaaaaaaaaa aaaaaaaaaa a                       3521
```

<210> SEQ ID NO 46
<211> LENGTH: 1081
<212> TYPE: PRT
<213> ORGANISM: Arabidopsis thaliana

<400> SEQUENCE: 46

Met Gly Lys Gln Lys Gln Gln Thr Ile Ser Arg Phe Phe Ala Pro Lys
1               5                   10                  15

```
Pro Lys Ser Pro Thr His Glu Pro Asn Pro Val Ala Glu Ser Ser Thr
            20                  25                  30

Pro Pro Pro Lys Ile Ser Ala Thr Val Ser Phe Ser Pro Ser Lys Arg
        35                  40                  45

Lys Leu Leu Ser Asp His Leu Ala Ala Ser Pro Lys Lys Pro Lys
    50                  55                  60

Leu Ser Pro His Thr Gln Asn Pro Val Pro Asp Pro Asn Leu His Gln
65                  70                  75                  80

Arg Phe Leu Gln Arg Phe Leu Glu Pro Ser Pro Glu Glu Tyr Val Pro
                85                  90                  95

Glu Thr Ser Ser Ser Arg Lys Tyr Thr Pro Leu Glu Gln Gln Val Val
            100                 105                 110

Glu Leu Lys Ser Lys Tyr Pro Asp Val Val Leu Met Val Glu Val Gly
            115                 120                 125

Tyr Arg Tyr Arg Phe Phe Gly Glu Asp Ala Glu Ile Ala Ala Arg Val
130                 135                 140

Leu Gly Ile Tyr Ala His Met Asp His Asn Phe Met Thr Ala Ser Val
145                 150                 155                 160

Pro Thr Phe Arg Leu Asn Phe His Val Arg Arg Leu Val Asn Ala Gly
                165                 170                 175

Tyr Lys Ile Gly Val Val Lys Gln Thr Glu Thr Ala Ala Ile Lys Ser
            180                 185                 190

His Gly Ala Asn Arg Thr Gly Pro Phe Phe Arg Gly Leu Ser Ala Leu
            195                 200                 205

Tyr Thr Lys Ala Thr Leu Glu Ala Ala Glu Asp Ile Ser Gly Gly Cys
210                 215                 220

Gly Gly Glu Glu Gly Phe Gly Ser Gln Ser Asn Phe Leu Val Cys Val
225                 230                 235                 240

Val Asp Glu Arg Val Lys Ser Glu Thr Leu Gly Cys Gly Ile Glu Met
                245                 250                 255

Ser Phe Asp Val Arg Val Gly Val Val Gly Val Glu Ile Ser Thr Gly
                260                 265                 270

Glu Val Val Tyr Glu Glu Phe Asn Asp Asn Phe Met Arg Ser Gly Leu
            275                 280                 285

Glu Ala Val Ile Leu Ser Leu Ser Pro Ala Glu Leu Leu Leu Gly Gln
            290                 295                 300

Pro Leu Ser Gln Gln Thr Glu Lys Phe Leu Val Ala His Ala Gly Pro
305                 310                 315                 320

Thr Ser Asn Val Arg Val Glu Arg Ala Ser Leu Asp Cys Phe Ser Asn
                325                 330                 335

Gly Asn Ala Val Asp Glu Val Ile Ser Leu Cys Glu Lys Ile Ser Ala
            340                 345                 350

Gly Asn Leu Glu Asp Asp Lys Glu Met Lys Leu Glu Ala Ala Glu Lys
            355                 360                 365

Gly Met Ser Cys Leu Thr Val His Thr Ile Met Asn Met Pro His Leu
    370                 375                 380

Thr Val Gln Ala Leu Ala Leu Thr Phe Cys His Leu Lys Gln Phe Gly
385                 390                 395                 400

Phe Glu Arg Ile Leu Tyr Gln Gly Ala Ser Phe Arg Ser Leu Ser Ser
                405                 410                 415

Asn Thr Glu Met Thr Leu Ser Ala Asn Thr Leu Gln Gln Leu Glu Val
            420                 425                 430

Val Lys Asn Asn Ser Asp Gly Ser Glu Ser Gly Ser Leu Phe His Asn
```

-continued

```
            435                 440                 445
Met Asn His Thr Leu Thr Val Tyr Gly Ser Arg Leu Leu Arg His Trp
450                 455                 460
Val Thr His Pro Leu Cys Asp Arg Asn Leu Ile Ser Ala Arg Leu Asp
465                 470                 475                 480
Ala Val Ser Glu Ile Ser Ala Cys Met Gly Ser His Ser Ser Ser Gln
                485                 490                 495
Leu Ser Ser Glu Leu Val Glu Glu Gly Ser Glu Arg Ala Ile Val Ser
            500                 505                 510
Pro Glu Phe Tyr Leu Val Leu Ser Ser Val Leu Thr Ala Met Ser Arg
        515                 520                 525
Ser Ser Asp Ile Gln Arg Gly Ile Thr Arg Ile Phe His Arg Thr Ala
    530                 535                 540
Lys Ala Thr Glu Phe Ile Ala Val Met Glu Ala Ile Leu Leu Ala Gly
545                 550                 555                 560
Lys Gln Ile Gln Arg Leu Gly Ile Lys Gln Asp Ser Glu Met Arg Ser
                565                 570                 575
Met Gln Ser Ala Thr Val Arg Ser Thr Leu Leu Arg Lys Leu Ile Ser
            580                 585                 590
Val Ile Ser Ser Pro Val Val Asp Asn Ala Gly Lys Leu Leu Ser
        595                 600                 605
Ala Leu Asn Lys Glu Ala Ala Val Arg Gly Asp Leu Leu Asp Ile Leu
    610                 615                 620
Ile Thr Ser Ser Asp Gln Phe Pro Glu Leu Ala Glu Ala Arg Gln Ala
625                 630                 635                 640
Val Leu Val Ile Arg Glu Lys Leu Asp Ser Ser Ile Ala Ser Phe Arg
                645                 650                 655
Lys Lys Leu Ala Ile Arg Asn Leu Glu Phe Leu Gln Val Ser Gly Ile
            660                 665                 670
Thr His Leu Ile Glu Leu Pro Val Asp Ser Lys Val Pro Met Asn Trp
        675                 680                 685
Val Lys Val Asn Ser Thr Lys Lys Thr Ile Arg Tyr His Pro Pro Glu
    690                 695                 700
Ile Val Ala Gly Leu Asp Glu Leu Ala Leu Ala Thr Glu His Leu Ala
705                 710                 715                 720
Ile Val Asn Arg Ala Ser Trp Asp Ser Phe Leu Lys Ser Phe Ser Arg
                725                 730                 735
Tyr Tyr Thr Asp Phe Lys Ala Val Gln Ala Leu Ala Ala Leu Asp
            740                 745                 750
Cys Leu His Ser Leu Ser Thr Leu Ser Arg Asn Lys Asn Tyr Val Arg
        755                 760                 765
Pro Glu Phe Val Asp Asp Cys Glu Pro Val Glu Ile Asn Ile Gln Ser
    770                 775                 780
Gly Arg His Pro Val Leu Glu Thr Ile Leu Gln Asp Asn Phe Val Pro
785                 790                 795                 800
Asn Asp Thr Ile Leu His Ala Glu Gly Glu Tyr Cys Gln Ile Ile Thr
                805                 810                 815
Gly Pro Asn Met Gly Gly Lys Ser Cys Tyr Ile Arg Gln Val Ala Leu
            820                 825                 830
Ile Ser Ile Met Ala Gln Val Gly Ser Phe Val Pro Ala Ser Phe Ala
        835                 840                 845
Lys Leu His Val Leu Asp Gly Val Phe Thr Arg Met Gly Ala Ser Asp
    850                 855                 860
```

| | | | | | | | | | | | | | |
|---|---|---|---|---|---|---|---|---|---|---|---|---|---|
|Ser|Ile|Gln|His|Gly|Arg|Ser|Thr|Phe|Leu|Glu|Glu|Leu|Ser|Glu|Ala|
|865| | | | |870| | | | |875| | | | |880|

Ser His Ile Ile Arg Thr Cys Ser Ser Arg Ser Leu Val Ile Leu Asp
           885                 890                 895

Glu Leu Gly Arg Gly Thr Ser Thr His Asp Gly Val Ala Ile Ala Tyr
        900                 905                 910

Ala Thr Leu Gln His Leu Leu Ala Glu Lys Arg Cys Leu Val Leu Phe
        915                 920                 925

Val Thr His Tyr Pro Glu Ile Ala Glu Ile Ser Asn Gly Phe Pro Gly
        930                 935                 940

Ser Val Gly Thr Tyr His Val Ser Tyr Leu Thr Leu Gln Lys Asp Lys
945                 950                 955                 960

Gly Ser Tyr Asp His Asp Asp Val Thr Tyr Leu Tyr Lys Leu Val Arg
                965                 970                 975

Gly Leu Cys Ser Arg Ser Phe Gly Phe Lys Val Ala Gln Leu Ala Gln
        980                 985                 990

Ile Pro Pro Ser Cys Ile Arg Arg Ala Ile Ser Met Ala Ala Lys Leu
        995                 1000                1005

Glu Ala Glu Val Arg Ala Arg Glu Arg Asn Thr Arg Met Gly Glu
        1010                1015                1020

Pro Glu Gly His Glu Glu Pro Arg Gly Ala Glu Glu Ser Ile Ser
        1025                1030                1035

Ala Leu Gly Asp Leu Phe Ala Asp Leu Lys Phe Ala Leu Ser Glu
        1040                1045                1050

Glu Asp Pro Trp Lys Ala Phe Glu Phe Leu Lys His Ala Trp Lys
        1055                1060                1065

Ile Ala Gly Lys Ile Arg Leu Lys Pro Thr Cys Ser Phe
        1070                1075                1080

<210> SEQ ID NO 47
<211> LENGTH: 7080
<212> TYPE: DNA
<213> ORGANISM: Arabidopsis thaliana

<400> SEQUENCE: 47
ctcttcgccg actgtttcac tccccttctc tctcactctc tgtgcgcttt attccactct      60
ccgatggctc cgtctcgccg acagatcagc ggaagatctc cgttggtgaa ccagcagcgt     120
caaatcacct ccttctttgg gaaatctgct tcatcatctt cttctccgtc tccatctcct     180
tcaccatctc tctccaataa gaaacccccc aaatctaaca ccctaacccc taaatctccg     240
tctccgtcac catctccgcc taagaaaacc cccaaattga accctaaccc tagttctaat     300
cttcctgctc gtagtcctag ccctggtcct gatactcctt ctcctgtaca gtccaagttt     360
aagaagcccc ttctcgtcat cggacagaca ccttcgcctc ctcaatcggt ggtaattact     420
tacggtgacg aggtggtggg gaagcaagtt agggtttatt ggccttttga taaaaaatgg     480
tatgatggga gcgtgacgtt ttatgataag ggtgagggta agcatgtggt tgagtatgaa     540
gatggggaag aagagtcttt ggatttggga aaggagaaga ctgagtgggt ggttggggaa     600
aaatcaggag ataggtttaa tcgattgaaa cgaggcgctt cggctttgag aaaagttgtg     660
acggatagtg atgatgatgt ggagatgggt aatgtggaag aagataaaag tgacggtgat     720
gattctagcg atgaggattg gggaaagaat gttgggaagg aggtttgtga gagtgaagaa     780
gatgatgtgg agttggttga tgagaatgaa atggatgaag aagagttggt ggaagagaaa     840
gatgaagaaa cttctaaagt taatagagta tccaaaactg actctagaaa gcggaagact     900

```
agtgaagtaa cgaaatcagg tggtgagaag aaaagcaaga ctgatacagg cactatcttg    960
aaaggtttta aggcttctgt tgtggagcct gcgaagaaga ttggacaagg taaaccgaag   1020
agtctcttgt tgtaatcata tgcttgtatt tgcattgttt tagtttgtgg tatgtctctt   1080
gcactgactt ttgtttcaga tagtgtatgt tgttggttgc ttaatattat ttgtgtctta   1140
ctacagctga tagggtggtc aagggtttgg aagataacgt gttggatggg gatgctcttg   1200
ctagatttgg tgctcgtgat tctgagaaat tccgcttttt gggagtgtaa gtctttcaca   1260
aaaaaaattc catcttagag gctatttgct acggtggtta ggagtagaga atgtaaattt   1320
gtgtcttaag caatattgac ttctctactg gcaggagcat ctctggtttt cttttatctt   1380
catgatgtat tagtaggctg catgatccct attctagcta agttagttct gttaattatt   1440
tttggtgaac agagaccgaa gggatgctaa aggagacgc cctactgatg agaattatga    1500
tccgaggaca ctctacctcc ctcctgattt tgtgaaaaaa ttaactggag gccaggtcag   1560
aagagcgcat ggaaatctgg ttcaggattt ttggtgaagc taatcaactt tcacttatat   1620
gattttgtgg ccttttttca gagacaatgg tgggagttta aagcaaagca tatggacaaa   1680
gttgtattct tcaaggtaga acgataatta cttatttcgt tataacttat ttattgatgg   1740
gagattctag gataaatggt cttcttttgt ggcaagcaga tgggtaaatt ctatgagctt   1800
tttgagatgg atgcacatgt cggagctaag gaactggata tacaatacat gaaggtaact   1860
gtttgttatg actcataact aggtgatgca tttgaagaca tctgttaaaa atgttaaaaa   1920
accgaaaatt tggcatcaga ttatgctaaa agggttcttt tcattggtgt tacattacaa   1980
atttctcctg tattgtctct aatgtatctc tctttacaag cccctgacat atgcatttat   2040
tttgtaggga gagcaacctc attgtggatt tccggagaag aattttttctg taaacattga   2100
gaaattagtt agaaaggttt gtttccagaa atatagcaac tccagttcaa gcgtgatcta   2160
tttcttgtta cgtgtagaga aattacattc atggcaaatg ctgtactttg ggtagaaata   2220
aagttgattg aattgaatgg aacagggcta tcgggtttta gttgtcgaac aaacagaaac   2280
acctgatcag ctggagcaac gccgaaaaga gacaggttcc aaggataaag tatgtcccac   2340
tatgaatcta atttagttgg cattatcagt tcaagtcaat ttgtttgctc ttgaaactaa   2400
aatttgttca ctttgggtga tgcctatgta gaaaaattat gatagggagg gctcatagtg   2460
acagaacttc tgttttttata ggttgtgaag cgcgaagtat gtgcagttgt tacaaaaggc   2520
acgctgacag atggggagat gctattaact aatccggatg catcttatct aatggccttg   2580
actgaaggag gagaaagttt aactaatcct acagcagagc acaattttgg tgtatgtttg   2640
gttgatgttg cgacacagaa gataatactg ggccaggtga gttctagttg atgaatggta   2700
cctggttgca cttatacgta acatttctcg gtgtatattg atggcatttt ttttcattc    2760
gtaccagttt aaggatgatc aagattgcag tgcattatct tgcctgctat ctgagatgag   2820
gccggtggaa attattaaac cagctaaggt gttgagttat gcaacagaga gaacaatagt   2880
tagacaaacc agaaatccct tagtaaataa tctcgttcca ctttctgaat tttgggattc   2940
ggagaagacc atatatgaag ttggaattat ctacaagcga atcaattgtc aaccgtcttc   3000
tgcttattct agtgagggaa agattctagg tgatggttca agctttcttc caaaaatgtt   3060
gtctgaatta gcaactgaag ataagaatgg tagcctggca ctctctgctc ttggtggtgc   3120
catttactac ctgcgacaag cattcttgga tgagagtctg cttagatttg caaagtttga   3180
atccctgcct tactgtgatt tcagcaacgt taatgagaag cagcacatgg ttcttgatgc   3240
tgctgctctt gaaaaccttg agatatttga aaacagtaga aatggaggct attcagggta   3300
```

-continued

```
aagtttctct atcttaccat gtattattaa acataattga tgtgttctaa atctagagtg  3360
ttgtcttttg aagaacgctg tatgctcaac tgaatcaatg tatcactgca tctgggaaac  3420
ggttactgaa acatggctg gcaagacctt tatataatac ggaactgatc aaggaacgac   3480
aagatgctgt agcaattctg cgggtgagtc tttcaacaag ttgtttgact ttgctgctgt  3540
catttctctg tctctcaact agacaataac ttggcatctt ggtttcacat ttgatcattt  3600
ttcatgtctg tttcgctatc catggatctc tcctcagaat tacactattt ccccattatg  3660
ggtgttcaag accatttttg ccactgtttc actggcaaag atgatgtttt cctatgcgtt  3720
caactaacca tctatttcta gaacttattc cctaagatta taaaacttac tctgcttctt  3780
cagcatgtca aggctttcgt ttacactatc catctgacaa tgtattatgg tactgtccct  3840
tccctcaggg tgaaaatctt ccgtactcac tggaattccg gaagtcgttg tccagacttc  3900
cagacatgga acggttgatt gcacgtatgt tttctagcat gtaagggatt agctagattg  3960
agatgttaat tcttacatta tatgtttata ccaaagactt actaaacata tttgttaaac  4020
ttgtgttacg tgttatagtg aagctagtgg aagaaatggc gataaagtgg tgctatatga  4080
agatacagct aagaagcagg tacaggaatt catatcaact ctacgtggtt gtgaaacaat  4140
ggcagaagca tgctcttctc tccgtgctat cttgaagcat gatacatcca ggcggctgct  4200
tcatttacta actcctggta taatcaattt gctccatatt cacattctta tactggcaaa  4260
ttgcacagca tctcatatca tttctctgcc aggtcaaagt cttccaaata tatcatcctc  4320
cataaagtat ttcaaggatg cttttgactg ggtagaagct cacaattctg gacgtgtaat  4380
accccatgaa ggagcagatg aagagtatga ttgtgcctgc aaaacagtag aagaatttga  4440
gtccagtttg aaaaaacatc tgaaagagca acggaaatta ctcggagatg catcagtgag  4500
aattacttca ctattttttt ttactcctta aatggctaat caaccgaggg ttttctgatc  4560
agatctttgg tgctcttttg tcttcttatc cagataaact atgttacagt tggaaaagat  4620
gaatacctct tggaagttcc tgaaagttta agtgggagtg ttcctcatga ttatgaatta  4680
tgctcatcga aaaaggtaaa agttgtacca agtttcacat tctaaagaaa ttggcatttc  4740
gctttcgtca taacaagtcg atagtcttct cgtaattgct gtctgctgat atatttacta  4800
tatagagacc cttaatttta aacatgagat tttcttactt tttactctct ttcagggtgt  4860
ctctcgatat tggactccta ccataaagaa attattaaaa gagctatcac aagcaaaatc  4920
tgaaaagag tcggccctga agagcatttc acagagattg attggacgtt tctgcgagca   4980
tcaagaaaaa tggagacaat tggtttctgc aacagctggt atggacaagt tcatgtttta  5040
aaaaaaaaaa attgtttaag gaattttcag catcttcctt cagaatatgt atcttgctta  5100
tccaattcct gttaattact gtcacccagt gttagctttg tgggtcgtcg cttggacccct 5160
tttcgttgtg aacatttgtt gagctagtta gaattgagtt tgatcccaca ctttatagat  5220
tgagttagaa gtaggcatgc agaagaaaat gaatcttagg cagacgtata gttcaatcac  5280
atcttataag caagaggttt cttgggtgga agattgtttt atagaattag gcatgcaaac  5340
aactttgcac ttagaccttt atgtggatac atttttgaca tgaattcttt ctattgcaga  5400
gctggacgtg ttgatcagcc tcgcttttgc aagtgattct tatgaaggag taagatgccg  5460
cccagtaata tctggttcta catctgatgg tgttccacac ttgtctgcca ctggtctagg  5520
gcatccagtt ctaaggggtg attcgttagg cagaggctct tttgtaccaa ataatgtaaa  5580
gataggtggt gctgagaaag ccagtttcat cctcctcaca ggccctaata tgggtggaaa  5640
atcaacccctt cttcgccaag tttgcttggc tgtaatcttg gctcaggtaa gctatcattt  5700
```

-continued

```
gaaaaaactt tgtaggcaat gggctttgac ccgtttaatt ttgatgaaag aaactcaagc    5760
aatgatgatc ttttcacaga ttggagcaga tgtcccagca gaaacctttg aggtttcgcc    5820
tgttgacaaa atttgtgtcc ggatgggtgc aaaagatcat atcatggcag acaaagcac     5880 gttttaaca gaactttcag aaactgcggt aatgttggta agtaatgttc attctgtttg     5940
tcaaattgat tacatgaagc tttctaagat aaatgtgaaa cttgccacag tggttaccct    6000
tttgagagtt ggtcacaggc tttgttaaac tatgcgaatg ccaacaaacg cactgataga    6060
atgttttata ttaataatat gcagacatca gccacccgaa actcgctggt ggtgctagat    6120
gagcttggac gaggaacagc cacatcagat gggcaagcca ttgcgtatgt tgaatcaatt    6180
attgcgtatc atgttttttg ggacttactg ttattgttca ctttatctaa aatatcttaa    6240
ctatttacag gaatccgta cttgagcact tcatagaaaa ggtgcagtgt agaggattct     6300
tctctactca ttatcatcgt ctctctgtgg attatcaaac caatccaaag gtattgtgaa    6360
aagtgtctgc ttcagtttct gggtttgaaa gacttgagaa ctatcaataa taatctgatt    6420
gtttgtgtac attctgaaac ttgtcaaaaa ccgatcagtc ttgaatattt gtttggatag    6480
gtctcacttt gccatatggc atgtcaaata ggagaaggaa tcggtggagt agaagaagtt    6540
acatttctct atagattgac tcctggtgca tgtcctaaaa gttatggagt taacgttgct    6600
cggttagctg gtaagaacac tgaattctct actccatcac ctctactcag ttaaacagaa    6660
gcagtcactc atcaaattgt tttggtttta atctccatag gtcttccaga ttacgtactc    6720
cagagagccg tgataaaatc ccaagaattc gaggctttgt acggtaaaaa ccatagaaaa    6780
accgatcata aattagcagc aatgataaag cagatcatca gcagtgttgc atcagattct    6840
gattactcag cttcaaagga ctcattgtgt gagctacact ccatggccaa tacatttctc    6900
cggttaacca actaatttaa cagctctacg cctttccggt ttgtcgttct tcttgtaact    6960
ctttaaccaa ggtcaatcca cgagcttcgt cgtgtcaaat actaaaacct gagtcagcct    7020
gaaactaaac tcctgagtag agactcagtt ttgaggtgtg ggtttagctt ctgagtcttt    7080
```

<210> SEQ ID NO 48
<211> LENGTH: 1324
<212> TYPE: PRT
<213> ORGANISM: Arabidopsis thaliana

<400> SEQUENCE: 48

```
Met Ala Pro Ser Arg Arg Gln Ile Ser Gly Arg Ser Pro Leu Val Asn
1               5                   10                  15

Gln Gln Arg Gln Ile Thr Ser Phe Phe Gly Lys Ser Ala Ser Ser Ser
            20                  25                  30

Ser Ser Pro Ser Pro Ser Pro Ser Pro Ser Leu Ser Asn Lys Lys Thr
        35                  40                  45

Pro Lys Ser Asn Asn Pro Asn Pro Lys Ser Pro Ser Pro Ser Pro Ser
    50                  55                  60

Pro Pro Lys Lys Thr Pro Lys Leu Asn Pro Asn Ser Ser Asn Leu
65                  70                  75                  80

Pro Ala Arg Ser Pro Ser Pro Gly Pro Asp Thr Pro Ser Pro Val Gln
            85                  90                  95

Ser Lys Phe Lys Lys Pro Leu Leu Val Ile Gly Gln Thr Pro Ser Pro
            100                 105                 110

Pro Gln Ser Val Val Ile Thr Tyr Gly Asp Glu Val Gly Lys Gln
        115                 120                 125

Val Arg Val Tyr Trp Pro Leu Asp Lys Lys Trp Tyr Asp Gly Ser Val
    130                 135                 140
```

```
Thr Phe Tyr Asp Lys Gly Glu Gly Lys His Val Val Glu Tyr Glu Asp
145                 150                 155                 160

Gly Glu Glu Glu Ser Leu Asp Leu Gly Lys Glu Lys Thr Glu Trp Val
                165                 170                 175

Val Gly Glu Lys Ser Gly Asp Arg Phe Asn Arg Leu Lys Arg Gly Ala
            180                 185                 190

Ser Ala Leu Arg Lys Val Val Thr Asp Ser Asp Asp Val Glu Met
        195                 200                 205

Gly Asn Val Glu Glu Asp Lys Ser Asp Gly Asp Ser Ser Asp Glu
    210                 215                 220

Asp Trp Gly Lys Asn Val Gly Lys Glu Val Cys Glu Ser Glu Glu Asp
225                 230                 235                 240

Asp Val Glu Leu Val Asp Glu Asn Glu Met Asp Glu Glu Glu Leu Val
                245                 250                 255

Glu Glu Lys Asp Glu Glu Thr Ser Lys Val Asn Arg Val Ser Lys Thr
            260                 265                 270

Asp Ser Arg Lys Arg Lys Thr Ser Glu Val Thr Lys Ser Gly Gly Glu
        275                 280                 285

Lys Lys Ser Lys Thr Asp Thr Gly Thr Ile Leu Lys Gly Phe Lys Ala
290                 295                 300

Ser Val Val Glu Pro Ala Lys Lys Ile Gly Gln Ala Asp Arg Val Val
305                 310                 315                 320

Lys Gly Leu Glu Asp Asn Val Leu Asp Gly Asp Ala Leu Ala Arg Phe
                325                 330                 335

Gly Ala Arg Asp Ser Glu Lys Phe Arg Phe Leu Gly Val Asp Arg Arg
            340                 345                 350

Asp Ala Lys Arg Arg Arg Pro Thr Asp Glu Asn Tyr Asp Pro Arg Thr
        355                 360                 365

Leu Tyr Leu Pro Pro Asp Phe Val Lys Lys Leu Thr Gly Gly Gln Arg
    370                 375                 380

Gln Trp Trp Glu Phe Lys Ala Lys His Met Asp Lys Val Val Phe Phe
385                 390                 395                 400

Lys Met Gly Lys Phe Tyr Glu Leu Phe Glu Met Asp Ala His Val Gly
                405                 410                 415

Ala Lys Glu Leu Asp Ile Gln Tyr Met Lys Gly Glu Gln Pro His Cys
            420                 425                 430

Gly Phe Pro Glu Lys Asn Phe Ser Val Asn Ile Glu Lys Leu Val Arg
        435                 440                 445

Lys Gly Tyr Arg Val Leu Val Val Glu Gln Thr Glu Thr Pro Asp Gln
    450                 455                 460

Leu Glu Gln Arg Arg Lys Glu Thr Gly Ser Lys Asp Lys Val Val Lys
465                 470                 475                 480

Arg Glu Val Cys Ala Val Val Thr Lys Gly Thr Leu Thr Asp Gly Glu
                485                 490                 495

Met Leu Leu Thr Asn Pro Asp Ala Ser Tyr Leu Met Ala Leu Thr Glu
            500                 505                 510

Gly Gly Glu Ser Leu Thr Asn Pro Thr Ala Glu His Asn Phe Gly Val
        515                 520                 525

Cys Leu Val Asp Val Ala Thr Gln Lys Ile Ile Leu Gly Gln Phe Lys
    530                 535                 540

Asp Asp Gln Asp Cys Ser Ala Leu Ser Cys Leu Leu Ser Glu Met Arg
545                 550                 555                 560

Pro Val Glu Ile Ile Lys Pro Ala Lys Val Leu Ser Tyr Ala Thr Glu
```

```
                    565                 570                 575
Arg Thr Ile Val Arg Gln Thr Arg Asn Pro Leu Val Asn Asn Leu Val
                580                 585                 590

Pro Leu Ser Glu Phe Trp Asp Ser Glu Lys Thr Ile Tyr Glu Val Gly
                595                 600                 605

Ile Ile Tyr Lys Arg Ile Asn Cys Gln Pro Ser Ser Ala Tyr Ser Ser
610                 615                 620

Glu Gly Lys Ile Leu Gly Asp Gly Ser Ser Phe Leu Pro Lys Met Leu
625                 630                 635                 640

Ser Glu Leu Ala Thr Glu Asp Lys Asn Gly Ser Leu Ala Leu Ser Ala
                645                 650                 655

Leu Gly Gly Ala Ile Tyr Tyr Leu Arg Gln Ala Phe Leu Asp Glu Ser
                660                 665                 670

Leu Leu Arg Phe Ala Lys Phe Glu Ser Leu Pro Tyr Cys Asp Phe Ser
                675                 680                 685

Asn Val Asn Glu Lys Gln His Met Val Leu Asp Ala Ala Leu Glu
                690                 695                 700

Asn Leu Glu Ile Phe Glu Asn Ser Arg Asn Gly Gly Tyr Ser Gly Thr
705                 710                 715                 720

Leu Tyr Ala Gln Leu Asn Gln Cys Ile Thr Ala Ser Gly Lys Arg Leu
                725                 730                 735

Leu Lys Thr Trp Leu Ala Arg Pro Leu Tyr Asn Thr Glu Leu Ile Lys
                740                 745                 750

Glu Arg Gln Asp Ala Val Ala Ile Leu Arg Gly Glu Asn Leu Pro Tyr
                755                 760                 765

Ser Leu Glu Phe Arg Lys Ser Leu Ser Arg Leu Pro Asp Met Glu Arg
                770                 775                 780

Leu Ile Ala Arg Met Phe Ser Ser Ile Glu Ala Ser Gly Arg Asn Gly
785                 790                 795                 800

Asp Lys Val Val Leu Tyr Glu Asp Thr Ala Lys Lys Gln Val Gln Glu
                805                 810                 815

Phe Ile Ser Thr Leu Arg Gly Cys Glu Thr Met Ala Glu Ala Cys Ser
                820                 825                 830

Ser Leu Arg Ala Ile Leu Lys His Asp Thr Ser Arg Arg Leu Leu His
                835                 840                 845

Leu Leu Thr Pro Gly Gln Ser Leu Pro Asn Ile Ser Ser Ile Lys
850                 855                 860

Tyr Phe Lys Asp Ala Phe Asp Trp Val Glu Ala His Asn Ser Gly Arg
865                 870                 875                 880

Val Ile Pro His Glu Gly Ala Asp Glu Tyr Asp Cys Ala Cys Lys
                885                 890                 895

Thr Val Glu Glu Phe Glu Ser Ser Leu Lys Lys His Leu Lys Glu Gln
                900                 905                 910

Arg Lys Leu Leu Gly Asp Ala Ser Ile Asn Tyr Val Thr Val Gly Lys
                915                 920                 925

Asp Glu Tyr Leu Leu Glu Val Pro Glu Ser Leu Ser Gly Ser Val Pro
930                 935                 940

His Asp Tyr Glu Leu Cys Ser Ser Lys Lys Gly Val Ser Arg Tyr Trp
945                 950                 955                 960

Thr Pro Thr Ile Lys Lys Leu Leu Lys Glu Leu Ser Gln Ala Lys Ser
                965                 970                 975

Glu Lys Glu Ser Ala Leu Lys Ser Ile Ser Gln Arg Leu Ile Gly Arg
                980                 985                 990
```

```
Phe Cys Glu His Gln Glu Lys Trp Arg Gln Leu Val Ser Ala Thr Ala
        995                 1000                1005

Glu Leu Asp Val Leu Ile Ser Leu Ala Phe Ala Ser Asp Ser Tyr
    1010                1015                1020

Glu Gly Val Arg Cys Arg Pro Val Ile Ser Gly Ser Thr Ser Asp
    1025                1030                1035

Gly Val Pro His Leu Ser Ala Thr Gly Leu Gly His Pro Val Leu
    1040                1045                1050

Arg Gly Asp Ser Leu Gly Arg Gly Ser Phe Val Pro Asn Asn Val
    1055                1060                1065

Lys Ile Gly Gly Ala Glu Lys Ala Ser Phe Ile Leu Leu Thr Gly
    1070                1075                1080

Pro Asn Met Gly Gly Lys Ser Thr Leu Leu Arg Gln Val Cys Leu
    1085                1090                1095

Ala Val Ile Leu Ala Gln Ile Gly Ala Asp Val Pro Ala Glu Thr
    1100                1105                1110

Phe Glu Val Ser Pro Val Asp Lys Ile Cys Val Arg Met Gly Ala
    1115                1120                1125

Lys Asp His Ile Met Ala Gly Gln Ser Thr Phe Leu Thr Glu Leu
    1130                1135                1140

Ser Glu Thr Ala Val Met Leu Thr Ser Ala Thr Arg Asn Ser Leu
    1145                1150                1155

Val Val Leu Asp Glu Leu Gly Arg Gly Thr Ala Thr Ser Asp Gly
    1160                1165                1170

Gln Ala Ile Ala Glu Ser Val Leu Glu His Phe Ile Glu Lys Val
    1175                1180                1185

Gln Cys Arg Gly Phe Phe Ser Thr His Tyr His Arg Leu Ser Val
    1190                1195                1200

Asp Tyr Gln Thr Asn Pro Lys Val Ser Leu Cys His Met Ala Cys
    1205                1210                1215

Gln Ile Gly Glu Gly Ile Gly Gly Val Glu Glu Val Thr Phe Leu
    1220                1225                1230

Tyr Arg Leu Thr Pro Gly Ala Cys Pro Lys Ser Tyr Gly Val Asn
    1235                1240                1245

Val Ala Arg Leu Ala Gly Leu Pro Asp Tyr Val Leu Gln Arg Ala
    1250                1255                1260

Val Ile Lys Ser Gln Glu Phe Glu Ala Leu Tyr Gly Lys Asn His
    1265                1270                1275

Arg Lys Thr Asp His Lys Leu Ala Ala Met Ile Lys Gln Ile Ile
    1280                1285                1290

Ser Ser Val Ala Ser Asp Ser Asp Tyr Ser Ala Ser Lys Asp Ser
    1295                1300                1305

Leu Cys Glu Leu His Ser Met Ala Asn Thr Phe Leu Arg Leu Thr
    1310                1315                1320

Asn

<210> SEQ ID NO 49
<211> LENGTH: 2501
<212> TYPE: DNA
<213> ORGANISM: Oryza sativa

<400> SEQUENCE: 49
cggcacgaga ttttgcagtc tcctctcctc ctccgctcga gcgagtgagt cccgaccacg    60
tcgctgccct cgcctcaccg ccggccaacc gccgtgacga gagatcgagc agggcggggc   120
```

-continued

```
atggacgagc cttcgccgcg cggaggtggg tgcgccgggg agccgccccg catccggagg    180
ttggaggagt cggtggtgaa ccgcatcgcg gcggggaggg tgatccagcg gccgtcgtcg    240
gcggtgaagg agctcatcga aacagcctc gacgctggcg cctccagcgt ctccgttgcg     300
gtgaaggacg gtggcctcaa gctcatccag gtctccgatg acggccatgg catcaggttt    360
gaggatttgg caatattgtg cgaaaggcat actacctcaa agttatctgc atacgaggat    420
ctgcagacca taaaatcgat ggggttcaga ggggaggctt tggctagtat gacttatgtt    480
ggccatgtta ccgtgacaac gataacagaa ggccaattgc acggctacag ggtttcttac    540
agagatggtg taatgagaa tgagcctaag ccttgcgctg cggtgaaagg aactcaagtc     600
atggttgaaa atctatttta caacatggta gcccgcaaga aaacattgca gaactccaat    660
gatgactacc ccaagatcgt agacttcatc agtcggtttg cagtccatca catcaacgtt    720
accttctctt gcagaaagca tggagccaat agagcagatg ttcatagtgc aagtacatcc    780
tcaaggttag atgctatcag gagtgtctat ggggcttctg tcgttcgtga tctcatagaa    840
ataaaggttt catatgagga tgctgcagat tcaatcttca agatggatgg ttacatctca    900
aatgcaaatt atgtggcaaa gaagattaca atgattcttt tcataaatga taggcttgta    960
gactgtactg ctttgaaaag agctattgaa tttgtgtact ctgcaacatt gcctcaagca   1020
tccaaacctt tcatatacat gtccatacat cttccatcag aacacgtgga tgttaatata   1080
cacccaacca agaaagaggt tagccttttg aatcaagagc gtattattga acaataaga    1140 aatgctattg aggaaaaact gatgaattct aatacaacca ggatattcca aactcaggca   1200
ttaaacttat cagggattgc tcaagctaac ccacaaaagg ataaggtttc tgaggccagt   1260
atgggttctg gaacaaaatc tcaaaaaatt cctgtgagcc aaatggtcag aacagatcca   1320
cgcaatccat ctggaagatt gcacacctac tggcacgggc aatcttcaaa tcttgaaaag   1380
aaatttgatc ttgtatctgt aagaaatgtt gtaagatcaa ggagaaacca aaaagatgct   1440
ggtgatttgt caagccgtca tgagctcctt gtggaaatag attctagctt ccatcctggc   1500
cttttggaca ttgtcaagaa ctgcacatat gttggacttg ccgatgaagc ctttgctttg   1560
atacaacaca tacccgctt ataccttgta aatgtggtaa atattagtaa agaacttatg    1620
taccagcaag ctttgtgccg ttttgggaac ttcaatgcta ttcagctcag tgaaccagct   1680
ccacttcagg agttgctggt gatggcactg aaagacgatg aattgatgag tgatgaaaag   1740
gatgatgaga aactggagat tgcagaagta aacactgaga tactaaaaga aaatgctgag   1800
atgattaatg agtactttc tattcacatt gatcaagatg gcaaattgac aagacttcct    1860
gttgtactgg accagtacac ccctgatatg gaccgtcttc cagaatttgt gttggcttta   1920
ggaaatgatg ttacttggga tgacgagaaa gagtgcttca gacagtagc ttctgctgta    1980 ggaaacttct atgcacttca tcccccaatc cttccaaatc catctgggaa tggcattcat   2040
ttatacaaga aaatagaga ttcaatggct gatgaacatg ctgagaatga tctaatatca    2100
gatgaaaatg acgttgatca agaacttctt gcggaagcag aagcagcatg ggcccaacgt   2160
gagtggacca ttcagcatgt cttgtttcca tccatgcgac ttttcctcaa gcccccgaag   2220
tcaatggcaa cagatggaac gtttgtgcag gttgcttcct tggagaaact ctacaagatt   2280
tttgaaaggt gttagctcat aagtgagaaa atgaaggcag agtaagatca tgattcatgg   2340 agtgttttg aaaatgtgta taatttcacc gtattatgta ctttgatagt gtctgtagaa    2400
actgaagaaa gaaagatggc tttacttctg aattgaaagt taacgatgcc agcaattgta   2460
tattctgatc aaccaaaaaa aaaaaaaaaa aaaaaaaaa a                         2501
```

<210> SEQ ID NO 50
<211> LENGTH: 724
<212> TYPE: PRT
<213> ORGANISM: Oryza sativa

<400> SEQUENCE: 50

Met Asp Glu Pro Ser Pro Arg Gly Gly Gly Cys Ala Gly Glu Pro Pro
1               5                   10                  15

Arg Ile Arg Arg Leu Glu Glu Ser Val Val Asn Arg Ile Ala Ala Gly
            20                  25                  30

Glu Val Ile Gln Arg Pro Ser Ser Ala Val Lys Glu Leu Ile Glu Asn
        35                  40                  45

Ser Leu Asp Ala Gly Ala Ser Ser Val Ser Val Ala Val Lys Asp Gly
    50                  55                  60

Gly Leu Lys Leu Ile Gln Val Ser Asp Asp Gly His Gly Ile Arg Phe
65                  70                  75                  80

Glu Asp Leu Ala Ile Leu Cys Glu Arg His Thr Thr Ser Lys Leu Ser
                85                  90                  95

Ala Tyr Glu Asp Leu Gln Thr Ile Lys Ser Met Gly Phe Arg Gly Glu
            100                 105                 110

Ala Leu Ala Ser Met Thr Tyr Val Gly His Val Thr Val Thr Thr Ile
        115                 120                 125

Thr Glu Gly Gln Leu His Gly Tyr Arg Val Ser Tyr Arg Asp Gly Val
    130                 135                 140

Met Glu Asn Glu Pro Lys Pro Cys Ala Ala Val Lys Gly Thr Gln Val
145                 150                 155                 160

Met Val Glu Asn Leu Phe Tyr Asn Met Val Ala Arg Lys Lys Thr Leu
                165                 170                 175

Gln Asn Ser Asn Asp Asp Tyr Pro Lys Ile Val Asp Phe Ile Ser Arg
            180                 185                 190

Phe Ala Val His His Ile Asn Val Thr Phe Ser Cys Arg Lys His Gly
        195                 200                 205

Ala Asn Arg Ala Asp Val His Ser Ala Ser Thr Ser Ser Arg Leu Asp
    210                 215                 220

Ala Ile Arg Ser Val Tyr Gly Ala Ser Val Val Arg Asp Leu Ile Glu
225                 230                 235                 240

Ile Lys Val Ser Tyr Glu Asp Ala Ala Asp Ser Ile Phe Lys Met Asp
                245                 250                 255

Gly Tyr Ile Ser Asn Ala Asn Tyr Val Ala Lys Lys Ile Thr Met Ile
            260                 265                 270

Leu Phe Ile Asn Asp Arg Leu Val Asp Cys Thr Ala Leu Lys Arg Ala
        275                 280                 285

Ile Glu Phe Val Tyr Ser Ala Thr Leu Pro Gln Ala Ser Lys Pro Phe
    290                 295                 300

Ile Tyr Met Ser Ile His Leu Pro Ser Glu His Val Asp Val Asn Ile
305                 310                 315                 320

His Pro Thr Lys Lys Glu Val Ser Leu Leu Asn Gln Glu Arg Ile Ile
                325                 330                 335

Glu Thr Ile Arg Asn Ala Ile Glu Glu Lys Leu Met Asn Ser Asn Thr
            340                 345                 350

Thr Arg Ile Phe Gln Thr Gln Ala Leu Asn Leu Ser Gly Ile Ala Gln
        355                 360                 365

Ala Asn Pro Gln Lys Asp Lys Val Ser Glu Ala Ser Met Gly Ser Gly
    370                 375                 380

-continued

```
Thr Lys Ser Gln Lys Ile Pro Val Ser Gln Met Val Arg Thr Asp Pro
385                 390                 395                 400
Arg Asn Pro Ser Gly Arg Leu His Thr Tyr Trp His Gly Gln Ser Ser
                405                 410                 415
Asn Leu Glu Lys Lys Phe Asp Leu Val Ser Val Arg Asn Val Val Arg
            420                 425                 430
Ser Arg Arg Asn Gln Lys Asp Ala Gly Asp Leu Ser Ser Arg His Glu
        435                 440                 445
Leu Leu Val Glu Ile Asp Ser Ser Phe His Pro Gly Leu Leu Asp Ile
    450                 455                 460
Val Lys Asn Cys Thr Tyr Val Gly Leu Ala Asp Glu Ala Phe Ala Leu
465                 470                 475                 480
Ile Gln His Asn Thr Arg Leu Tyr Leu Val Asn Val Val Asn Ile Ser
                485                 490                 495
Lys Glu Leu Met Tyr Gln Gln Ala Leu Cys Arg Phe Gly Asn Phe Asn
            500                 505                 510
Ala Ile Gln Leu Ser Glu Pro Ala Pro Leu Gln Glu Leu Leu Val Met
        515                 520                 525
Ala Leu Lys Asp Asp Glu Leu Met Ser Asp Glu Lys Asp Asp Glu Lys
    530                 535                 540
Leu Glu Ile Ala Glu Val Asn Thr Glu Ile Leu Lys Glu Asn Ala Glu
545                 550                 555                 560
Met Ile Asn Glu Tyr Phe Ser Ile His Ile Asp Gln Asp Gly Lys Leu
                565                 570                 575
Thr Arg Leu Pro Val Val Leu Asp Gln Tyr Thr Pro Asp Met Asp Arg
            580                 585                 590
Leu Pro Glu Phe Val Leu Ala Leu Gly Asn Asp Val Thr Trp Asp Asp
        595                 600                 605
Glu Lys Glu Cys Phe Arg Thr Val Ala Ser Ala Val Gly Asn Phe Tyr
    610                 615                 620
Ala Leu His Pro Pro Ile Leu Pro Asn Pro Ser Gly Asn Gly Ile His
625                 630                 635                 640
Leu Tyr Lys Lys Asn Arg Asp Ser Met Ala Asp Glu His Ala Glu Asn
                645                 650                 655
Asp Leu Ile Ser Asp Glu Asn Asp Val Asp Gln Glu Leu Leu Ala Glu
            660                 665                 670
Ala Glu Ala Ala Trp Ala Gln Arg Glu Trp Thr Ile Gln His Val Leu
        675                 680                 685
Phe Pro Ser Met Arg Leu Phe Leu Lys Pro Pro Lys Ser Met Ala Thr
    690                 695                 700
Asp Gly Thr Phe Val Gln Val Ala Ser Leu Glu Lys Leu Tyr Lys Ile
705                 710                 715                 720
Phe Glu Arg Cys
```

METHODS OF GENERATING HIGH-PRODUCTION OF ANTIBODIES FROM HYBRIDOMAS CREATED BY IN VITRO IMMUNIZATION

CROSS-REFERENCE TO RELATED APPLICATIONS

This is a divisional of U.S. application Ser. No. 10/714,228, filed Nov. 14, 2003, which claims the benefit of U.S. Provisional Application No. 60/427,165 filed Nov. 15, 2002 and U.S. Provisional Application No. 60/501,650 filed Sep. 10, 2003. The disclosures of each of these applications are hereby incorporated by reference in their entirety.

FIELD OF THE INVENTION

The invention relates to the generation of hybridoma cells that produce high-affinity antibodies in high titers. More specifically, the invention relates to the use of an in vitro immunization method in conjunction with hybridoma technology using dominant negative mismatch repair genes or chemical inhibitors of mismatch repair to produce high titers of antigen specific antibodies of the IgG subclass, that bind to the antigen with high affinity.

BACKGROUND OF THE RELATED ART

The use of antibodies to block the activity of foreign and/or endogenous polypeptides provides an effective and selective strategy for treating the underlying cause of disease. In particular is the use of monoclonal antibodies (MAb) as effective therapeutics such as the FDA approved ReoPro (Glaser, (1996) *Nat. Biotechnol.* 14:1216-1217), an anti-platelet MAb from Centocor; Herceptin (Weiner, (1999) *Semin. Oncol.* 26:43-51), an anti-Her2/neu MAb from Genentech; and Synagis (SaezLlorens, et al. (1998) *Pediat. Infect. Dis. J.* 17:787-791), an anti-respiratory syncytial virus MAb produced by Medimmune.

Standard methods for generating MAbs against candidate protein targets are known by those skilled in the art. Briefly, rodents such as mice or rats are injected with a purified antigen in the presence of adjuvant to generate an immune response (Shield, et al. (1996) *Am. J. Kidney Dis.* 27: 855-864). Rodents with positive immune sera are sacrificed and splenocytes are isolated. Isolated splenocytes are fused to melanomas to produce immortalized cell lines that are then screened for antibody production. Positive lines are isolated and characterized for antibody production. The direct use of rodent MAbs as human therapeutic agents were confounded by the fact that human anti-rodent antibody (HARA) responses occurred in a significant number of patients treated with the rodent-derived antibody (Khazaeli, et al., (1994) *Immunother.* 15:42-52). In order to circumvent the problem of HARA, the grafting of the complementarity determining regions (CDRs), which are the critical motifs found within the heavy and light chain variable regions of the immunoglobulin (Ig) subunits making up the antigen binding domain, onto a human antibody backbone found these chimeric molecules are able to retain their binding activity to antigen while lacking the HARA response (Emery and Harris, "Strategies for humanizing antibodies" In: ANTIBODY ENGINEERING, C. A. K. Borrebaeck (Ed.) Oxford University Press, NY, 1995. pp. 159-183. A common problem that exists during the "humanization" of rodent-derived MAbs (referred to hereafter as HAb) is the loss of binding affinity due to conformational changes in the three-dimensional structure of the CDR domain upon grafting onto the human Ig backbone (U.S. Pat. No. 5,530,101 to Queen et al.). To overcome this problem, additional HAb vectors are usually needed to be engineered by inserting or deleting additional amino acid residues within the framework region and/or within the CDR coding region itself in order to recreate high affinity HAbs (U.S. Pat. No. 5,530,101 to Queen et al.). This process is a very time consuming procedure that involves the use of expensive computer modeling programs to predict changes that may lead to a high affinity HAb. In some instances the affinity of the HAb is never restored to that of the MAb, rendering them of little therapeutic use.

Another problem that exists in antibody engineering is the generation of stable, high yielding producer cell lines that is required for manufacturing of the molecule for clinical materials. Several strategies have been adopted in standard practice by those skilled in the art to circumvent this problem. One method is the use of Chinese Hamster Ovary (CHO) cells transfected with exogenous Ig fusion genes containing the grafted human light and heavy chains to produce whole antibodies or single chain antibodies, which are a chimeric molecule containing both light and heavy chains that form an antigen-binding polypeptide (Reff, M. E. (1993) *Curr. Opin. Biotechnol.* 4:573-576). Another method employs the use of human lymphocytes derived from transgenic mice containing a human grafted immune system or transgenic mice containing a human Ig gene repertoire. Yet another method employs the use of monkeys to produce primate MAbs, which have been reported to lack a human anti-monkey response (Neuberger and Gruggermann (1997) *Nature* 386:25-26). In all cases, the generation of a cell line that is capable of generating sufficient amounts of high affinity antibody poses a major limitation for producing sufficient materials for clinical studies. Because of these limitations, the utility of other recombinant systems such as plants are currently being explored as systems that will lead to the stable, high-level production of humanized antibodies (Fiedler and Conrad (1995) *Bio/Technology* 13:1090-1093).

One strategy to overcome the problem of human reactions against foreign antibodies is to stimulate human immunoglobulin-producing cells in vitro. Various attempts to stimulate human antibody production in vitro typically have resulted in low affinity antibodies of the IgM subclass (Zafiropoulos et al. (1997) *J. Immunological Methods* 200:181-190).

A method for generating diverse antibody sequences within the variable domain that results in HAbs and MAbs with high binding affinities to antigens would be useful for the creation of more potent therapeutic and diagnostic reagents respectively. Moreover, the generation of randomly altered nucleotide and polypeptide residues throughout an entire antibody molecule will result in new reagents that are less antigenic and/or have beneficial pharmacokinetic properties. The invention described herein is directed to the use of random genetic mutation throughout an antibody structure in vitro by blocking the endogenous mismatch repair (MMR) activity of a host cell producing immunoglobulins that encode biochemically active antibodies. The invention also relates to methods for repeated in vitro genetic alterations and selection for antibodies with enhanced binding and pharmacokinetic profiles.

In addition, the ability to develop genetically altered host cells that are capable of secreting increased amounts of antibody also will provide a valuable method for creating cell hosts for product development. The invention described herein is further directed to the creation of genetically altered cell hosts with increased antibody production via the blockade of MMR. The invention facilitates the generation of high affinity antibodies and the production of cell lines with elevated levels of antibody production derived from hybridoma cells. The invention described herein provides methods for generating antigen-specific monoclonal antibodies (mAbs). Other advantages of the present invention are described in the examples and figures described herein.

SUMMARY OF THE INVENTION

The invention provides methods for producing hybridoma cells producing high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

In some embodiments, the dominant negative allele of a mismatch repair gene comprises a truncation mutation of the PMS2 gene (e.g., a PMS2-134 gene). In some embodiments of the method of the invention, antibodies are screened using an ELISA-based assay or other assays that can measure antibody-antigen binding. In some embodiments, the screening assays screen for hypermutated hybridomas that produce higher affinity antibodies than those produced by the parental hybridomas. In other embodiments, the screening assays screen for hypermutated hybridomas that produce antibodies in higher titers than the parental hybridomas.

In some embodiments of the method of the invention, the method further comprises inactivation of the dominant negative allele of the mismatch repair gene, thereby stabilizing the genome of said hypermutated hybridoma.

In some embodiments of the method of the invention, the dominant negative mismatch repair gene is introduced into the hybridoma cell after the fusion of said myeloma with the immunoglobulin-producing cells. In other embodiments, the dominant negative mismatch repair gene is introduced into the myeloma cell prior to the fusion with the immunoglobulin-producing cells.

The invention also comprises antibodies produced by the hybridoma cells.

The invention also comprises methods for producing hybridoma cells that produce high titers of antibodies from in vitro immunized immunoglobulin-producing cells comprising: (a) combining donor blood cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by the parental hybridoma cells.

In some embodiments, the dominant negative allele of a mismatch repair gene comprises a truncation mutation of the PMS2 gene (e.g., a PMS2-134 gene). In some embodiments of the method of the invention, antibodies are screened using an ELISA-based assay. In some embodiments, the screening assays screen for hypermutated hybridomas that produce higher affinity antibodies than those produced by the parental hybridomas. In other embodiments, the screening assays screen for hypermutated hybridomas that produce antibodies in higher titers than the parental hybridomas.

In some embodiments of the method of the invention, the method further comprising inactivation of the dominant negative allele of the mismatch repair gene, thereby stabilizing the genome of said hypermutated hybridoma.

In some embodiments of the method of the invention, the dominant negative mismatch repair gene is introduced into the hybridoma cell after the fusion of said myeloma with the immunoglobulin-producing cells. In other embodiments, the dominant negative mismatch repair gene is introduced into the myeloma cell prior to the fusion with the immunoglobulin-producing cells.

In some embodiments of the method of the invention, the dominant negative allele of the mismatch repair gene is subsequently inactivated in order to restabilize the genome of the cell.

The dominant negative allele of the mismatch repair gene may be introduced into the myeloma cell prior to fusion with the immunoglobulin producing cells. Thus, the resulting hybridoma cells express the same dominant negative allele of the mismatch repair gene as the myeloma cells. Alternatively, the dominant negative allele of the mismatch repair gene may be introduced into the hybridoma cells.

The invention also comprises antibodies produced by the hybridoma cells.

The invention further provides recombinant myeloma cells comprising a polynucleotide sequence encoding a dominant negative mismatch repair protein. The dominant negative mismatch repair protein may be a dominant negative form of, for example, a PMS2, PMS1, PMSR3, PMSR2, PMSR6, MLH1, GTBP, MSH3, MSH2, MLH3, or MSH1, and PMSR proteins encoded by homologs of the PMSR genes as described in Nicolaides et al. (1995) *Genomics* 30:195-206 and Horii et al. (1994) *Biochem. Biophys. Res. Commun.* 204:1257-1264. In some embodiments, the recombinant myeloma cell expresses a polynucleotide encoding a dominant negative allele of a PMS2 gene (e.g., a truncation mutation of the PMS2 gene, such as the PMS2-134 gene).

In some embodiments, the recombinant myeloma cell is a human cell. In other embodiments, the recombinant myeloma cell does not express immunoglobulin genes and/or Epstein-Barr virus. In other embodiments, the myeloma cells are HAT sensitive.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell, wherein said mammalian expression cell expresses a dominant negative allele of a mismatch repair gene; (e) performing a screen for mammalian expression cells that secrete antibodies with higher affinity for antigen as compared to antibodies produced from said hybridoma cells;

thereby producing mammalian expression cells that produce high titers of high-affinity antibodies from in vitro immunized immunoglobulin-producing cells.

In some embodiments, the dominant negative allele of a mismatch repair gene is introduced into said mammalian expression cell prior to introduction of the immunoglobulin genes. In other embodiments, the dominant negative allele of a mismatch repair gene is introduced into said mammalian expression cell after introduction of said immunoglobulin genes. In other embodiments, the dominant negative allele of a mismatch repair gene is introduced into the mammalian expression cell with the immunoglobulin genes simultaneously.

The invention also comprises antibodies produced by the mammalian expression cells.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells, wherein said hybridoma cells express a dominant negative allele of a mismatch repair gene; (c) incubating said parental hybridoma cells to allow for mutagenesis, thereby forming hypermutated hybridoma cells; (d) performing a screen for binding of antibodies to antigen for antibodies produced from said hypermutated hybridoma cells; (e) selecting hypermutated hybridoma cells that produce antibodies with greater affinity for said antigen than antibodies produced by said parental hybridoma cells; (f) cloning immunoglobulin genes from said hybridoma into a mammalian expression cell; thereby producing mammalian expression cells that produce high titers of high-affinity antibodies from in vitro immunized human immunoglobulin-producing cells.

In some embodiments, the dominant negative allele of a mismatch repair gene is present in the myeloma cell prior to cell fusion. In other embodiments, the dominant negative allele of the mismatch repair gene is introduced into the hybridoma cell after cell fusion.

The invention also comprises antibodies produced by the mammalian expression cells.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form hybridoma cells; (c) performing a screen for binding of antibodies produced from the hybridoma cells to antigen; (d) cloning immunoglobulin genes from the hybridoma into a parental mammalian expression cell, wherein the mammalian expression cell expresses a dominant negative allele of a mismatch repair gene; (e) incubating the parental mammalian expression cell to allow for mutagenesis, thereby forming hypermutated mammalian expression cells; (f) performing a screen of hypermutable mammalian expression cells that secrete antibodies with higher affinity for antigen as compared to antibodies produced from the hybridoma cells; and (g) performing a screen of hypermutable mammalian expression cells that secrete higher titers of antibodies than parental mammalian expression cells; thereby producing mammalian expression cells that produce high titers of high-affinity antibodies from in vitro immunized immunoglobulin-producing cells.

In some embodiments, the dominant negative allele of a mismatch repair gene is introduced into said mammalian expression cell prior to introduction of the immunoglobulin genes. In other embodiments, the dominant negative allele of a mismatch repair gene is introduced into said mammalian expression cell after introduction of said immunoglobulin genes. In other embodiments, the dominant negative allele of a mismatch repair gene is introduced into the mammalian expression cell with the immunoglobulin genes simultaneously.

The invention also provides antibodies produced by the mammalian expression cells.

The invention also provides recombinant, hypermutable mammalian expression cells comprising a polynucleotide sequence encoding a dominant negative mismatch repair protein.

The mismatch repair gene may be a dominant negative mismatch repair gene, including, but not limited to a dominant negative form of PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264. A non-limiting example includes a dominant negative truncation mutant of PMS2 (e.g., a PMS2-134 gene).

The invention also provides methods for producing hybridoma cells producing high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen for antigen binding for antibodies produced from the hypermutated hybridoma cells; and (e) selecting hypermutated hybridoma cells that produce antibodies with greater affinity for the antigen than antibodies produced by said parental hybridoma cells; thereby producing hybridoma cells producing high-affinity antibodies.

The invention also comprises antibodies produced by the hybridoma cells.

The invention also provides methods for producing hybridoma cells that produce high titers of antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by said parental hybridoma cells; thereby producing hybridoma cells producing high titers of antibodies.

In some embodiments of the method of the invention, the hypermutated hybridoma cells also are screened for the production of higher titers of antibodies than that produced by the parental hybridomas. The screening may be using an ELISA-based assay, or any other means to measure antibody-antigen binding.

The invention also comprises antibodies produced by the hybridoma cells.

The invention also provides methods for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form hybridoma cells; (c) performing a screen for antigen binding of antibodies produced from the hybridoma cells; (d) cloning immunoglobulin genes from the hybridoma cells into a mammalian expression cell; (e) incubating the mammalian expression cell in the presence of at least one chemical inhibitor of mismatch repair; (f) performing a screen for mammalian expression cells that secrete antibodies with higher affinity for antigen as compared to antibodies produced from the hybridoma cells; thereby producing mammalian expression cells that produce high titers of high-affinity antibodies from in vitro immunized immunoglobulin-producing cells.

In some embodiments of the method of the invention the method may further comprise the removal of the chemical inhibitor from the hypermutated mammalian expression cells, thereby stabilizing the genome of said hypermutated mammalian expression cells.

The invention also comprises antibodies produced by the mammalian expression cells The invention also provides methods for producing mammalian expression cells that produce high titers of high affinity antibodies to a selected antigen from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form hybridoma cells; (c) incubating the hybridoma cells in the presence of at least one chemical inhibitor of mismatch repair to form hypermutated hybridoma cells; (d) performing a screen for antigen binding for antibodies produced from the hypermutated hybridoma cells; (e) selecting hypermutated hybridoma cells that produce antibodies with greater affinity for the antigen than antibodies produced by the parental hybridoma cells; (f) cloning immunoglobulin genes from the hypermutated hybridoma cells into a mammalian expression cell, thereby forming parental mammalian expression cells; thereby producing mammalian expression cells that produce high titers of high-affinity antibodies from in vitro immunized immunoglobulin-producing cells.

In some embodiments, the parental mammalian expression cell is further incubated in the presence of at least one chemical inhibitor of mismatch repair, thereby forming a hypermutated mammalian expression cell; and the hypermutated mammalian expression cells are screened for higher production of antibodies than that of the parental mammalian expression cells.

In some embodiments of the method of the invention the method may further comprise the removal of the chemical inhibitor from the hypermutated hybridoma and/or hypermutated mammalian expression cells, thereby stabilizing the genome of said hypermutated hybridoma cells and/or hypermutated mammalian expression cells.

The invention also comprises antibodies produced by the mammalian expression cells.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell; (e) incubating said mammalian expression cell in the presence of at least one chemical inhibitor of mismatch repair, thereby forming a hypermutated mammalian expression cell; (f) performing a screen for hypermutated mammalian expression cells that secrete antibodies with higher affinity for antigen as compared to antibodies produced from said parental mammalian expression cells; and (g) performing a second screen for hypermutated mammalian expression cells that produce higher titers of antibodies than that produced by parental mammalian expression cells; thereby producing mammalian expression cells that produce high titers of high-affinity antibodies from in vitro immunized immunoglobulin-producing cells.

In some embodiments of the method of the invention the method may further comprise the removal of the chemical inhibitor from the hypermutated hybridoma and/or hypermutated mammalian expression cells, thereby stabilizing the genome of said hypermutated hybridoma cells and/or hypermutated mammalian expression cells.

The invention also comprises antibodies produced by the mammalian expression cells.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; (g) selecting hypermutated hybridoma cells that produce antibodies in higher titers than produced by the parental hybridoma cells; thereby producing hybridoma cells producing high titers of high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; (g) selecting hypermutated hybridoma cells that produce antibodies in higher titers than produced by the parental hybridoma cells; thereby producing hybridoma cells producing high titers of high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing mammalian expression cells that produce high-affinity antibodies in high titers from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) cloning immunoglobulin genes from said hypermutated hybridoma into a mammalian expression cell; thereby producing a mammalian expression cell that produces high titers of high-affinity antibodies in high titer from in vitro immunized immunoglobulin-producing cells.

In some embodiments, the parental mammalian expression cell is further incubated in the presence of at least one chemical inhibitor of mismatch repair, thereby forming a hypermutated mammalian expression cell; and the hypermutated mammalian expression cells are screened for higher production of antibodies than that of the parental mammalian expression cells.

In some embodiments of the method of the invention the method may further comprise the removal of the chemical inhibitor from the hypermutated mammalian expression cells, thereby stabilizing the genome of said hypermutated mammalian expression cells.

The invention also comprises antibodies produced by the mammalian expression cells.

In another embodiment, the invention comprises a method for producing mammalian expression cells that produce high-affinity antibodies in high titer from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; and (f) cloning immunoglobulin genes from said hypermutated hybridoma cell into a mammalian expression cell; thereby producing mammalian expression cells that produce high titers of high-affinity antibodies from in vitro immunized immunoglobulin-producing cells.

In some embodiments, the parental mammalian expression cell is further incubated in the presence of at least one chemical inhibitor of mismatch repair, thereby forming a hypermutated mammalian expression cell; and the hypermutated mammalian expression cells are screened for higher production of antibodies than that of the parental mammalian expression cells.

In some embodiments of the method of the invention the method may further comprise the removal of the chemical inhibitor from the hypermutated mammalian expression cells, thereby stabilizing the genome of said hypermutated mammalian expression cells.

The invention also comprises antibodies produced by the hybridoma cells.

In some embodiments of the methods of the invention, the immunoglobulin-producing cells are mammalian cells, including but not limited to, mouse cells, rat cells, goat cells, cow cells, horse cells, dog cells, cat cells, rabbit cells, bird cells, monkey cells and human cells. In preferred embodiments, the cells are human cells.

In some embodiments the dominant negative allele of a mismatch repair gene is a dominant negative allele of PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264. However, the mismatch repair genes are not limit to these examples.

In some embodiments of the method of the invention, the immunogenic antigen is conjugated to a mitogenic polypeptide comprising at least a portion of a polypeptide including, but not limited to tetanus toxoid, ovalbumin, bovine serum albumen, thyroglobulin, diptheria toxoid, BCG, and cholera toxin. In some embodiments, the antigen is generated by denaturing the mature protein.

In some embodiments of the method of the invention, the antibodies produced have an affinity of at least about $1\times10^7$ $M^{-1}$. In other embodiments, the antibodies have an affinity of at least about $1\times10^8$ $M^{-1}$. In other embodiments, the antibodies have an affinity of at least about $1\times10^9$ $M^{-1}$. In other embodiments, the antibodies have an affinity of at least about $1\times10^{10}$ $M^{-1}$. In other embodiments, the antibodies have an affinity of at least about $1\times10^{11}$ $M^{-1}$. In other embodiments, the antibodies have an affinity of at least about $1\times10^{12}$ $M^{-1}$. In other embodiments, the antibodies have an affinity of at least about $1\times10^{13}$ $M^{-1}$. In other embodiments, the antibodies have an affinity of at least about $1\times10^{14}$ $M^{-1}$.

In some embodiments, the antibodies are produced in a higher titer than the parental cell lines, such as in an amount of at least about 1.5 fold higher than the parental cell line. In other embodiments, the titer is at least about 1.5-3 fold higher than the parental cell line. In other embodiments, the titer is at least about 3-5 fold higher than the parental cell line. In other embodiments, the titer is at least about 5-7 fold higher than the parental cell line. In other embodiments, the titer is at least about 7-9 fold higher than the parental cell line. In other embodiments, the titer is at least about 9-10 fold higher than the parental cell line.

In some embodiments of the method of the invention, mutation rates are further enhanced by incubating the hybridoma cells with a chemical mutagen, such as, but not limited to N-ethyl-N-nitrosourea, N-methyl-N-nitrosourea, procarbazine hydrochloride, chlorambucil, cyclophosphamide, methyl methanesulfonate, ethyl methanesulfonate, diethyl sulfate, acrylamide monomer, triethylene melamin, melphalan, nitrogen mustard, vincristine, dimethylnitrosamine, N-methyl-N'-nitro-nitrosoguanidine, 7,12 dimethylbenz (a) anthracene, ethylene oxide, hexamethylphosphoramide, and bisulfan.

The chemical inhibitors of mismatch repair used in certain embodiments of the methods of the invention include, but are not limited to, at least one of an anthracene, an ATPase inhibitor, a nuclease inhibitor, an RNA interference molecule, a polymerase inhibitor and an antisense oligonucleotide that specifically hybridizes to a nucleotide encoding a mismatch repair protein. In some embodiments, the chemical inhibitor is an anthracene having the formula:

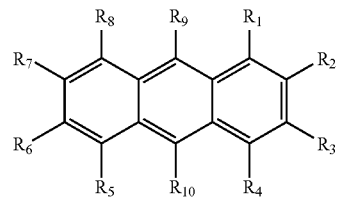

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups; wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups. In certain embodiments, $R_5$ and $R_6$ are hydrogen. In other embodiments, $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl. Non-limiting examples of the anthracenes include 1,2-dimethylanthracene, 9,10-dimethylanthracene, 7,8-dimethylanthracene, 9,10-duphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolylanthracene.

The chemical inhibitor may be introduced into the growth medium of the cells. In some embodiments, the chemical inhibitor may be withdrawn from the hypermutated hybridoma cells in order to re-stabilize the genome of the cells.

The invention also comprises a method for in vitro production of antigen-specific immunoglobulin-producing cells comprising: (a) isolating donor cells from an animal; (b) treating said cells with L-leucyl-L-leucine methy ester hydrobromide; (c) incubating said donor cells with an immunogenic antigen in vitro, at 25-37° C., 5-10% $CO_2$, in medium supplemented with 5-15% serum, and a growth promoting cytokine for 4 days; (d) washing said cells in medium; and (e) culturing said cells in medium supplemented with 5-15% serum an additional 8 days; thereby stimulating the production of antigen-specific immunoglobulin-producing cells.

In some embodiments, the immunoglobulin-producing cells are human cells.

In some embodiments of the method of the invention, the immunogenic antigen is conjugated to a mitogenic polypeptide comprising at least a portion of a polypeptide including, but not limited to tetanus toxoid, ovalbumin, bovine serum albumen, thyroglobulin, diptheria toxoid, BCG, and cholera toxin. In some embodiments, the antigen is generated by denaturing the mature protein.

In some embodiments of the method of the invention, the antibodies produced have an affinity of at least about $1\times10^7$ $M^{-1}$. In other embodiments, the antibodies have an affinity of at least about $1\times10^8$ $M^{-1}$. In other embodiments, the antibodies have an affinity of at least about $1\times10^9$ $M^{-1}$. In other embodiments, the antibodies have an affinity of at least about $1\times10^{10}$ $M^{-1}$. In other embodiments, the antibodies have an affinity of at least about $1\times10^{11}$ $M^{-1}$. In other embodiments, the antibodies have an affinity of at least about $1\times10^{12}$ $M^{-1}$. In other embodiments, the antibodies have an affinity of at least about $1\times10^{13}$ $M^{-1}$. In other embodiments, the antibodies have an affinity of at least about $1\times10^{14}$ $M^{-1}$.

In some embodiments, the antibodies are produced in a higher titer than the parental cell lines, such as in an amount of at least about 1.5 fold higher than the parental cell line. In other embodiments, the titer is at least about 1.5-3 fold higher than the parental cell line. In other embodiments, the titer is at least about 3-5 fold higher than the parental cell line. In other embodiments, the titer is at least about 5-7 fold higher than the parental cell line. In other embodiments, the titer is at least about 7-9 fold higher than the parental cell line. In other embodiments, the titer is at least about 9-10 fold higher than the parental cell line.

In some embodiments of the method of the invention, mutation rates are further enhanced by incubating the hybridoma cells and/or mammalian expression cells with a chemical mutagen, such as, but not limited to N-ethyl-N-nitrosourea, N-methyl-N-nitrosourea, procarbazine hydrochloride, chlorambucil, cyclophosphamide, methyl methanesulfonate, ethyl methanesulfonate, diethyl sulfate, acrylamide monomer, triethylene melamin, melphalan, nitrogen mustard, vincristine, dimethylnitrosamine, N-methyl-N'-nitro-nitrosoguanidine, 7,12 dimethylbenz (a) anthracene, ethylene oxide, hexamethylphosphoramide, and bisulfan.

The mammalian expression cells used in the methods of the invention may include, but are not limited to, Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK$^{31}$ cells, mouse sertoli cells, human cervical carcinoma cells, buffalo rat liver cells, human lung cells, human liver cells, mouse mammary tumor cells, TRI cells, MRC 5 cells, and FS4 cells.

These and other embodiments are described more fully in the next section and include certain non-limiting examples.

DETAILED DESCRIPTION OF THE INVENTION

Figure 1:
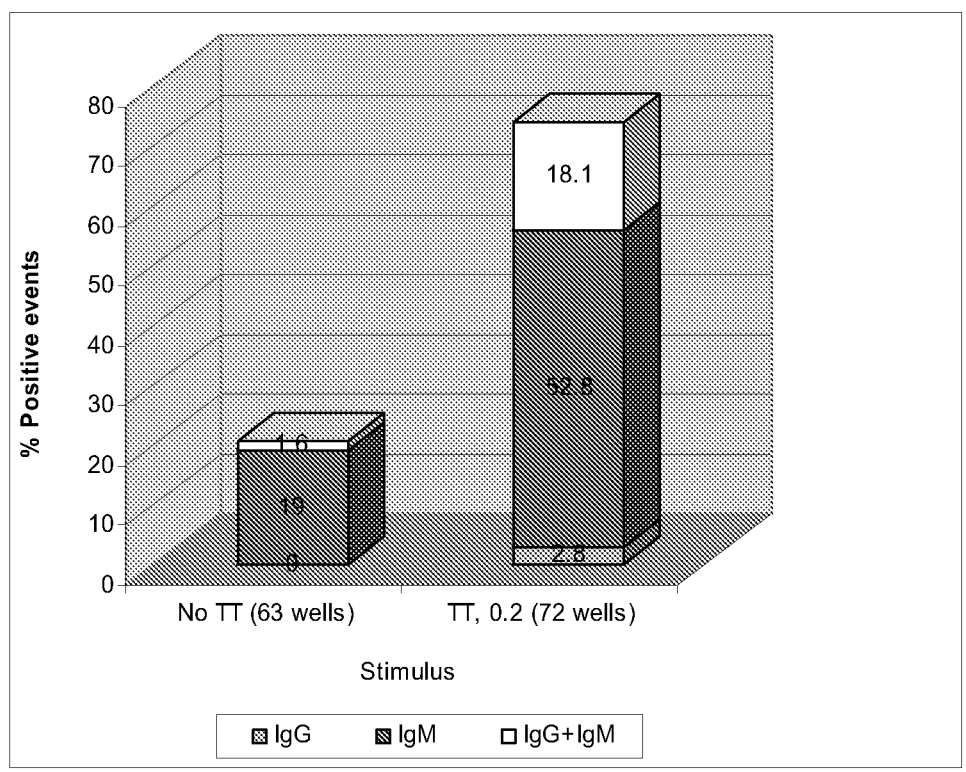
FIG. 1 shows the immune response of PBMCs to antigen stimulation. PBMCs were cultured in the presence or absence of TT for 4 days then washed with medium and cultured in the presence or absence of TT for an additional eight days. Culture supernates were collected and tested for the presence of antibody reactive to TT. Antibodies bound to TT pre-coated on the solid phase were detected with HRP-labeled goat anti-human IgG, or HRP-labeled goat anti-human IgM.

The referenced patents, patent applications, and scientific literature, including accession numbers to GenBank database sequences, referred to herein are hereby incorporated by reference in their entirety. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include, but are not limited to Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

The invention provides various embodiments of a method for producing antibody-producing cells and antibodies from in vitro immunized cells with high affinity, and/or increased production. In some embodiments, the cells that produce the antibodies are hybridoma cells, formed by fusing myeloma cells with the lymphoid cells that have been immunized against an antigen in vitro. In other embodiments, the cells that produce the antibodies are mammalian cells that have been transfected with immunoglobulin genes cloned from lymphoid cells that have been immunized against an antigen in vitro. In some embodiments, the method employs both hybridoma cells and mammalian cells. Some basic embodiments of the method of the invention may be described as follows.

In one embodiment, the invention provides a method for generating hybridoma cells producing high-affinity antibodies from in vitro immunized, immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with greater affinity for the antigen than antibodies produced by the parental hybridoma cells; thereby producing hybridoma cells producing high-affinity antibodies.

In another embodiment, the invention provides methods of producing hybridoma cells that produce high titers of antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by the parental hybridoma cells; thereby producing hybridoma cells that produce high titers of antibodies.

In another embodiment, the invention provides a method for producing hybridoma cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell, wherein said mammalian expression cell expresses a dominant negative allele of a mismatch repair gene; and (e) performing a screen for mammalian expression cells that secrete antibodies with higher affinity for antigen as compared to antibodies produced from said hybridoma cells; thereby producing hybridoma cells that produce high titers of high-affinity antibodies from in vitro immunized immunoglobulin-producing cells.

In another embodiment, the invention provides a method for producing mammalian expression cells that produce high titers of high-affinity antibodies from in vitro immunized immunoglobulin-producing cells are produced by: (a) combining donor cells comprising immunoglobulin-producing cells with an immunogenic antigen in vitro; (b) fusing said immunoglobulin-producing cells with myeloma cells to form hybridoma cells, wherein said hybridoma cells express a dominant negative allele of a mismatch repair gene; (c) incubating said parental hybridoma cells to allow for mutagenesis, thereby forming hypermutated hybridoma cells; (d) performing a screen for binding of antibodies to antigen for antibodies produced from said hypermutated hybridoma cells; (e) selecting hypermutated hybridoma cells that produce antibodies with greater affinity for said antigen than antibodies produced by said parental hybridoma cells; and (f) cloning immunoglobulin genes from said hybridoma into a mammalian expression cell; thereby producing high titers of high-affinity antibodies from in vitro immunized immunoglobulin-producing cells.

In yet another embodiment, the invention provides mammalian expression cells that produce high titers of high-affinity antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form hybridoma cells; (c) performing a screen for binding of antibodies produced from the hybridoma cells to antigen; (d) cloning immunoglobulin genes from the hybridoma into a parental mammalian expression cell, wherein the mammalian expression cell expresses a dominant negative allele of a mismatch repair gene; (e) incubating the parental mammalian expression cell to allow for mutagenesis, thereby forming hypermutated mammalian expression cells; (f) performing a screen of hypermutable mammalian expression cells that secrete antibodies with higher affinity for antigen as compared to antibodies produced from the hybridoma cells; and (g) performing a screen of hypermutable mammalian expression cells that secrete higher titers of antibodies than parental mammalian expression cells; thereby producing mammalian expression cells that produce high titers of high-affinity antibodies from in vitro immunized immunoglobulin-producing cells.

In yet another embodiment, the invention provides a method of producing hybridoma cells that produce high-affinity antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen for antigen binding for antibodies produced from the hypermutated hybridoma cells; and (e) selecting hypermutated hybridoma cells that produce antibodies with greater affinity for the antigen than antibodies produced by said parental hybridoma cells; thereby producing hybridoma cells that produce high-affinity antibodies.

In still another embodiment, the invention provides a method of producing hybridoma cells that produce high titers of antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by said parental hybridoma cells; thereby producing hybridoma cells producing high titers of antibodies.

In another embodiment, the invention provides methods for producing mammalian expression cells that produce high titers of high-affinity antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form hybridoma cells; (c) performing a screen for antigen binding of antibodies produced from the hybridoma cells; (d) cloning immunoglobulin genes from the hybridoma cells into a mammalian expression cell; (e) incubating the mammalian expression cell in the presence of at least one chemical inhibitor of mismatch repair; and (f) performing a screen for mammalian expression cells that secrete antibodies with higher affinity for antigen as compared to antibodies produced from the hybridoma cells; thereby producing mammalian expression cells that produce high titers of high-affinity antibodies from in vitro immunized immunoglobulin-producing cells.

In yet another embodiment, the invention provides a method for producing mammalian expression cells that produce high affinity antibodies to a selected antigen from in vitro immunized immunoglobulin-producing cells are produced in high titers by: (a) combining donor cells comprising immunoglobulin-producing cells with an immunogenic antigen in vitro; (b) fusing the immunoglobulin-producing cells with myeloma cells to form hybridoma cells; (c) incubating the hybridoma cells in the presence of at least one chemical inhibitor of mismatch repair to form hypermutated hybridoma cells; (d) performing a screen for antigen binding for antibodies produced from the hypermutated hybridoma cells; (e) selecting hypermutated hybridoma cells that produce antibodies with greater affinity for the antigen than antibodies produced by the parental hybridoma cells; and (f) cloning immunoglobulin genes from the hypermutated hybridoma cells into a mammalian expression cell, thereby forming parental mammalian expression cells; thereby producing mammalian expression cells that produce high titers of high-affinity antibodies from in vitro immunized immunoglobulin-producing cells.

In yet another embodiment, the invention also provides methods for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell; (e) incubating said mammalian expression cell in the presence of at least one chemical inhibitor of mismatch repair, thereby forming a hypermutated mammalian expression cell; (f) performing a screen for hypermutated mammalian expression cells that secrete antibodies with higher affinity for antigen as compared to antibodies produced from said parental mammalian expression cells; and (g) performing a second screen for hypermutated mammalian expression cells that produce higher titers of antibodies that produced by parental mammalian expression cells; thereby producing mammalian expression cells that produce high titers of high-affinity antibodies from in vitro immunized immunoglobulin-producing cells.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; and (g) selecting hypermutated hybridoma cells that produce antibodies in higher titers than produced by the parental hybridoma cells; thereby producing hybridoma cells producing high titers of high-affinity antibodies.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; and (g) selecting hypermutated hybridoma cells that produce antibodies in higher titers than produced by the parental hybridoma cells; thereby producing hybridoma cells producing high titers of high-affinity antibodies.

In another embodiment, the invention comprises a method for producing mammalian expression cells that produce high-affinity antibodies in high titers from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; and (f) cloning immunoglobulin genes from said hypermutated hybridoma into a mammalian expression cell; thereby producing a mammalian expression cell that produce high titers of high-affinity antibodies in high titer from in vitro immunized immunoglobulin-producing cells.

In another embodiment, the invention comprises a method for producing mammalian expression cells that produce high-affinity antibodies in high titer from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; and (f) cloning immunoglobulin genes from said hypermutated hybridoma cell into a mammalian expression cell; thereby producing mammalian expression cells that produce high titers of high-affinity antibodies from in vitro immunized immunoglobulin-producing cells.

The invention also provides hybridoma cells, expression cells produced by any of the methods of the invention, as well as antibodies produced by any of the hybridoma cells and expression cells of the invention.

In still another embodiment, antigen-specific immunoglobulin-producing cells are produced by: (a) isolating donor cells from an animal; (b) treating said cells with L-leucyl-L-leucine methy ester hydrobromide; (c) incubating said donor cells with an immunogenic antigen in vitro, at 25-37° C., 5-10% $CO_2$, in medium supplemented with 5-15% serum, and a growth promoting cytokine for 4 days; (d) washing said cells in medium; and (e) culturing said cells in medium supplemented with 5-15% serum an additional 8 days; thereby stimulating the production of antigen-specific immunoglobulin-producing cells.

The blood cells used in the methods of the invention may be derived from any animal that produces antibodies. Preferably, the donor cells are derived from mammals, including, but not limited to humans, monkeys, mice, rats, guinea pigs, hamsters, gerbils, birds, rabbits, sheep, goats, pigs, horses, and cows. The source of blood is not necessarily limited, but may be whole blood or fractions containing lymphocytes. The blood may be donor or cord blood, for example. In some embodiments, the blood cells are preferably human donor cells.

The myeloma cells used to create the hybridoma cells in the method of the invention may be derived from any species known to have suitable myeloma cells. For example, but not by way of limitation, the myeloma cells may be conveniently derived from humans or mice. Suitable examples of myeloma cells include, but are not limited to the HuNS1 myeloma as described in U.S. Pat. No. 4,720,459 to Winkelhake, and deposited with the American Type Culture Collection (ATCC) as CRL 8644; GM4672; RPMI 8226; and murine myeloma cell lines (e.g., P3-NS1/1-Ag4-1; P3-x63-Ag8.653; Sp2/O-Ag14; NS/O, NS/1, SP2 and S194).

The mammalian expression cells suitable for use in certain embodiments of the method of the invention include, but are not limited to Chinese Hamster Ovary cells (CHO cells, Urlaub and Chasin (1980) *Proc. Natl. Acad. Sci. USA*, 77: 4216), baby hamster kidney (BHK cells), human embryonic kidney line 293 (HeLa cells, Graham et al., (1977) *J. Gen Virol.*, 36: 59), normal dog kidney cell line (e.g., MDCK, ATCC CCL 34), normal cat kidney cell line (CRFK cells), monkey kidney cells (CV1 ATCC CCL 70); African green monkey kidney cells (VERO-76, ATCC CRL-1587), COS (e.g., COS-7) cells, and non-tumorigenic mouse myoblast G8 cells (e.g., ATCC CRL 1246), fibroblast cell lines (e.g., human, murine or chicken embryo fibroblast cell lines), myeloma cell lines, mouse NIH/3T3 cells, LMTK$^{31}$ cells, mouse sertoli cells (TM4, Mather, (1980) *Biol. Reprod.*, 23:243-251); human cervical carcinoma cells (HELA, ATCC CCL 2); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51), TRI cells (Mather et al. (1982) *Annals N.Y. Acad. Sci.* 383:44-68); MRC 5 cells; FS4 cells; and the human hepatoma line (Hep G2).

As an alternative to mammalian expression cells, other non-mammalian cells may be used to express the cloned immunoglobulin genes. Such non-mammalian cells include, but are not limited to insect cells (e.g., *Spodoptera frugiperda* cells and the like). Vectors and non-mammalian host cells are well known in the art and are continually being optimized and developed. Any host cell system capable of expressing antibodies may be used in the methods of the invention.

As used herein, "dominant negative allele of a mismatch repair gene" refers to an allele of a mismatch repair gene that, when expressed, exerts a dominant phenotype in the cell or organism that leads to an inhibition of the mismatch repair system, even in the presence of a wild-type allele. Cells expressing a dominant negative allele of a mismatch repair gene are hypermutable and accumulate mutations at a higher rate than wild-type cells. Examples of nucleic acid sequences encoding mismatch repair proteins useful in the method of the invention include, but are not limited to the following: PMS1 (SEQ ID NO:1); PMS2 (SEQ ID NO:3); PMS2-134 (SEQ ID NO:5); PMSR2 (SEQ ID NO:7); PMSR3 (SEQ ID NO:9); MLH1 (SEQ ID NO:11); MLH3 (SEQ ID NO:13); MSH2 (SEQ ID NO:15); MSH3 (SEQ ID NO:17); MSH4 (SEQ ID NO:19); MSH5 (SEQ ID NO:21); MSH6 (SEQ ID NO:23); PMSR6 (SEQ ID NO:25); PMSL9 (SEQ ID NO:27); yeast MLH1 (SEQ ID NO:29); mouse PMS2 (SEQ ID NO:31); mouse PMS2-134 (SEQ ID NO:33); *Arabidopsis thaliana* PMS2 (SEQ ID NO:35); *A. thaliana* PMS2-134 (SEQ ID NO:37) *A. thaliana* PMS1 (SEQ ID NO:39); *A. thaliana* MSH7 (SEQ ID NO:41) *A. thaliana* MSH2 (SEQ ID NO:43); *A. thaliana* MSH3 (SEQ ID NO:45); *A. thaliana* MSH6-1 (SEQ ID NO:47); and *Oryza satvia* MLH1 (SEQ ID NO:49). The corresponding amino acid sequences for the listed nucleic acid sequences are: PMS1 (SEQ ID NO:2); PMS2 (SEQ ID NO:4); PMS2-134 (SEQ ID NO:6); PMSR2 (SEQ ID NO:8); PMSR3 (SEQ ID NO:10); MLH1 (SEQ ID NO:12); MLH3 (SEQ ID NO:14); MSH2 (SEQ ID NO:16); MSH3 (SEQ ID NO:18); MSH4 (SEQ ID NO:20); MSH5

(SEQ ID NO:22); MSH6 (SEQ ID NO:24); PMSR6 (SEQ ID NO:26); PMSL9 (SEQ ID NO:28); yeast MLH1 (SEQ ID NO:30); mouse PMS2 (SEQ ID NO:32); mouse PMS2-134 (SEQ ID NO:34); Arabidopsis thaliana PMS2 (SEQ ID NO:36); A. thaliana PMS2-134 (SEQ ID NO:38); A. thaliana PMS1 (SEQ ID NO:40); A. thaliana MSH7 (SEQ ID NO:42) A. thaliana MSH2 (SEQ ID NO:44); A. thaliana MSH3 (SEQ ID NO:46); A. thaliana MSH6-1 (SEQ ID NO:48); and Oryza satvia MLH1 (SEQ ID NO:50).

As used herein, "high titer" refers to an titer of at least about 1.5 fold higher than the parental cell line. In some embodiments, the titer is at least about 1.5-3 fold higher, 3-5 fold higher, 5-7 fold higher, 7-9 fold higher, or 9-10 fold higher than the parental cell line.

As used herein, "high affinity" refers to a high antibody binding affinity, that may be calculated according to standard methods by the formula $K_a=8/3$ (It−Tt) where "It" is the total molar concentration of inhibitor uptake at 50% tracer and "Tt" is the total molar concentration of tracer. See Muller (1980) *J. Immunol. Meth.* 34:345-352. Binding affinity may also be calculated using the formula $B/T=n \cdot N_{Ab} \cdot W^{108}[(V-V_m)K+Q \cdot W]$ (See Antoni and Mariani (1985) *J. Immunol. Meth.* 83:61-68). As used herein, "high affinity" is at least about $1 \times 10^7$ M$^{-1}$. In some embodiments, the antibodies have an affinity of at least about $1 \times 10^8$ M$^{-1}$. In other embodiments, the antibodies have an affinity of at least about $1 \times 10^9$ M$^{-1}$. In other embodiments, the antibodies have an affinity of at least about $1 \times 10^{10}$ M$^{-1}$. In other embodiments, the antibodies have an affinity of at least about $1 \times 10^{11}$ M$^{-1}$. In other embodiments, the antibodies have an affinity of at least about $1 \times 10^{12}$ M$^{-1}$. In other embodiments, the antibodies have an affinity of at least about $1 \times 10^{13}$ M$^{-1}$. In other embodiments, the antibodies have an affinity of at least about $1 \times 10^{14}$ M$^{-1}$.

As used herein, "antigen-specific" refers to an interaction between the CDR regions of the immunoglobulin molecule with an epitope of the antigen wherein the CDR regions of the immunoglobulin molecule binds to the epitope.

As used herein, "cured" refers to a state of the cells wherein the dominant negative mismatch repair gene has been eliminated from the cell or wherein the expression of the dominant negative allele has been turned off, leading to a stabilized genome, producing stable biological products such as immunoglobulins.

In some embodiments of the methods of the invention, mismatch repair is inhibited by introducing a dominant negative allele of a mismatch repair gene into a cell.

In other embodiments of the methods of the invention, mismatch repair is inhibited by exposing cells that express an antibody to a compound that inhibits mismatch repair. In some embodiments, the compound is an ATPase inhibitor. Suitable ATPase inhibitors include, but not limited to ATP analogs that are capable of blocking the ATPase activity necessary for mismatch repair in the cell. Examples of ATP analogs that may be used in the methods of the invention, include, but are not limited to non-hydrolyzable forms of ATP, such as AMP-PNP and ATPγS, which block mismatch repair activity (Galio et al. (1999) *Nucl. Acids Res.* 27:2325-2331; Allen et al. (1997) *EMBO J.* 16:4467-4476; Bjornson et al. (2000) *Biochem.* 39:3176-3183). Other suitable ATPase inhibitors may be identified using mismatch repair reporter cells that may be screened with candidate ATPase inhibitors to identify those compounds which effectively block ATPase activity in the cells.

In other embodiments of the methods of the invention, mismatch repair is inhibited by exposing cells that express an antibody to a nuclease inhibitor. The nuclease inhibitors are capable of blocking exonuclease activity in the mismatch repair biochemical pathway. Mismatch repair reporter cells may be screened with candidate nuclease inhibitors to identify compounds that effectively block the exonuclease activity of the mismatch repair system. Suitable nuclease inhibitors which may be used in the methods of the invention include, but are not limited to analogs of N-ethylmaleimide, an endonuclease inhibitor (Huang et al. (1995) *Arch. Biochem. Biophys.* 316:485); heterodimeric adenosine-chain-acridine compounds, exonuclease III inhibitors (Belmont et al. (2000) *Bioorg. Med. Chem Lett.* 10:293-295); as well as antibiotic compounds such as heliquinomycin, which have helicase inhibitory activity (Chino et al. (1998) *J. Antibiot. (Tokyo)* 51:480-486). Other suitable nuclease inhibitors may be identified using mismatch repair reporter cells that may be screened with candidate nuclease inhibitors to identify those compounds which effectively block nuclease activity in the cells.

In other embodiments of the methods of the invention, mismatch repair is inhibited by exposing the cells producing antibodies to DNA polymerase inhibitors. DNA polymerase inhibitors are capable of blocking the polymerization of DNA which is required for functional mismatch repair. Examples of suitable DNA polymerase inhibitors include, but are not limited to actinomycin D (Martin et al. (1990) *J. Immunol.* 145:1859); aphidicolin (Kuwakado et al. (1993) *Biochem. Pharmacol.* 46:1909); 1-(2'-deoxy-2'-fluoro-beta-L-arabino-furanosyl)-5-methyluracil (L-FMAU) (Kukhanova et al. (1998) *Biochem. Pharmacol.* 55:1181-1187); and 2'3'-dideoxyribonucleoside 5'-triphosphates (ddNTPs) (Ono et al. (1984) *Biomed. Pharmacother.* 38:382-389). Other suitable DNA polymerase inhibitors may be identified using mismatch repair reporter cells that may be screened with candidate DNA polymerase inhibitors to identify those compounds which effectively block DNA polymerase activity in the cells.

In other embodiments of the methods of the invention, mismatch repair is inhibited by exposing the cells producing antibody to an anthracene. As used herein the term "anthracene" refers to the compound anthracene. However, when referred to in the general sense, such as "anthracenes," "an anthracene" or "the anthracene," such terms denote any compound that contains the fused triphenyl core structure of anthracene, i.e.,

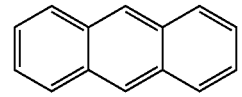

regardless of extent of substitution. The anthracene may be substituted or unsubstituted.

As used herein, "alkyl" refers to a hydrocarbon containing from 1 to about 20 carbon atoms. Alkyl groups may straight, branched, cyclic, or combinations thereof Alkyl groups thus include, by way of illustration only, methyl, ethyl, propyl, isopropyl, butyl, isobutyl, cyclopentyl, cyclopentylmethyl, cyclohexyl, cyclohexylmethyl, and the like. Also included within the definition of "alkyl" are fused and/or polycyclic aliphatic cyclic ring systems such as, for example, adamantane. As used herein the term "alkenyl" denotes an alkyl group having at least one carbon-carbon double bond. As used herein the term "alkynyl" denotes an alkyl group having at least one carbon-carbon triple bond.

In some preferred embodiments, the alkyl, alkenyl, alkynyl, aryl, aryloxy, and heteroaryl substituent groups described above may bear one or more further substituent groups; that is, they may be "substituted". In some preferred embodiments these substituent groups can include halogens (for example fluorine, chlorine, bromine and iodine), CN, NO$_2$, lower alkyl groups, aryl groups, heteroaryl groups, aralkyl groups, aralkyloxy groups, guanidino, alkoxycarbonyl, alkoxy, hydroxy, carboxy and amino groups. In addition, the alkyl and aryl portions of aralkyloxy, arylalkyl, arylsulfonyl, alkylsulfonyl, alkoxycarbonyl, and aryloxycarbonyl groups also can bear such substituent groups. Thus, by way of example only, substituted alkyl groups include, for example, alkyl groups fluoro-, chloro-, bromo- and iodoalkyl groups, aminoalkyl groups, and hydroxyalkyl groups, such as hydroxymethyl, hydroxyethyl, hydroxypropyl, hydroxybutyl, and the like. In some preferred embodiments such hydroxyalkyl groups contain from 1 to about 20 carbons.

As used herein the term "aryl" means a group having 5 to about 20 carbon atoms and which contains at least one aromatic ring, such as phenyl, biphenyl and naphthyl. Preferred aryl groups include unsubstituted or substituted phenyl and naphthyl groups. The term "aryloxy" denotes an aryl group that is bound through an oxygen atom, for example a phenoxy group.

In general, the prefix "hetero" denotes the presence of at least one hetero (i.e., non-carbon) atom, which is in some preferred embodiments independently one to three O, N, S, P, Si or metal atoms. Thus, the term "heteroaryl" denotes an aryl group in which one or more ring carbon atom is replaced by such a heteroatom. Preferred heteroaryl groups include pyridyl, pyrimidyl, pyrrolyl, furyl, thienyl, and imidazolyl groups.

The term "aralkyl" (or "arylalkyl") is intended to denote a group having from 6 to 15 carbons, consisting of an alkyl group that bears an aryl group. Examples of aralkyl groups include benzyl, phenethyl, benzhydryl and naphthylmethyl groups.

The term "alkylaryl" (or "alkaryl") is intended to denote a group having from 6 to 15 carbons, consisting of an aryl group that bears an alkyl group. Examples of aralkyl groups include methylphenyl, ethylphenyl and methylnaphthyl groups.

The term "arylsulfonyl" denotes an aryl group attached through a sulfonyl group, for example phenylsulfonyl. The term "alkylsulfonyl" denotes an alkyl group attached through a sulfonyl group, for example methylsulfonyl.

The term "alkoxycarbonyl" denotes a group of formula —C(=O)—O—R where R is alkyl, alkenyl, or alkynyl, where the alkyl, alkenyl, or alkynyl portions thereof can be optionally substituted as described herein.

The term "aryloxycarbonyl" denotes a group of formula —C(=O)—O—R where R is aryl, where the aryl portion thereof can be optionally substituted as described herein.

The terms "arylalkyloxy" or "aralkyloxy" are equivalent, and denote a group of formula —O—R'—R", where R' is R is alkyl, alkenyl, or alkynyl which can be optionally substituted as described herein, and wherein R" denotes a aryl or substituted aryl group.

The terms "alkylaryloxy" or "alkaryloxy" are equivalent, and denote a group of formula —O—R'—R", where R' is an aryl or substituted aryl group, and R" is alkyl, alkenyl, or alkynyl which can be optionally substituted as described herein.

As used herein, the term "aldehyde group" denotes a group that bears a moiety of formula —C(=O)—H. The term "ketone" denotes a moiety containing a group of formula —R—C(=O)—R=, where R and R= are independently alkyl, alkenyl, alkynyl, aryl, heteroaryl, aralkyl, or alkaryl, each of which may be substituted as described herein.

As used herein, the term "ester" denotes a moiety having a group of formula —R—C(=O)—O—R= or —R—O—C (=O)—R= where R and R= are independently alkyl, alkenyl, alkynyl, aryl, heteroaryl, aralkyl, or alkaryl, each of which may be substituted as described herein.

The term "ether" denotes a moiety having a group of formula —R—O—R= or where R and R= are independently alkyl, alkenyl, alkynyl, aryl, heteroaryl, aralkyl, or alkaryl, each of which may be substituted as described herein.

The term "crown ether" has its usual meaning of a cyclic ether containing several oxygen atoms. As used herein the term "organosulfur compound" denotes aliphatic or aromatic sulfur containing compounds, for example thiols and disulfides. The term "organometallic group" denotes an organic molecule containing at least one metal atom.

The term "organosilicon compound" denotes aliphatic or aromatic silicon containing compounds, for example alkyl and aryl silanes.

The term "carboxylic acid" denotes a moiety having a carboxyl group, other than an amino acid.

Suitable anthracenes that may be used in the method of the invention comprise compounds having the formula:

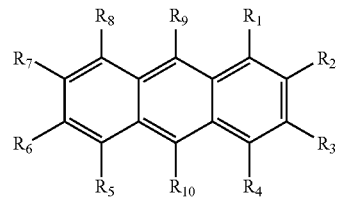

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, NO$_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups; wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, NO$_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups. In some embodiments, the $R_5$ and $R_6$ are hydrogen. In other embodiments, $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl. Suitable anthracenes for use in the methods of the invention include, but are not limited to 1,2-dimethylanthracene, 9,10-dimethylanthracene, 7,8-dimethylanthracene, 9,10-duphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolylanthracene.

Other suitable anthracenes may be identified using mismatch repair reporter cells that may be screened with candidate anthracenes to identify those compounds which effectively block mismatch repair activity in the cells. In some embodiments, the chemical inhibitor of mismatch repair is an RNA interference molecule that is homologous to a mismatch repair gene of the invention. The technique for generating sequence-specific RNA interference molecules is well-known in the art and may be found in, for example, Sharp et al. (2000) *Science* 287:2431-2433; Marx (2000) *Science* 288:1370-1372; Grishok et al. (2001) *Science* 287:2494-2497; and Fire et al. (1998) *Nature* 391:806-811, the disclosures of which are specifically incorporated by reference in their entirety.

In other embodiments of the method of the invention, mismatch repair is inhibited by exposing the cells producing antibody to "antisense compounds" which specifically hybridize with one or more nucleic acids encoding a mismatch repair gene. As used herein, the terms "target nucleic acid" and "nucleic acid encoding a mismatch repair gene" encompass DNA encoding a mismatch repair gene, RNA (including pre-mRNA and mRNA) transcribed from such DNA, and also cDNA derived from such RNA. The specific hybridization of an antisense compound with its target nucleic acid interferes with the normal function of the nucleic acid, such as replication and transcription. The functions of RNA disrupted by antisense compounds include such functions as, for example, translocation of the RNA to the site of protein translation, translation of protein from the RNA, and splicing of the RNA to yield one or more mRNA species. The antisense compound thereby inhibits the expression or function of a mismatch repair gene.

It is preferred to target specific nucleic acids for antisense inhibition of mismatch repair in order to reversibly disrupt the function of a given mismatch repair gene. "Targeting" an antisense compound to a particular nucleic acid, in the context of this invention, is a multistep process, beginning with the identification of a nucleic acid sequence whose function is to be modulated. As disclosed herein, there are several mismatch repair genes that may be targeted by an antisense strategy. Among the various mismatch repair genes that may be targeted are PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264, including DNA or RNA. The next step of targeting involves the determination of a site or sites within this gene for the antisense interaction to occur, such that inhibition of the function of the mismatch repair gene occurs. In one embodiment, an intragenic site is targeted. An "intragenic site" is a region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a mismatch repair gene, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. Complementarity of the antisense oligonucleotide is preferably 100%, however, degeneracy may be introduced into the oligonucleotide such that the complementarity, in some embodiments, is 80-85%, 85-90%, 90-95% or 95-100%.

Antisense and other compounds of the invention which hybridize to the target and inhibit expression of the target are identified through experimentation, and the sequences of these compounds are herein below identified as preferred embodiments of the invention. The target sites to which these preferred sequences are complementary comprise the region of PMS2, for example, which inhibits the translation of the C-terminal portion of the PMS2 protein, effectively forming a truncation mutant. The region targeted comprises a portion of the PMS2 gene that encodes the 134 amino acid of PMS2, for example.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e., from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. In some embodiments, the antisense oligonucleotides are at least about 15 nucleotides in length and may be at least 20, 25, 30, 35, 40, 45, 50, 55, 60, 65, 70, 75, 80, 85, 90, 95, 100 or more nucleotides in length.

In some embodiments, the antisense oligonucleotides comprise a sequence that is complementary to a portion of the mismatch repair sequence shown in SEQ ID NO:1; SEQ ID NO:3; SEQ ID NO:5; SEQ ID NO:7; SEQ ID NO:9; SEQ ID NO:11; SEQ ID NO:13; SEQ ID NO:15; SEQ ID NO:17; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; SEQ ID NO:45; SEQ ID NO:47; or SEQ ID NO:49. In certain embodiments, the oligonucleotide is at least 15-50 nucleotides in length with 85-100% complementarity.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage, i.e., a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., (1991) *Science* 254:1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al. (1995) *Helv. Chim. Acta* 78:486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_2$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin- 2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in THE CONCISE ENCYCLOPEDIA OF POLYMER SCIENCE AND ENGINEERING, Kroschwitz, (Ed.) John Wiley & Sons, 1990, pages 858-859, those disclosed by Englisch et al. (1991) *Angewandte Chemie* (International Edition) 30:613, and those disclosed by Sanghvi, ANTISENSE RESEARCH AND APPLICATIONS, Crooke and Lebleu (Eds.), CRC Press, 1993, pages 289-302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, ANTISENSE RESEARCH AND APPLICATIONS, Crooke and Lebleu (Eds.), CRC Press, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,750,692; 5,830,653; 5,763,588; 6,005,096; and 5,681,941, each of which is herein incorporated by reference in its entirety.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al. (1989) *Proc. Natl. Acad. Sci. USA* 86:6553-6556), cholic acid (Manoharan et al. (1994) *Bioorg. Med. Chem. Let.* 4:1053-1060), a thioether, e.g., hexyl-S-tritylthiol (Manoharan et al. (1992) *Ann. N.Y. Acad. Sci.* 660:306-309; Manoharan et al. (1993) *Bioorg. Med. Chem. Let.* 3:2765-2770), a thiocholesterol (Oberhauser et al. (1992) *Nucl. Acids Res.* 20:533-538), an aliphatic chain, e.g., dodecandiol or undecyl residues (Saison-Behmoaras et al. (1991) *EMBO J.* 10:1111-1118; Kabanov et al. (1990) *FEBS Lett.* 259:327-330; Svinarchuk et al. (1993) *Biochimie* 75:49-54), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.* 36:3651-3654; Shea et al. (1990) *Nucl. Acids Res.* 18:3777-3783), a polyamine or a polyethylene glycol chain (Manoharan et al. (1995) *Nucleosides & Nucleotides* 14:969-973), or adamantane acetic acid (Manoharan et al. (1995) *Tetrahedron Lett.* 36:3651-3654), a palmityl moiety (Mishra et al. (1995) *Biochim. Biophys. Acta* 1264:229-237), or an octadecylamine or hexylamino-carbonyl-oxycholesterol moiety (Crooke et al. (1996) *J. Pharmacol. Exp. Ther.* 277:923-937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

As used herein "donor cells comprising immunoglobulin-producing cells" or "donor cells comprising immunoglobulin-producing cells" sometimes referred to simply as "donor cells" or "donor blood cells" refers to cells that are capable of producing antibodies when immunized with an antigenic compound. Examples of sources of such donor cells suitable for use in the invention include, but are not limited to spleen cells, lymph node cells, bone marrow cells, and immortalizing tumor infiltrating lymphocytes.

As used herein, the term "amino acid" denotes a molecule containing both an amino group and a carboxyl group. In some preferred embodiments, the amino acids are α-, β-, γ- or δ-amino acids, including their stereoisomers and racemates. As used herein the term "L-amino acid" denotes an α-amino acid having the L configuration around the α-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the D-configuration around the α-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, BIOCHEMISTRY, Second Edition, Worth Publishers, Inc., 1975, pages 72-77 (incorporated herein by reference). Amino acid substituents may be attached through their carbonyl groups through the oxygen or carbonyl carbon thereof, or through their amino groups, or through functionalities residing on their sidechain portions.

As used herein "polynucleotide" refers to a nucleic acid molecule and includes genomic DNA cDNA, RNA, mRNA and the like.

As used herein "inhibitor of mismatch repair" refers to an agent that interferes with at least one function of the mismatch repair system of a cell and thereby renders the cell more susceptible to mutation.

As used herein "hypermutable" refers to a state in which a cell in vitro or in vivo is made more susceptible to mutation through a loss or impairment of the mismatch repair system.

As used herein "agents," "chemicals," and "inhibitors" when used in connection with inhibition of MMR refers to chemicals, oligonucleotides, RNA interference molecules, analogs of natural substrates, and the like that interfere with normal function of MMR.

As used herein, "about" refers to an amount within a range of +/−10% of the cited value.

As used herein, "mitogenic polypeptide" refers to a polypeptide when in combination with the antigen provides stimulation of appropriate cells to increase the immune response against the subject antigen.

As used herein, "hybridoma" refers to the result of a cell fusion between an immunoglobulin-producing cell and a transformed cell, such as a myeloma cell.

As used herein, "IgG subclass" refers to a category of immunoglobulins comprising IgG1, IgG2, IgG2a, IgG2b, IgG3, and IgG4.

As used herein, "mismatch repair gene" refers to a gene that encodes one of the proteins of the mismatch repair complex. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base which is complementary to the older DNA strand. In this way, cells eliminate many mutations that occur as a result of mistakes in DNA replication. Dominant negative alleles cause a mismatch repair defective phenotype even in the presence of a wild-type allele in the same cell. A non-limiting example of a dominant negative allele of a mismatch repair gene is the human gene hPMS2-134, which carries a truncation mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations which accumulate in cells after DNA replication. Thus, expression of a dominant negative allele of a mismatch repair gene results in impairment of mismatch repair activity, even in the presence of the wild-type allele.

As used herein, "HAT-sensitive" refers to a lethal effect on cells when cultured in medium containing hypoxanthine, aminopterin and thymidine.

As used herein, "EBV-negative" refers to lack of infection of Epstein-Barr virus in a cell as measured by production of EBNA protein, or detection of EBV nucleic acids.

As used herein, "Ig-negative" refers to lack of production in a cell of any light or heavy chains of immunoglobulins.

As used herein, "screening" refers to an assay to assess the genotype or phenotype of a cell or cell product including, but not limited to nucleic acid sequence, protein sequence, protein function (e.g., binding, enzymatic activity, blocking activity, cross-blocking activity, neutralization activity, and the like). The assays include ELISA-based assays, Biacore analysis, and the like.

As used herein, "isolated" refers to a nucleic acid or protein that has been separated and/or recovered from a component of its natural environment. Contaminant components of its natural environment are materials which would interfere with diagnostic or therapeutic uses for the polypeptide, and may include enzymes, hormones, and other proteinaceous or non-proteinaceous solutes. In some embodiments, the nucleic acid or protein is purified to greater than 95% by weight of protein. In other embodiments, the nucleic acid or protein is purified to greater than 99% by weight of protein. Determination of protein purity may be by any means known in the art such as the Lowry method, by SDS-PAGE under reducing or non-reducing conditions using a stain such as a Coomassie blue or silver stain. Purification of nucleic acid may be assessed by any known method, including, but not limited to spectroscopy, agarose or polyacrylamide separation with fluorescent or chemical staining such as methylene blue, for example.

The invention provides an in vitro immunization method for obtaining antigen-specific immunoglobulin producing cells wherein the cells produce immunoglobulins of the IgG subclass, and cells produced by this method. The in vitro immunization procedure comprises combining donor cells with an immunogenic antigen in culture. In one embodiment, the buffy coat of donor cells is used. The donor may be from any source, including, but not limited to cord blood, venous blood, and the like. The source of the blood cells may be from any animal producing immune cells, particularly mammals. Non-limiting examples of blood cell sources include, mice, rats, humans, monkeys, dogs, cats, horses, pigs, sheep, goats, rabbits, birds, cows, guinea pigs and fish. The blood or buffy coat may be further enriched for lymphocytes by any known method, such as, but not limited to differential centrifugation, filtration, and the like.

Donor cells such as peripheral blood mononuclear cells (PBMC) may be incubated in L-leucyl-L-lysine methyl ester hydrobromide (LLOMe). While not wishing to be bound by any particular theory of operation, LLOme is believed to lysosomotropic and specifically kills cytotoxic cells in the PBMC pool such as NK cells, cytotoxic T cells, and CD8+ suppressor T cells, while not having an effect on B cells, T helper cells accessory cells and fibroblasts (Borrebaeck (1988) *Immunol. Today* 9(11):355-359). Generally, the PBMCs may be incubated with LLOMe for a period of 1-30 minutes. In some embodiments, the incubation is performed for 10-20 minutes. In other embodiments, the incubation is performed for 15 minutes. The LLOMe is generally a component of culture medium, such as, for example, RPMI 1640, and is provided in a concentration of about 0.10 to 1 mM. In some embodiments, LLOMe is provided in an amount of about 0.10 to 0.50 mM. In other embodiments, LLOMe is provided in an amount of about 0.25 mM.

The antigen may be any antigen provided that it is immunogenic. Whole proteins or peptides may be used. In addition, one may use, for example, membrane preparations (including those from tumors), lymphoma cells, whole cells, single cells, homogenized cells, pathogens, inclusion bodies, cell lysates, protein preparations, and minced tissue (including tumor tissue). Whole proteins may be in native or denatured conformation. Peptides may be conjugated to carrier molecules to provide immunogenicity. While not wishing to be bound by any particular theory of operation, carrier molecules may provide additional T cell epitopes which may be useful in stimulating a more robust in vitro antibody response. Examples of carriers that are suitable for use in the method of the invention include tetanus toxoid, diptheria toxin, thyroglobulin, cholera toxin, BCG, bovine serum albumen (BSA), ovalbumin (OVA), and the like. These carriers are referred to herein as "mitogenic polypeptides."

Antigens may be conjugated to mitogenic polypeptides in any way known in the art. For example, fusion proteins may be generated by expressing a polypeptide in a recombinant expression system comprising the polynucleotide encoding at least a portion of the antigen joined in-frame to a polynucleotide encoding at least a portion of the mitogenic polypeptide. The fusion protein may have the mitogenic polypeptide joined at either the amino- or carboxy terminus of the antigen. In some embodiments, more that one antigen may be expressed as a fusion protein in combination with a mitogenic polypeptide. In other embodiments, more than one mitogenic polypeptide may be expressed as a fusion protein with the antigen or antigens. In other embodiments, more than one mitigenic polypeptide and more than one antigen may be expressed together as a single fusion protein.

In an alternative embodiment, at least a portion of the mitogenic polypeptide is conjugated to at least a portion of the antigen using chemical cross-linkers. Examples of chemical cross-linkers include, but are not limited to gluteraldehyde, formaldehyde, 1,1-bis(diazoacetyl)-2-phenylethane, N-hydroxysuccinimide esters (e.g., esters with 4-azidosalicylic acid, homobifunctional imidoesters including disuccinimidyl esters such as 3,3'-dithiobis(succinimidyl-propionate), and bifunctional maleimides such as bis-N-maleimido-1,8-octane). Derivatizing agents such as methyl-3-[(p-azido-phenyl)dithio]propioimidate yield photoactivatable intermediates which are capable of forming cross-links in the presence of light. Alternatively, for example, a lysine residue in the mitogenic polypeptide or antigen may be coupled to a C-terminal or other cysteine residue in the antigen or mitogenic polypeptide, respectively, by treatment with N-γ-maleimidobutyryloxy-succinimide (Kitagawa and Aikawa (1976) *J. Biochem.* 79, 233-236). Alternatively, a lysine residue in the mitogenic polypeptide or antigen may be conjugated to a glutamic or aspartic acid residue in the antigen or mitogenic polypeptide, respectively, using isobutylchloroformate (Thorell and De Larson (1978) RADIOIMMUNOASSAY AND RELATED TECHNIQUES: METHODOLOGY AND CLINICAL APPLICATIONS, p. 288). Other coupling reactions and reagents have been described in the literature.

The conditions for the in vitro immunization procedure comprise incubating the cells at about 25-37° C., (preferably 37° C.) supplied with about 5-10% $CO_2$. In some embodiments, the incubation is performed with between about 6-9% $CO_2$. In other embodiments the incubation is performed in about 8% $CO_2$. The cell density is between about 2.5 to $5\times10^6$ cells/ml in culture medium. In some embodiments, the culture medium is supplemented with about 2-20% FBS. In other embodiments, the culture medium is supplemented with about 5-15% FBS. In other embodiments, the culture medium is supplemented with about 7-12% FBS. In other embodiments, the culture medium is supplemented with about 10% FBS.

The in vitro stimulation culture medium is supplemented with cytokines to stimulate the cells and increase the immune response. In general IL-2 is supplied in the culture medium. However, other cytokines and additives may also be included to increase the immune response. Such cytokines and factors may include, for example, IL-4 and anti-CD40 antibodies.

The fusion of myeloma cells with the immunoglobulin-producing cells may be by any method known in the art for the creation of hybridoma cells. These methods include, but are not limited to, the hybridoma technique of Kohler and Milstein, (1975, *Nature* 256:495-497; and U.S. Pat. No. 4,376, 110) (see also, Brown et al. (1981) *J. Immunol.* 127:539-546; Brown et al. (1980) *J. Biol. Chem.* 255 (11):4980-4983; Yeh et al. (1976) *Proc. Natl. Acad. Sci. USA* 76:2927-2931; and Yeh et al. (1982) *Int. J. Cancer* 29:269-275), the human B-cell hybridoma technique (Kosbor et al., 1983, *Immunology Today* 4:72; Cole et al., 1983, *Proc. Natl. Acad. Sci. USA* 80:2026-2030), and the EBV-hybridoma technique (Cole et al., 1985, MONOCLONAL ANTIBODIES AND CANCER THERAPY, Alan R. Liss, Inc., pp. 77-96). The hybridoma producing the mAb of this invention may be cultivated in vitro or in vivo.

The technology for producing monoclonal antibody hybridomas is well-known to those of skill in the art and is described, for example in Kenneth, in MONOCLONAL ANTIBODIES: A NEW DIMENSION IN BIOLOGICAL ANALYSES, Plenum Publishing Corp., New York, N.Y. (1980); Lerner (1981) *Yale J. Biol. Med.,* 54:387-402; Galfre et al. (1977) *Nature* 266: 55052; and Gefter et al. (1977) *Somatic Cell Genet.* 3:231-236). However, many variations of such methods are possible and would be appreciated by one of skill in the art. Thus, the techniques for generation of hybridomas is not limited to the disclosures of these references.

Any myeloma cell may be used in the method of the invention. Preferably, the myeloma cells are human cells, but the invention is not limited thereto or thereby. In some embodiments, the cells are sensitive to medium containing hypoxanthine, aminopterin, an thymidine (HAT medium). In some embodiments, the myeloma cells do not express immunoglobulin genes. In some embodiments the myeloma cells are negative for Epstein-Barr virus (EBV) infection. In preferred embodiments, the myeloma cells are HAT-sensitive, EBV negative and Ig expression negative. Any suitable myeloma may be used. An example of such a myeloma is that described in U.S. Pat. No. 4,720,459 to Winkelhake, and deposited with the American Type Culture Collection (ATCC) as CRL 8644. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC.

In some embodiments of the method of the invention, the hybridoma cells and/or mammalian expression cells may be rendered hypermutable by the introduction of a dominant negative allele of a mismatch repair gene. The dominant negative allele of the mismatch repair gene may be introduced into the hybridoma cell (i.e., after the fusion of immunoglobulin-producing cells with the myeloma cells) or may be introduced into the myeloma cell prior to the fusions. The invention, therefore, also provides hypermutable myeloma cells for use in the generation of hybridoma cells. The dominant negative allele may also be introduced into the mammalian expression cells.

The dominant negative allele of the mismatch repair gene is in the form of a polynucleotide which may be in the form of genomic DNA, cDNA, RNA, or a chemically synthesized polynucleotide. The polynucleotide can be cloned into an expression vector containing a constitutively active promoter segment (such as, but not limited to, CMV, SV40, EF-1 Dor LTR sequences) or to inducible promoter sequences such as those from tetracycline, or ecdysone/glucocorticoid inducible vectors, where the expression of the dominant negative mismatch repair gene can be regulated. The polynucleotide can be introduced into the cell by transfection.

Transfection is any process whereby a polynucleotide is introduced into a cell. The process of transfection can be carried out in vitro, e.g., using a suspension of one or more isolated cells in culture. The cell can be any immortalized cell used for creating hybridomas for the production of monoclonal antibodies, or the cell may be the hybridoma itself. The hybridomas may be heterohybridoma cells (e.g. human-mouse cell fusions) or homohybridoma cells (e.g., human-human hybridoma cells and mouse-mouse hybridoma cells).

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the mismatch repair gene, the cell can be grown and reproduced in culture. If the transfection is stable, such that the gene is expressed at a consistent level for many cell generations, then a cell line results.

The dominant negative allele of the mismatch repair gene may be derived from any known mismatch repair gene including, but not limited to PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264 and the like. "Dominant negative alleles" as used herein, refers to the ability of the allele to confer a hypermutable status to the cell expressing the allele. Any allele which produces such effect can be used in this invention. The dominant negative alleles of a mismatch repair gene can be obtained from the cells of humans, animals, yeast, bacteria, or other organisms. Dominant negative alleles of mismatch repair genes that are suitable for use in the invention have certain functional characteristics associated with structural features. A non-limiting example of a dominant negative mismatch repair gene is the PMS2 truncation mutant, PMS2-134. This gene contains a mutation which truncates the PMS2 protein after amino acid 133. The lack of the C-terminus in the PMS2 protein is believed to interfere with the binding of PMS2 with Screening cells for defective mismatch repair activity can identify such alleles. Cells from animals or humans with cancer can be screened for defective mismatch repair. Cells from colon cancer patients may be particularly useful. Genomic DNA, cDNA, or mRNA from any cell encoding a mismatch repair protein can be analyzed for variations from the wild type sequence. Dominant negative alleles of a mismatch repair gene can also be created artificially, for example, by producing variants of the hPMS2-134 allele or other mismatch repair genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

Dominant negative alleles of such genes, when introduced into cells or transgenic animals, increase the rate of spontaneous mutations by reducing the effectiveness of DNA repair and thereby render the cells or animals hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The hypermutable hybridoma cells will accumulate new mutations in gene(s) to produce new output traits within the hybridoma. The hybridoma cells can be screened for desired characteristics and cell lines bearing these characteristics may be expanded. Furthermore, the hybridoma cells may be "cured" of the mismatch repair defect by eliminating the dominant negative mismatch repair gene in the cell or by turning of its expression, leading to stable biological products consisting of altered genes, RNAs, or polypeptides.

The dominant negative alleles of the mismatch repair gene may be introduced as part of a vector. The polynucleotide encoding the dominant negative mismatch repair protein allele may be operably linked to a promoter that functions in the cell to drive expression of the dominant negative allele of the mismatch repair gene. Other elements of the vector may include an origin of replication, one or more selectable markers, such as a drug resistance gene that allows the cells to grow in the presence of a growth inhibitory compound.

In embodiments of the invention that utilize myeloma cells or donor immunoglobulin-producing cells that are naturally deficient in mismatch repair, the invention may further comprise the step of restoring genetic stability of the hybridoma by introducing a wild-type mismatch repair gene into the cell to complement the deficiency and restore genetic stability.

Another aspect of the invention is the use of cells lacking MMR (either due to defects in endogenous mismatch repair genes, or due to the introduction of a dominant negative MMR gene) and chemical mutagens to cause an enhanced rate of mutations in a host's genome. The lack of MMR activity has been known to make cells more resistant to the toxic effects of DNA damaging agents. This invention comprises making proficient MMR cells mismatch repair defective via the expression of a dominant negative MMR gene allele and then enhancing the genomic hypermutability with the use of a DNA mutagen. Chemical mutagens are classifiable by chemical properties, e.g., alkylating agents, cross-linking agents, etc. The following chemical mutagens are useful, as are others not listed here, according to the invention and may be used to further enhance the rate of mutation in any of the embodiments of the method of the invention: N-ethyl-N-nitrosourea (ENU), N-methyl-N-nitrosourea (MNU), procarbazine hydrochloride, chlorambucil, cyclophosphamide, methyl methanesulfonate (MMS), ethyl methanesulfonate (EMS), diethyl sulfate, acrylamide monomer, triethylene melamin (TEM), melphalan, nitrogen mustard, vincristine, dimethylnitrosamine, N-methyl-N'-nitro-nitrosoguanidine (MNNG), 7,12 dimethylbenz (a) anthracene (DMBA), ethylene oxide, hexamethylphosphoramide, bisulfan. In a preferred aspect of the invention, a mutagenesis technique is employed that confers a mutation rate in the range of 1 mutation out of every 100 genes; 1 mutation per 1,000 genes. The use of such combination (MMR deficiency and chemical mutagens will allow for the generation of a wide array of genome alterations (such as but not limited to expansions or deletions of DNA segments within the context of a gene's coding region, a gene's intronic regions, or 5' or 3' proximal and/or distal regions, point mutations, altered repetitive sequences) that are preferentially induced by each particular agent.

Mutations can be detected by analyzing for alterations in the genotype of the cells or animals, for example by examining the sequence of genomic DNA, cDNA, messenger RNA, or amino acids associated with the gene of interest. Mutations can also be detected by screening the phenotype of the gene. An altered phenotype can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to measuring protein secretion, chemical-resistance, pathogen resistance, etc.

In some embodiments of the method of the invention, inducible vectors that control the expression of a dominant negative and normally functioning MMR gene are used. This strategy restores DNA stability once a host cell or organism exhibiting a new output trait, altered gene, RNA or polypeptide has been generated via trait selection with or without the combination of chemical mutagens to establish a genetically stable version of this cell or organism. In the case of MMR defective cells as a result of ectopically expressing a dominant negative MMR gene allele, the MMR activity is decreased or completely eliminated by removing the inducer molecule from the cell culture or organism's environment. In addition, the expression of a dominant negative MMR gene can be suppressed by knocking out the MMR gene allele using methods that are standard to those skilled in the art of DNA knockout technology in germ or somatic cells (Waldman et al. (1995) *Cancer Res.* 55:5187-5190).

The chiral position of the side chains of the anthracenes is not particularly limited and may be any chiral position and any chiral analog. The anthracenes may also comprise a stereoisomeric form of the anthracenes and include any isomeric analog.

Examples of hosts are but not limited to cells or whole organisms from human, primate, mammal, rodent, plant, fish, reptiles, amphibians, insects, fungi, yeast or microbes of prokaryotic origin.

A more detailed disclosure of particular embodiments of the invention follows in the specific examples, however, the invention is not limited thereto or thereby.

EXAMPLES

Example 1

Generation of Hybridomas Secreting Human Monoclonal Antibodies to Tetanus Toxin (TT)

Figure 2A:
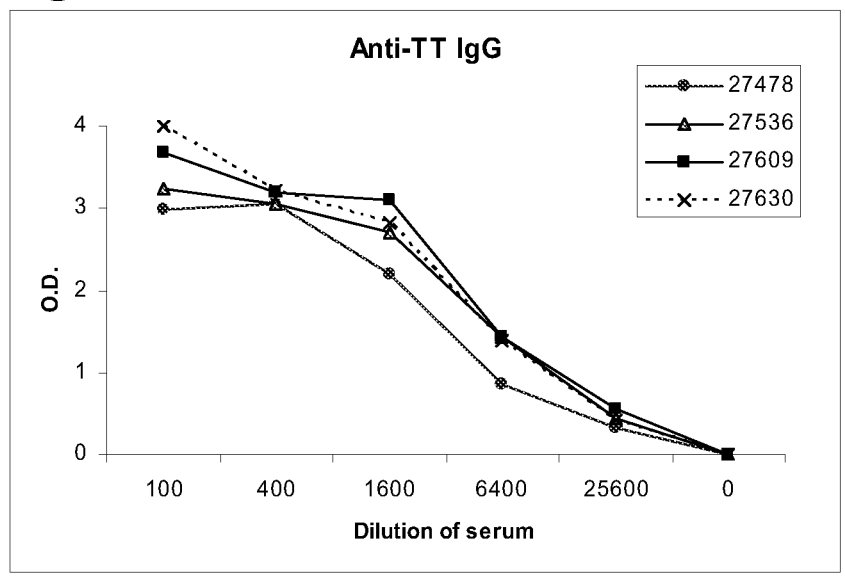
FIG. 2A shows reactivity of donor serum to TT by detection of donor anti-TT IgG.
Figure 2B:
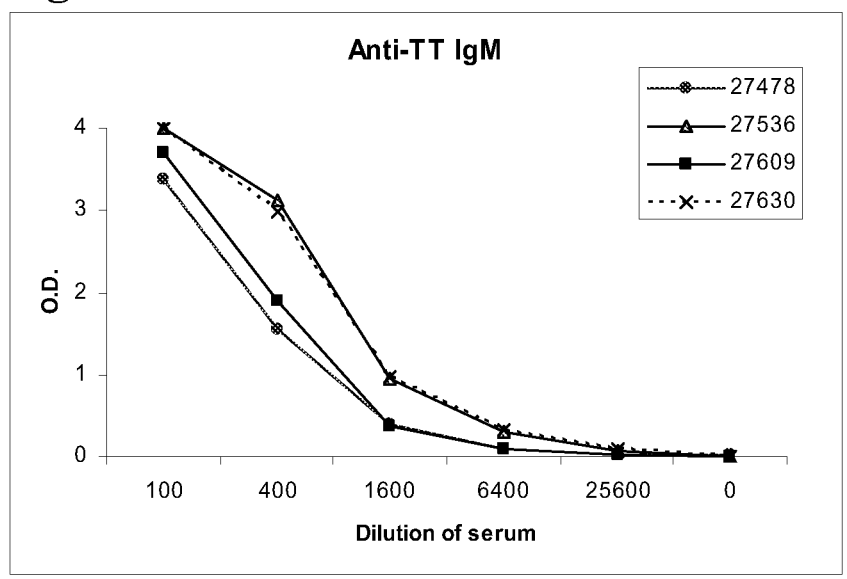
FIG. 2B shows reactivity of donor serum to TT by detection of donor anti-TT IgM.
Figure 3:
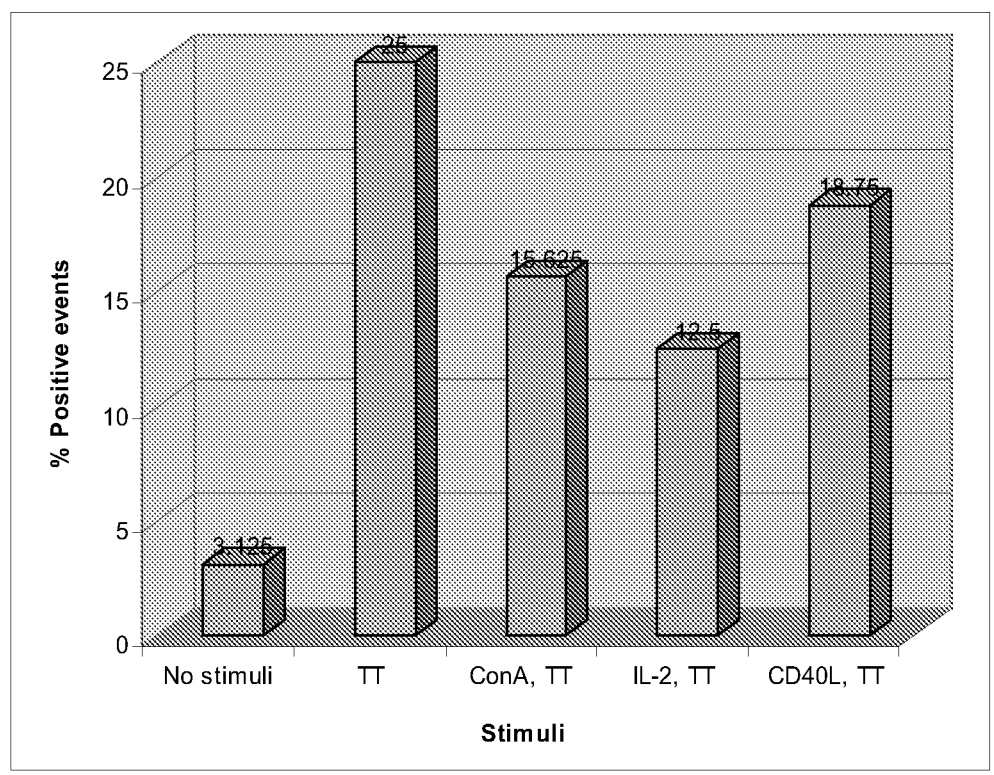
FIG. 3 shows the frequency of the anti-TT response of PBMCs upon in vitro immunization with TT, or with TT in combination with IL-2, or CD40L.
Figure 4:
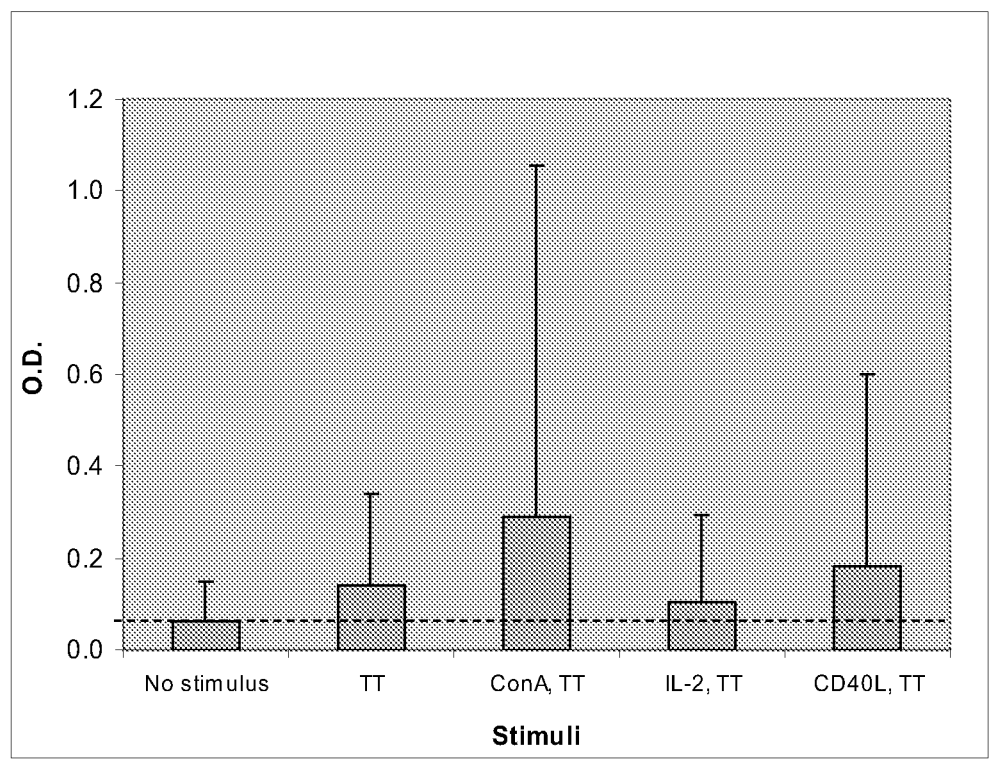
FIG. 4 shows the intensity of the response of PBMCs upon in vitro immunization with TT, or with TT in combination with IL-2, or CD40L.

A. Generation and Assaying of TT-Specific B Lymphocytes
  Isolation of Lymphocytes from Donor.
  Lymphocytes were isolated from whole blood by centrifugation through Ficoll-Paque according to the manufacturer's instructions. Isolated lymphocytes were incubated with 0.25 mM Leu-Leu methyl ester hydrobromide (LLOMe) prepared in RPMI 1640 medium containing 2% fetal bovine serum (FBS) for 15 minutes at room temperature. The cells were then washed three times with culture medium.
  In Vitro Stimulation of Isolated Lymphocytes.
  The cells were incubated at 37° C. in a incubator, supplied with 8% $CO_2$, at a density between 2.5 to $5 \times 10^6$ cells/ml in culture medium supplemented with 10% FBS and TT and IL-2 at various concentrations. After four days of culture, the cells were washed four times with medium and the culture was continued for additional eight days.
  Measurement of the B Cell Response.
  Lymphocyte culture supernatants were collected on day 12 of the culture and tested in an ELISA for the presence of anti-TT antibodies. Briefly, TT or BSA at 0.5 µg/ml in 0.05 M carbonate-bicarbonate buffer was immobilized onto an EIA plate. After blocking with 1% bovine serum albumin (BSA) in PBS containing 0.05% Tween 20, the supernatant was added to the wells. Antibodies bound to TT were detected with peroxidase-labeled goat anti-human IgG or anti-human IgM. TMB was used for color development. The plate was read using a Microplate reader with a 450 nm filter. A supernatant sample that had antibody bound to TT, but not to BSA, and in which the signal was two times the assay background was considered positive. The positive cells were pooled, and used for hybridoma production (FIG. 1).
  Notably, peripheral blood mononuclear cells (PBMCs) from some donors contain a fraction of B cells that secret TT-specific antibodies in culture. This is due to the fact that about 90% of the population in the United States has been vaccinated against TT. Such sera also has a titer of higher than 1000 (FIG. 2). However, the percentage of positive events is greatly increased when PBMCs are immunized in vitro with TT (FIG. 3). The intensity of the PBMC response is also enhanced with the stimulation of TT alone or in combination with IL-2 or CD40L (FIG. 4). Similar effects were observed with other antigens (data not shown).
  Generation of Hybridomas Secreting Human Antibodies.
  To prepare activated lymphocytes, cells were pooled and cultured in T flasks at $0.5-1 \times 10^6$ cells/ml in culture medium supplemented with 10% FBS one day prior to the fusion. To prepare the fusion partner, mouse myeloma NS0 cells were transfected with human PMS2-134 expression vector as described in Nicolaides et al. (1998) *Mol. Cell. Biol.* 18(3): 1635-1641. The cells were cultured in RPMI 1640 supplemented with 10% FBS and 2 mM glutamine (Complete Medium) and the culture was kept in log phase.
  Next, lymphocytes were harvested and counted. An equal number of myeloma cells was harvested. Both types of cells were combined and washed three times with RPMI 1640 medium. Polyethylene glycol (PEG) was added dropwise to the loosened cell pellet, and the PEG was subsequently diluted out slowly with 25 ml of RPMI medium in a course of 2.5 minutes. After diluting out the PEG, fused cells were suspended in Complete Medium supplemented with HAT and 20% FBS, and seeded onto 96-well plates.

Screening and Characterization of Antigen-Specific Hybridoma Clones.

Figure 5:
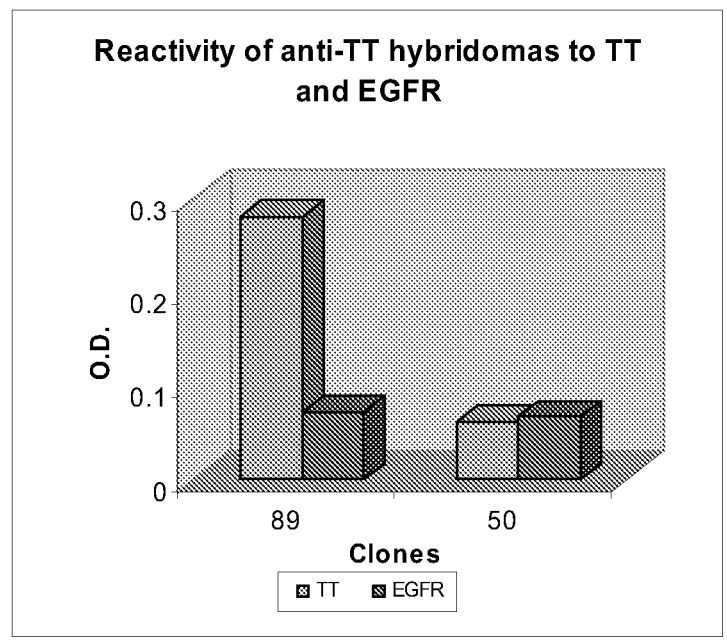
FIG. 5 shows the response of hybridomas expressing anti-TT antibodies.
Figure 6A:
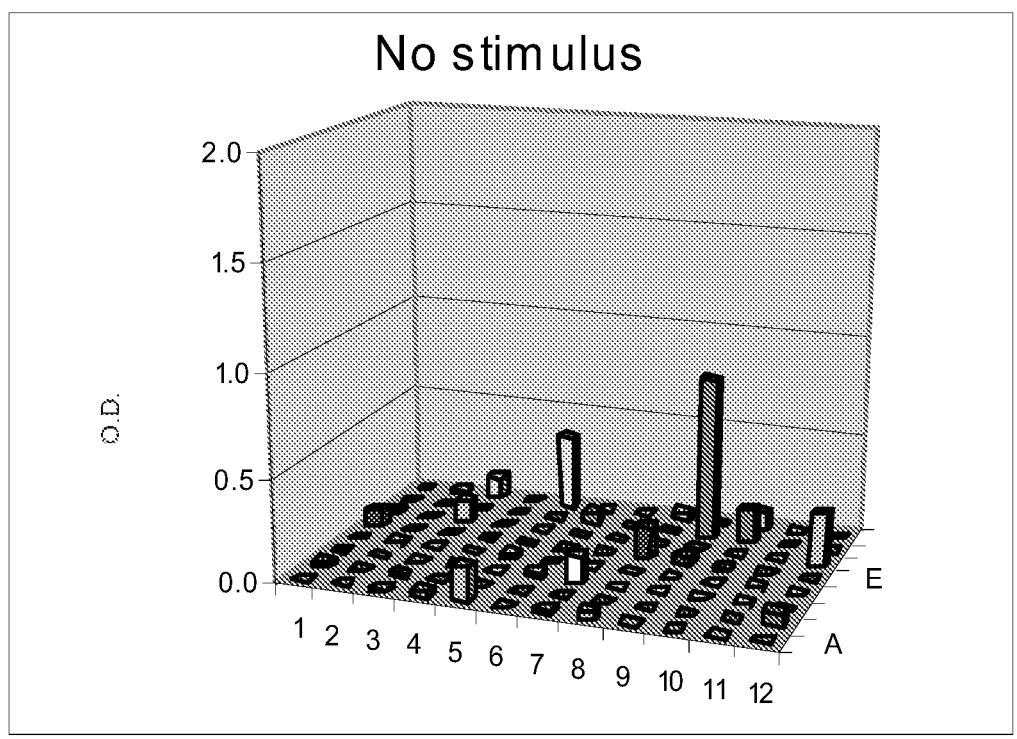
FIG. 6A shows the reactivity of unstimulated PBMCs to EGFR.
Figure 6B:
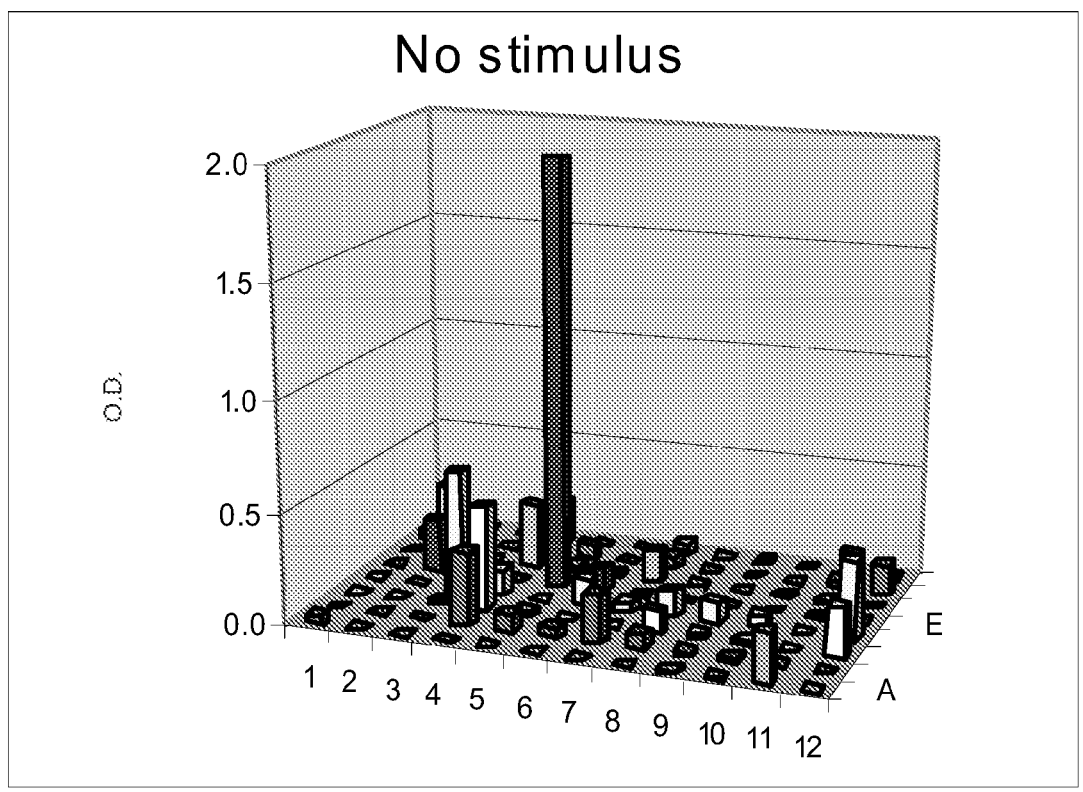
FIG. 6B shows the reactivity of PBMCs to EGFR after immunization with EGFR-TT.
Figure 6C:
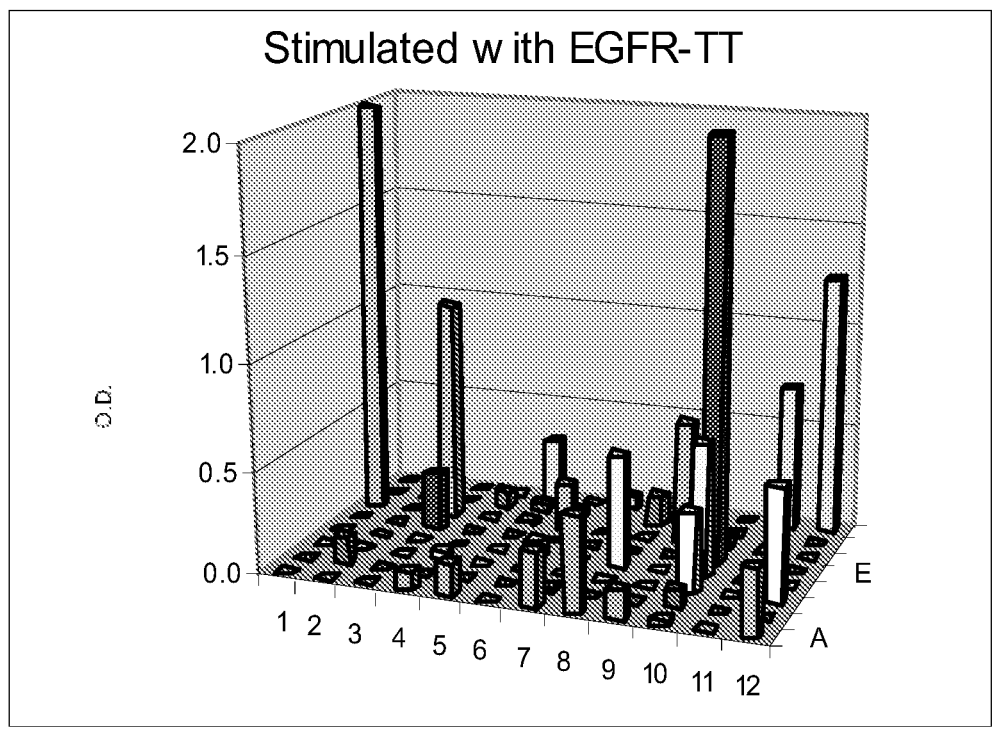
FIG. 6C shows the reactivity of unstimulated PBMCs to EGFR-TT.
Figure 6D:
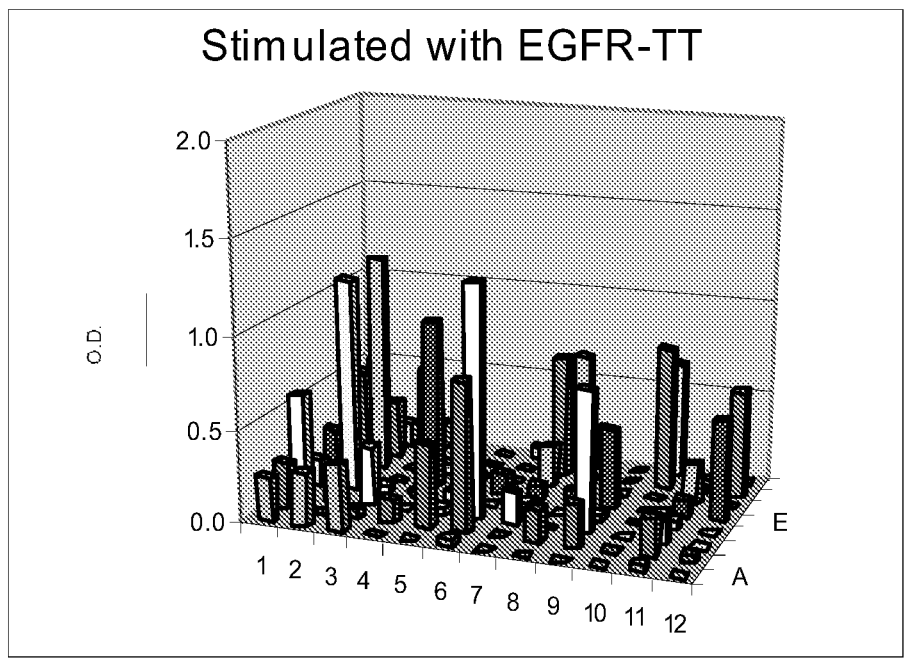
FIG. 6D shows the reactivity of PBMCs to EGFR-TT after immunization with EGFR-TT.

When the hybridoma cells grew to semi-confluence, supernatants were collected and subjected to an ELISA for antigen-specific reactivity. As an example, hybridomas derived from TT-immunized lymphocytes were tested. Briefly, TT or BSA at 0.5 ug/ml in 0.05 M carbonate-bicarbonate buffer was immobilized onto the EIA plate. After blocking with 1% bovine serum albumen in PBS containing 0.05% Tween 20, the cell culture supernate was added to the wells. Antibodies bound to TT were detected with peroxidase-labeled goat anti-human IgG or anti-human IgM. TMB was used for color development. The plate was read in the Microplate reader with a 450 nm filter. A cell clone that showed reactivity to TT but not to BSA was considered positive (FIG. 5). Positive clones were expanded and subcloned by limiting dilution to generate monoclonal cells.

Example 2

Generation of Hybridomas Secreting Human Monoclonal Antibodies to Epidermal Growth Factor Receptor (EGFR) (Self Antigen)

A. Generation of EGFR-Specific B Lymphocytes

Preparation of Antigen.

Human epidermal growth factor receptor (EGFR), purified from A431 cells, was purchased from Sigma. Previous studies found that immune responses to this antigen were very weak, most likely due to tolerance. In order to enhance immunization, we conjugated the EGFR to tetanus toxin C (EGFR-TT) and the conjugate was used as immunogen for in vitro immunization in order to overcome any immunotolerance.

Preparation of EGFR-TT Conjugate.

100 ug of purified EGFR was reconstituted in 100 ul of sterile MilliQ-grade water. 1 mg of purified, lyophilized recombinant tetanus toxin C fragment (TT-C) was dissolved in sterile MilliQ-grade water to yield a 2 mg/ml TT-C solution. Crosslinking was performed in 50 mM sodium carbonate buffer pH 9.0 at equimolar ratios of EGFR to TT-C, using glutaraldehyde at a final concentration of 0.5% for 3 hours at room temperature, followed by 4° C. overnight. Glutaraldehyde was quenched by addition of a fresh 100 mg/ml solution of sodium borohydride in 50 mM sodium carbonate pH 9.0, under open atmosphere for 1 hour at 4° C. Crosslinked products were dialyzed against $Ca^{2+}$, $Mg^{2+}$-free phosphate-buffered saline overnight at 4° C., using 3.5K MWCO Slide-A-Lyzer cassettes. The reaction was monitored by Western blotting, using commercial anti-EGFR (mAb-15) and anti-TT-C (Roche) monoclonal antibodies. By this method, greater than 70% of the components are crosslinked, and appear as immunoreactive species of greater MW than the starting material (data not shown).

In Vitro Stimulation of Peripheral Blood Mononuclear Cells (PBMC).

LLOMe-pretreated PBMC were incubated at a density of $3 \times 10^6$ cells/ml in culture medium supplemented with 10% FBS and a stimuli mixture. The stimuli mixture was composed of EGFR-TT at a concentration of 50 ng/ml with or without recombinant human IL-2 at 20 IU, mouse anti-human CD40 antibody as CD40L at 0.5 ug/ml (used to enhance IgG class switching). After four days of culture, the cells were re-fed with complete medium, in the absence of added stimulus, every three or four days. Culture supernatants were collected on days 12-18 and tested for EGFR-specific antibodies.

Detection of EGFR-Specific Antibody Response.

The PBMC response to the stimulation was examined in a EGFR-specific ELISA. Briefly, EGFR, TT, or BSA at 0.5 ug/ml in 0.05 M carbonate-bicarbonate buffer, pH 9.6, was immobilized onto EIA plates. After blocking the plates with 5% non-fat dry milk in PBS containing 0.05% Tween 20, the supernatant was added to the wells. Antibodies from the supernatant bound to immobilized antigens were detected with peroxidase-labeled goat anti-human IgG+IgM (H+L). TMB substrate kit was used for color development. The plates were read in a Microplate reader with a 450 nm filter. A supernatant sample containing antibody that bound to EGFR, but not to TT and BSA, was considered positive. A robust response was observed in cultures immunized to the EGFR-TT as compared to controls. While anti-EGFR responses were observed in PBMCs for a small fraction of donors, the percentage of positive clones was greatly increased when PBMCs were immunized in vitro with EGFR complexed with TT (FIG. 6). Positive cells were pooled and used for hybridoma production.

Generation of Hybridomas.

To prepare activated lymphocytes, cells were pooled and cultured in T flasks at $0.5-1 \times 10^6$ cells/ml in culture medium supplemented with 10% FBS one day prior to the fusion. To prepare the fusion partner, mouse myeloma NS0 cells were transfected with human PMS2-134 expression vector as described in Nicolaides et al. (1998) *Mol. Cell. Biol.* 18(3): 1635-1641. The cells were cultured in RPMI 1640 supplemented with 10% FBS and 2 mM glutamine (Complete Medium) and the culture was kept in log phase.

Screening and Characterization of Antigen-Specific Hybridoma Clones.

Figure 7:
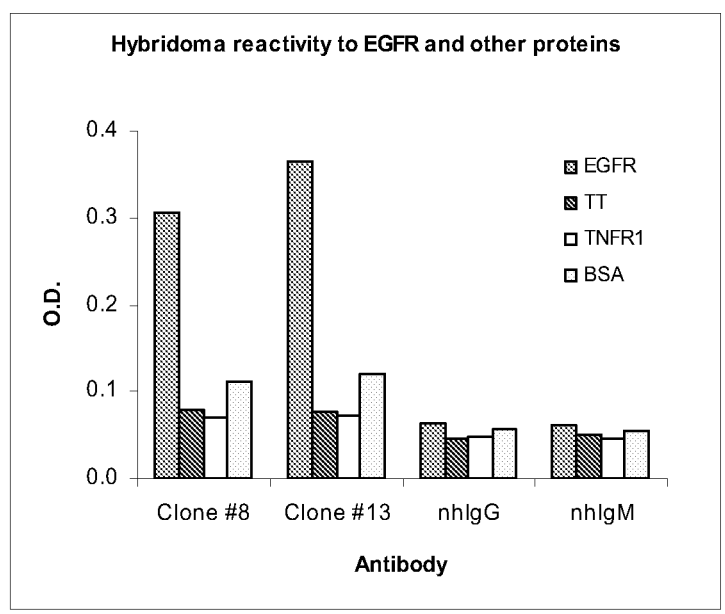
FIG. 7 shows the response of hybridomas expressing antibodies against human EGFR. Antibodies bound to EGFR or BSA (control) pre-coated on the solid phase were detected with HRP-labeled goat anti-human IgG or HRP-labeled goat anti-human IgM.

When the hybridoma cells grew to semi-confluence, supernatants were collected and subjected to an ELISA for antigen-specific reactivity. As an example, hybridomas derived from EGFR-immunized lymphocytes were tested. Briefly, EGFR, TT TNFR1 or BSA at 0.5 ug/ml in 0.05 M carbonate-bicarbonate buffer was immobilized onto the EIA plate. After blocking with 1% bovine serum albumen in PBS containing 0.05% Tween 20, the cell culture supernate was added to the wells. Antibodies bound were detected with peroxidase-labeled goat anti-human IgG or anti-human IgM. TMB was used for color development. Normal human IgG (nhIgG) and IgM (nhIgM) were used as controls. The plate was read in the Microplate reader with a 450 nm filter. A cell clone that showed reactivity to EGFR, but not to BSA was considered positive (FIG. 7).

Example 3

A. Isolation of PBMC from Whole Blood

Approximately 200 ml of whole blood mixed with 200 ml $PBS^{-/-}$ was centrifuged through Ficoll-Paque at 2000 rpm for 30 min. Serum was aspirated, the interface layer containing lymphocytes was collected and diluted 1:3 with $PBS^{-/-}$ and centrifuged at 2000 rpm for 10 min. The supernatant fluid was aspirated and the pellet was resuspended in 10 ml $PBS^{-/-}$. The cell suspension was split into two 50 ml conical tubes and $PBS^{-/-}$ was added to each tube to adjust the volume to 35 ml each. The tubes were centrifuged at 800 rpm for 7 minutes to remove the platelets. After aspirating the supernatant fluid, the pellet was resuspended in 10 ml ACK Lysing Buffer and incubated for 5 minutes at room temperature. Following lysis, 35 ml $PBS^{-/-}$ was added to the tubes and the tubes were centrifuged at 1000 rpm for 7 minutes. The cells were then washed with 45 ml RPMI medium.

B. Preparation of Dendritic Cells

Cells were centrifuged at 1000 rpm for 7 minutes and resuspended at $1\times10^8$ cells per 40 ml cRPMI for a density of $2.5\times10^6$ cells/ml. The cells were incubated at 37° C./8% $CO_2$ for 2 hours. Non-adherent cells were removed for further treatment (see Step C), and the adherent cells were carefully rinsed twice with $PBS^{-/-}$. Adherent cells were cultured in cRPMI supplemented with 400 IU/ml IL-4 and 50 ng/ml GM-CSF.

C. LLOMe Treatment and Cryopreservation of Non-Adherent Culture

The non-adherent cell culture was centrifuged at 1000 rpm for 7 minutes. The supernatant fluid was aspirated and the pellet was resuspended in 10 ml RPMI supplemented with 2% FBS and freshly thawed 85 µg/ml LLOMe. The cells were incubated for 15 minutes at room temperature. The cells were washed twice with cRPMI and resuspended in 45 ml cRPMI. The cells were transferred to an upright T25 flask at a density of $5\times10^6$ cells/ml in cRPMI supplemented with 2 µg/ml PHA and incubated at 37° C./8% $CO_2$ for 24 hours. The non-adherent cells were harvested, centrifuged at 1000 rpm for 7 minutes, and the cell pellet was resuspended in 5 ml cold cRPMI/5% DMSO. The tubes containing the cells were wrapped in paper towels and stored at −80° C. until needed.

D. Tumor Immunization

On day 6 of the procedure for isolation of dendritic cells, tumor cells were thawed in 2.5 ml pre-warmed medium at 37° C. The flask of dendritic cells was rinsed twice with 10 ml $PBS^{-/-}$. The dendritic cells were incubated with gentle rocking in 5 ml Cell Dissociation Buffer (Invitrogen Cat. No. 13151-014), and the solution was collected (scraping the remaining cells from the flask. The flask was rinsed with 10 ml cRPMI and the medium was collected. The cells were centrifuged at 1000 rpm for 7 minutes and the pellet was resuspended at $4\times10^6$ cells/ml cRPMI. Cells were distributed in a culture plate at a density of $1\times10^6$ cells/well. A tumor sample was chopped into fine pieces of approximately 1-3 $mm^3$. An aliquot of the tumor suspension was transferred to all but 1 well, titrating the amount of tumor per well. An aliquot of 0.25 ml cRPMI was added to the control well. The total volume in the wells was 0.5 ml/well. The dendritic cells and tumor cells were co-cultured at 37° C./8% $CO_2$ for 24 hours.

E. Co-Culture of PBMC with DC

Frozen PBMC were thawed by adding 40 ml cRPMI/30 IU/ml IL-2/600 IU/ml IL-4/0.75 µg/ml CD-40L pre-warmed to 50° C. to the frozen cells. When thawed, the cells were incubated for 1-2 hours at 37° C. The cells were centrifuged at 1000 rpm for 7 minutes and the pellet was resuspended in 5 ml of a 2× cocktail of cRPMI/60 IU/ml IL-2/1200 IU/ml IL-4/1.5 µg/ml CD-40L. The cell suspension was divided among wells in a tissue culture plate at 0.5 ml/well of suspension and diluted with 0.5 ml medium for a final concentration of 30 IU/ml IL-2, 600 IU/ml IL-4, and 0.75 µg/ml CD-40L. Cells were fed with cRPMI supplemented with 20 IU/ml IL-2, 400 IU/ml IL-4, 100 IU/ml IL-10, and 0.5 µg/ml CD-40L.

F. Fusion

Figure 8:
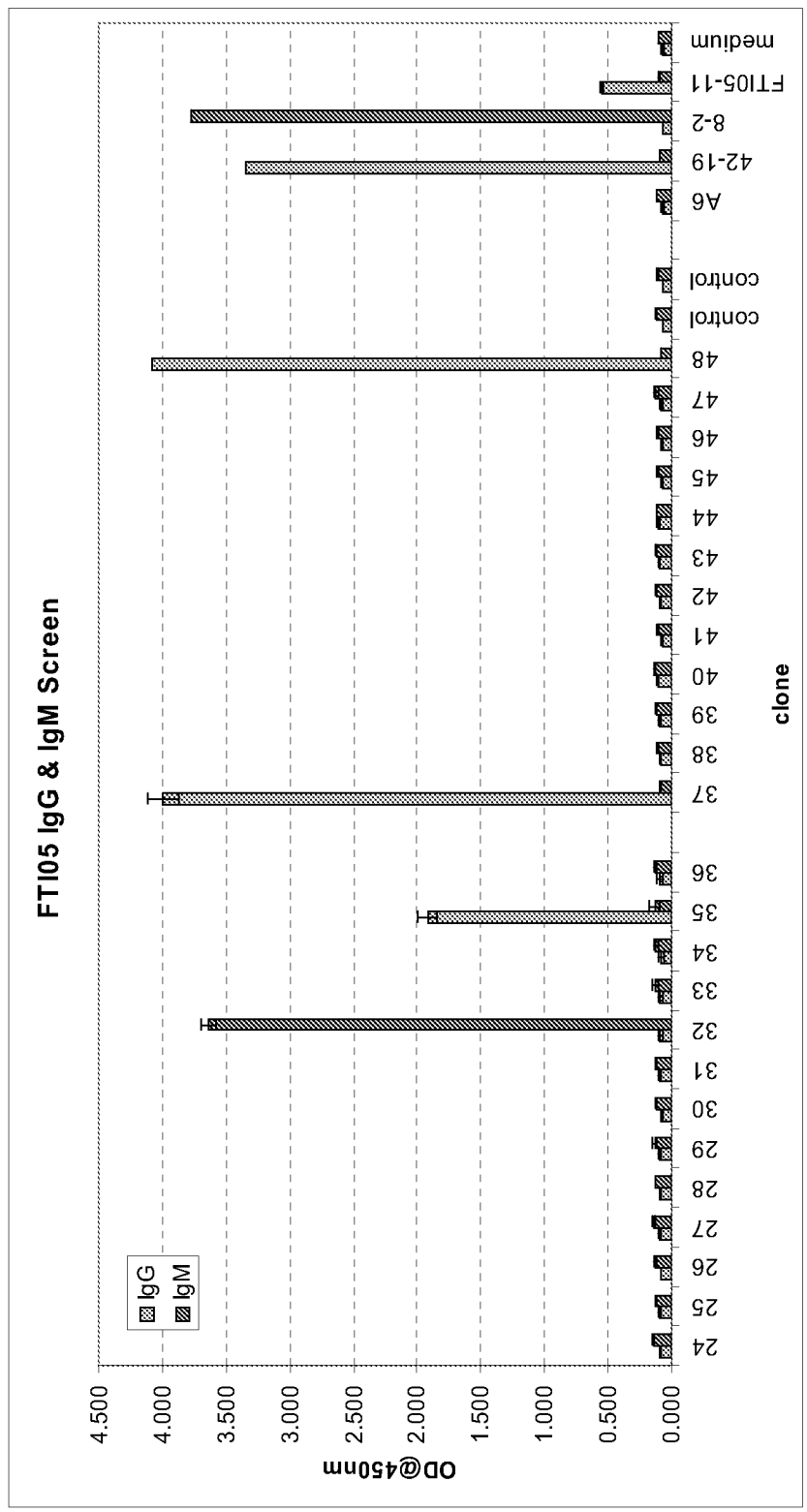
FIG. 8 shows the IgG and IgM responses of cells immunized with tumor cells in vitro.

Tumor-immunized PBMCs were then fused with A6 myeloma cells to generate hybridomas. Briefly, lymphocytes were harvested from 75% tumor and 100% tumor wells, rinsed with 1 ml RPMI, transfer to conical tubes, and the volume was adjusted to 5 ml with cRPMI. The cells were centrifuged through Ficoll-Paque, and the supernatant fluid was aspirated. Interfaces containing cells from all tubes were combined and the cells were rinsed with cRPMI. The cells were then resuspended in 7.5 ml cRPMI. Viable cells were assessed by trypan blue exclusion. A6 cell viability was also assessed by trypan blue exclusion. A6 cells and tumor-immunized lymphocytes were centrifuged separately at 1200 rpm for 10 minutes. The supernatant fluids were aspirated and the cells were washed with 10 ml $DPBS^{-/-}$/tube. Each cell line was washed three times with 2 ml cold Mannitol Fusion Medium (MFM) (0.3M Mannitol, 0.18 mM $MgCl_2$, 0.18 mM $CaCl_2$, 1 mM Hepes) and the cells were combined and resuspended in MFM at a density of $3\times10^6$ A6 cells and $3\times10^6$ PBMCs in 200 µl for a total of $6\times10^6$ cells in 200 µl. BTX 450 microslides were sterilized with 65 µL 100% EtOH and prewetted with 65 µl MFM. A 40 µl aliquot of cell suspension was distributed evenly onto a BTX 450-1 microslide. To fuse the cells, the ECM 2001 conditions were set as follows: alignment conditions, 20V for 30 seconds; pulse conditions, 150V for 30 µseconds (1×); compression conditions, 20V for 9 seconds. After fusion, the cells were transferred to one well of a 24 well plate containing 1 ml phenol red-free cRPMI. The fusion steps were repeated for the remaining cell suspensions, rinsing slide between fusions with 65 µL MFM. The culture plate containing fused cell cultures was incubated overnight at 37° C./8% $CO_2$. The fused cells were cloned and assessed by ELISA for IgG and IgM production. The results are shown in FIG. 8.

Example 4

In Vitro Immunization

Purified GM-CSF from a commercial source is administered in vitro to peripheral blood mononuclear cells (PBMC).

A. Generation and Assaying of GM-CSF-Specific B Lymphocytes

Isolation of Lymphocytes from Peripheral Blood.

Lymphocytes are isolated from whole blood by centrifugation through Ficoll-Paque according to the manufacturer's instructions. Isolated lymphocytes are incubated with 0.25 mM Leu-Leu methyl ester hydrobromide (LLOMe) prepared in RPMI 1640 medium containing 2% fetal bovine serum (FBS) for 15 minutes at room temperature. The cells are then washed three times with culture medium.

In Vitro Stimulation of Isolated Lymphocytes.

The cells are incubated at 37° C. in an incubator, supplied with 8% $CO_2$, at a density between 2.5 to $5\times10^6$ cells/ml in culture medium supplemented with 10% FBS and GM-CSF and IL-2 at various concentrations. After four days of culture, the cells are washed four times with medium and the culture was continued for additional eight days.

Measurement of the B Cell Response.

Lymphocyte culture supernatants are collected on day 12 of the culture and tested in an ELISA for the presence of anti-GM-CSF antibodies. Briefly, GM-CSF or BSA at 0.5 µg/ml in 0.05 M carbonate-bicarbonate buffer is immobilized onto an EIA plate. After blocking with 1% bovine serum albumin (BSA) in PBS containing 0.05% Tween 20, the supernatant is added to the wells. Antibodies bound to GM-CSF are detected with peroxidase-labeled goat anti-human IgG or anti-human IgM. TMB is used for color development. The plate is read using a Microplate reader with a 450 nm filter. A supernatant sample that had antibody bound to GM-CSF, but not to BSA, and in which the signal was two times the assay background is considered positive. The positive cells are pooled, and used for hybridoma production.

Generation of Hybridomas Secreting Human Antibodies.

To prepare activated lymphocytes, cells are pooled and cultured in T flasks at $0.5-1\times10^6$ cells/ml in culture medium supplemented with 10% FBS one day prior to the fusion. To prepare the fusion partner, mouse myeloma NS0 cells are transfected with human PMS2-134 expression vector as described in Nicolaides et al. (1998) *Mol. Cell. Biol.* 18(3): 1635-1641. The cells are cultured in RPMI 1640 supplemented with 10% FBS and 2 mM glutamine (Complete Medium) and the culture is kept in log phase.

Next, lymphocytes are harvested and counted. An equal number of myeloma cells is harvested. Both types of cells are combined and washed three times with RPMI 1640 medium. Polyethylene glycol (PEG) is added dropwise to the loosened cell pellet, and the PEG is subsequently diluted out slowly with 25 ml of RPMI medium in a course of 2.5 minutes. After diluting out the PEG, fused cells are suspended in Complete Medium supplemented with HAT and 20% FBS, and seeded onto 96-well plates.

Screening and Characterization of Antigen-Specific Hybridoma Clones.

When the hybridoma cells grew to semi-confluence, supernatants are collected and subjected to an ELISA for antigen-specific reactivity. As an example, hybridomas derived from TT-immunized lymphocytes are tested. Briefly, TT or BSA at 0.5 ug/ml in 0.05 M carbonate-bicarbonate buffer is immobilized onto the EIA plate. After blocking with 1% bovine serum albumin in PBS containing 0.05% Tween 20, the cell culture supernate is added to the wells. Antibodies bound to GM-CSF are detected with peroxidase-labeled goat anti-human IgG or anti-human IgM. TMB is used for color development. The plate is read in the Microplate reader with a 450 nm filter. A cell clone that showed reactivity to GM-CSF but not to BSA is considered positive. Positive clones are expanded and subcloned by limiting dilution to generate monoclonal cells.

Example 5

Generation of Hybridomas Secreting Human Monoclonal Antibodies to GM-CSF-KLH

A. Generation of GM-CSF-Specific B Lymphocytes
Preparation of Antigen.

Human GM-CSF was purchased from a vendor. In order to enhance immunization, GM-CSF was conjugated to keyhole limpet hemocyanin (KLH) (GM-CSF-KLH) and the conjugate was used as immunogen for in vitro immunization in order to overcome any immunotolerance.

Preparation of GM-CSF-KLH Conjugate.

Purified GM-CSF was reconstituted in sterile MilliQ-grade water to yield a 1 mg/ml solution. Purified, lyophilized recombinant KLH was dissolved in sterile MilliQ-grade water to yield a 1 mg/ml KLH solution. A 0.2% solution of glutaraldehyde in PBS was prepared. Crosslinking was performed by combining 25 ul of 1 mg/ml KLH, 25 ul of 1 mg/ml GM-CSF, and 50 ul 0.2% glutaraldehyde in a microcentrifuge tube wrapped in aluminum foil at room temperature, with shaking for 1 hour. Following cross-linking, 25 ul of 1 M glycine was added to the tube and the solution was incubated an additional 1 hour at room temperature with shaking. Crosslinked products were dialyzed against three changes of 300 ml PBS. The reaction was monitored by Western blotting, using a commercial anti-GM-CSF and anti-KLH monoclonal antibodies. By this method, greater than 80% of the components are crosslinked, and appeared as immunoreactive species of greater MW than the starting material (data not shown).

In Vitro Stimulation of Peripheral Blood Mononuclear Cells (PBMC).

LLOMe-pretreated PBMC were incubated at a density of $3 \times 10^6$ cells/ml in culture medium supplemented with 10% FBS and a stimuli mixture. The stimuli mixture was composed of GM-CSF-KLH at a concentration of 50 ng/ml with or without recombinant human IL-2 at 20 IU, mouse anti-human CD40 antibody as CD40L at 0.5 ug/ml (used to enhance IgG class switching). After four days of culture, the cells were re-fed with complete medium, in the absence of added stimulus, every three or four days. Culture supernatants were collected on days 12-18 and tested for GM-CSF-specific antibodies.

Detection of GM-CSF-Specific Antibody Response.

The PBMC response to the stimulation was examined in a GM-CSF-specific ELISA. Briefly, GM-CSF, KLH, or chick ovalbumin (CAB) at 0.5 ug/ml in 0.05 M carbonate-bicarbonate buffer, pH 9.6, was immobilized onto EIA plates. After blocking the plates with 1% BSA containing 0.05% Tween 20, the supernatant were added to the wells. Antibodies from the supernatant bound to immobilized antigens were detected with peroxidase-labeled goat anti-human IgG+IgM (H+L). TMB substrate kit was used for color development. The plates were read in a Microplate reader with a 450 nm filter. A supernatant sample containing antibody that bound to GM-CSF, but not to KLH and CAB, was considered positive. There was a robust response observed in cultures immunized to the GM-CSF-KLH as compared to controls. While anti-GM-CSF responses were observed in PBMCs for a small fraction of donors, the percentage of positive clones was greatly increased when PBMC were immunized in vitro with GM-CSF complexed with KLH. Positive cells were pooled and used for hybridoma production.

Generation of Hybridomas.

To prepare activated lymphocytes, cells were pooled and cultured in T flasks at $0.5-1 \times 10^6$ cells/ml in culture medium supplemented with 10% FBS one day prior to the fusion. To prepare the fusion partner, mouse myeloma NS0 cells were transfected with human PMS2-134 expression vector as described in Nicolaides et al. (1998) *Mol. Cell. Biol.* 18(3): 1635-1641. The cells were cultured in RPMI 1640 supplemented with 10% FBS and 2 mM glutamine (Complete Medium) and the culture was kept in log phase.

Screening and Characterization of Antigen-Specific Hybridoma Clones.

Figure 9:
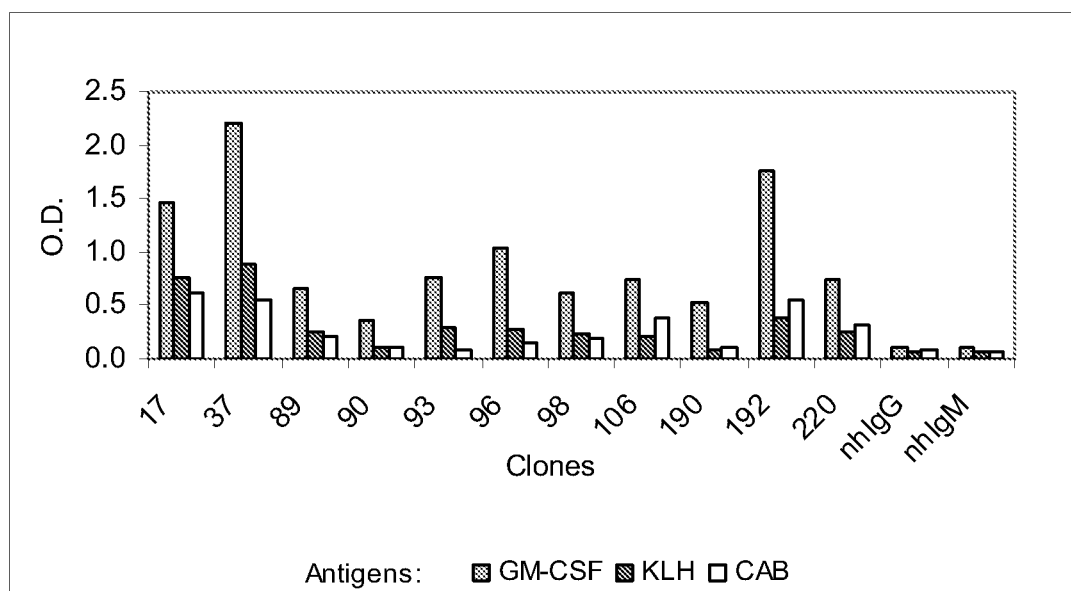
FIG. 9 shows reactivity of clones to GM-CSF, chick ovalbumin (CAB), or keyhole limpet hemocyanin.

When the hybridoma cells grew to semi-confluence, supernatants were collected and subjected to an ELISA for antigen-specific reactivity. As an example, hybridomas derived from GM-CSF-immunized lymphocytes were tested. Briefly, GM-CSF, KLH, or CAB at 0.5 ug/ml in 0.05 M carbonate-bicarbonate buffer was immobilized onto the EIA plate. After blocking with 1% bovine serum albumin in PBS containing 0.05% Tween 20, the cell culture supernate was added to the wells. Antibodies bound were detected with peroxidase-labeled goat anti-human IgG or anti-human IgM. TMB was used for color development. Normal human IgG (nhIgG) and IgM (nhIgM) were used as controls. The plate is read in the Microplate reader with a 450 nm filter. A cell clone that showed reactivity to GM-CSF, but not to CAB was considered positive. The results are shown in FIG. 9.

Example 6

Inhibition of Proliferation Assays

Figure 10:
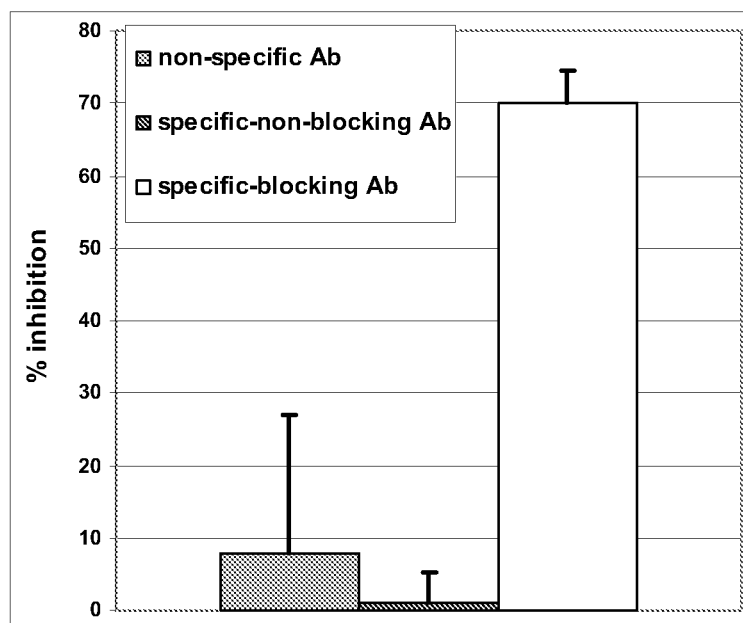
FIG. 10 shows inhibitory effect of anti-GM-CSF antibodies on proliferation of TF-1 cells. Shown are the effects of a GM-CSF-specific, blocking antibody; a GM-CSF-specific, non-blocking antibody; and a non-specific antibody.

TF-1 cells were seeded at $0.2 \times 10^6$/ml in RPMI supplemented with 10% FBS and 0.5 ng/ml recombinant human GM-CSF. TF-1 cells were serum starved for 24 hours in medium containing 0.5% BSA, without rhGM-CSF. Cells were then cultured in the presence of 0.275 ng/ml of GM-CSF for 3 days, with or without 4 ug/ml of various antibodies. Cell proliferation was measured using the ATPLite assay (Perkin Elmer). In this assay, ATP was released by lysis of viable cells and utilized by the enzyme luciferase to convert luciferin into oxyluciferin. Light was emitted (luminescence) as a result of the reaction, and the intensity of the emission was ultimately proportional to the ATP content and thus to the cell number. Counts per second (CPS) were obtained by reading the reactions with a luminometer and the percentage of inhibition was calculated according to the formula: 100−(CPS no Ab:CPS with Ab)×100%. The results are shown in FIG. 10.

The foregoing examples are merely illustrative of the invention and are not to be construed to limit the scope of the invention in any way. The scope of the invention is defined by the appended claims.

What is claimed is:

1. A method for producing hybridoma cells producing high-affinity antibodies from in vitro immunized immunoglobulin-producing cells comprising:
   (a) combining donor cells comprising immunoglobulin-producing cells with an immunogenic antigen in vitro;
   (b) fusing said immunoglobulin-producing cells with myeloma cells to form parental hybridoma cells, wherein said hybridoma cells express a dominant negative allele of a mismatch repair gene;
   (c) incubating said parental hybridoma cells with a chemical mutagen;
   (d) incubating said parental hybridoma cells to allow for mutagenesis, thereby forming hypermutated hybridoma cells;
   (e) performing a screen for binding of antibodies to antigen for antibodies produced from said hypermutated hybridoma cells; and
   (f) selecting hypermutated hybridoma cells that produce antibodies with greater affinity for said antigen than antibodies produced by said parental hybridoma cells;
   thereby producing hybridoma cells producing high-affinity antibodies.

2. The method of claim 1 wherein said dominant negative allele of a mismatch repair gene comprises a dominant negative allele of a gene selected from the group consisting of PMS2, PMS1, PMSR3, PMSR2, PMSR6, MLH1, GTBP, MSH3, MSH2, MLH3, or MSH1, and homologs of PMSR genes.

3. The method of claim 1 wherein said dominant negative allele of a mismatch repair gene comprises a dominant negative allele of a PMS2 gene.

4. The method of claim 1 further comprising a screen for hypermutated hybridomas that also produce antibodies in higher titers than said parental hybridomas.

5. The method of claim 1 further comprising inactivation of said dominant negative allele of said mismatch repair gene, thereby stabilizing the genome of said hypermutated hybridoma.

6. The method of claim 4 further comprising inactivation of said dominant negative allele of said mismatch repair gene, thereby stabilizing the genome of said hypermutated hybridoma.

7. The method of claim 1 wherein said high affinity antibodies have an affinity of at least about $1 \times 10^7$ $M^{-1}$ to about $1 \times 10^{14}$ $M^{-1}$.

8. The method of claim 4 wherein said higher titer of said antibodies is at least about 1.5-8 fold greater than the titer produced by said parental hybridoma cell.

9. The method of claim 1 further comprising the step of inactivating said dominant negative allele of a mismatch repair gene by knocking out said dominant negative allele or removing an inducer of said dominant negative allele.

10. The method of claim 1 wherein the dominant negative mismatch repair gene is introduced into said hybridoma cell after the fusion of said myeloma with said immunoglobulin-producing cells.

11. The method of claim 1 wherein said myeloma cells express a dominant negative mismatch repair gene which is also expressed in said hybridoma cells.

12. The method of claim 4 further comprising the step of inactivating said dominant negative allele of a mismatch repair gene by knocking out said dominant negative allele or removing an inducer of said dominant negative allele.

13. A method for producing hybridoma cells that produce high titers of antibodies from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form parental hybridoma cells, wherein said hybridoma cells express a dominant negative allele of a mismatch repair gene;
(c) incubating said parental hybridoma cells with a chemical mutagen;
(d) incubating said parental hybridoma cells to allow for mutagenesis, thereby forming hypermutated hybridoma cells;
(e) performing a screen of said hypermutated hybridoma cells for antibodies produced in higher titers than that produced by said parental hybridoma cells; and
(f) selecting hypermutated hybridoma cells that produce higher titers of antibodies than that produced by said parental hybridoma cells;
thereby producing hybridoma cells that produce high titers of antibodies.

14. The method of claim 13 wherein said dominant negative allele of a mismatch repair gene is selected from the group consisting of a dominant negative allele of PMS2, PMS1, PMSR3, PMSR2, PMSR6, MLH1, GTBP, MSH3, MSH2, MLH3, or MSH1, and homologs of PMSR.

15. The method of claim 13 wherein said dominant negative allele of a mismatch repair gene comprises a dominant negative allele of a PMS2 gene.

16. The method of claim 13 further comprising inactivation of said dominant negative allele of said mismatch repair gene, thereby stabilizing the genome of said hypermutated hybridoma.

17. The method of claim 13 wherein said higher titer of said antibodies is at least about 1.5-8 fold greater than the titer produced by said parental hybridoma cell.

18. The method of claim 16 wherein said dominant negative allele of a mismatch repair gene is inactivated by knocking out said dominant negative allele or removing an inducer of said dominant negative allele.

19. The method of claim 13 wherein the dominant negative mismatch repair gene is introduced into said hybridoma cell after the fusion of said myeloma with said immunoglobulin-producing cells.

20. The method of claim 13 wherein said myeloma cells express a dominant negative mismatch repair gene which is also expressed in said hybridoma cells.

21. A method for producing mammalian expression cells that produce high-affinity antibodies from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form hybridoma cells;
(c) performing a screen for binding of antibodies produced from said hybridoma cells to antigen;
(d) cloning immunoglobulin genes from said hybridoma into a mammalian expression cell, wherein said mammalian expression cell expresses a dominant negative allele of a mismatch repair gene;
(e) incubating said mammalian expression cell with a chemical mutagen;
(f) performing a screen for mammalian expression cells that secrete antibodies with higher affinity for antigen as compared to antibodies produced from said hybridoma cells;
thereby producing mammalian expression cells that produce high-affinity antibodies from in vitro immunized human immunoglobulin-producing cells.

22. The method of claim 21 wherein said dominant negative allele of a mismatch repair gene is introduced into said mammalian expression cell prior to introduction of said immunoglobulin genes.

23. The method of claim 21 wherein said dominant negative allele of a mismatch repair gene is introduced into said mammalian expression cell after introduction of said immunoglobulin genes.

24. The method of claim 21 wherein said dominant negative allele of a mismatch repair gene is introduced into said mammalian expression cell simultaneously said immunoglobulin genes.

25. The method of claim 21 wherein said mismatch repair gene is selected from the group consisting of PMS2, PMS1, PMSR3, PMSR2, PMSR6, MLH1, GTBP, MSH3, MSH2, MLH3, or MSH1, and homologs of PMSR genes.

26. The method of claim 21 wherein said dominant negative allele of a mismatch repair gene comprises a dominant negative allele of a PMS2 gene.

27. The method of claim 21 wherein said high affinity antibodies have an affinity of at least about $1 \times 10^7$ $M^{-1}$ to about $1 \times 10^{14}$ $M^{-1}$.

28. A method for producing mammalian expression cells that produce high-affinity antibodies from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form hybridoma cells, wherein said hybridoma cells express a dominant negative allele of a mismatch repair gene;
(c) incubating said hybridoma cells with a chemical mutagen;
(d) incubating said hybridoma cells to allow for mutagenesis, thereby forming hypermutated hybridoma cells;
(e) performing a screen for binding of antibodies to antigen for antibodies produced from said hypermutated hybridoma cells;
(f) selecting hypermutated hybridoma cells that produce antibodies with greater affinity for said antigen than antibodies produced by said parental hybridoma cells;
(g) cloning immunoglobulin genes from said hybridoma into a mammalian expression cell;
thereby producing mammalian expression cells that produce high-affinity antibodies from in vitro immunized immunoglobulin-producing cells.

29. The method of claim 28 wherein said dominant negative allele of a mismatch repair gene is expressed in said myeloma cell and in said hybridoma cell.

30. The method of claim 28 wherein said dominant negative allele of a mismatch repair gene is introduced into said hybridoma cell after said fusion.

31. The method of claim 28 wherein said mismatch repair gene is selected from the group consisting of PMS2, PMS1, PMSR3, PMSR2, PMSR6, MLH1, GTBP, MSH3, MSH2, MLH3, or MSH1, and homologs of PMSR genes.

32. The method of claim 28 wherein said dominant negative allele of a mismatch repair gene comprises a dominant negative allele of a PMS2 gene.

33. The method of claim 28 wherein said high affinity antibodies have an affinity of at least about $1 \times 10^7$ $M^{-1}$ to about $1 \times 10^{14}$ $M^{-1}$.

34. A method for producing mammalian expression cells that produce high titers of high-affinity antibodies from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form hybridoma cells;
(c) performing a screen for binding of antibodies produced from said hybridoma cells to antigen;
(d) cloning immunoglobulin genes from said hybridoma into a parental mammalian expression cell, wherein said mammalian expression cell expresses a dominant negative allele of a mismatch repair gene;
(e) incubating said parental mammalian expression cell with a chemical mutagen;
(f) incubating said parental mammalian expression cell to allow for mutagenesis, thereby forming hypermutated mammalian expression cells;
(g) performing a screen of hypermutable mammalian expression cells that secrete antibodies with higher affinity for antigen as compared to antibodies produced from said hybridoma cells; and
(h) performing a screen of hypermutable mammalian expression cells that secrete higher titers of antibodies than parental mammalian expression cells;
thereby producing mammalian expression cells that produce high titers of high-affinity antibodies from in vitro immunized immunoglobulin-producing cells.

35. The method of claim 34 wherein said dominant negative allele of a mismatch repair gene is introduced into said mammalian expression cell prior to introduction of said immunoglobulin genes.

36. The method of claim 34 wherein said dominant negative allele of a mismatch repair gene is introduced into said mammalian expression cell after introduction of said immunoglobulin genes.

37. The method of claim 34 wherein said dominant negative allele of a mismatch repair gene is introduced into said mammalian expression cell simultaneously said immunoglobulin genes.

38. The method of claim 34 wherein said mismatch repair gene is selected from the group consisting of PMS2, PMS1, PMSR3, PMSR2, PMSR6, MLH1, GTBP, MSH3, MSH2, MLH3, or MSH1, and homologs of PMSR genes.

39. The method of claim 34 wherein said dominant negative allele of a mismatch repair gene comprises a dominant negative allele of a PMS2 gene.

40. The method of claim 34 wherein said high affinity antibodies have an affinity of at least about $1 \times 10^7$ $M^{-1}$ to about $1 \times 10^{14}$ $M^{-1}$.

41. The method of claim 34 wherein said higher titer of said antibodies is at least about 1.5-8 fold greater than the titer produced by said parental hybridoma cell.

* * * * *